United States Patent
Cady et al.

(10) Patent No.: US 12,215,144 B2
(45) Date of Patent: *Feb. 4, 2025

(54) ACUTE TREATMENT AND RAPID TREATMENT OF HEADACHE USING ANTI-CGRP ANTIBODIES

(71) Applicant: H. LUNDBECK A/S, Valby (DK)

(72) Inventors: Roger K. Cady, Bothell, WA (US);
Jeffrey T.L. Smith, Dublin (IE);
Joseph Hirman, Bothell, WA (US);
Barbara Schaeffler, Bothell, WA (US);
Lahar Mehta, Valby (DK)

(73) Assignee: H. LUNDBECK A/S, Valby (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/609,223

(22) Filed: Mar. 19, 2024

(65) Prior Publication Data

US 2024/0270832 A1    Aug. 15, 2024

Related U.S. Application Data

(62) Division of application No. 18/173,116, filed on Feb. 23, 2023, which is a division of application No. 16/736,925, filed on Jan. 8, 2020, now Pat. No. 11,639,380.

(60) Provisional application No. 62/872,989, filed on Jul. 11, 2019, provisional application No. 62/842,162, filed on May 2, 2019, provisional application No. 62/789,828, filed on Jan. 8, 2019.

(51) Int. Cl.
| | |
|---|---|
| *C07K 16/18* | (2006.01) |
| *A61K 9/00* | (2006.01) |
| *A61K 31/4172* | (2006.01) |
| *A61K 38/00* | (2006.01) |
| *A61K 39/00* | (2006.01) |
| *A61K 39/395* | (2006.01) |
| *A61K 45/06* | (2006.01) |
| *A61K 47/26* | (2006.01) |
| *A61P 25/06* | (2006.01) |

(52) U.S. Cl.
CPC ............ *C07K 16/18* (2013.01); *A61K 9/0019* (2013.01); *A61K 31/4172* (2013.01); *A61K 39/3955* (2013.01); *A61K 45/06* (2013.01); *A61K 47/26* (2013.01); *A61P 25/06* (2018.01); *A61K 38/00* (2013.01); *A61K 2039/505* (2013.01); *A61K 2039/545* (2013.01); *C07K 2317/24* (2013.01)

(58) Field of Classification Search
CPC .. C07K 16/18; C07K 2317/24; A61K 9/0019; A61K 39/3955; A61K 45/06; A61K 2039/505; A61K 2039/545; A61K 31/4172; A61K 47/26; A61K 38/00; A61P 25/06

See application file for complete search history.

(56) References Cited

U.S. PATENT DOCUMENTS

| | | |
|---|---|---|
| 5,116,964 A | 5/1992 | Capon et al. |
| 5,266,561 A | 11/1993 | Cooper et al. |
| 5,364,841 A | 11/1994 | Cooper et al. |
| 5,585,089 A | 12/1996 | Queen et al. |
| 5,624,821 A | 4/1997 | Winter et al. |
| 5,648,260 A | 7/1997 | Winter et al. |
| 5,942,227 A | 8/1999 | Cooper et al. |
| 6,180,370 B1 | 1/2001 | Queen et al. |
| 6,313,097 B1 | 11/2001 | Eberlein et al. |
| 6,509,014 B1 | 1/2003 | De Lacharriere et al. |
| 6,521,609 B1 | 2/2003 | Doods et al. |
| 6,737,056 B1 | 5/2004 | Presta |
| 6,956,107 B2 | 10/2005 | Fung et al. |
| 7,279,471 B2 | 10/2007 | Mueller et al. |
| 7,479,488 B2 | 1/2009 | Mueller et al. |
| 7,696,209 B2 | 4/2010 | Mueller et al. |
| 7,700,735 B2 | 4/2010 | Young et al. |
| 7,879,991 B2 | 2/2011 | Vater et al. |
| 7,927,863 B2 | 4/2011 | Cregg et al. |
| 7,935,340 B2 | 5/2011 | Garcia-Martinez et al. |
| 8,007,794 B2 | 8/2011 | Zeller et al. |
| 8,293,239 B2 | 10/2012 | Poulsen et al. |
| 8,298,536 B2 | 10/2012 | Poulsen et al. |
| 8,586,045 B2 | 11/2013 | Zeller et al. |
| 8,597,649 B2 | 12/2013 | Zeller et al. |
| 8,623,366 B2 | 1/2014 | Pios et al. |
| 8,734,802 B1 | 5/2014 | Zeller et al. |
| 9,073,991 B2 | 7/2015 | Allan et al. |
| 9,708,393 B2 | 7/2017 | Russo et al. |

(Continued)

FOREIGN PATENT DOCUMENTS

| | | |
|---|---|---|
| AU | 2006313434 | 5/2007 |
| CA | 2611433 | 12/2006 |

(Continued)

OTHER PUBLICATIONS

Alder Biopharmaceuticals. "Alder BioPharmaceuticals announces positive eptinezumab Phase 3 results for prevention of frequent episodic migraine." (2017).

Dodick, David W., et al. "Eptinezumab demonstrated efficacy in sustained prevention of episodic and chronic migraine beginning on day 1 after dosing." Headache: The Journal of Head and Face Pain 60.10 (2020): 2220-2231.

Dodick, David W., et al. "Safety and efficacy of ALD403, an antibody to calcitonin gene-related peptide, for the prevention of frequent episodic migraine: a randomised, double-blind, placebo-controlled, exploratory phase 2 trial." the lancet neurology 13.11 (2014): 1100-1107.

(Continued)

*Primary Examiner* — Olga N Chernyshev
(74) *Attorney, Agent, or Firm* — Robin L. Teskin; Baker, Donelson, Bearman, Caldwell & Berkowitz PC

(57) ABSTRACT

Methods for rapid treatment of chronic migraine are provided. Exemplary methods provide relief from migraine within 24 hours of administration. Also provided are methods for acute treatment of migraine. Exemplary methods comprise administration of an anti-CGRP antagonist antibody to a patient in need thereof.

31 Claims, 63 Drawing Sheets

Specification includes a Sequence Listing.

(56) References Cited

U.S. PATENT DOCUMENTS

| | | | |
|---|---|---|---|
| 9,745,373 B2 | 8/2017 | Kovacevich et al. | |
| 9,855,332 B2 | 1/2018 | Russo et al. | |
| 10,066,009 B2* | 9/2018 | Kovacevich | C07K 16/26 |
| 10,179,809 B2 | 1/2019 | Kovacevich et al. | |
| 10,189,895 B2 | 1/2019 | Kovacevich et al. | |
| 10,208,112 B2 | 2/2019 | Kovacevich et al. | |
| 10,214,582 B2 | 2/2019 | Kovacevich et al. | |
| 10,266,587 B2 | 4/2019 | Russo et al. | |
| 10,533,048 B2 | 1/2020 | Kovacevich et al. | |
| 11,639,380 B2* | 5/2023 | Cady | A61P 25/06 |
| | | | 424/130.1 |
| 11,639,381 B2* | 5/2023 | Cady | A61K 47/26 |
| | | | 424/133.1 |
| 2001/0036647 A1 | 11/2001 | Choudary et al. | |
| 2002/0162125 A1 | 10/2002 | Salmon et al. | |
| 2002/0164707 A1 | 11/2002 | Adamou et al. | |
| 2003/0027213 A1 | 2/2003 | Zhu et al. | |
| 2003/0181462 A1 | 9/2003 | Doods et al. | |
| 2003/0194404 A1 | 10/2003 | Greenfeder et al. | |
| 2004/0110170 A1 | 6/2004 | Pisegna et al. | |
| 2004/0132824 A1 | 7/2004 | Gil et al. | |
| 2005/0234054 A1 | 10/2005 | Mueller et al. | |
| 2006/0183700 A1 | 8/2006 | Vater et al. | |
| 2006/0270045 A1 | 11/2006 | Cregg et al. | |
| 2009/0023644 A1 | 1/2009 | Southard et al. | |
| 2009/0028784 A1 | 1/2009 | Garcia-Martinez et al. | |
| 2009/0220489 A1 | 9/2009 | Zeller et al. | |
| 2010/0152171 A1 | 6/2010 | Rudolf et al. | |
| 2011/0054150 A1 | 3/2011 | Poulsen et al. | |
| 2011/0257371 A1 | 10/2011 | Poulsen et al. | |
| 2011/0305711 A1 | 12/2011 | Allan et al. | |
| 2012/0000192 A1 | 1/2012 | Zeller et al. | |
| 2012/0114741 A1 | 5/2012 | Aung-Din | |
| 2012/0225075 A1 | 9/2012 | Pios et al. | |
| 2012/0294797 A1 | 11/2012 | Kovacevich et al. | |
| 2012/0294802 A1 | 11/2012 | Russo et al. | |
| 2012/0294822 A1 | 11/2012 | Russo et al. | |
| 2013/0216535 A1 | 8/2013 | Zeller et al. | |
| 2013/0295087 A1 | 11/2013 | Poulsen et al. | |
| 2013/0295088 A1 | 11/2013 | Poulsen et al. | |
| 2015/0266948 A1 | 9/2015 | Bigal et al. | |
| 2017/0088612 A1 | 3/2017 | Bigal | |
| 2018/0127490 A1 | 5/2018 | Bigal et al. | |
| 2018/0142029 A1 | 5/2018 | Boone et al. | |
| 2018/0161434 A1 | 6/2018 | Russo et al. | |
| 2019/0211085 A1 | 7/2019 | Kovacevich et al. | |
| 2019/0240331 A1 | 8/2019 | Russo et al. | |
| 2019/0367590 A1 | 12/2019 | Russo et al. | |
| 2020/0010537 A1 | 1/2020 | Baker et al. | |
| 2020/0216524 A1 | 7/2020 | Cady et al. | |
| 2020/0216525 A1 | 7/2020 | Cady et al. | |

FOREIGN PATENT DOCUMENTS

| | | |
|---|---|---|
| CA | 2626120 | 12/2012 |
| CN | 101309704 | 11/2008 |
| CN | 101979650 | 2/2011 |
| CN | 103421114 | 12/2013 |
| EA | 015526 | 10/2008 |
| EP | 0212432 | 3/1987 |
| EP | 1031350 | 8/2000 |
| EP | 1770091 | 4/2007 |
| EP | 1556020 | 2/2009 |
| EP | 1957106 | 10/2013 |
| JP | Hei6-87890 | 3/1994 |
| JP | 08-268874 | 10/1996 |
| JP | 2005523418 | 8/2005 |
| JP | 2007517911 | 7/2007 |
| JP | 2009-515942 | 4/2009 |
| JP | 2011046710 | 3/2011 |
| JP | 2011513386 | 4/2011 |
| JP | 2011513387 | 4/2011 |
| JP | 5123197 | 1/2013 |
| JP | 2014-517699 | 7/2014 |
| JP | 2017-515579 | 6/2017 |
| KR | 10-1250049 | 4/2013 |
| RU | 2329062 | 7/2008 |
| WO | WO 1996/004928 | 2/1996 |
| WO | WO 97/09046 | 3/1997 |
| WO | WO 98/09630 | 3/1998 |
| WO | WO 98/11128 | 3/1998 |
| WO | WO 98/56779 | 12/1998 |
| WO | WO 00/18764 | 4/2000 |
| WO | WO 2001/022972 | 4/2001 |
| WO | WO 2003/045424 | 6/2003 |
| WO | WO 2003/093472 | 11/2003 |
| WO | WO 03/104236 | 12/2003 |
| WO | WO 2004/003019 | 1/2004 |
| WO | WO 2004/014351 | 2/2004 |
| WO | WO 2004/050683 | 6/2004 |
| WO | WO 2004058184 | 7/2004 |
| WO | WO 2004/082605 | 9/2004 |
| WO | WO 2004/082678 | 9/2004 |
| WO | WO 2004/083187 | 9/2004 |
| WO | WO 2004/0826002 | 9/2004 |
| WO | WO 2004/087649 | 10/2004 |
| WO | WO 2004/091514 | 10/2004 |
| WO | WO 2004/092166 | 10/2004 |
| WO | WO 2004/092168 | 10/2004 |
| WO | WO 2004096122 | 11/2004 |
| WO | WO 2004097421 | 11/2004 |
| WO | WO 2005/009962 | 2/2005 |
| WO | WO 2005/040395 | 5/2005 |
| WO | WO 2005041757 | 5/2005 |
| WO | WO 2005070444 | 8/2005 |
| WO | WO 2005/100360 | 10/2005 |
| WO | WO 2006/077212 | 7/2006 |
| WO | WO 2007/025212 | 3/2007 |
| WO | WO 2007/048026 | 4/2007 |
| WO | WO 2007/054800 | 5/2007 |
| WO | WO 2007/054809 | 5/2007 |
| WO | WO 2007/061676 | 5/2007 |
| WO | WO 2007/076336 | 7/2007 |
| WO | WO 2007/141285 | 12/2007 |
| WO | WO 2008/011190 | 1/2008 |
| WO | 2008144757 | 11/2008 |
| WO | WO 2009/109908 | 9/2009 |
| WO | WO 2009/109911 | 9/2009 |
| WO | WO 2010075238 | 7/2010 |
| WO | WO 2011/024113 | 3/2011 |
| WO | WO 2011/156324 | 12/2011 |
| WO | 2012162243 | 11/2012 |
| WO | 2015143409 | 9/2015 |
| WO | 2015173539 | 11/2015 |
| WO | 2016171742 | 10/2016 |
| WO | 2016205037 | 12/2016 |
| WO | 2017186928 | 11/2017 |
| WO | 2020146527 | 7/2020 |

OTHER PUBLICATIONS

Edvinsson, L. "The Trigeminovascular pathway: role of CGRP and CGRP receptors in migraine. Headache. 57 (Suppl 2): 47-55." (2017).

George, Judy. "Eptinezumab Effective in Chronic Migraine: Intravenous CGRP blocker shows rapid treatment effect," MedPage Today, Apr. 27, 2018.

Lee, Mi Ji, et al. "Feasibility of serum CGRP measurement as a biomarker of chronic migraine: a critical reappraisal." the journal of headache and pain 19.1 (2018): 1-8.

Maasumi, Kasra, Rebecca L. Michael, and Alan M. Rapoport. "CGRP and migraine: the role of blocking calcitonin gene-related peptide ligand and receptor in the management of migraine." Drugs 78 (2018): 913-928.

Marmura MJ, et al. Preventive migraine treatment with eptinezumab reduced acute headache medication and headache frequency to below diagnostic thresholds in patients with chronic migraine and medication-overuse headache. Headache: the Journal of Head and Face Pain. Oct. 2021;61(9):1421-31.

Peters, Golden L. "Migraine overview and summary of current and emerging treatment options." Am J Manag Care 25.2 Suppl (2019): S23-S34.

(56) References Cited

OTHER PUBLICATIONS

Raffaelli, Bianca, and Uwe Reuter. "The biology of monoclonal antibodies: focus on calcitonin gene-related peptide for prophylactic migraine therapy." Neurotherapeutics 15.2 (2018): 324-335.
Silberstein, S. D., et al. "Eptinezumab results for the prevention of episodic migraine over one year in the PROMISE-1 (PRevention of migraine via intravenous Eptinezumab safety and efficacy-1) trial." Headache. Vol. 58. No. 8. 111 River St, Hoboken 07030-5774, NJ USA: Wiley, 2018. p. 1298.
Singh SR, Zhang J, O'Dell C, Hsieh MC, Goldstein J, Liu J, Srivastava A. Effect of polysorbate 80 quality on photostability of a monoclonal antibody. Aaps Pharmscitech. Jun. 2012; 13:422-30.
Tepper, Stewart J. "CGRP and headache: a brief review." Neurological Sciences 40 (2019): 99-105.
The Department of Health and Human Services U.S. Food and Drug Administration, the Pediatric Exclusivity Provision, Jan. 2001 Status Report to Congress (Year 2001).
The International Classification of Headache Disorders, second edition, Cephalalgia, 24(Suppl 1) 2004 (Year: 2004).
Warne, Nicholas W. "Development of high concentration protein biopharmaceuticals: the use of platform approaches in formulation development." European journal of pharmaceutics and biopharmaceutics 78.2 (2011): 208-212.
Dodick, David, et al. "A single intravenous administration of ALD403 (eptinezumab) reduces use of triptans among patients with chronic migraine." Cephalalgia. vol. 37. 1 Olivers Yard, 55 City Road, London EC1Y 1SP, England: Sage Publications LTD, 2017.
Alstadhaug, Karl B et al. "Preventing and treating medication overuse headache." Pain reports vol. 2,4 e612. Jul. 26, 2017, doi: 10.1097/PR9.0000000000000612.
[No Author Attributed] Clinical Trial No. LY2951742, started Mar. 2015, "A Study of LY2951742 in Participants With Episodio Cluster Headache," from ClinicalTrials.gov [database online], Retrieved from the Internet: <https://clinicaltrials.gov/ct2/show/study/NCT02397473?term=LY2951742&rank=9>, retrieved Sep. 3, 2016. 6 pages.
[No Author Attributed] [machine translated from website] "Dysfunction of the temporomandibular joint," as published on the Colgate-Palmolive Company website [online], Retrieved from the Internet: <http://www.colgate.ru/ru/ru/oc/oral-health/conditions/temporomandibular-disorder> 2017; 7 pages.
Androulakis, X Michelle et al. "Central Executive and Default Mode Network Intranet work Functional Connectivity Patterns in Chronic Migraine." Journal of neurological disorders vol. 6,5 (2018): 393. doi:10.4172/2329-6895.1000393.
Carlsen, Louise Ninett, et al. "Complete detoxification is the most effective treatment of medication-overuse headache: a randomized controlled open-label trial." Cephalalgia 38.2 (2018): 225-236.
Cevoli, Sabina, et al. "Family history for chronic headache and drug overuse as a risk factor for headache chronification." Headache: the Journal of Head and Face Pain 49.3 (2009): 412-418.
Chen, Zhiye, et al. "Altered functional connectivity architecture of the brain in medication overuse headache using testing state fMRI." the Journal of Headache and Pain 18.1 (2017): 1-9.
Ferrari, Anna, et al. "Need for analgesics/drugs of abuse: a comparison between headache patients and addicts by the Leeds Dependence Questionnaire (LDQ)." Cephalalgia 26.2 (2006): 187-193.
Ferraro, Stefania et al. "In medication overuse headache, fMRI shows long-lasting dysfunction in midbrain areas." Headache vol. 52,10 (2012): 1520-34. doi: 10.1111/j.1526-4610.2012.02276.x.
Find, Ninette Louise et al. "Medication overuse headache in Europe and Latin America: general demographic and clinical characteristics, referral pathways and national distribution of painkillers in a descriptive, multinational, multicenter study." the journal of headache and pain 17.1 (2016): 1-12.
Fuh, Jong-Ling et al. "Does medication overuse headache represent a behavior of dependence?." Pain vol. 119,1-3 (2005): 49-55. doi:10.1016/j.pain.2005.09.034.

Fumal, Arnaud, et al. "Orbitofrontal cortex involvement in chronic analgesic-overuse headache evolving from episodic migraine." Brain 129.2 (2006): 543-550.
"Headache Classification Committee of the International Headache Society (IHS) the International Classification of Headache Disorders, 3rd edition." Cephalalgia : an international journal of headache vol. 38,1 (2018): 1-211. doi:10.1177/0333102417738202.
Grande, Ragnhild Berling, et al. "The Severity of Dependence Scale detects people with medication overuse: the Akershus study of chronic headache." Journal of Neurology, Neurosurgery & Psychiatry 80.7 (2009): 784-789.
Lai, Tzu-Hsien, et al. "Gray matter changes related to medication overuse in patients with chronic migraine." Cephalalgia 36.14 (2016): 1324-1333.
Lundqvist, C., et al. "An adapted Severity of Dependence Scale is valid for the detection of medication overuse: the Akershus study of chronic headache." European Journal of Neurology 18.3 (2011): 512-518.
Newman-Norlund, Roger D., et al. "Cortical and subcortical changes following sphenopalatine ganglion blocks in chronic migraine with medication overuse headache: a preliminary longitudinal study." Women's midlife health 6.1 (2020): 1-8.
Riederer, Franz, et al. "Decrease of gray matter volume in the midbrain is associated with treatment response in medication-overuse headache: possible influence of orbitofrontal cortex." Journal of Neuroscience 33.39 (2013): 15343-15349.
Riederer, Franz, et al. "Grey matter changes associated with medication-overuse headache: correlations with disease related disability and anxiety." the world journal of biological psychiatry 13.7 (2012): 517-525.
Torta, D. M., et al. "Nucleus accumbens functional connectivity discriminates medication-overuse headache." NeuroImage: Clinical 11 (2016): 686-693.
Lundqvist, Christofer, et al. "The severity of dependence score correlates with medication overuse in persons with secondary chronic headaches. The Akershus study of chronic headache." Pain® 148.3 (2010): 487-491.
Scuteri et al. "New trends in migraine pharmacology: targeting calcitonin gene-related peptide (CGRP) with monoclonal antibodies." Frontiers in pharmacology. Apr. 9, 2019;10:363.
Winner et al. "Effects of Intravenous Eptinezumab vs Placebo on Headache Pain and Most Bothersome Symptom When Initiated During a Migraine Attack: a Randomized Clinical Trial." JAMA. Jun. 15, 2021;325(23):2348-56.
Goadsby et al. Pathophysiology of Migraine: A Disorder of Sensory Processing, Physiological reviews. Apr. 97 (2):553-622. 1997.
Messlinger et al. "The Big CGRP Flood-sources, Sinks and Signalling Sites in the Trigeminovascular System." The Journal of Headache and Pain. Dec. 2018;19(1):1-7.
Kumar et al. "Protective role of a-calcitonin gene-related peptide in cardiovascular diseases." Frontiers in physiology. Jul. 2, 2019;10:821.
Van Dongen et al. "Migraine biomarkers in cerebrospinal fluid: a systematic review and meta-analysis." Cephalalgia. Jan. 2017;37(1):48-63.
Christensen et al. "Migraine induction with calcitonin gene-related peptide in patients from erenumab trials." The Journal of Headache and Pain. Dec. 2018;19(1):1-9.
Covasala et al. "Calcitonin gene-related peptide receptors in rat trigeminal ganglion do not control spinal trigeminal activity." Journal of neurophysiology. Jul. 15, 2012;108(2):431.40.
Storer et al. "Calcitonin gene-related peptide (CGRP) modulates nociceptive trigeminovascular transmission in the cat." British journal of pharmacology. Aug. 2004;142(7):1171-81.
Burstein et al. "The neurobiology of photophobia." Journal of neuro-ophthalmology: the official journal of the North American Neuro-Ophthalmology Society. Mar. 2019:39(1):94.
Wang et al. "Monoclonal antibody exposure in rat and cynomolgus monkey cerebrospinal fluid following systemic administration." Fluids and Barriers of the CNS. Dec. 2018; 15(1):1.0.
Kelman L. "Pain characteristics of the acute migraine attack." Headache: The Journal of Head and Face Pain. Jun. 2006;46(6):942-53.

(56) References Cited

OTHER PUBLICATIONS

Kopruszinski et al. "Prevention of stress-or nitric oxide donor-induced medication overuse headache by a calcitonin gene-related peptide antibody in rodents." Cephalalgia. May 2017;37(6):560-70.
Iranian Office Action dated Apr. 15, 2022, for Pat. Appl. No. 140050140003002468, filed Jun. 15, 2021 entitled "Treatment of Medication Overuse Headache Using Anticgrp or Anti-CGRP-R Antibodies".
Iranian Office Action dated Feb. 7, 2022, for Pat. Appl. No. 140050140003002305, filed Jun. 9, 2021 entitled "Acute Treatment and Rapid Treatment of Headache Using Anti-CGRP Antibodies.".
"Cluster Headache," Wolff's Headache 1974, p. 348.
"Highlights of Prescribing Information" BLA STN 103000/5215—FDA Approved Labeling Text, Botox Package Insert, Oct. 2010, 25 pages.
"Teva to Acquire Labrys Biologics, Inc.: Novel Migraine Prophylaxis Treatment Adds Significant New Dimension to Teva's Growing Pain Care Franchise Business Wire Jun. 3, 2014." 4 pages.
"TMJ Disorders," National Institute of Dental and Craniofacial Research, NIH Publication No. 15-3487, Apr. 2015. 20 pages.
Abdiche YN, et al. "Probing the binding mechanism and affinity of tanezumab, a recombinant humanized anti-NGF monoclonal antibody, using a repertoire of biosensors," Protein Sci. Aug. 2008;17(8):1326-35.
Adwanikar H, et al. Spinal CGRP1 receptors contribute to supraspinally organized pain behavior and pain-related sensitization of amygdala neurons. Pain. Nov. 2007;132(1-2):53- 66. Epub Mar. 1, 2007.
Akerman S, et al. "Nitric oxide synthase inhibitors can antagonize neurogenic and calcitonin gene-related peptide induced dilation of dural meningeal vessels," Br J Pharmacol. Sep. 2002;137(1):62-8.
Akerman, S., et al. "Pearls and pitfalls in experimental in vivo models of migraine: dural trigeminovascular nociception," Cephalalgia. Jun. 2013;33(8):577-92.
Alder Biopharmaceuticals Inc., "Alder Presents Positive ALD403 Clinical Data at European Headache and Migraine Trust International Congress," Press Release, Sep. 15, 2016.
Alder Biopharmaceuticals Inc., "Alder Presents Positive Clinical Data for ALD403 at the 17th Congress of the International Headache Society" Press Release, May 15, 2015. (3 pages).
Alder Biopharmaceuticals Inc., "Alder Reports Phase 2b Trial of ALD403 Meets Primary and Secondary Endpoints Demonstrating Migraine Prevention in Patients with Chronic Migraine," Press Release, Mar. 28, 2016. (4 pages).
Alder Biopharmaceuticals Inc., "Alder Reports Positive Top-Line 24-Week Data Demonstrating Persistent Migraine Prevention in Phase 2b Study of ALD403 in Patients with Chronic Migraine" Press Release, Jul. 25, 2016. (3 pages).
Alder Biopharmaceuticals Inc., "Data From Proof-of-Concept Clinical Trial of ALD403, a Monoclonal Antibody Against CGRP for the Prevention of Migraine, to be Presented at 56th Annual Scientific Meeting of the American Headache Society," Press Release, Jun. 26, 2014. 2 pages.
Almagro JC et al. "Chapter 13 Antibody Engineering: Humanization, Affinity Maturation, and Selection Techniques." Therapeutic Monoclonal Antibodies: From Bench to Clinic (Zhiqiang An (Editor)) Oct. 2009:311-34.
Amara SG, et al. "Expression in brain of a messenger RNA encoding a novel neuropeptide homologous to calcitonin gene-related peptide." Science. Sep. 13, 1985;229(4718):1094-7.
Ambalavanar R., et al. "Deep tissue inflammation upregulates neuropeptides and evokes nociceptive behaviors which are modulated by a neuropeptide antagonist." Pain. Jan. 2006;120(1-2):53-68. Epub Dec. 13, 2005.
Amrutkar DV. "Calcitonin gene-related peptide (CGRP) uptake and release in rat dura mater, trigeminal ganglion and trigeminal nucleus caudalis," PhD thesis, Faculty of Health and Medical Sciences University of Copenhagen, Academic advisor: Inger Jansen-Olesen and Jes Olesen, Submitted: Feb. 20, 2013.
An Z. "Therapeutic Monoclonal Antibodies: From Bench to Clinic." Wiley & Sons, Inc., 2009 Chapter 31, 711-62.

Andersen DC, et al. "Production technologies for monoclonal antibodies and their fragments," Carr Opin Biotechnol. Oct. 2004;15(5):456-62.
Andrew DP, et al. "Monoclonal antibodies distinguishing alpha and beta forms of calcitonin gene-related peptide." J Immunol Methods. Nov. 6, 1990;134(1):87-94.
Antibody Structure and Function, Chapter 4 of Elgert's Immunology: Understanding the Immune System, pp. 58-78. Wiley 1998.
Aoki KR. "Review of a proposed mechanism for the antinociceptive action of botulinum toxin type A," Neurotoxicology. Oct. 2005;26(5):785-93.
Aoki-Nagase T, et al. "Attenuation of antigen-induced airway hyperresponsiveness in CGRP-deficient mice," Am J Physiol Lung Cell Mol Physiol. Nov. 2002;283(5):L963-70.
Armour KL, et al. "Recombinant human IgG molecules lacking Fcgamma receptor 1 binding and monocyte triggering activities," Eur J Immunol. Aug. 1999;29(8):2613-24.
Arulmani U, et al. "Calcitonin gene-related peptide and its role in migraine pathophysiology." Eur J Pharmacol. Oct. 1, 2004:500(1-3):315-30.
Arulmani U, et al. "Experimental migraine models and their relevance in migraine therapy," Cephalalgia. Jun. 2006;26(6):642-59.
Arulmozhi DK, et al., "Migraine: current concepts and emerging therapies." Vascul Pharmacol. Sep. 2005;43(3):176-87.
Asghar, MS, et al. "Evidence for a vascular factor in migraine," Ann Neurol. Apr. 2011;69(4):635-45.
Ashina M, "Vascular changes have a primary role in migraine," Cephalalgia. Apr. 2012;32(5):428-30.
Ashina M, et al. "Evidence for increased plasma levels of calcitonin gene-related peptide in migraine outside of attacks." Pain. May 2000;86(1-2):133-8.
Ashina M, et al. "Pearls and pitfalls in human pharmacological models of migraine: 30 years' experience," Cephalalgia. Jun. 2013;33(8):540-53.
Ashina M, et al. "Plasma levels of calcitonin gene-related peptide in chronic tension-type headache," Neurology. Nov. 14, 2000;55(9):1335-40.
Ashina M. "Calcitonin gene-related peptide in tension-type headache," ScientificWorldJournal. Jun. 7, 2002;2:1527-31.
Aziz Q., "Visceral hypersensitivity: fact or fiction." Gastroenterology. Aug. 2006;131(2):661-4.
Bagdy, G, et al. "Headache-type adverse effects of No donors: vasodilation and beyond," Br J Pharmacol. May 2010: 160(1):20-35.
Balint RF, et al. "Antibody engineering by parsimonious mutagenesis." Gene. Dec. 27, 1993;137(1):109-18.
Barker JN, et al. "Progress in psoriasis. Psoriasis: from gene to clinic. London, UK, Dec. 5-7, 1996," Mol Med Today. May 1997:3(5):193-4.
Batra SK, et al. "Pharmacokinetics and biodistribution of genetically engineered antibodies," Curr Opin Biotechnol. Dec. 2002;13(6):603-8.
Baxter LT, et al. "Biodistribution of monoclonal antibodies: scale-up from mouse to human using a physiologically based pharmacokinetic model," Cancer Res. Oct. 15, 1995;55(20):4611-22.
Bell RD, et al. "Breaching the blood-brain barrier for drug delivery," Neuron. Jan. 8, 2014;81(1):1-3.
Benarroch EE. "CGRP: sensory neuropeptide with multiple neurologic implications," Neurology. Jul. 19, 2011;77(3):281-7.
Benemei S, et al. "CGRP receptors in the control of pain and inflammation," Curr Opin Pharmacol. Feb. 2009;9(1):9-14.
Benemei S, et al. "Migraine," Handb Exp Pharmacol. 2009;(194):75-89.
Benemei S, et al. "Pain pharmacology in migraine: focus on CGRP and CGRP receptors," Neurol Sci. May 2007;28 Suppl 2:S89-93.
Benincosa LJ, et al. "Pharmacokinetics and Pharmacodynamics of a Humanized Monoclonal Antibody to Factor IX in Cynomolgus Monkeys," J Pharmacol Exp Ther, Feb. 2000;292(2):810-6.
Bennett AD, et al. "Alleviation of mechanical and thermal allodynia by CGRP(8-37) in a rodent model of chronic central pain." Pain. May 2000:86(1-2):163-75.
Benschop Provisional U.S. Appl. No. 60/753,044, filed Dec. 22, 2005. File History, 48 pages.

(56) References Cited

OTHER PUBLICATIONS

Biacore 3000 Instrument Handbook, Mar. 1999. 201 pages.
Bigal and Krymchantowski, "Emerging drugs for migraine prophylaxis and treatment," Med. Gen. Med. 2006;8(2):31.
Bigal M, "Clinical Trials Update—2012: Year in Review—a Comment" Headache. Jun. 2013;53(6):1003-4.
Bigal ME, et al. "Emerging drugs for migraine prophylaxis and treatment," MedGenMed. May 4, 2006;8(2):31.
Bigal ME, et al. "Ergotamine and dihydroergotamine: a review," Curr Pain Headache Rep. Feb. 2003;7(1):55-62.
Bigal ME, et al. "Headache prevention outcome and body mass index," Cephalalgia. Apr. 2006:26(4):445-50.
Bigal ME, et al. "Migraine in the Triptan Era: Lessons From Epidemiology, Pathophysiology, and Clinical Science," Headache, Feb. 2009;49 Suppl 1:S21-33.
Bigal ME, et al. "Migraine in the triptan era: progresses achieved, lessons learned and future developments," Arq Neuropsiquiatr. Jun. 2009:67(2B):559-69.
Bigal ME, et al. "Modifiable risk factors for migraine progression," Headache. Oct. 2006;46(9):1334-43.
Bigal ME, et al. "Monoclonal Antibodies for Migraine: Preventing Calcitonin Gene-Related Peptide Activity," CNS Drugs, May 2014;28(5):389-99.
Bigal ME, et al. "New developments in migraine prophylaxis," Expert Opin Pharmacother. Apr. 2003;4(4):433-43.
Bigal ME, et al. "New migraine preventive options: an update with pathophysiological considerations," Rev Hosp Clin Fac Med Sao Paulo. Nov.-Dec. 2002 57(6):293-8.
Bigal ME, et al. "Obesity and migraine: a population study," Neurology. Feb. 28, 2006;66(4):545-50.
Bigal ME, et al. "Obesity is a risk factor for transformed migraine but not chronic tension-type headache," Neurology. Jul. 25, 2006;67(2):252-7.
Bigal ME, et al. "Prophylactio migraine therapy: emerging treatment options," Curr Pain Headache Rep. Jun. 2004;8(3):178-84.
Bigal ME, et al. "Safety and tolerability of LBR-101, a humanized monoclonal antibody that blocks the binding of CGRP to its receptor: Results of the Phase 1 program," Cephalalgia. Dec. 23, 2013;34(7):483-492.
Bigal ME, et al. "Safety, tolerability, and efficacy of TEV-48125 for preventive treatment of high-frequency episodio migraine: a multicentre, randomised, double-blind, placebo-controlled, phase 2b study," Lancet Neurol. Nov. 2015;14(11):1081-90.
Bigal ME, et al. "The preventive treatment of migraine." Neurologist, Jul. 2006;12(4):204-13.
Bigal ME, et al. "The triptans," Expert Rev Neurother, May 2009:9(5):649-59.
Bigal, ME "Glutamate Receptor Antagonists," Headache Currents, 1:20-21. Jul. 2004.
Birder L, et al. "Neural control of the lower urinary tract: peripheral and spinal mechanisms," Neurourol Urodyn. 2010;29(1):128-39.
Boeckh M, et al. "Phase 1 Evaluation of the Respiratory Syncytial Virus—Specific Monoclonal Antibody Palivizumab in Recipients of Hematopoietic Stem Cell Transplants," J Infect Dis. Aug. 1, 2001;184(3):350-4.
Bolay H, et al. "Intrinsic brain activity triggers trigeminal meningeal afferents in a migrane model," Nat Med. Feb. 2002;8(2):136-42.
Brain SD, et al. "CGRP receptors: a headache to study, but will antagonists prove therapeutic in migraine?" Trends Pharmacol Sci. Feb. 2002;23(2):51-3.
Brain SD, et al. "Vascular actions of calcitonin gene-related peptide and adrenomedullin." Physiol Rev. Jul. 2004;84(3):903-34.
Brekke OH, et al. "Therapeutic Antibodies For Human Diseases at the Dawn of the Twenty-First Century," Nat Rev Drug Discov. Jan. 2003;2(1):52-62.
Brorson K, et al. "Mutational analysis of avidity and fine specificity of anti-levan antibodies." J Immunol. Dec. 15, 1999;163(12):6694-701.
Brüggemann M, et al. "The Immunogenicity of Chimeric Antibodies," J Exp Med. Dec. 1, 1989;170(6):2153-7.
Brummell DA, et al. "Probing the combining site of an anti-carbohydrate antibody by saturation-mutagenesis: role of the heavy-chain CDR3 residues." Biochemistry. Feb. 2, 1993;32(4):1180-7.
Buckley TL, et al. "The partial inhibition of inflammatory responses induced by capsaicin using the Fab fragment of a selective calcitonin gene-related peptide antiserum in rabbit skin." Neuroscience. Jun. 1992;48(4):963-8.
Burks EA, "In vitro scanning saturation mutagenesis of an antibody binding pocket." Proc Natl Acad Sci U S A. Jan. 21, 1997;94(2):412-7.
Buzzi MG, et al. "The antimigraine drug, sumatriptan (GR43175), selectively blocks neurogenic plasma extravasation from blood vessels in dura mater," Br J Pharmacol. Jan. 1990;99(1):202-6.
Carter PJ. "Potent antibody therapeutics by design," Nat Rev Immunol. May 2006;6(5):343-57.
Casset F, et al. "A peptide mimetic of an anti-CD4 monoclonal antibody by rational design." Biochem Biophys Res Commun. Jul. 18, 2003;307(1):198-205.
Castaño A, et al. "Headache in symptomatic intracranial hypertension secondary to leptospirosis: a case report," Cephalalgia. Apr. 2005;25(4):309-11.
Cernuda-Morollón E, et al. "CGRP and VIP levels as predictors of efficacy of Onabotulinumtoxin type A in chronic migraine," Headache. Jun. 2014;54(6):987-95.
Chancellor MB, et al. "Neurophysiology of stress urinary incontinence," Rev Urol. 2004;6 Suppl 3:S19-28.
Charbit, A et al. "Dopamine: what's new in migraine?" Curr Opin Neurol. Jun. 2010;23(3):275-81.
Charles A, "Migraine is not primarily a vascular disorder," Cephalalgia. Apr. 2012;32(5):431-2.
Chauhan M. et al. "Studies on the effects of the N-terminal domain antibodies of calcitonin receptor-like receptor and receptor activity-modifying protein 1 on calcitonin gene-related peptide-induced vasorelaxation in rat uterine artery," Biol Reprod. Jun. 2004;70(6):1658-63.
Chen JT, et al. "Menopausal flushes and calcitonin-gene-related peptide," Lancet. Jul. 3, 1993;342(8862):49.
Chen Y, et al. "Selection and analysis of an optimized anti-VEGF antibody: crystal structure of an affinity-matured Fab in complex with antigen." J Mol Biol. Nov. 5, 1999;293(4):865-81.
Cheung B et al. "Adrenomedullin: Its Role in the Cardiovascular System," Semin Vasc Med. May 2004;4(2):129-34.
Chowdhury PS, et al. "Tailor-made antibody therapeutics," Methods. May 2005:36(1):11-24.
Chuang YC, et al. "Intraprostatic botulinum toxin a injection inhibits cyclooxygenase-2 expression and suppresses prostatic pain on capsaicin induced prostatitis model in rat," J Urol. Aug. 2008:180(2):742-8.
Chuang YC, et al. "Urodynamic and immunohistochemical evaluation of intravesical botulinum toxin a delivery using liposomes," J Urol. Aug. 2009;182(2):786-92.
Clanchetti C. "The role of the neurovascular scalp structures in migraine," Cephalalgia. Jul. 2012;32(10):778-84.
Colcher D, et al. "Pharmacokinetics and biodistribution of genetically-engineered antibodies," Q J Nucl Med. Dec. 1998;42(4):225-41.
Colman PM. "Effects of amino acid sequence changes on antibody-antigen interactions." Res Immunol. Jan. 1994;145(1):33-6.
Conner AC, et al. "Interaction of calcitonin-gene-related peptide with its receptors." Biochem Soc Trans. Aug. 2002;30(4):451-5.
Conner AC, et al. "Ligand binding and activation of the CGRP receptor," Biochem Soc Trans. Aug. 2007;35(Pt 4):729-32.
Connor K M et al: "Randomized, controlled trial of telcagepant for the acute treatment of migraine.", Neurology Sep. 22, 2009, vol. 73, No. 12, Sep. 22, 2009 (Sep. 22, 2009), pp. 970-977, XP002732737, ISSN: 1526-632X.
Correia IR. "Stability of IgG isotypes in serum," MAbs. May-Jun. 2010;2(3):221-32.
Cottrell GS, et al. "Localization of calcitonin receptor-like receptor (CLR) and receptor activity-modifying protein 1 (RAMP1) in human gastrointestinal tract," Peptides. Jun. 2012;35(2):202-11.

(56) References Cited

OTHER PUBLICATIONS

Covell DG, et al. "Pharmacokinetics of monoclonal immunoglobulin G1, F(ab')2, and Fab' in mice." Cancer Res. Aug. 1986;46(8):3969-78.
Cutrer F. "Pathophysiology of Migraine," Semin Neurol. Apr. 2006;26(2):171-80.
Cutrer F. "Pathophysiology of Migraine," Semin Neurol. Apr. 2010;30(2):120-30.
Dakhama A, et al. "Calcitonin gene-related peptide: role in airway homeostasis," Curr Opin Pharmacol. Jun. 2004;4(3):215-20.
Davies J, et al. "Affinity improvement of single antibody VH domains: residues in all three hypervariable regions affect antigen binding." Immunotechnology. Sep. 1996;2(3):169-79.
Davis CD et al. "The Tortuous Road to an Ideal CGRP Function Blocker for the Treatment of Migraine," Curr Top Med Chem. 2008;8(16):1468-79.
Davietov B, et al. "Beyond Botox: advantages and limitations of individual botulinum neurotoxins," Trends Neurosci. Aug. 2005;28(8):446-52.
De Pascalis R, et al. "Grafting of "abbreviated" complementarity-determining regions containing specificity-determining residues essential for ligand contact to engineer a less immunogenic humanized monoclonal antibody." J Immunol. Sep. 15, 2002;169(6):3076-84.
Delafoy L, et al. "Interactive involvement of brain derived neurotrophic factor, nerve growth factor, and calcitonin gene related peptide in colonic hypersensitivity in the rat." Gut. Jul. 2006;55(7):940-5. Epub Jan. 9, 2006.
Denekas T, et al. "Inhibition of stimulated meningeal blood flow by a calcitonin gene-related peptide binding mirror-image RNA oligonucleotide," Br J Pharmacol. Jun. 2006;148(4):536-43.
Deng R et al. "Projecting human pharmacokinetics of therapeutic antibodies from nonclinical data," MAbs. Jan.-Feb. 2011;3(1):61-6.
Derosa G, et al. "Optimizing combination treatment in the management of type 2 diabetes," Vasc Health Risk Manag. 2007;3(5):665-71.
Diamond S, et al. "Patterns of diagnosis and acute and preventive treatment for migraine in the United States: results from the American Migraine Prevalence and Prevention study," Headache. Mar. 2007;47(3):355-63.
Diener HC, et al. "Utility of topiramate for the treatment of patients with chronic migraine in the presence or absence of acute medication overuse," Cephalalgia. Oct. 2009;29(10):1021-7.
Dockray et al., "Immunoneutralization studies with calcitonin gene-related peptide," Ann. NY Acad Sci. 1992;657:258-67.
Dodick D, et al. "Cluster Headache: Diagnosis, Management and Treatment," Wolff's Headache 2001, p. 283.
Dodick DW, et al. "Safety and efficacy of ALD403, an antibody to calcitonin gene-related peptide, for the prevention of frequent episodic migraine: a randomised, double-blind, placebo-controlled, exploratory phase 2 trial," Lancet Neurol. Nov. 2014;13(11):1100-7.
Doggrell S. "Migraine and beyond: cardiovascular therapeutic potential for CGRP modulators," Expert Opin Investig Drugs. Jun. 2001;10(6):1131-8.
Dolgin E. "Antibody drugs set to revive flagging migraine target." Nat Rev Drug Discov. Apr. 2013;12(4):249-50.
Doods H, et al. "Pharmacological profile of BIBN4096BS, the first selective small molecule CGRP antagonist." Br J Pharmacol. Feb. 2000;129(3):420-3.
Doods, H et al. "CGRP antagonists: unravelling the role of CGRP in migraine," Trends Pharmacol Sci. Nov. 2007;28(11):580-7.
Dooley JS, et al. "Antibiotics in the treatment of biliary infection," Gut. Sep. 1984;25(9):988-98.
Drake AW, et al. "Characterizing high-affinity antigen/antibody complexes by kinetic- and equilibrium-based methods," Anal Biochem. May 1, 2004;328(1):35-43.
Dressler and Saberi, "Botulinum toxin: mechanisms of action," Eur. Neurol, 2008:53:3-9.
Dressler D, et al. "Botulinum toxin: mechanisms of action," Arq Neuropsiquiatr. Mar. 2005;63(1):180-5.
Dufner P, et al. "Harnessing phage and ribosome display for antibody optimisation." Trends Biotechnol. Nov. 2006;24(11):523-9. Epub Sep. 26, 2006.
Durham P. "CGRP-receptor antagonists—a fresh approach to migraine therapy?" N Engl J Med. Mar. 11, 2004;350(11):1073-5.
Durham Paul L et al: "Calcitonin Gene-Related Peptide (CGRP) Receptor Antagonists in the Treatment of Migraine", CNS Drugs, vol. 24, No. 7, 2010, pp. 539-548.
Durham PL et al. "New insights into the molecular actions of serotonergic antimigraine drugs," Pharmacol Ther. Apr.-May 2022;94(1-2):77-92.
Durham PL, et al. "Regulation of calcitonin gene-related peptide secretion from trigeminal nerve cells by botulinum toxin type A : implications for migraine therapy," Headache. Jan. 2004;44(1):35-42; discussion 42-3.
Durham PL. "Calcitonin Gene-Related Peptide (CGRP) and Migraine," Headache. Jun. 2006;46 Suppl 1:S3~8.
Durham PL. "Inhibition of calcitonin gene-related peptide function: a promising strategy for treating migraine," Headache. Sep. 2008;48(8):1269-75.
Edvinsson L et al. "Blockade of CGRP receptors in the intracranial vasculature: a new target in the treatment of headache," Cephalalgia. Aug. 2004;24(8):611-22.
Edvinsson L et al. "CGRP Receptor Antagonism and Migraine," Neurotherapeutics. Apr. 2010;7(2):164-75.
Edvinsson L et al. "Extracerebral manifestations in migraine. A peptidergic involvement?" J Intern Med. Oct. 1990;228(4):299-304.
Edvinsson L et al. "Neurobiology in primary headaches," Brain Res Brain Res Rev. Jun. 2005;48(3):438-56.
Edvinsson L et al. "Perivascular neuropeptides (NPY, VIP, CGRP and SP) in human brain vessels after subarachnoid haemorrhage," Acta Neurol Scand. Nov. 1994;90(5):324-30.
Edvinsson L et al. "The blood-brain barrier in migraine treatment," Cephalalgia. Dec. 2008;28(12):1245-58.
Edvinsson L et al.: "New drugs in migraine treatment and prophylaxis: telcagepant and topiramate", The Lancet, The Lancet Publishing Group, GB, vol. 376, No. 9741, Aug. 21, 2010 (Aug. 21, 2010), pp. 645-655.
Edvinsson L, et al. "Calcitonin gene-related peptide and cerebral blood vessels: distribution and vasomotor effects," J Cereb Blood Flow Metab. Dec. 1987;7(6):720-8.
Edvinsson L, et al. "Inhibitory effect of BIBN4096BS, CGRP(8-37), a CGRP antibody and an RNA-Spiegelmer on CGRP induced vasodilatation in the perfused and non-perfused rat middle cerebral artery." Br J Pharmacol. Mar. 2007;150(5):633-40. Epub Jan. 22, 2007.
Edvinsson L, et al. "Innervation of the human middle meningeal artery; immunohistochemistry, ultrastructure, and role of endothelium for vasomotility," Peptides. 1998;19(7):1213-25.
Edvinsson L, et al. "Neuropeptides in migraine and cluster headache," Cephalalgia. Oct. 1994;14(5):320-7.
Edvinsson L. "Aspects on the Pathophysiology of Migraine and Cluster Headache," Pharmacol Toxicol. Aug. 2001;89(2):65-73.
Edvinsson L. "Calcitonin Gene-Related Peptide (CGRP) and the Pathophysiology of Headache Therapeutic Implications," CNS Drugs. 2001;15(10):745-53.
Edvinsson L. "CGRP blockers in migraine therapy: where do they act?" Br J Pharmacol. Dec. 2008;155(7): 967-9.
Edvinsson L. "CGRP-receptor antagonism in migraine treatment." Lancet. Dec. 20, 2008:372(9656):2089-90.
Edvinsson L. "Clinical Data on the CGRP Antagonist BIBN4096BS for Treatment of Migraine Attacks," CNS Drug Rev. 2005 Spring;11(1):69-76.
Edvinsson L. "Innervation and effects of dilatory neuropeptides on cerebral vessels. New aspects," Blood Vessels. 1991;28(1-3):35-45.
Edvinsson L. "Neuronal Signal Substances as Biomarkers of Migraine," Headache. Jul.-Aug. 2006 46(7):1088-94.
Edvinsson L. "New therapeutic target in primary headaches—blocking the CGRP receptor," Expert Opin Ther Targets. Jun. 2003;7(3):377-83.
Edvinsson L. "Novel migraine therapy with calcitonin gene-regulated peptide receptor antagonists," Expert Opin Ther Targets. Sep. 2007:11(9):1179-88.

(56) References Cited

OTHER PUBLICATIONS

Edvinsson L: "CGRP blockers in migraine therapy: where do they act?", British Journal of Pharmacology, vol. 155, No. 7, Dec. 2008 (Dec. 2008), pp. 967-969.
Edvinsson Lars: "CGRP-receptor antagonism in migraine treatment.", LANCET Dec. 20, 2008, vol. 372, No. 9656, Dec. 20, 2008 (Dec. 20, 2008), pp. 2089-2090.
Eftekhari S et al. "Differentiation of Nerve Fibers Storing CGRP and CGRP Receptors in the Peripheral Trigeminovascular System," J Pain. Nov. 2013;14(11):1289-303.
Elshourbagy NA, et al. "Molecular cloning and characterization of the porcine calcitonin gene-related peptide receptor." Endocrinology. Apr. 1998;139(4):1678-83.
Emerick GT. "Migraines in the Presence of Glaucoma. Recent advances in diagnosis and management," Glaucoma Today, Sep./Oct. 2008, 21-23.
Escott et al., "Effect of a calcitonin gene-related peptide antagonist (CGRP8-37) on skin vasodilatation and oedema induced by stimulation of the rat saphenous nerve," Br. J. Pharmacol. 1993;110:772-6.
Escott KJ, et al. "Trigeminal ganglion stimulation increases facial skin blood flow in the rat: a major role for calcitonin gene-related peptide." Brain Res. Jan. 9, 1995,669(1):93-9.
Esfandyari T. "The Role of Calcitonin Gene-Related Peptide (CGRP) in Colonic Inflammation, and Secretion in the Rat Distal Colon," Thesis, University of Calagary, Department of Neuroscience and Gastrointestinal Sciences. 1999. 145 pages.
Evans BN, et al. "CGRP-RCP, a novel protein required for signal transduction at calcitonin gene-related peptide and adrenomedullin receptors," J Biol Chem. Oct. 6, 2000;275(40):31438-43.
Evans RW, et al. "Target doses and titration schedules for migraine preventive medications," Headache. Jan. 2006;46(1):160-4.
Evans RW. "Exploding head syndrome followed by sleep paralysis: a rare migraine aura," Headache. Apr. 2006:46(4):682-3.
Everitt DE et al. "The Pharmacokinetics, Antigenicity, and Fusion-Inhibition Activity of RSHZ19, a Humanized Monoclonal Antibody to Respiratory Syncytial Virus, in Healthy Volunteers," J Infect Dis. Sep. 1996;174(3):463-9.
Faraci FM, et al. "Vascular responses of dura mater," Am J Physiol. Jul. 1989;257(1 Pt 2):H157-61.
Farinelli, I et al. "Future drugs for migraine," Intern Emerg Med. Oct. 2009;4(5):367-73.
Feuerstein G et al. "Clinical perspectives of calcitonin gene related peptide pharmacology," Can J Physiol Pharmacol. Jul. 1995;73(7):1070-4.
File History U.S. Appl. No. 60/736,623, filed Nov. 14, 2005, Zeller, et al. Antagonist Antibodies Directed Against Calcitonin Gene-Related Peptide and Methods Using Same. 110 pages.
Fischer MJ et al. "The Nonpeptide Calcitonin Gene-Related Peptide Receptor Antagonist BIBN4096BS Lowers the Activity of Neurons with Meningeal Input in the Rat Spinal Trigeminal Nucleus," J Neurosci. Jun. 22, 2005;25(25):5877-83.
Fischer MJ, "Calcitonin gene-related peptide receptor antagonists for migraine," Expert Opin Investig Drugs. Jul. 2010;19(7):815-23.
Forssman B, et al. "Atenolol for migraine prophylaxis," Headache, Jul. 1983;23(4):188-90.
Forster ER, et al. "The role of calcitonin gene-related peptide in gastric mucosal protection in the rat," Exp Physiol. Jul. 1991;76(4):623-6.
Friend PJ, et al. "Phase I study of an engineered aglycosylated humanized CD3 antibody in renal transplant rejection," Transplantation. Dec. 15, 1999;68(11):1632-7.
Frobert Y, et al. "A sensitive sandwich enzyme immunoassay for calcitonin gene-related peptide (CGRP): characterization and application." Peptides. 1999;20(2):275-84.
Galitsky BA, et al. "Predicting amino acid sequences of the antibody human VH chains from its first several residues," Proc Natl Acad Sci U S A. Apr. 28, 1998;95(9):5193-8.

Gallai V, et al. "Vasoactive peptide levels in the plasma of young migraine patients with and without aura assessed both interictally and ictally." Cephalalgia. Oct. 1995;15(5):384-90.
Gangula PR, et al. "Increased blood pressure in alpha-calcitonin gene-related peptide/calcitonin gene knockout mice," Hypertension. Jan. 2000;35(1 Pt 2):470-5.
Gearing D, et al. "A fully caninised anti-NGF monoclonal antibody for pain relief in dogs," BMC Vet Res. Nov. 9, 2013;9:226.
Geppetti P et al. "Antidromic vasodilatation and the migraine mechanism," J Headache Pain. Mar. 2012;13(2):103-11.
Geppetti P et al., "CGRP and migraine: neurogenic inflammation revisited," J Headache Pain. Apr. 2005;6(2):61-70.
Geppetti P et al. "Novel therapeutic targets," Neurol Sci. May 2006;27 Suppl 2;S111-4.
Giamberardino MA, et al. "Emerging drugs for migraine treatment," Expert Opin Emerg Drugs. Mar. 2015;20(1):137-47.
Gillies S et al. "Improving the efficacy of antibody-interleukin 2 fusion proteins by reducing their interaction with Fc receptors," Cancer Res. May 1, 1999:59(9):2159-66.
Giniatullin R et al. "Molecular Mechanisms of Sensitization of Pain-transducing P2X3 Receptors by the Migraine Mediators CGRP and NGF," Mol Neurobiol, Feb. 2008;37(1):83-90.
Glennie MJ, et al. "Clinical trials of antibody therapy," Immunol Today. Aug. 2000:21(8):403-10.
Glover V, et al. "Can the vascular and neurogenic theories of migraine finally be reconciled?" Trends Pharmacol Sol. Jan. 1989;10(1):1-3.
Goadsby PJ et al. "Release of vasoactive peptides in the extracerebral circulation of humans and the cat during activation of the trigeminovascular system," Ann Neurol. Feb. 1988;23(2):193-6.
Goadsby PJ, et al. "Migraine—current understanding and treatment." N Engl J Med. Jan. 24, 2002;346(4):257-70.
Goadsby PJ, et al. "Vasoactive peptide release in the extracerebral circulation of humans during migraine headache." Ann Neurol. Aug. 1990;28(2):183-7.
Goadsby PJ, "Advances in the understanding of headache," Br Med Bull. Oct. 5, 2005;73-74:83-92. Print 2005.
Goadsby PJ. "Calcitonin gene-related peptide antagonists as treatments of migraine and other primary headaches," Drugs. 2005;65(18):2557-67.
Goadsby PJ. "Can we develop neurally acting drugs for the treatment of migraine?" Nat Rev Drug Discov. Sep. 2005;4(9):741-50.
Goadsby PJ. "Headache: a good year for research," Lancet Neurol. Jan. 2006;5(1):5-6.
Goadsby PJ. "Migraine Pathophysiology," Headache. Apr. 2005;45 Suppl 1:S14-24.
Goadsby PJ. "New targets in the acute treatment of headache," Curr Opin Neurol. Jun. 2005;18(3):283-8.
Goadsby PJ. "The vascular theory of migraine—a great story wrecked by the facts," Brain. Jan. 2009;132(Pt 1):6-7.
Goadsby, PJ, et al. "Randomized, double-blind, placebo-controlled trial of ALD403, an anti-CGRP antibody in the prevention of frequent episodio migraine." 56th Annual Scientific Meeting of the American Headache Society, Jun. 2014. 4 pages.
Gómez-Foix AM, et al., "Anti-insulin effects of amylin and calcitonin-gene-related peptide on hepatic glycogen metabolism," Biochem J. Jun. 15, 1991:276 ( Pt 3):607-10.
Green LL, et al. "Antigen-specific human monoclonal antibodies from mice engineered with human Ig heavy and light chain YACs," Nat Genet. May 1994;7(1):13-21.
Grunenberger F. "[Calcitonin gene-related peptide (CGRP): a vasodilator neuropeptide with many potential applications]" Pathol Biol (Paris). Dec. 1993;41(10):936-42.
Gupta S et al. "Evidence for CGRP re-uptake in rat dura mater encephali," Br J Pharmacol. Dec. 2010;161(8):1885-98.
Gupta S et al. "Intravital microscopy on a closed cranial window in mice: a model to study trigeminovascular mechanisms involved in migraine," Cephalalgia. Nov. 2006;26(11):1294-303.
Gupta S et al. "Potential role of female sex hormones in the pathophysiology of migraine," Pharmacol Ther. Feb. 2007;113(2):321-40.

(56) References Cited

OTHER PUBLICATIONS

Gupta S et al. "The relevance of preclinical research models for the development of antimigraine drugs: focus on 5-HT(1B/1D) and CGRP receptors," Pharmacol Ther. Oct. 2010;128(1):170-90.
Hakala JM, et al. "Modelling constrained calcitonin gene-related peptide analogues." Protein Eng. Feb. 1996;9(2):143-8.
Halimi S, et al. "Combination treatment in the management of type 2 diabetes: focus on vildagliptin and metformin as a single tablet," Vasc Health Risk Manag. 2008;4(3):481-92.
Hanes J et al. "Picomolar affinity antibodies from a fully synthetic naive library selected and evolved by ribosome display," Nat Biotechnol. Dec. 2000;18(12):1287-92.
Hansen JM, et al. "Calcitonin gene-related peptide triggers migraine-like attacks in patients with migraine with aura." Cephalalgia. Oct. 2010:30(10):1179-86.
Hargreaves R. "New Migraine and Pain Research," Headache. Apr. 2007,47 Suppl 1:S26-43.
Hatcher JP, et al, "Biologics: the next-generation therapeutics for analgesia?" Expert Rev Neurother. Nov. 2011:11(11):1653-8.
Hay D et al. "A comparison of the actions of BIBN4096BS and CGRP(8-37) on CGRP and adrenomedullin receptors expressed on Sk-N-Mc, L6. Col 29 and Rat 2 cells," Br J Pharmacol. Sep. 2002;137(1):80-6.
Hay D et al. "International Union of Pharmacology. LXIX. Status of the Calcitonin Gene-Related Peptide Subtype 2 Receptor," Pharmacol Rev. Jun. 2008;60(2):143-5.
Hay D et al. "The pharmacology of CGRP-responsive receptors in cultured and transfected cells," Peptides. Nov. 2004;25(11):2019-26.
Hay D et al. "The Preclinical Pharmacology of BIBN4096BS, a CGRP Antagonist," Cardiovasc Drug Rev. 2005 Spring:23(1):31-42.
Hay D. "What Makes a CGRP2 Receptor?" Clin Exp Pharmacol Physiol. Oct. 2007;34(10):963-71.
Hay DL, et al. "CU/RAMP2 and CL/RAMP3 produce pharmacologically distinct adrenomedullin receptors: a comparison of effects of adrenomedullin22-52, CGRP8-37 and BIBN4096BS," Br J Pharmacol. Oct. 2003;140(3):477-86. Epub Aug. 26, 2003.
Hershey JC, et al. "Investigation of the species selectivity of a nonpeptide CGRP receptor antagonist using a novel pharmacodynamic assay," Regul Pept. Apr. 15, 2005;127(1-3):71-7.
Hill RG et al. "Neuropeptide and Kinin Antagonists," Handb Exp Pharmacol. 2007;(177):181-216.
Hillmen P, et al. "Effect of eculizumab on hemolysis and transfusion requirements in patients with paroxysmal nocturnal hemoglobinuria," N Engl J Med. Feb. 5, 2004;350(6):552-9.
Hinton PR, et al. "Engineered human IgG antibodies with longer serum half-lives in primates," J Biol Chem. Feb. 20, 2004:279(8):6213-6.
Hirsch S et al, "The CGRP receptor antagonist BIBN4096BS peripherally alleviates inflammatory pain in rats," Pain. May 2013:154(5):700-7.
Ho TW et al. "CGRP and its receptors provide new insights into migraine pathophysiology," Nat Rev Neurol. Oct. 2010;6(10):573-82.
Ho TW, et al. "Impact of recent prior opioid use on rizatriptan efficacy. a post hoc pooled analysis," Headache. Mar. 2009;49(3):395-403.
Ho TW, et al. "Randomized controlled trial of the CGRP receptor antagonist telcagepant for migraine prevention," Neurology. Sep. 9, 2014;83(11):958-66.
Ho TW, et al. "Efficacy and tolerability of MK-0974 (telcagepant), a new oral antagonist of calcitonin gene-related peptide receptor, compared with zolmitriptan for acute migraine: a randomised, placebo-controlled, parallel-treatment trial," Lancet. Dec. 20, 2008;372(9656):2115-23.
Hoff AO et al. "Increased bone mass is an unexpected phenotype associated with deletion of the calcitonin gene," J Clin Invest. Dec. 2002;110(12):1849-57.
Hoffmann J, et al. "New Agents for Acute Treatment of Migraine: CGRP Receptor Antagonists, iNOS Inhibitors," Curr Treat Options Neurol. Feb. 2012;14(1):50-9.
Holland J et al. "Calcitonin Gene-Related Peptide Reduces Brain Injury in a Rat Model of Focal Cerebral Ischemia," Stroke. Oct. 1994;25(10):2055-8; discussion 2058-9.
Holliger P, et al. "Engineered antibody fragments and the rise of single domains," Nat Biotechnol. Sep. 2005;23(9):1126-36.
Holm P, et al. "Functional mapping and single chain construction of the anti-cytokeratin 8 monoclonal antibody TS1." Mol Immunol. Feb. 2007;44(6):1075-84. Epub Sep. 20, 2006.
Holman JJ, et al. "Human alpha- and beta-CGRP and rat alpha-CGRP are coronary vasodilators in the rat." Peptides. Mar.-Apr. 1986;7(2):231-5.
Holt LJ, et al. "Domain antibodies: proteins for therapy," Trends Biotechnol. Nov. 2003;21(11):484-90.
Holzer P et al. "Afferent Nerve-Mediated Protection Against Deep Mucosal Damage in the Rat Stomach," Gastroenterology. Apr. 1990:98(4):838-48.
Holzer P et al. "Sensory neurons mediate protective vasodilatation in rat gastric mucosa," Am J Physiol. Mar. 1991;260(3 Pt 1):G363-70.
Holzer P et al. "Stimulation of Afferent Nerve Endings By Intragastric Capsaicin Protects Against Ethanol-Induced Damage of Gastric Mucosa," Neuroscience. Dec. 1988;27(3):981-7.
Holzer P. "Implications of tachykinins and calcitonin gene-related peptide in inflammatory bowel disease," Digestion. Jul.-Aug. 1998;59(4):269-83.
Holzer P. "Capsaicin: Cellular Targets, Mechanisms of Action, and Selectivity for Thin Sensory Neurons," Pharmacol Rev. Jun. 1991;43(2):143-201.
Hong KW, et al. "Effect of omega-conotoxin GVIA and omega-agatoxin IVA on the capsaicin-sensitive calcitonin gene-related peptide release and autoregulatory vasodilation in rat pial arteries," J Cereb Blood Flow Metab. Jan. 1999;19(1):53-60.
Hong KW, et al. "Pharmacological coupling and functional role for CGRP receptors in the vasodilation of rat pial arterioles," Am J Physiol. Jan. 1996:270(1 Pt 2):H317-23.
Hong KW, et al. "Pharmacological evidence that calcitonin gene-related peptide is implicated in cerebral autoregulation," Am J Physiol. Jan. 1994;266(1 Pt 2):H11-6.
Hoogenboom HR, et al. "Multi-subunit proteins on the surface of filamentous phage: methodologies for displaying antibody (Fab) heavy and light chains," Nucleic Acids Res. Aug. 11, 1991;19(15):4133-7.
Hoogenboom HR. "Selecting and screening recombinant antibody libraries," Nat Biotechnof. Sep. 2005:23(9):1105-16.
Hopkins, CR. "ACS Chemical Neuroscience Molecule Spotlight on Telcagepant (MK-0974)," ACS Chem Neurosci. Jul. 20, 2011;2(7):334-5,.
Hu H. et al. "Acute migraine treatment with rizatriptan in real world settings—focusing on treatment strategy, effectiveness, and behavior," Headache. Feb. 2009;49 Suppl 1:S34-42.
Hubbard JA, et al. "Identification of the epitopes of calcitonin gene-related peptide (CGRP) for two anti CGRP monoclonal antibodies by 2D NMR," Protein Sci. Sep. 1997;6(9):1945-52.
Hudson PJ, et al. "Engineered antibodies," Nat Med. Jan. 2003;9(1):129-34.
Hughes SR et al. "A calcitonin gene-related peptide (CGRP) antagonist (CGRP8-37) inhibits microvascular responses induced by CGRP and capsaicin in skin," Br J Pharmacol. Nov. 1991;104(3):738-42.
Hurley D. "CGRP Drug Improves Wellness on Headache-Free Days, Study Finds," Neurology Today, p. 31, Jul. 2016.
Hwang WY, et al. "Immunogenicity of engineered antibodies," Methods. May 2005;36(1):3-10.
Ibrahimi K, et al. "Development of an experimental model to study trigeminal nerve-mediated vasodilation on the human forehead," Cephalalgia. Jan. 3, 2014;34(7):514-522.
Idusogie EE, at al. "Mapping of the C1q Binding Site on Rituxan, a Chimeric Antibody with a Human IgG1 Fc," J Immunol. Apr. 15, 2000;164(8):4178-84.
Iovino M, et al. "Safety, tolerability and pharmacokinetics of BIBN 4096 BS, the first selective small molecule calcitonin gene-related

(56) References Cited

OTHER PUBLICATIONS peptide receptor antagonist, following single intravenous administration in healthy volunteers," Cephalalgia. Aug. 2004;24(8):645-56.
Janeway CA et al. "Immuno Biology: the Immune System in Health and Disease." Current Biology Ltd./Garland Publishing Inc. 1994 Glossary page G:2.
Jang YJ, et al. "The structural basis for DNA binding by an anti-DNA autoantibody." Mol Immunol. Dec. 1998; 35(18):1207-17.
Jansen-Olesen I, et al. "In-depth characterization of CGRP receptors in human intracranial arteries," Eur J Pharmacol. Nov. 28, 2003;481(2-3):207-16.
Jones PT, et al. "Replacing the complementarity-determining regions in a human antibody with those from a mouse," Nature. May 29-Jun 4, 1986:321(6069):522-5.
Juaneda C, et al. "The molecular pharmacology of CGRP and related peptide receptor subtypes," Trends Pharmacol Sci. Nov. 2000;21(11):432-8.
Juhasz G, et al. "No-induced migraine attack: strong increase in plasma calcitonin gene-related peptide (CGRP) concentration and negative correlation with platelet serotonin release." Pain. Dec. 2003;106(3):461-70.
Juhl L, et al. "Effect of two novel CGRP-binding compounds in a closed cranial window rat model," Eur J Pharmacol. Jul. 12, 2007;567(1-2):117-24.
Julia V, et al. "Tachykininergic mediation of viscerosensitive responses to acute inflammation in rats: role of CGRP." Am J Physiol. Jan. 1997;272(1 Pt 1):G141-6.
Jung ST, et al. "Bypassing glycosylation: engineering aglycosylated full-length IgG antibodies for human therapy," Curr Opin Biotechnol. Dec. 2011;22(6):858-67.
Kaiser EA, et al. "CGRP and migraine: could PACAP play a role too?" Neuropeptides. Dec. 2013;47(6):451-61.
Kapoor K, et al. "Effects of BIBN4096BS on cardiac output distribution and on CGRP-induced carotid haemodynamic responses in the pig," Eur J Pharmacol. Aug. 15, 2003;475(1-3):69-77.
Kapoor K, et al. "Effects of the CGRP receptor antagonist BIBN4096BS on capsaicin-induced carotid haemodynamic changes in anaesthetised pigs," Br J Pharmacol. Sep. 2003;140(2):329-38.
Kapoor, K. "Novel Potential Antimigraine Compounds: Carotid and Systemic Haemodynamic Effects in a Porcine Model of Migraine," Thesis, Erasmus University, Rotterdam. With summary in Dutch. 2003. 157 pages.
Karasek C., et al. "Characterization of the intrinsic binding features of three anti-CGRP therapeutic antibodies effective in preventing migraine: a comparative pre-clinical case study of ALD403, LY-2951742, TEV-48125." 5th European Headache and Migraine Trust International Congress, Sep. 2016. 4 pages.
Kato K, et al. "CGRP antagonists enhance gastric acid secretion in 2-h pylorus-ligated rats," Peptides. 1995;16(7):1257-62.
Kawamura M, et al. "Antinociceptive effect of intrathecally administered antiserum against calcitonin gene-related peptide on thermal and mechanical noxious stimuli in experimental hyperalgesic rats." Brain Res. Sep. 11, 1989;497(1):199-203.
Kaymakcalan Z, et al. "Comparisons of affinities, avidities, and complement activation of adalimumab, infliximab, and etanercept in binding to soluble andmembrane tumor necrosis factor," Clin Immunol. May 2009;131(2):306-16.
Keates AC, et al. "CGRP upregulation in dorsal root ganglia and ileal mucosa during Clostridium difficile toxin A-induced enteritis," Am J Physiol. Jan. 1998;274(1 Pt 1):G196-202.
Kennel SJ, et al. "Direct Binding of Radioiodinated Monoclonal Antibody to Tumor Cells: Significance of Antibody Purity and Affinity for Drug Targeting or Tumor Imaging," Hybridoma. 1983;2(3):297-310.
Kim SJ, et al. "Antibody Engineering for the Development of Therapeutic Antibodies," Mol Cells. Aug. 31, 2005;20(1):17-29.
Kipriyanov S, et al. "Generation and Production of Engineered Antibodies," Mol Biotechnol. Jan. 2004;26(1):39-60.
Kipriyanov S. "Generation of Antibody Molecules Through Antibody Engineering" from Methods in Molecular Biology, vol. 207: Recombinant Antibodies for Cancer Therapy Methods and Protocols, 2003 pp. 3-25.
Knotkova H, et al. "Imaging intracranial plasma extravasation in a migraine patient: a case report," Pain Med. May-Jun. 2007;8(4):383-7.
Kobayashi D, et al. "Calcitonin Gene-Related Peptide Mediated Neurogenic Vasorelaxation in the Isolated Canine Lingual Artery," Jpn J Pharmacol. Apr. 1995;67(4):329-39.
Kobayashi H, et al. "Tryptophan H33 plays an important role in pyrimidine (6-4) pyrimidone photoproduct binding by a high-affinity antibody." Protein Eng. Oct. 1999;12(10):879-84.
Krymchantowski AV, et al. "New and emerging prophylactic agents for migraine," CNS Drugs. 2002;16(9):611-34.
Krymchantowski AV, et al. "Rizatriptan in migraine," Expert Rev Neurother. Sep. 2005;5(5):597-603.
Krymchantowski AV, et al. "Rizatriptan vs. rizatriptan plus trimebutine for the acute treatment of migraine: a double-blind, randomized, cross-over, placebo-controlled study," Cephalalgia, Jul. 2006:26(7):871-4.
Krymchantowski AV, et al. "Topiramate plus nortriptyline in the preventive treatment of migraine: a controlled study for nonresponders," J Headache Pain. Jan. 2012;13(1):53-9.
Kumar S, et al. "Molecular cloning and expression of the Fabs of human autoantibodies in *Escherichia coli*. Determination of the heavy or light chain contribution to the anti-DNA/-cardiolipin activity of the Fab." J Biol Chem. Nov. 10, 2000:275(45):35129-36.
Kunkel RS, et al. "Surgical treatment of chronic migrainous neuralgia," Cleve Clin Q. 1974 Winter;41(4):189-92.
Kuraishi Y, et al. "Antinociception induced in rats by intrathecal administration of antiserum against calcitonin gene-related peptide." Neurosci Lett. Oct. 17, 1988;92(3):325-9.
Kurosawa M, et al. "Increase of meningeal blood flow after electrical stimulation of rat dura mater encephali: mediation by calcitonin gene-related peptide," Br J Pharmacol. Apr. 1995:114(7):1397-402.
Kuus-Reichel K, et al. "Will Immunogenicity Limit the Use, Efficacy, and Future Development of Therapeutic Monoclonal Antibodies?" Clin Diagn Lab Immunol. Jul. 1994;1(4):365-72.
Lambrecht N, et al. "Role of calcitonin gene-related peptide and nitric oxide in the gastroprotective effect of capsaicin in the rat," Gastroenterology. May 1993;104(5):1371-80.
Lance J. "Migraine Pain Originates from Blood Vessels." Headache Pathogenesis: Monoamines, Neuropeptides, Purines, and Nitric Oxide, edited by J. Olesen and L. Edvinsson, Lippincott-Raven Publishers, Philedelphia, 1997. Chapter 1, pp. 3-9.
Lassen LH, et al. "CGRP may play a causative role in migraine." Cephalalgia. Feb. 2002;22(1):54-61.
Lassen LH, et al. "Involvement of calcitonin gene-related peptide in migraine: regional cerebral blood flow and blood flow velocity in migraine patients," J Headache Pain. Jun. 2008;9(3):151-7.
Lazzeria M, et al. "The Challenge of the Overactive Bladder: From Laboratory to New Drugs," European Association of Urology, vol. 5, Issue 6, Dec. 2007, pp. 250-258.
Lee CV, et al. "High-affinity human antibodies from phage-displayed synthetic Fab libraries with a single framework scaffold," J Mol Biol. Jul. 23, 2004;340(5):1073-93.
Leighton B, et al. "Pancreatic amylin and calcitonin gene-related peptide cause resistance to insulin in skeletal muscle in vitro," Nature. Oct. 13, 1988;335(6191):632-5.
Lévéque D, et al. "Pharmacokinetics of therapeutic monoclonal antibodies used in oncology." Anticancer Res. May-Jun. 2005;25(3c):2327-43.
Levy D. et al. "A critical view on the role of migraine triggers in the genesis of migraine pain," Headache. Jun. 2009;49(6):953-7.
Levy D, et al. "Calcitonin gene-related peptide does not excite or sensitize meningeal nociceptors: implications for the pathophysiology of migraine," Ann Neurol. Nov. 2005;58(5):698-705.
Levy D, et al. "Migraine pain and nociceptor activation—where do we stand?" Headache. May 2010;50(5):909-16.
Levy D, et al. "The vascular theory of migraine: leave it or love it?" Ann Neurol. Apr. 2011;69(4):800-1.

(56) References Cited

OTHER PUBLICATIONS

Li DS, et al. "Role of calcitonin gene-related peptide in gastric hyperemic response to intragastric capsaicin," Am J Physiol. Oct. 1991;261(4 Pt 1):G657-61.

Lin HC, et al. "Immunoneutralization of Calcitonin Gene-Related Peptide (CGRP) During Inhibition of Intestinal Transit by Fat," Gastroenterology vol. 114, No. 4. 1998. 1 page, Abstract No. G3253.

Lin YS, et al. "Preclinical pharmacokinetics, interspecies scaling, and tissue distribution of a humanized monoclonal antibody against vascular endothelial growth factor," J Pharmacol Exp Ther. Jan. 1999;288(1):371-8.

Link AS, et al. "Treatment of migraine attacks based on the interaction with the trigemino-cerebrovascular system," J Headache Pain. Feb. 2008;9(1):5-12.

Lipton RB, et al. "CGRP antagonists in the acute treatment of migraine," Lancet Neurol. Jun. 2004;3(6):332.

Lipton RB, et al. "Headache: triumphs in translational research," Lancet Neurol. Jan. 2005;4(1):11-2.

Lipton RB, et al. "Moving forward–essential questions for the next 10 years," Headache. Feb. 2009;49 Suppl 1:S43-6.

Little M, et al. "Of mice and men: hybridoma and recombinant antibodies." Immunol Today. Aug. 2000;21(8):364-70.

Lonberg N, et al. "Antigen-specific human antibodies from mice comprising four distinct genetic modifications," Nature, Apr. 28, 1994;368(6474):856-9.

Lonberg N, et al. "Human antibodies from transgenic animals," Nat Biotechnol. Sep. 2005;23(9):1117-25.

Longoni M, et al. "Inflammation and excitotoxicity: role in migraine pathogenesis," Neurol Sci. May 2006:27 Suppl 2:S107-10.

Louis SM, et al. "Antibodies to calcitonin-gene related peptide reduce inflammation induced by topical mustard oil but not that due to carrageenin in the rat." Neurosci Lett. Jul. 31, 1989;102(2-3):257-60.

Louis SM, et al. "Immunization with calcitonin gene-related peptide reduces the inflammatory response to adjuvant arthritis in the rat." Neuroscience. 1990;39(3):727-31.

Louis SM, et al. "The role of substance P and calcitonin gene-related peptide in neurogenic plasma extravasation and vasodilatation in the rat." Neuroscience. 1989;32(3):581-6.

MacCallum RM, et al. "Antibody-antigen interactions: contact analysis and binding site topography." J Mol Biol. Oct. 11, 1996;262(5):732-45.

MacGregor EA, "Migraine in pregnancy and lactation; a clinical review," J Fam Plann Reprod Health Care. Apr. 2007;33(2):83-93.

Majima, M, et al. "Roles of calcitonin gene-related peptide in ehancement of angiogenesis," Inflammation and Regeneration vol. 31 No. 2 Mar. 2011, 146-150.

Mallee JJ, et al. "Receptor activity-modifying protein 1 determines the species selectivity of non-peptide CGRP receptor antagonists." J Biol Chem. Apr. 19, 2002;277(16):14294-8.

Marcelo E. Bigal et al: "Calcitonin Gene-Related Peptide (CGRP) and Migraine Current Understanding and State of Development", Headache, vol. 53, No. 8, Sep. 12, 2013 (Sep. 12, 2013), pp. 1230-1244.

Mareska M, et al. "Lambert-Eaton myasthenic syndrome," Semin Neurol. Jun. 2004;24(2):149-53.

Marquez de Prado B and Russo AF, "CGRP receptor antagonists; a new frontier of anti-migraine medications," Drug Discov Today Ther Strateg. 2006 Winter;3(4):593-597.

Marshall I, et al. "Human and rat alpha-CGRP but not calcitonin cause mesenteric vasodilatation in rats." Eur J Pharmacol. Apr. 16, 1986;123(2):217-22.

Martinez-Sáenz A, et al., "Role of calcitonin gene-related peptide in inhibitory neurotransmission to the pig bladder neck," J Urol. Aug. 2011;186(2):728-35.

Maynard JA, et al. "Protection against anthrax toxin by recombinant antibody fragments correlates with antigen affinity," Nat Biotechnol. Jun. 2002;20(6):597-601.

McCafferty J, et al. "Phage antibodies: filamentous phage displaying antibody variable domains," Nature. Dec. 6, 1990:348(6301):552-4.

McCulloch J, et al. "Calcitonin gene-related peptide: functional role in cerebrovascular regulation," Proc Natl Acad Sci U S A. Aug. 1986;83(15):5731-5.

McLatchie LM, et al. "RAMPs regulate the transport and ligand specificity of the calcitonin-receptor-like receptor," Nature. May 28, 1998;393(6683):333-9.

Mehrotra S, et al. "Current and prospective pharmacological targets in relation to antimigraine action," Naunyn Schmiedebergs Arch Pharmacol. Oct. 2008;378(4):371-94.

Mense S. "Pathophysiology of low back pain and the transition to the chronic state—experimental data and new concepts." Schmerz. Dec. 2001;15(6):413-7.

Messlinger K, et al. "Neuropeptide effects in the trigeminal system: pathophysiology and clinical relevance in migraine," Keio J Med. 2011;60(3):82-9.

Messlinger K. "Migraine: where and how does the pain originate?" Exp Brain Res. Jun. 2009;196(1):179-93.

Messlinger, et al. "Inhibition of neurogenic blood flow increases in the rat cranial dura matter by a CGRP-binding Spiegelmer," Cephalalgia, No. F022 2004.

Middlemiss DN. "Direct evidence for an interaction of beta-adrenergic blockers with the 5-HT receptor," Nature. May 19, 1977;267(5608):289-90.

Middlemiss DN. "Stereoselective blockade at [3H]5-HT binding sites and at the 5-HT autoreceptor by propranolol." Eur J Pharmacol. Jun. 1, 1984;101(3-4):289-93.

Mirick GR, et al. "A review of human anti-globulin antibody (HAGA, HAMA, HACA, HAHA) responses to monoclonal antibodies. Not four letter words," Q J Nucl Med Mol Imaging, Dec. 2004;48(4):251-7.

Molina JM, et al. "Induction of insulin resistance in vivo by amylin and calcitonin gene-related peptide," Diabetes. Feb. 1990;39(2):260-5.

Moore CK, et al. "Urological Applications of Botulinum Toxin," Female Urology: A Practical Clinical Guide. 2007 Chapter 14:213-217.

Moore EL, et al. "Targeting a family B GPCR/RAMP receptor complex: CGRP receptor antagonists and migraine," Br J Pharmacol. May 2012;166(1):66-78.

Morara S, et al. "Monoclonal antibodies reveal expression of the CGRP receptor in Purkinje cells, interneurons and astrocytes of rat cerebellar cortex," Neuroreport. Nov. 16, 1998;9(16):3755-9.

Morell A, et al. "Metabolic properties of IgG subclasses in man." J Clin Invest. Apr. 1970;49(4):673-80.

Morrison SL, et al. "Chimeric human antibody molecules: mouse antigen-binding domains with human constant region domains," Proc Natl Acad Sci U S A. Nov. 1984;81(21):6851-5.

Moskowitz MA, "Neurogenic inflammation in the pathophysiology and treatment of migraine," Neurology. Jun. 1993:43(6 Suppl 3):S16-20.

Moskowitz MA, et al. "CGRP: blood flow and more?" Cephalalgia. Aug. 1996;16(5):287.

Moskowitz MA. "Pathophysiology of headache—past and present," Headache. Apr. 2007;47 Suppl 1:S58-63.

Mould DR, et al. "A population pharmacokinetic-pharmacodynamic analysis of single doses of clenoliximab in patients with rheumatoid arthritis." Clin Pharmacol Ther, Sep. 1999;66(3):246-57.

Mountain A, et al. "Engineering antibodies for therapy," Biotechnol Genet Eng Rev. 1992;10:1-142.

Muff R, et al. "Calcitonin, calcitonin gene-related peptide, adrenomedullin and amylin: homologous peptides, separate receptors and overlapping biological actions," Eur J Endocrinol. Jul. 1995;133(1):17-20.

Mulderry PK, et al. "Differential expression of alpha-CGRP and beta-CGRP by primary sensory neurons and enteric autonomic neurons of the rat." Neuroscience. Apr. 1988:25(1):195-205.

Mullins MW, et al. "Characterization of a calcitonin gene-related peptide (CGRP) receptor on mouse bone marrow cells." Regul Pept. Nov. 19, 1993;49(1):65-72.

(56) References Cited

OTHER PUBLICATIONS

Nakamura-Craig M, et al. "Effect of neurokinin A, substance P and calcitonin gene related peptide in peripheral hyperalgesia in the rat paw." Neurosci Lett. Mar. 11, 1991;124(1):49-51.

Naot D, et al. "The role of peptides and receptors of the calcitonin family in the regulation of bone metabolism," Bone. Nov. 2008;43(5):813-8.

Negro A, et al. "CGRP receptor antagonists: an expanding drug class for acute migraine?" Expert Opin Investig Drugs. Jun. 2012;21(6):807-18.

Newman R, et al. "Modification of the Fc region of a primatized IgG antibody to human CD4 retains its ability to modulate CD4 receptors but does not deplete CD4(+) T cells in chimpanzees," Clin Immunol. Feb. 2001;98(2):164-74.

Ng-Mak DS, et al. "Migraine treatment with rizatriptan and almotriptan: a crossover study," Headache. May 2009;49(5):655-62.

Nippon Rinsho, "Recent Development of Calcitonin Gene-related Peptide (CGRP) receptor antagonist," 2005, vol. 63, Suppl. 10, pp. 263-266 [Original With English Translation].

Nishimoto N, et al. "Anti-interleukin-6 receptor antibody therapy in rheumatic diseases." Endocr Metab Immune Disord Drug Targets. Dec. 2006:6(4):373-81.

Oates PJ, et al. "Studies on the mechanism of ethanol-induced gastric damage in rats," Gastroenterology. Jan. 1988;94(1):10-21.

Ober RJ, et al. "Visualizing the site and dynamics of IgG salvage by the MHC class I-related receptor, FcRn," J Immunol. Feb. 15, 2004;172(4):2021-9.

O'Connell JP, et al. "On the role of the C-terminus of alpha-calcitonin-gene-related peptide (alpha CGRP). the structure of des-phenylalaninamide37-alpha CGRP and its interaction with the CGRP receptor," Biochem J. Apr. 1, 1993;291 ( Pt 1):205-10.

Oh-hashi Y, et al. "Elevated sympathetic nervous activity in mice deficient in alphaCGRP," Circ Res. Nov. 23, 2001;89(11):983-90.

Olesen J, et al. "Calcitonin gene-related peptide receptor antagonist BIBN 4096 BS for the acute treatment of migraine." N Engl J Med. Mar. 11, 2004;350(11):1104-10.

Olesen J, et al. "Chapter 16: Calcitonin Gene-Related Peptide and Other Peptides." the Headaches Third Edition. Lippincott Williams & Wilkins 2006 159-164.

Olesen J, et al. "Chapter 31: CGRP Involvement in Mirgaines." the Headaches Third Edition. Lippincott Williams & Wilkins 2006 289-99.

Olesen J, et al. "Emerging migraine treatments and drug targets," Trends Pharmacol Sci. Jun. 2011;32(6):352-9.

Olesen J, et al. "Finding new drug targets for the treatment of migraine attacks," Cephalalgia. Sep. 2009:29(9):909-20.

Olesen J, et al. "Migraine: a research field matured for the basic neurosciences," Trends Neurosci. Jan. 1991:14(1):3-5.

Olesen J, et al. "Origin of pain in migraine: evidence for peripheral sensitisation," Lancet Neurol. Jul. 2009;8(7):679-90.

Olesen J. "Migraine: a neural pathway for photophobia in migraine," Nat Rev Neurol. May 2010;6(5):241-2.

Ondo WG, et al. "Botulinum toxin A for chronic daily headache: a randomized, placebo-controlled, parallel design study," Cephalalgia. Jan. 2004;24(1):60-5.

O'Sullivan J, et al. "Migraine development, treatments, research advances, and anesthesia implications," AANA J. Feb. 2006;74(1):61-9.

Ottosson A, et al. "Release of histamine from dural mast cells by substance P and calcitonin gene-related peptide," Cephalalgia. May 1997;17(3):166-74.

Pabst MA, et al. "Ablation of capsaicin sensitive afferent nerves impairs defence but not rapid repair of rat gastric mucosa," Gut. Jul. 1993;34(7):897-903.

Panconesi A, et al. "Migraine pain: reflections against vasodilatation," J Headache Pain. Oct. 2009;10(5):317-25.

Panka DJ, et al. "Defining the structural correlates responsible for loss of arsonate affinity in an IDCR antibody isolated from an autoimmune mouse," Mol Immunol. Aug. 1993;30(11):1013-20.

Paone DV, et al. "Calcitonin gene-related peptide receptor antagonists for the treatment of migraine: a patent review," Expert Opin Ther Pat. Dec. 2009;19(12):1675-713.

Papadopoulos N, et al. "Binding and neutralization of vascular endothelial growth factor (VEGF) and related ligands by VEGF Trap, ranibizumab and bevacizumab." Angiogenesis. Jun. 2012;15(2):171-85.

Papp K, et al. "The treatment of moderate to severe psoriasis with a new anti-CD11a monoclonal antibody," J Am Acad Dermatol. Nov. 2001;45(5):665-74.

Pavlou AK, et al. "Recombinant protein therapeutics—success rates, market trends and values to 2010," Nat Biotechnol. Dec. 2004;22(12): 1513-9.

Peroutka SJ, et al. "Neurogenic inflammation and migraine: implications for the therapeutics." Mol Interv. Oct. 2005;5(5):304-11.

Peskar BM, et al. "A monoclonal antibody to calcitonin gene-related peptide abolishes capsaicin-induced gastroprotection." Eur J Pharmacol. Nov. 30, 1993;250(1):201-3.

Petersen KA, et al. "BIBN4096BS antagonizes human alpha-calcitonin gene related peptide-induced headache and extracerebral artery dilatation." Clin Pharmacol Ther. Mar. 2005;77(3):202-13.

Petersen KA, et al. "Effect of hypotension and carbon dioxide changes in an improved genuine closed cranial window rat model," Cephalalgia. Jan. 2005;25(1):23-9.

Petersen KA, et al. "Inhibitory effect of BIBN4096BS on cephalic vasodilatation induced by CGRP or transcranial electrical stimulation in the rat." Br J Pharmacol. Nov. 2004;143(6):697-704.

Petersen KA, et al. "Presence and function of the calcitonin gene-related peptide receptor on rat pial arteries investigated in vitro and in vivo," Cephalalgia. Jun. 2005;25(6):424-32.

Petersen KA, et al. "The effect of nonpeptide CGRP-antagonist, BIBN4096BS on human-alphaCGRP induced headache and hemodynamics in healthy volunteers," Cephalalgia, vol. 23, extract from Abstracts of the XI Congress of the International Headache Society, p. 725, 2003.

Petkova SB, et al. "Enhanced half-life of genetically engineered human lgG1 antibodies in a humanized FcRn mouse model: potential application in humorally mediated autoimmune disease," Int Immunol. Dec. 2006;18(12):1759-69.

Pietrobon D, et al. "Pathophysiology of migraine," Annu Rev Physiol. 2013;75:365-91.

Plessas IN, et al. "Migraine-like episodic pain behavior in a dog: can dogs suffer from migraines?" J Vet Intem Med. Sep.-Oct. 2013;27(5):1034-40.

Plourde V, et al. "CGRP antagonists and capsaicin on celiac ganglia partly prevent postoperative gastric ileus." Peptides. Nov.-Dec. 1993;14(6):1225-9.

Poyner DR, et al. "International Union of Pharmacology. XXXII. The mammalian calcitonin gene-related peptides, adrenomedullin, amylin, and calcitonin receptors," Pharmacol Rev. Jun. 2002;54(2):233-46.

Presta L. "Antibody engineering for therapeutics," Curr Opin Struct Biol. Aug. 2003;13(4):519-25.

Presta LG, et al. "Engineering therapeutic antibodies for improved function," Biochem Soc Trans. Aug. 2002:30(4):487-90.

Prewett M, et al. "The biologic effects of C225, a chimeric monoclonal antibody to the EGFR, on human prostate carcinoma." J Immunother Emphasis Tumor Immunol. Nov. 1996;19(6):419-27.

Qing-Hui Niu, et al. "Expression of mast cell and calcition gene related peptides in the mucosa of irritable bowel syndrome," World Chinese Journal of Digestology, Jan. 18, 2009 p. 213-217; ISSN 1099-3079.

Raddant AC, et al. "Calcitonin gene-related peptide in migraine: intersection of peripheral inflammation and central modulation," Expert Rev Mol Med. Nov. 29, 2011;13:e36.

Ramadan NM, et al. "New and future migraine therapy," Pharmacol Ther. Oct. 2006;112(1):199-212.

Ramadan NM. "Acute treatments: future developments," Curr Med Res Opin. 2001;17 Suppl 1:s81-6.

Ramos ML, et al. "AMG 334 CGRP antibody for migraine: time to celebrate?" Lancet Neurol. Apr. 2016;15(4):347-9.

Rapoport AM, Bigal ME, et al. "Naratriptan in the preventive treatment of refractory chronic migraine." in Olsen J, Silberstein

(56) References Cited

OTHER PUBLICATIONS

SD, Tfelt-Hansen P, eds. Preventive Pharmacotherapy of Headache Disorders. Copenhagen: Oxford University Press, 2004, Chapter 31.
Rapoport AM, et al. "Intranasal medications for the treatment of migraine and cluster headache," CNS Drugs. 2004;18(10):671-85.
Rapoport AM, et al. "Levetiracetam in the preventive treatmentof transformed migraine: a prospective, open-label, pilot study," Curr Ther Res Clin Exp. May 2005;66(3):212-21.
Rapoport AM, et al. "Migraine preventive therapy: current and emerging treatment options," Neurol Sci. May 2005;26 Suppl 2:s111-20.
Rapoport AM, et al. "Preventive migraine therapy: what is new," Neurol Sci. Oct. 2004;25 Suppl 3:S177-85.
Raybould HE, et al. "Selective ablation of spinal afferent neurons containing CGRP attenuates gastric hyperemic response to acid," Peptides. Mar.-Apr. 1992;13(2):249-54.
Reasbeck PG, et al. "Calcitonin gene-related peptide: enteric and cardiovascular effects in the dog," Gastroenterology. Oct. 1988;95(4):966-71.
Recober A, et al. "Calcitonin gene-related peptide: a molecular link between obesity and migraine?" Drug News Perspect. Mar. 2010;23(2):112-7.
Recober A, et al. "Calcitonin gene-related peptide: an update on the biology," Curr Opin Neurol. Jun. 2009;22(3):241-6.
Recober A, et al. "Olcegepant, a non-peptide CGRP1 antagonist for migraine treatment," IDrugs. Aug. 2007;10(8):566-74.
Recober A, et al., "Role of calcitonin gene-related peptide in light-aversive behavior: implications for migraine," J Neurosci. Jul. 8, 2009;29(27):8798-804.
Reddy MP, et al. "Elimination of Fc receptor-dependent effector functions of a modified lgG4 monoclonal antibody to human CD4," J Immunol. Feb. 15, 2000;164(4):1925-33.
Reff ME, et al. "A review of modifications to recombinant antibodies: attempt to increase efficacy in oncology applications." Crit Rev Oncol Hematol. Oct. 2001;40(1):25-35.
Reff ME, et al. "Depletion of B cells in vivo by a chimeric mouse human monoclonal antibody to CD20," Blood. Jan. 15, 1994;83(2):435-45.
Reichert JM, et al. "Monoclonal antibody successes in the clinic," Nat Biotechnol. Sep. 2005;23(9):1073-8.
Reinshagen M, et al. "Calcitonin gene-related peptide mediates the protective effect of sensory nerves in a model of colonic injury." J Pharmacol Exp Ther. Aug. 1998;286(2):657-61.
Reuter U, et al. "Experimental models of migraine," Funct Neurol. 2000;15 Suppl 3:9-18.
Reuter U. "Anti-CGRP antibodies: a new approach to migraine prevention," Lancet Neurol. Sep. 2014;13(9):857-9.
Rolston RK, et al., "Intravenous calcitonin gene-related peptide stimulates net water secretion in rat colon in vivo," Dig Dis Sci. Apr. 1989;34(4):612-6.
Roon KI, et al. "No acute antimigraine efficacy of CP-122,288, a highly potent inhibitor of neurogenic inflammation: results of two randomized, double-blind, placebo-controlled clinical trials," Ann Neurol. Feb. 2000;47(2):238-41.
Roopenian DC, et al. "FcRn: the neonatal Fc receptor comes of age," Nat Rev Immunol. Sep. 2007;7(9):715-25.
Roque AC, et al. "Antibodies and genetically engineered related molecules: production and purification," Biotechnol Prog. May-Jun. 2004;20(3):639-54.
Roskos LK, et al. "The Clinical Pharmacology of Therapeutic Monoclonal Antibodies," Drug Development Research 2004 61:108-120.
Rother RP, et al. "Discovery and development of the complement inhibitor eculizumab for the treatment of paroxysmal nocturnal hemoglobinuria." Nat Biotechnol. Nov. 2007;25(11):1256-64.
Rovero P, et al. "CGRP antagonist activity of short C-terminal fragments of human alpha CGRP, CGRP(23-37) and CGRP(19-37)." Peptides. Sep.-Oct. 1992;13(5):1025-7.

Rudikoff S, et al. "Single amino acid substitution altering antigen-binding specificity." Proc Natl Acad Sci U S A. Mar. 1982;79(6):1979-83.
Ruiz-Gayo M, et al. "Vasodilatory effects of cholecystokinin: new role for an old peptide?" Regul Pept. Dec. 10, 2006;137(3):179-84.
Russo AF, et al., "A Potential Preclinical Migraine Model: CGRP-Sensitized Mice," Mol Cell Pharmacol. 2009;1(5):264-270.
Russo AF. "Calcitonin gene-related peptide (CGRP): a new target for migraine," Annu Rev Pharmacol Toxicol. 2015;55:533-52.
Russo. "CGRP Meeting Abstract Book," the 4th International Meeting on CGRP, Copenhagen, Sep. 2001, 71 pages.
Russo. "CGRP Meeting Abstract Book," Joint International Symposium on Calictonin Gene-Related Peptide, Amylin and Calcitonin; 4th Symposium on Adrenomedullin and Proadrenomedullin N-20 Peptide, Zurich, Switzerland, Mar. 2004. 38 pages.
Ryan AM, et al. "Preclinical safety evaluation of rhuMAbVEGF, an antiangiogenic humanized monoclonal antibody," Toxicol Pathol. Jan.-Feb. 1999;27(1):78-86.
Ryan S. "Medicines for migraine," Arch Dis Child Educ Pract Ed. Apr. 2007;92(2):ep50-5.
Saleh MN, et al. "Phase I trial of the chimeric anti-GD2 monoclonal antibody ch14.18 in patients with malignant melanoma." Hum Antibodies Hybridomas, Jan. 1992;3(1):19-24.
Salonen R, et al. "Triptans: do they differ?" Curr Pain Headache Rep. Apr. 2002;6(2):133-9.
Salvatore CA, et al. "Pharmacological characterization of MK-0974 [N-[(3R,6S)-6-(2,3-difluorophenyl)-2-oxo-1-(2,2,2-trifluoroethyl)azepan-3-yl]-4-(2-oxo-2,3-dihydro-1H-imidazo[4,5-b]pyridin-1-yl)piperidine-1-carboxamide], a potent and orally active calcitonin gene-related peptide receptor antagonist for the treatment of migraine," J Pharmacol Exp Ther. Feb. 2008;324(2):416-21.
Sarns-Nielsen A, et al. "Pharmacological evidence for CGRP uptake into perivascular capsaicin sensitive nerve terminals," Br J Pharmacol. Mar. 2001;132(5):1145-53.
Saphire EO, et al. "Crystal structure of a neutralizing human IGG against HIV-1: a template for vaccine design," Science. Aug. 10, 2001;293(5532):1155-9.
Schaible HG, et al. "Mechanisms of pain in arthritis." Ann N Y Acad Sci. Jun. 2002;966:343-54.
Schelstraete C, et al. "CGRP antagonists: hope for a new era in acute migraine treatment," Acta Neurol Belg. Dec. 2009;109(4):252-61.
Schier R, et al. "Isolation of high-affinity monomeric human anti-c-erbB-2 single chain Fv using affinity-driven selection," J Mol Biol. Jan. 12, 1996;255(1):28-43.
Schier R, et al. "Isolation of picomolar affinity anti-c-erbB-2 single-chain Fv by molecular evolution of the complementarity determining regions in the center of the antibody binding site," J Mol Biol. Nov. 8, 1996;263(4):551-67.
Schifter S. "Circulating concentrations of calcitonin gene-related peptide (CGRP) in normal man determined with a new, highly sensitive radioimmunoassay," Peptides. Mar.-Apr. 1991;12(2):365-9.
Schindler M, et al. "Binding properties of the novel, non-peptide CGRP receptor antagonist radioligand, [(3)H]BIBN4096BS," Eur J Pharmacol. May 10, 2002;442(3):187-93.
Schoenen J, et al. "Almotriptan and its combination with aceclofenac for migraine attacks; a study of efficacy and the influence of auto-evaluated brush allodynia," Cephalalgia. Oct. 2008;28(10):1095-105.
Schreiber CP, "The pathophysiology of migraine," Dis Mon, Oct. 2006:52(10):385-401.
Schwenger N, et al. "Interaction of calcitonin gene-related peptide, nitric oxide and histamine release in neurogenic blood flow and afferent activation in the rat cranial dura mater," Cephalalgia. Jun. 2007;27(6):481-91.
Schytz HW, et al. "What have we learnt from triggering migraine?" Curr Opin Neurol. Jun. 2010;23(3):259-65.
Seike M, et al. "Increased synthesis of calcitonin gene-related peptide stimulates keratinocyte proliferation in murine UVB-irradiated skin," J Dermatol Sci. Feb. 2002;28(2):135-43.

(56) References Cited

OTHER PUBLICATIONS

Selenko N, et al. "CD20 antibody (C2B8)-induced apoptosis of lymphoma cells promotes phagocytosis by dendritic cells and cross-priming of CD8+ cytotoxic T cells," Leukemia. Oct. 2001;15(10):1619-26.
Seong J, et al. "Radiation-induced alteration of pain-related signals in an animal model with bone invasion from cancer." Ann N Y Acad Sci. Dec. 2004;1030:179-86.
Seybold VS. "The role of peptides in central sensitization," Handb Exp Pharmacol. 2009;(194):451-91.
Shaw NE, et al. "The effect of monoclonal antibodies to calcitonin gene-related peptide (CGRP) on CGRP-induced vasodilatation in pig coronary artery rings," Br J Pharmacol. May 1992:106(1):196-8.
Sheets MD, et al. "Efficient construction of a large nonimmune phage antibody library: the production of high-affinity human single-chain antibodies to protein antigens," Proc Natl Acad Sci U S A. May 26, 1998;95(11):6157-62.
Sheftell FD, et al. "Naratriptan in the preventive treatment of refractory transformed migraine: a prospective pilot study," Headache. Nov.-Dec. 2005;45(10):1400-6.
Shen YT, et al. "Functional role of alpha-calcitonin gene-related peptide in the regulation of the cardiovascular system." J Pharmacol Exp Ther, Aug. 2001:298(2):551-8.
Shevel E. "The extracranial vascular theory of migraine—a great story confirmed by the facts," Headache. Mar. 2011;51(3):409-17.
Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.
Shulkes A, et al. "Production of calcitonin gene related peptide, calcitonin and PTH-related protein by a prostatic adenocarcinoma," Clin Endocrinol (Oxf). May 1991;34(5):387-93.
Silberstein S, et al. "Botulinum toxin type a as a migraine preventive treatment. For the Botox Migraine Clinical Research Group," Headache. Jun. 2000;40(6):445-50.
Silberstein SD, "Practice parameter: evidence-based guidelines for migraine headache (an evidence-based review): report of the Quality Standards Subcommittee of the American Academy of Neurology," Neurology. Sep. 26, 2000:55(6):754-62.
Silberstein SD. "Emerging target-based paradigms to prevent and treat migraine," Clin Pharmacol Ther. Jan. 2013;93(1):78-85.
Silverman AJ, et al. "Mast cells migrate from blood to brain," J Neurosci. Jan. 1, 2000;20(1):401-8.
Simmons LC, et al. "Expression of full-length immunoglobulins in *Escherichia coli*: rapid and efficient production of aglycosylated antibodies," J Immunol Methods. May 1, 2002:263(1-2):133-47.
Sixt ML, et al. "Calcitonin gene-related peptide receptor antagonist olcegepant acts in the spinal trigeminal nucleus," Brain. Nov. 2009;132(Pt 11):3134-41.
Skofitsch G, et al. "Comparative immunohistochemical distribution of amylin-like and calcitonin gene related peptide like immunoreactivity in the rat central nervous system," Can J Physiol Pharmacol. Jul. 1995;73(7):945-58.
Smillie SJ, et al. "Calcitonin gene-related peptide (CGRP) and its role in hypertension," Neuropeptides. Apr. 2011;45(2):93-104.
Smith KA, et al. "Demystified . . . recombinant antibodies," J Clin Pathol, Sep. 2004;57(9):912-7.
Smith TW, et al. "Reversal of advanced digoxin intoxication with Fab fragments of digoxin-specific antibodies." N Engl J Med. Apr. 8, 1976;294(15):797-800.
Smith-Gill SJ, et al. "Contributions of immunoglobulin heavy and light chains to antibody specificity for lysozyme and two haptens." J Immunol. Dec. 15, 1987;139(12):4135-44.
Solomon S. "Major therapeutic advances in the past 25 years," Headache. Apr. 2007;47 Suppl 1:S20-2.
Song MK, et al. "Light chain of natural antibody plays a dominant role in protein antigen binding." Biochem Biophys Res Commun. Feb. 16, 2000;268(2):390-4.

Spetz AC, et al. "Momentary increase in plasma calcitonin gene-related peptide is involved in hot flashes in men treated with castration for carcinoma of the prostate," J Urol. Nov. 2001;166(5):1720-3.
Sprenger T, et al. "Migraine pathogenesis and state of pharmacological treatment options," BMC Med. Nov. 16, 2009;7:71.
Stensrud P, et al. "Comparative trial of Tenormin (atenolol) and Inderal (propranolol) in migraine," Headache. Jul. 1980;20(4):204-7.
Storer RJ, et al. "Calcitonin gene-related peptide (CGRP) modulates nociceptive trigeminovascular transmission in the cat," Br J Pharmacol. Aug. 2004;142(7):1171-81.
Stovner LJ, et al. "New drugs for migraine," J Headache Pain. Dec. 2009;10(6):395-406.
Strassman AM, et al. "On the origin of headaches," Endeavour. 1997;21(3):97-100.
Strassman AM, et al. "Response properties of dural nociceptors in relation to headache," J Neurophysiol. Mar. 2006;95(3):1298-306.
Subramanian KN, et al. "Safety, tolerance and pharmacokinetics of a humanized monoclonal antibody to respiratory syncytial virus in premature infants and infants with bronchopulmonary dysplasia," MEDI-493 Study Group, Pediatr Infect Dis J. Feb. 1998;17(2):110-5.
Tam SH, et al. "Abciximab (ReoPro, chimeric 7E3 Fab) demonstrates equivalent affinity and functional blockade of glycoprotein llb/llla and alpha(v)beta3 integrins." Circulation, Sep. 15, 1998;98(11):1085-91.
Tamura M, et al. "Structural correlates of an anticarcinoma antibody: identification of specificity-determining residues (SDRs) and development of a minimally immunogenic antibody variant by retention of SDRs only." J Immunol. Feb. 1, 2000;164(3):1432-41.
Tan et al., "Demonstration of the neurotransmitter role of calcitonin gene-related peptides (CGRP) by immunoblockade with anti-CGRP monoclonal antibodies," Br J Pharmacol. Mar. 1994;111(3):703-10.
Tan KK, et al. "Calcitonin gene-related peptide as an endogenous vasodilator: immunoblockade studies in vivo with an anti-calcitonin gene-related peptide monoclonal antibody and its Fab' fragment." Clin Sci (Lond). Dec. 1995;89(6):565-73.
Tanaka H, et al. "Inhibition of calcitonin gene-related peptide (CGRP) has the potential to extend first-phase insulin secretion," Exp Clin Endocrinol Diabetes. May 2013;121(5):260-5.
Taylor AW, et al. "Suppression of nitric oxide generated by inflammatory macrophages by calcitonin gene-related peptide in aqueous humor," Invest Ophthalmol Vis Sci. Jul. 1998;39(8):1372-8.
Tedstone, et al. "The effect of islet amyloid polypeptide (amylin) and calcitonin gene-related peptide on glucose removal in the anaesthetized rat and on insulin secretion from rat pancreatic islets in vitro," Biosci Rep. Aug. 1990;10(4):339-45.
Tepper SJ, Bigal ME, et al. "Botulinum toxin type a in the treatment of refractory headache." in Olsen J. Silberstein SD, Tfelt-Hansen P, eds. Preventive Pharmacotherapy of Headache Disorders. Copenhagen: Oxford University Press, 2004, Chapter 20.
Tepper SJ, et al. "Botulinum neurotoxin type A in the preventive treatment of refractory headache: a review of 100 consecutive cases," Headache. Sep. 2004;44(8):794-800.
Tepper SJ, et al. "Clinical and preclinical rationale for CGRP-receptor antagonists in the treatment of migraine," Headache. Sep. 2008;48(8):1259-68.
Tepper SJ, et al. "Mechanisms of action of the 5-HT1B/1D receptor agonists," Arch Neurol. Jul. 2002:59(7):1084-8.
Teva Pharmaceutical Industries Ltd., Press Release, "Teva to Acquire Labrys Biologics, Inc.", Jun. 3, 2014. 4 pages.
Tfelt-Hansen P, et al. "Effervescent metoclopramide and aspirin (Migravess) versus effervescent aspirin or placebo for migraine attacks: a double-blind study," Cephalalgia. Jun. 1984;4(2):107-11.
Tfelt-Hansen P. et al. "Possible site of action of CGRP antagonists in migraine," Cephalalgia. Apr. 2011;31(6):748-50.
Tfelt-Hansen PC. "Verisimilitude (or "truthlikeness") as an alternative to pro and cons: migraine and cluster headache mechanisms," J Headache Pain. Oct. 2010;11(5):379-89.
Theoharides TC, et al. "The role of mast cells in migraine pathophysiology," Brain Res Brain Res Rev. Jul. 2005;49(1):65-76.

(56) References Cited

OTHER PUBLICATIONS

Thomas TC, et al. "Inhibition of complement activity by humanized anti-C5 antibody and single-chain Fv," Mol Immunol. Dec. 1996:33(17-18):1389-401.
Tjen-A-Looi S, et al. "CGRP and somatostatin modulate chronic hypoxic pulmonary hypertension," Am J Physiol. Sep. 1992;263(3 Pt 2):H681-90.
Toda M, et al. "Neuronal system-dependent facilitation of tumor angiogenesis and tumor growth by calcitonin gene-related peptide." Proc Natl Acad Sci U S A. Sep. 9, 2008;105(36):13550-5.
Todd J. Schwedt et al: "14th International Headache Congress: Basic Science Highlights", Headache, vol. 50, No. 3, Mar. 1, 2010 (Mar. 1, 2010), pp. 520-526.
Tokuda Y, et al. "Dose escalation and pharmacokinetic study of a humanized anti-HER2 monoclonal antibody in patients with HER2/neu-overexpressing metastatic breast cancer," Br J Cancer. Dec. 1999;81(8):1419-25.
Tsujikawa K, et al. "Hypertension and dysregulated proinflammatory cytokine production in receptor activity-modifying protein 1-deficient mice," Proc Natl Acad Sci U S A. Oct. 16, 2007;104(42):16702-7.
Turner LC, et al. "A neural shift theory of migraine," Neuroepidemiology. 1993; 12(4):249-50.
Tvedskov JF, et al. "No increase of calcitonin gene-related peptide in jugular blood during migraine." Ann Neurol. Oct. 2005;58(4):561-8.
Tzabazis AZ, et al. "Antihyperalgesic effect of a recombinant herpes virus encoding antisense for calcitonin gene-related peptide." Anesthesiology. Jun. 2007;106(6):1196-203.
Uhr M, et al. "Penetration of endogenous steroid hormones corticosterone, cortisol, aldosterone and progesterone into the brain is enhanced in mice deficient for both mdr1a and mdr1b P-glycoproteins," J Neuroendocrinol. Sep. 2002;14(9):753-9.
Unger J. "Migraine headaches: a historical prospective, a glimpse into the future, and migraine epidemiology," Dis Mon. Oct. 2006;52(10):367-84.
Vajdos FF, et al. "Comprehensive functional maps of the antigen-binding site of an anti-ErbB2 antibody obtained with shotgun scanning mutagenesis." J Mol Biol. Jul. 5, 2002:320(2):415-28.
Van der Schueren BJ, et al. " Calcitonin gene-related peptide8-37 antagonizes capsaicin-induced vasodilation in the skin: evaluation of a human in vivo pharmacodynamic model," J Pharmacol Exp Ther. Apr. 2008;325(1):248-55.
Van Rossum D, et al. "Neuroanatomical localization, pharmacological characterization and functions of CGRP, related peptides and their receptors," Neurosci Biobehav Rev. Sep. 1997;21(5):649-78.
Vater A, et al. "Short bioactive Spiegelmers to migraine-associated calcitonin gene-related peptide rapidly identified by a novel approach: tailored-SELEX." Nucleic Acids Res. Nov. 1, 2003:31(21):e130.
Vaughan TJ, et al. "Human antibodies with sub-nanomolar affinities isolated from a large non-immunized phage display library," Nat Biotechnol. Mar. 1996;14(3):309-14.
Villalón CM, et al. "The role of CGRP in the pathophysiology of migraine and efficacy of CGRP receptor antagonists as acute antimigraine drugs," Pharmacol Ther. Dec. 2009;124(3):309-23.
Vincent A, et al. "Molecular targets for autoimmune and genetic disorders of neuromuscular transmission," Eur J Biochem. Dec. 2000;267(23):6717-28.
Vogler B, et al. "Role of melatonin in the pathophysiology of migraine: implications for treatment," CNS Drugs. 2006;20(5):343-50.
Volcy M, et al. "Botulinum toxin A for the treatment of greater occipital neuralgia and trigeminal neuralgia: a case report with pathophysiological considerations," Cephalalgia. Mar. 2006;26(3):336-40.
Von Mehren M, et al. "Monoclonal antibody therapy for cancer," Annu Rev Med. 2003:54:343-69.
Wachter C, et al. "Visceral vasodilatation and somatic vasoconstriction evoked by acid challenge of the rat gastric mucosa: diversity of mechanisms," J Physiol. Jul. 15, 1995:486 ( Pt 2):505-16.
Wacnik PW, et al. "Tumor-induced mechanical hyperalgesia involves CGRP receptors and altered innervation and vascularization of DsRed2 fluorescent hindpaw tumors." Pain. May 2005;115(1-2):95-106.
Waeber C, et al. "Migraine as an inflammatory disorder." Neurology, May 24, 2005,64(10 Suppl 2):S9-15.
Walker CS, et al. "Mice lacking the neuropeptide alpha-calcitonin gene-related peptide are protected against diet-induced obesity," Endocrinology. Sep. 2010;151(9):4257-69.
Walker CS, et al. "Regulation of signal transduction by calcitonin gene-related peptide receptors," Trends Pharmacol Sci. Oct. 2010;31(10):476-83.
Ward ES, et al. "Binding activities of a repertoire of single immunoglobulin variable domains secreted from *Escherichia coli*." Nature. Oct. 12, 1989;341(6242):544-6.
Weir AN, et al. "Formatting antibody fragments to mediate specific therapeutic functions," Biochem Soc Trans. Aug. 2002;30(4):512-6.
Welch KM, et al. "Mismatch in how oestrogen modulates molecular and neuronal function may explain menstrual migraine," Neurol Sci. May 2006;27 Suppl 2:S190-2.
Werther WA, et al. "Humanization of an anti-lymphocyte function-associated antigen (LFA)-1 monoclonal antibody and reengineering of the humanized antibody for binding to rhesus LFA-1," J Immunol. Dec. 1, 1996;157(11):4986-95.
Wick EC, et al. "Transient receptor potential vanilloid 1, calcitonin gene-related peptide, and substance P mediate nociception in acute pancreatitis." Am J Physiol Gastrointest Liver Physiol. May 2006;290(5):G959-69. Epub Jan. 6, 2006.
Willats WG. "Phage display: practicalities and prospects," Plant Mol Biol. Dec. 2002;50(6):837-54.
Williamson DJ, et al. "Intravital microscope studies on the effects of neurokinin agonists and calcitonin gene-related peptide on dural vessel diameter in the anaesthetized rat," Cephalalgia. Jun. 1997:17(4):518-24.
Williamson DJ, et al. "Neurogenic inflammation in the context of migraine," Microsc Res Tech. May 1, 2001:53(3):167-78.
Williamson DJ, et al. "Sumatriptan inhibits neurogenic vasodilation of dural blood vessels in the anaesthetized rat—intravital microscope studies," Cephalalgia. Jun. 1997;17(4):525-31.
Williamson DJ, et al. "The anti-migraine 5-HT(1B/1D) agonist rizatriptan inhibits neurogenic dural vasodilation in anaesthetized guinea-pigs," Br J Pharmacol. Aug. 2001;133(7):1029-34.
Williamson DJ, et al. "The novel anti-migraine agent rizatriptan inhibits neurogenic dural vasodilation and extravasation," Eur J Pharmacol. Jun. 5, 1997;328(1):61-4.
Wimalawansa SJ, et al. "Comparative study of distribution and biochemical characterization of brain calcitonin gene-related peptide receptors in five different species," Neuroscience. May 1993;54(2):513-9.
Wimalawansa SJ, et al. "Validation, role in perioperative assessment, and clinical applications of an immunoradiometric assay for human calcitonin," Peptides. 1995;16(2):307-12.
Wimalawansa SJ. "Amylin, calcitonin gene-related peptide, calcitonin, and adrenomedullin: a peptide superfamily," Crit Rev Neurobiol. 1997;11(2-3):167-239.
Wimalawansa SJ. "Calcitonin gene-related peptide and its receptors: molecular genetics, physiology, pathophysiology, and therapeutic potentials," Endocr Rev. Oct. 1996;17(5):533-85.
Wimalawansa SJ. "Effects of in vivo stimulation on molecular forms of circulatory calcitonin and calcitonin gene-related peptide in man," Mol Cell Endocrinol. May 28, 1990;71(1):13-9.
Winkler K, et al. "Changing the antigen binding specificity by single point mutations of an anti-p24 (HIV-1) antibody." J Immunol. Oct. 15, 2000;165(8):4505-14.
Winter G, et al. "Making antibodies by phage display technology," Annu Rev Immunol. 1994;12:433-55.
Wong G, et al. "Safety and tolerability of LBR-101, a humanized monoclonal antibody that blocks the binding of CGRP to its receptor," Labrys Biologics Poster, 1 page, 2013 International Headache Congress.
Wong HC, et al. "Monoclonal antibody to rat alpha-CGRP: production, characterization, and in vivo immunoneutralization activity." Hybridoma. Feb. 1993;12(1):93-106.

(56) References Cited

OTHER PUBLICATIONS

Wong HC, et al. "Preparation of a monoclonal antibody to rat alpha-CGRP for in vivo immunoneutralization of peptides." Ann N Y Acad Sci. Jun. 30, 1992;657:525-7.
Wu D, et al. "Development and potential of non-peptide antagonists for calcitonin-gene-related peptide (CGRP) receptors: evidence for CGRP receptor heterogeneity," Biochem Soc Trans. Aug. 2002;30(4):468-73.
Wu H, et al. "Humanization of a murine monoclonal antibody by simultaneous optimization of framework and CDR residues." J Mol Biol. Nov. 19, 1999;294(1):151-62.
Wu H, et al. "Humanized antibodies and their applications," Methods. May 2005;36(1):1-2.
Wyon Y, et al. "Postmenopausal women with vasomotor symptoms have increased urinary excretion of calcitonin gene-related peptide," Maturitas. Nov. 16, 1998:30(3):289-94.
Xu, F.T. Study on the Mechanism of SP and CGRP in the Chronic Pain and Knee Joint. Master Thesis. Guangxi Medical University. May 2005. (in Chinese with English abstract).
Yallampalli C, et al. "Calcitonin gene-related peptide in pregnancy and its emerging receptor heterogeneity," Trends Endocrinol Metab. Aug. 2002:13(6):263-9.
Yoshikawa R, et al. "Suppression of ovalbumin-induced allergic diarrhea by diminished intestinal peristalsis in RAMP1-deficient mice," Biochem Biophys Res Commun. Jul. 8, 2011;410(3):389-93.
Yu LC, et al. "Roles of calcitonin gene-related peptide and its receptors in pain-related behavioral responses in the central nervous system," Neurosci Biobehav Rev. Sep. 2009;33(8):1185-91.
Zeller J, et al. "CGRP function-blocking antibodies inhibit neurogenic vasodilatation without affecting heart rate or arterial blood pressure in the rat." Br J Pharmacol. Dec. 2008;155(7):1093-103. doi: 10.1038/bjp.2008.334. Epub Sep. 8, 2008.
Zhang L, et al. "Arthritic calcitonin/alpha calcitonin gene-related peptide knockout mice have reduced nociceptive hypersensitivity," Pain. Jan. 2001:89(2-3):265-73.
Zhang M, et al. "Rheumatoid factor specificity of a VH3-encoded antibody is dependent on the heavy chain CDR3 region and is independent of protein A binding." J Immunol. Sep. 1, 1998;161(5):2284-9.
Zhuang X, et al. "Brain mast cell degranulation regulates blood-brain barrier," J Neurobiol. Dec. 1996;31(4):393-403.
Zittel et al., "Role of spinal afferents and calcitonin gene-related peptide in the postoperative gastric ileus in anesthetized rats," Ann Surg. Jan. 1994;219(1):79-87.
Zittel TT, et al. "Calcitonin gene-related peptide and spinal afferents partly mediate postoperative colonic ileus in the rat," Surgery. May 1998;123(5):518-27.
Zuckier LS, et al. "Chimeric human-mouse IgG antibodies with shuffled constant region exons demonstrate that multiple domains contribute to in vivo half-life," Cancer Res. Sep. 1, 1998;58(17):3905-8.
Misura, et al. "The Eptinezumab: CGRP Complex Structure and Characterization of the Ligand Binding Interface," poster Presented at the American Headache Society (AHS) 61$^{st}$ Annual Scientific Meeting Jul. 11-14, 2019.
Rita Costa A, Elisa Rodrigues M, Henriques M, Azeredo J, Oliveira R. Guidelines to cell engineering for monoclonal antibody production. Eur J Pharm Biopharm. 2010;74(2):127-138. doi:10.1016/j.ejpb.2009.10.002.
Potgieter TI, Cukan M, Drummond JE, et al. Production of monoclonal antibodies by glycoengineered Pichia pastoris. J Biotechnol. 2009;139(4):318-325. doi:10.1016/j.jbiotec.2008.12.015.
Trill JJ, Shatzman AR, Ganguly S. Production of monoclonal antibodies in COS and CHO cells. Curr Opin Biotechnol. 1995;6(5):553-560. doi:10.1016/0958-1669(95)80092-1.

\* cited by examiner

Figure 1A - Heavy Chain Protein Sequence

| Sequence Name | FR1 | CDR1 | FR2 | CDR2 |
|---|---|---|---|---|
| Ab1 | QSLEESGGRLVTPGTPLTLTCTVSGLDLS | SYYMQ | WVRQAPGKGLEWIG | VIGINDNTYYASWAKG |
| Ab2 | EVQLVESGGGLVQPGGSLRLSCAVSGLDLS | SYYMQ | WVRQAPGKGLEWVG | VIGINDNTYYASWAKG |
| Ab3 | EVQLVESGGGLVQPGGSLRLSCAVSGLDLS | SYYMQ | WVRQAPGKGLEWVG | VIGINDNTYYASWAKG |
| Ab4 | QSLEESGGRLVTPGTPLTLTCTVSVSGIDLS | GYYMN | WVRQAPGKGLEWIG | VIGINGATYYASWAKG |
| Ab5 | EVQLVESGGGLVQPGGSLRLSCAVSGIDLS | GYYMN | WVRQAPGKGLEWVG | VIGINGATYYASWAKG |
| Ab6 | EVQLVESGGGLVQPGGSLRLSCAVSGIDLS | GYYMN | WVRQAPGKGLEWVG | VIGINGATYYASWAKG |
| Ab7 | QEQLKESGGRLVTPGTSLTLTCTVSGIDLS | NHYMQ | WVRQAPGKGLEWIG | VVGINGRTYYASWAKG |
| Ab8 | EVQLVESGGGLVQPGGSLRLSCAVSGIDLS | NHYMQ | WVRQAPGKGLEWVG | VVGINGRTYYASWAKG |
| Ab9 | QSLEESGGRLVTPGTPLTLTCTVSGIGLS | SYYMQ | WVRQSPGRGLEWIG | VIGSDGKTYYATWAKG |
| Ab10 | EVQLVESGGGLVQPGGSLRLSCAVSGIGLS | SYYMQ | WVRQAPGKGLEWVG | VIGSDGKTYYATWAKG |
| Ab11 | QSLEESGGRLVTPGGSLTLTCTVSGIDVT | NYYMQ | WVRQAPGKGLEWIG | VIGVNGKRYYASWAKG |
| Ab12 | EVQLVESGGGLVQPGGSLRLSCAVSGIDVT | NYYMQ | WVRQAPGKGLEWVG | VIGVNGKRYYASWAKG |
| Ab13 | QSVEESGGGLVQPEGSLTLTCTASGFDFS | SNAMW | WVRQAPGKGLEWIG | CIYNGDGSTYYASWVNG |
| Ab14 | EVQLVESGGGLVQPGGSLRLSCAVSGIGLS | SYYMQ | WVRQAPGKGLEWVG | VIGSDGKTYYATWAKG |

Figure 1B - Heavy Chain Protein Sequence

| Sequence Name | FR3 | CDR3 | FR4 |
|---|---|---|---|
| Ab1 | RFTISRASSTTVDLKMTISLTTEDTATYFCAR | GDI | WGPGTLVTVSS |
| Ab2 | RFTISRDNSKTTVYLQMNSLRAEDTAVYFCAR | GDI | WGQGTLVTVSS |
| Ab3 | RFTISRDNSKTTVYLQMNSLRAEDTAVYFCAR | GDI | WGQGTLVTVSS |
| Ab4 | RFTISKTSSTTVDLKMTSLTTEDTATYFCAR | GDI | WGPGTLVTVSS |
| Ab5 | RFTISRDNSKTTVYLQMNSLRAEDTAVYFCAR | GDI | WGQGTLVTVSS |
| Ab6 | RFTISRDNSKTTVYLQMNSLRAEDTAVYFCAR | GDI | WGQGTLVTVSS |
| Ab7 | RFTISRTSSTTVDLKMTRLTTEDTATYFCAR | GDI | WGPGTLVTVSS |
| Ab8 | RFTISRDNSKTTVYLQMNSLRAEDTAVYFCAR | GDI | WGQGTLVTVSS |
| Ab9 | RFTISKTSSTTVDLRMASLTTEDTATYFCAR | GDI | WGPGTLVTVSS |
| Ab10 | RFTISRDNSKTTVYLQMNSLRAEDTAVYFCTR | GDI | WGQGTLVTVSS |
| Ab11 | RFTISKTSSTTVDLKMTSLTTEDTATYFCAR | GDI | WGPGTLVTVSS |
| Ab12 | RFTISRDNSKTTVYLQMNSLRAEDTAVYFCAR | GDI | WGQGTLVTVSS |
| Ab13 | RFSISKTSSTTVTLQINSLTVADTATYYCAR | DLDL | WGPGTLVTVSS |
| Ab14 | RFTISRDNSKTTVYLQMNSLRAEDTAVYFCTR | GDI | WGQGTLVTVSS |

Figure 1C - Heavy Chain Protein Sequence

| Sequence Name | Constant Region |
|---|---|
| Ab1 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab2 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab3 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab4 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab5 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab6 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab7 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab8 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab9 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab10 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab11 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab12 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab13 | ASTKGPSVFPLAPSSKSTSGGTAALGCLVKDYFPEPVTVSWNSGALTSGVHTFPAVLQSSGLYSLSSVVTVPSSSLGTQTYICNV |
| Ab14 | ASTKGPSVFPLAPSSKSTSGGTAALGCLVKDYFPEPVTVSWNSGALTSGVHTFPAVLQSSGLYSLSSVVTVPSSSLGTQTYICNV |

Figure 1D - Heavy Chain Protein Sequence

| Sequence Name | Constant Region |
|---|---|
| Ab1 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab2 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab3 | NHKPSNTKVDARVEPKSCDKTHTCPPCPAPELLGGPSVFLFPPKPKDTLMISRTPEVTCVVVDVSHEDPEVKFNWYVDGVEVHNA |
| Ab4 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab5 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab6 | NHKPSNTKVDARVEPKSCDKTHTCPPCPAPELLGGPSVFLFPPKPKDTLMISRTPEVTCVVVDVSHEDPEVKFNWYVDGVEVHNA |
| Ab7 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab8 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab9 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab10 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab11 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab12 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab13 | NHKPSNTKVDKRVEPKSCDKTHTCPPCPAPELLGGPSVFLFPPKPKDTLMISRTPEVTCVVVDVSHEDPEVKFNWYVDGVEVHNA |
| Ab14 | NHKPSNTKVDARVEPKSCDKTHTCPPCPAPELLGGPSVFLFPPKPKDTLMISRTPEVTCVVVDVSHEDPEVKFNWYVDGVEVHNA |

Figure 1E - Heavy Chain Protein Sequence

| Sequence Name | Constant Region | |
|---|---|---|
| Ab1 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 1) |
| Ab2 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 41) |
| Ab3 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 81) |
| Ab4 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 121) |
| Ab5 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 161) |
| Ab6 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 201) |
| Ab7 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 241) |
| Ab8 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 281) |
| Ab9 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 321) |
| Ab10 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 361) |
| Ab11 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 401) |
| Ab12 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 441) |
| Ab13 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 481) |
| Ab14 | KTKPREEQYASTYRVVSVLTVLHQDWLNGKEYKCKVSNKALPAPIEKTISKAKGQPREPQVYTLPPSREEMTKNQVSLTCLVKGF | (SEQ ID NO: 521) |

Figure 1F - Heavy Chain Protein Sequence

| Sequence Name | Constant Region | |
|---|---|---|
| Ab1 | YPSDIAVEWESNGQPENNYKTTPPVLDSDGSFFLYSKLTVDKSRWQQGNVFSCSVMHEALHNHYTQKSLSLSPGK | (SEQ ID NO: 1) |
| Ab2 | YPSDIAVEWESNGQPENNYKTTPPVLDSDGSFFLYSKLTVDKSRWQQGNVFSCSVMHEALHNHYTQKSLSLSPGK | (SEQ ID NO: 41) |
| Ab3 | YPSDIAVEWESNGQPENNYKTTPPVLDSDGSFFLYSKLTVDKSRWQQGNVFSCSVMHEALHNHYTQKSLSLSPGK | (SEQ ID NO: 81) |
| Ab4 | YPSDIAVEWESNGQPENNYKTTPPVLDSDGSFFLYSKLTVDKSRWQQGNVFSCSVMHEALHNHYTQKSLSLSPGK | (SEQ ID NO: 121) |
| Ab5 | YPSDIAVEWESNGQPENNYKTTPPVLDSDGSFFLYSKLTVDKSRWQQGNVFSCSVMHEALHNHYTQKSLSLSPGK | (SEQ ID NO: 161) |
| Ab6 | YPSDIAVEWESNGQPENNYKTTPPVLDSDGSFFLYSKLTVDKSRWQQGNVFSCSVMHEALHNHYTQKSLSLSPGK | (SEQ ID NO: 201) |
| Ab7 | YPSDIAVEWESNGQPENNYKTTPPVLDSDGSFFLYSKLTVDKSRWQQGNVFSCSVMHEALHNHYTQKSLSLSPGK | (SEQ ID NO: 241) |
| Ab8 | YPSDIAVEWESNGQPENNYKTTPPVLDSDGSFFLYSKLTVDKSRWQQGNVFSCSVMHEALHNHYTQKSLSLSPGK | (SEQ ID NO: 281) |
| Ab9 | YPSDIAVEWESNGQPENNYKTTPPVLDSDGSFFLYSKLTVDKSRWQQGNVFSCSVMHEALHNHYTQKSLSLSPGK | (SEQ ID NO: 321) |
| Ab10 | YPSDIAVEWESNGQPENNYKTTPPVLDSDGSFFLYSKLTVDKSRWQQGNVFSCSVMHEALHNHYTQKSLSLSPGK | (SEQ ID NO: 361) |
| Ab11 | YPSDIAVEWESNGQPENNYKTTPPVLDSDGSFFLYSKLTVDKSRWQQGNVFSCSVMHEALHNHYTQKSLSLSPGK | (SEQ ID NO: 401) |
| Ab12 | YPSDIAVEWESNGQPENNYKTTPPVLDSDGSFFLYSKLTVDKSRWQQGNVFSCSVMHEALHNHYTQKSLSLSPGK | (SEQ ID NO: 441) |
| Ab13 | YPSDIAVEWESNGQPENNYKTTPPVLDSDGSFFLYSKLTVDKSRWQQGNVFSCSVMHEALHNHYTQKSLSLSPGK | (SEQ ID NO: 481) |
| Ab14 | YPSDIAVEWESNGQPENNYKTTPPVLDSDGSFFLYSKLTVDKSRWQQGNVFSCSVMHEALHNHYTQKSLSLSPGK | (SEQ ID NO: 521) |

Figure 2A - Light Chain Protein Sequence

| Sequence Name | FR1 | CDR1 | FR2 | CDR2 |
|---|---|---|---|---|
| Ab1 | QVLTQTASPVSAAVGSTVTINC | QASQSVYDNNYLA | WYQQKPGQPPKQLIY | STSTLAS |
| Ab2 | QVLTQSPSSLSASVGDRVTINC | QASQSVYDNNYLA | WYQQKPGKVPKQLIY | STSTLAS |
| Ab3 | QVLTQSPSSLSASVGDRVTINC | QASQSVYDNNYLA | WYQQKPGKVPKQLIY | STSTLAS |
| Ab4 | QVLTQTPSPVSAAVGSTVTINC | QASQSVYHNTYLA | WYQQKPGQPPKQLIY | DASTLAS |
| Ab5 | QVLTQSPSSLSASVGDRVTINC | QASQSVYHNTYLA | WYQQKPGKVPKQLIY | DASTLAS |
| Ab6 | QVLTQSPSSLSASVGDRVTINC | QASQSVYHNTYLA | WYQQKPGKVPKQLIY | DASTLAS |
| Ab7 | QVLTQTASPVSAAVGSTVTINC | QASQSVYNYNYLA | WYQQKPGQPPKQLIY | STSTLAS |
| Ab8 | QVLTQSPSSLSASVGDRVTINC | QASQSVYNYNYLA | WYQQKPGKVPKQLIY | STSTLAS |
| Ab9 | QVLTQTPSPVSAAVGSTVTINC | QASQNVYNNNYLA | WYQQKPGQPPKQLIY | STSTLAS |
| Ab10 | QVLTQSPSSLSASVGDRVTINC | QASQNVYNNNYLA | WYQQKPGKVPKQLIY | STSTLAS |
| Ab11 | QVLTQTASPVSPAVGSTVTINC | RASQSVYYNNYLA | WYQQKPGQPPKQLIY | STSTLAS |
| Ab12 | QVLTQSPSSLSASVGDRVTINC | RASQSVYYNNYLA | WYQQKPGKVPKQLIY | STSTLAS |
| Ab13 | AIVMTQTPSSKSVPVGDTVTINC | QASESLYNNNALA | WFQQKPGQPPKRLIY | DASKLAS |
| Ab14 | QVLTQSPSSLSASVGDRVTINC | QASQNVYNNNYLA | WYQQKPGKVPKQLIY | STSTLAS |

Figure 2B - Light Chain Protein Sequence

| Sequence Name | FR3 | CDR3 | FR4 |
|---|---|---|---|
| Ab1 | GVSSRFKGSGSGTQFTLTITSDLECADAATYYC | LGSYDCSSGDCFV | FGGGTEVVKR |
| Ab2 | GVPSRFSGSGSGTDFTLTISSLQPEDVATYYC | LGSYDCSSGDCFV | FGGGTKVEIKR |
| Ab3 | GVPSRFSGSGSGTDFTLTISSLQPEDVATYYC | LGSYDCSSGDCFV | FGGGTKVEIKR |
| Ab4 | GVPSRFSGSGSGTQFTLTISGVQCNDAAAYYC | LGSYDCTNGDCFV | FGGGTEVVVKR |
| Ab5 | GVPSRFSGSGSGTDFTLTISSLQPEDVATYYC | LGSYDCTNGDCFV | FGGGTKVEIKR |
| Ab6 | GVPSRFSGSGSGTDFTLTISSLQPEDVATYYC | LGSYDCTNGDCFV | FGGGTKVEIKR |
| Ab7 | GVSSRFKGSGSGTQFTLTITSDVQCDDAATYYC | LGSYDCSTGDCFV | FGGGTEVVVKR |
| Ab8 | GVPSRFSGSGSGTDFTLTISSLQPEDVATYYC | LGSYDCSTGDCFV | FGGGTKVEIKR |
| Ab9 | GVSSRFKGSGSGTQFTLTISDVQCDDAATYYC | LGSYDCSRGDCFV | FGGGTEVVVKR |
| Ab10 | GVPSRFSGSGSGTDFTLTISSLQPEDVATYYC | LGSYDCSRGDCFV | FGGGTKVEIKR |
| Ab11 | GVSSRFKGSGSGTQFTLTISDVQCDDAATYYC | LGSYDCSNGDCFV | FGGGTEVVVKR |
| Ab12 | GVPSRFSGSGSGTDFTLTISSLQPEDVATYYC | LGSYDCSNGDCFV | FGGGTKVEIKR |
| Ab13 | GVPSRFSGGGSGTQFTLTISGVQCDDAATYYC | GGYRSDSVDGVA | FAGGTEVVVKR |
| Ab14 | GVPSRFSGSGSGTDFTLTISSLQPEDVATYYC | LGSYDCSRGDCFV | FGGGTKVEIKR |

Figure 2C - Light Chain Protein Sequence

| Sequence Name | Constant Region |
|---|---|
| Ab1 | TVAAPSVFIFPPSDEQLKSGTASVVCLLNNFYPREAKVQWKVDNALQSGNSQESVTEQDSKDSTYSLSSTLTLSKADYEKHKVYA |
| Ab2 | TVAAPSVFIFPPSDEQLKSGTASVVCLLNNFYPREAKVQWKVDNALQSGNSQESVTEQDSKDSTYSLSSTLTLSKADYEKHKVYA |
| Ab3 | TVAAPSVFIFPPSDEQLKSGTASVVCLLNNFYPREAKVQWKVDNALQSGNSQESVTEQDSKDSTYSLSSTLTLSKADYEKHKVYA |
| Ab4 | TVAAPSVFIFPPSDEQLKSGTASVVCLLNNFYPREAKVQWKVDNALQSGNSQESVTEQDSKDSTYSLSSTLTLSKADYEKHKVYA |
| Ab5 | TVAAPSVFIFPPSDEQLKSGTASVVCLLNNFYPREAKVQWKVDNALQSGNSQESVTEQDSKDSTYSLSSTLTLSKADYEKHKVYA |
| Ab6 | TVAAPSVFIFPPSDEQLKSGTASVVCLLNNFYPREAKVQWKVDNALQSGNSQESVTEQDSKDSTYSLSSTLTLSKADYEKHKVYA |
| Ab7 | TVAAPSVFIFPPSDEQLKSGTASVVCLLNNFYPREAKVQWKVDNALQSGNSQESVTEQDSKDSTYSLSSTLTLSKADYEKHKVYA |
| Ab8 | TVAAPSVFIFPPSDEQLKSGTASVVCLLNNFYPREAKVQWKVDNALQSGNSQESVTEQDSKDSTYSLSSTLTLSKADYEKHKVYA |
| Ab9 | TVAAPSVFIFPPSDEQLKSGTASVVCLLNNFYPREAKVQWKVDNALQSGNSQESVTEQDSKDSTYSLSSTLTLSKADYEKHKVYA |
| Ab10 | TVAAPSVFIFPPSDEQLKSGTASVVCLLNNFYPREAKVQWKVDNALQSGNSQESVTEQDSKDSTYSLSSTLTLSKADYEKHKVYA |
| Ab11 | TVAAPSVFIFPPSDEQLKSGTASVVCLLNNFYPREAKVQWKVDNALQSGNSQESVTEQDSKDSTYSLSSTLTLSKADYEKHKVYA |
| Ab12 | TVAAPSVFIFPPSDEQLKSGTASVVCLLNNFYPREAKVQWKVDNALQSGNSQESVTEQDSKDSTYSLSSTLTLSKADYEKHKVYA |
| Ab13 | TVAAPSVFIFPPSDEQLKSGTASVVCLLNNFYPREAKVQWKVDNALQSGNSQESVTEQDSKDSTYSLSSTLTLSKADYEKHKVYA |
| Ab14 | TVAAPSVFIFPPSDEQLKSGTASVVCLLNNFYPREAKVQWKVDNALQSGNSQESVTEQDSKDSTYSLSSTLTLSKADYEKHKVYA |

Figure 2D - Light Chain Protein Sequence

| Sequence Name | Constant Region | |
|---|---|---|
| Ab1 | CEVTHQGLSSPVTKSFNRGEC | (SEQ ID NO: 21) |
| Ab2 | CEVTHQGLSSPVTKSFNRGEC | (SEQ ID NO: 61) |
| Ab3 | CEVTHQGLSSPVTKSFNRGEC | (SEQ ID NO: 101) |
| Ab4 | CEVTHQGLSSPVTKSFNRGEC | (SEQ ID NO: 141) |
| Ab5 | CEVTHQGLSSPVTKSFNRGEC | (SEQ ID NO: 181) |
| Ab6 | CEVTHQGLSSPVTKSFNRGEC | (SEQ ID NO: 221) |
| Ab7 | CEVTHQGLSSPVTKSFNRGEC | (SEQ ID NO: 261) |
| Ab8 | CEVTHQGLSSPVTKSFNRGEC | (SEQ ID NO: 301) |
| Ab9 | CEVTHQGLSSPVTKSFNRGEC | (SEQ ID NO: 341) |
| Ab10 | CEVTHQGLSSPVTKSFNRGEC | (SEQ ID NO: 381) |
| Ab11 | CEVTHQGLSSPVTKSFNRGEC | (SEQ ID NO: 421) |
| Ab12 | CEVTHQGLSSPVTKSFNRGEC | (SEQ ID NO: 461) |
| Ab13 | CEVTHQGLSSPVTKSFNRGEC | (SEQ ID NO: 501) |
| Ab14 | CEVTHQGLSSPVTKSFNRGEC | (SEQ ID NO: 541) |

Figure 3A - Heavy Chain DNA Sequence

| Sequence Name | FR1 |
|---|---|
| Ab1 | CAGTCGCTGGAGGAGTCCGGGGGTCGCCCTGGTCACGCCTGGGACACCCTCACCTGCACAGTCTCTGGACTCGACCTCAGT |
| Ab2 | GAGGTGCAGCTTGTGGAGTCTGGGGGAGGCTTGGTCCAGCCTGGGGGGTCCCTGAGACTCTCCTGTGCAGTCTCTGGACTCGACCTCAGT |
| Ab3 | GAGGTGCAGCTTGTGGAGTCTGGGGGAGGCTTGGTCCAGCCTTCCAGCCTGGGGGGTCCCTGAGACTCTCCTGTGCAGTCTCTGGACTCGACCTCAGT |
| Ab4 | CAGTCGCTGGAGGAGTCCGGGGGTCGCCCTGGTCACGCCTGGGACACCCTCACCTGTTCCGTCTCTGGACATCGACCTCAGT |
| Ab5 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab6 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab7 | CAGGAGCAGCTGAAGGAGTCCGGGAGTCTCGCGCTGGTCGCCTGGGACATCCTCACCTGCACCGTCTCTGGATTCTCTGGAATCGACCTCAGT |
| Ab8 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab9 | CAGTCGCTGGAGGAGTCCGGGGGTCGCCCTGGTCACGCCTGGGACACCCTCACCTGCACAGTCTCTGGCCTCAGT |
| Ab10 | GAGGTGCAGCTTGTGGAGTCTGGGGGAGGCTTGGTCCAGCCTGGGGGGTCCCTGAGACTCTCCTGTGCAGTCTCTGGAATCGACCTCAGT |
| Ab11 | CAGTCGCTGGAGGAGTCCGGGGGTCGCCCTGGTCACGCCTCGCCTGGGAGGAGATCCCTGAGACTCTCCTGTGCAGTCTCTGGAATCGACGTCACT |
| Ab12 | GAGGTGCAGCTTGTGGAGGAGTCCGGGAGTCTCGGGGGCCCTGGTCCAGCCTGGGGGGTCCCTGAGACTCTCCTGTGCAGTCTCTGGAATCGACGTCACT |
| Ab13 | CAGTCGGTGGAGGAGTCCGGGGGTCGCCCTGGTCACGCCTGAGGCCCTGAGACTCTCCTGCACAGCCTCACCTGCAGTCTCTGGATTCGACTTCAGT |
| Ab14 | GAGGTGCAGCTTGTGGAGTCTGGGGGAGGCTTGGTCCAGCCTCCAGCCTGGGGGGTCCCTGAGACTCTCCTGTGCAGTCTCTGGAATCGCCTCAGT |

Figure 3B - Heavy Chain DNA Sequence

| Sequence Name | CDR1 | FR2 |
|---|---|---|
| Ab1 | AGCTACTACATGCAA | TGGGTCCGCCAGGCTCCAGGGAAGGGGCTCCAGGGAAGGGGCTGGAATGGATCGGA |
| Ab2 | AGCTACTACATGCAA | TGGGTCCGTCAGGCTCCAGGGAAGGGGCTGGAGTGGGTCGGA |
| Ab3 | AGCTACTACATGCAA | TGGGTCCGTCAGGCTCCAGGGAAGGGGCTGGAGTGGGTCGGA |
| Ab4 | GGCTACTACATGAAC | TGGGTCCGCCAGGCTCCAGGGAAGGGGCTGGAATGGATCGGA |
| Ab5 | GGCTACTACATGAAC | TGGGTCCGCCAGGCTCCAGGGAAGGGGCTGGAGTGGGTCGGA |
| Ab6 | GGCTACTACATGAAC | TGGGTCCGCCAGGCTCCAGGGAAGGGGCTGGAGTGGGTCGGA |
| Ab7 | AACCACTACATGCAA | TGGGTCCGCCAGGCTCCAGGGAAGGGGCTGGAGTGGGATCGGA |
| Ab8 | AACCACTACATGCAA | TGGGTCCAGTCAGGCTCTCCAGGGAAGGGGCTGGAGTGGGTCGGA |
| Ab9 | AGCTACTACATGCAG | TGGGTCCGCCAGGCTCCAGGGAAGGGGCTGGAATGGATCGGA |
| Ab10 | AGCTACTACATGCAA | TGGGTCCGTCAGGCTCCAGGGAAGGGGCTGGAGTGGGTCGGA |
| Ab11 | AACTACTATATGCAA | TGGGTCCGCCAGGCTCCAGGGAAGGGGCTGGAATGGATCGGA |
| Ab12 | AACTACTACATGCAA | TGGGTCCGTCAGGCTCCAGGGAAGGGGCTGGAATGGATCGGA |
| Ab13 | AGCAATGCAATGTGG | TGGGTCCGCCAGGCTCCAGGGAAGGGGCTGGAGTGGATCGGA |
| Ab14 | AGCTACTACATGCAA | TGGGTCCGTCAGGCTCCAGGGAAGGGGCTGGAGTGGGTCGGA |

Figure 3C - Heavy Chain DNA Sequence

| Sequence Name | CDR2 |
|---|---|
| Ab1 | GTCATTGGTATTAATGATAACACATACTACGCGAGCTGGGCGAAAGGC |
| Ab2 | GTCATTGGTATCAATGATAACACATACTACGCGAGCTGGGCGAAAGGC |
| Ab3 | GTCATTGGTATCAATGATAACACATACTACGCGAGCTGGGCGAAAGGC |
| Ab4 | GTCATTGGTATTAATGGTGCCACATACTACGCGAGCTGGGCGAAAGGC |
| Ab5 | GTCATTGGTATTAATGGTGCCACATACTACGCGAGCTGGGCGAAAGGC |
| Ab6 | GTCATTGGTATTAATGGTGCCACATACTACGCGAGCTGGGCGAAAGGC |
| Ab7 | GTCGTTGGTATTAATGGTCGCACATACTACGCGAGCTGGGCGAAAGGC |
| Ab8 | GTCGTTGGTATCAATGGTCGCACATACTACGCGAGCTGGGCGAAAGGC |
| Ab9 | GTCATTGGTAGTAGTGATGGTAAGACATACTACGCGACCTGGGCGAAAGGC |
| Ab10 | GTCATTGGTAGTAGTGATGGTAAGACATACTACGCGACCTGGGCGAAAGGC |
| Ab11 | GTCATTGGTGTGTGAATGGTAAGAGATACTACGCGAGCTGGGCGAAAGGC |
| Ab12 | GTCATTGGTGTGTGAATGGTAAGAGATACTACGCGAGCTGGGCGAAAGGC |
| Ab13 | TGCATTTACAATGGTGATGGCAGCAGACATACTACGCGAGCTGGGTGAATGGC |
| Ab14 | GTCATTGGTAGTGATGGTAAGACATACTACGCGACCTGGGCGAAAGGC |

Figure 3D - Heavy Chain DNA Sequence

| Sequence Name | FR3 |
|---|---|
| Ab1 | CGATTCACCATCTCCAGAGCCTCGTCGTCGACCACGGTGGATCTGAAATGACCAGTCTGACAACCGAGGACACGGCCACCTATTTCTGTGCCAGA |
| Ab2 | CGATTCACCATCTCCAGAGACACCATTCCAAGACACCACGGTGTATCTTCAAATGAACAGCCTGAGAGCTGAGGACACTGCTGTGTATTTCTGTGCTAGA |
| Ab3 | CGATTCACCATCTCCAGAGACACCATTCCAAGACACCACGGTGTATCTTCAAATGAACAGCCTGAGAGCTGAGGACACTGCTGTGTATTTCTGTGCTAGA |
| Ab4 | CGATTCACCATCTCCAGAGACACCATTCCAAAACCTCGTCGACCACGGTGGATCTGAAAATGAACAGTCTGAGAGCTGAGGACACTGCCACCTATTTCTGTGCCAGA |
| Ab5 | CGATTCACCATCTCCAGAGACACCATTCCAAAACCTCGTCGACCACGGTGGATCTGAAAATGAACAGTCTGAGAGCTGAGGACACTGCCACCTATTTCTGTGCCAGA |
| Ab6 | CGATTCACCATCTCCAGAGACAATTCCAAGACAATTCGTCGACCACGGTGTATCTTCAAATGAACAGCCTGAGAGCTGAGGACACTGCTGTCTGTATTTCTGTGCTAGA |
| Ab7 | CGATTCACCATCTCCAGAGACAATTCCAAGACAATTCGTCGACCACGGTGTATCTTCAAATGAACAGCCTGAGAGCTGAGGACACTGCTGTCTGTATTTCTGTGCTAGA |
| Ab8 | CGATTCACCATCTCCAGAGACAATTCCAAGACAATTCGTCGACCACGGTGTATCTTCAAATGAACAGCCTGAGAGCTGAGGACACTGCTGTCTGTATTTCTGTGCTAGA |
| Ab9 | CGATTCACCATCTCCAGAGACAATTCCAAGACAATTCGTCGACCACGGTGGATCTGTATCTTCAAATGGCCAGTCTGAGAATCTTCAAAATGACCAGTCTGAGAGCTGAGGACACTGCCACCTATTTCTGTACCAGA |
| Ab10 | CGATTCACCATCTCCAGAGACAATTCCAAGACAATTCGTGACCACGGTGGATCTGTATCTTCAAATGGCCAGTCTGAGAATCTTCAAAATGACCAGTCTGAGAGCTGAGGACACTGCCACCTATTTCTGTACCAGA |
| Ab11 | CGATTCACCATCTCCAAAACCTCCAAAAACCTCGTGACCACGGTGTATCTTCAAATGAACAGTCTGAGAGCTGAGGACACTGCTGTATTTCTGTGCCAGA |
| Ab12 | CGATTCACCATCTCCAGAGACAATTCCAAGACAATTCGTGACCACGGTGTATCTTGCAACTGAATAGTCTGACAGTCGCGGACACTGCTGTATTATTGTGCGAGA |
| Ab13 | CGATTCTCCATCTCCAAAACCTCCAAAAACCTCGTGACCACGGTGACTCTGCAACTCTGAATAGTCTGACAGTCGCGGACACTGCTGTATTATTGTGCGAGA |
| Ab14 | CGATTCACCATCTCCAGAGACAATTCCAAGACAATTCGTGACCACGGTGTATCTTCAAATGAACAGCCTGAGAGCTGAGGACACTGCTGTCTGTATTTCTGTACCAGA |

Figure 3E – Heavy Chain DNA Sequence

| Sequence Name | CDR3 | FR4 | Constant Region |
|---|---|---|---|
| Ab1 | GGGGACATC | TGGGGCCCAGGCACCCTCGTCACCGTCTCGAGC | GCCTCCACCAAGGGCCCATCGGTCTTCCCCCTGGCACCCTCCTCC |
| Ab2 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab3 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab4 | GGGGACATC | TGGGGCCCGGGCACCCTCGTCACCGTCTCGAGC | GCCTCCACCAAGGGCCCATCGGTCTTCCCCCTGGCACCCTCCTCC |
| Ab5 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab6 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab7 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab8 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab9 | GGGGACATC | TGGGGCCCGGGCACCCTCGTCACCGTCTCGAGC | GCCTCCACCAAGGGCCCATCGGTCTTCCCCCTGGCACCCTCCTCC |
| Ab10 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab11 | GGCGACATC | TGGGGCCCGGGCACCCTCGTCACCGTCTCGAGC | GCCTCCACCAAGGGCCCATCGGTCTTCCCCCTGGCACCCTCCTCC |
| Ab12 | GGGGACATC | TGGGGCCAAGGGACCCTCGTCACCGTCTCGAGC | GCCTCCACCAAGGGCCCATCGGTCTTCCCCCTGGCACCCTCCTCC |
| Ab13 | GATCTTTGACTTG | TGGGGCCCCGGGGACCCTCGTCACCGTCTCGAGC | GCCTCCACCAAGGGCCCATCGGTCTTCCCCCTGGCACCCTCCTCC |
| Ab14 | GGGGACATC | TGGGGCCAAGGGACCCTCGTCACCGTCTCGAGC | GCCTCCACCAAGGGCCCATCGGTCTTCCCCCTGGCACCCTCCTCC |

Figure 3F – Heavy Chain DNA Sequence

| Sequence Name | Constant Region |
|---|---|
| Ab1 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab2 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab3 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab4 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab5 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab6 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab7 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab8 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab9 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab10 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab11 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab12 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab13 | AAGAGCACCTCTGGGGGCACAGCGGCCCTGGGCTGCCTGGTCAAGGACTACTTCCCCGAACCGGTGACGGTGTCGTGGAACTCAGGCGCC |
| Ab14 | AAGAGCACCTCTGGGGGCACAGCGGCCCTGGGCTGCCTGGTCAAGGACTACTTCCCCGAACCGGTGACGGTGTCGTGGAACTCAGGCGCC |

Figure 3G – Heavy Chain DNA Sequence

| Sequence Name | Constant Region |
|---|---|
| Ab1 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab2 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab3 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab4 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab5 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab6 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab7 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab8 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab9 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab10 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab11 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab12 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab13 | CTGACCAGCGGCGTGCACACCTTCCCGGCTGTCCTACAGTCCTCAGGACTCTACTCCCTCAGCAGCGTGGTGACCGTGCCCTCCAGCAGC |
| Ab14 | CTGACCAGCGGCGTGCACACCTTCCCGGCTGTCCTACAGTCCTCAGGACTCTACTCCCTCAGCAGCGTGGTGACCGTGCCCTCCAGCAGC |

Figure 3H – Heavy Chain DNA Sequence

| Sequence Name | Constant Region |
|---|---|
| Ab1 | TTGGGCACCCAGACCTACATCTGCAACGTGAATCACAAGCCCAGCAACACCAAGGTGGACAAGAGAGTTGAGCCCAAATCTTGTGACAAA |
| Ab2 | TTGGGCACCCAGACCTACATCTGCAACGTGAATCACAAGCCCAGCAACACCAAGGTGGACAAGAGAGTTGAGCCCAAATCTTGTGACAAA |
| Ab3 | TTGGGCACCCAGACCTACATCTGCAACGTGAATCACAAGCCCAGCAACACCAAGGTGGACAAGAGAGTTGAGCCCAAATCTTGTGACAAA |
| Ab4 | TTGGGCACCCAGACCTACATCTGCAACGTGAATCACAAGCCCAGCAACACCAAGGTGGACAAGAGAGTTGAGCCCAAATCTTGTGACAAA |
| Ab5 | TTGGGCACCCAGACCTACATCTGCAACGTGAATCACAAGCCCAGCAACACCAAGGTGGACAAGAGAGTTGAGCCCAAATCTTGTGACAAA |
| Ab6 | TTGGGCACCCAGACCTACATCTGCAACGTGAATCACAAGCCCAGCAACACCAAGGTGGACAAGAGAGTTGAGCCCAAATCTTGTGACAAA |
| Ab7 | TTGGGCACCCAGACCTACATCTGCAACGTGAATCACAAGCCCAGCAACACCAAGGTGGACAAGAGAGTTGAGCCCAAATCTTGTGACAAA |
| Ab8 | TTGGGCACCCAGACCTACATCTGCAACGTGAATCACAAGCCCAGCAACACCAAGGTGGACAAGAGAGTTGAGCCCAAATCTTGTGACAAA |
| Ab9 | TTGGGCACCCAGACCTACATCTGCAACGTGAATCACAAGCCCAGCAACACCAAGGTGGACAAGAGAGTTGAGCCCAAATCTTGTGACAAA |
| Ab10 | TTGGGCACCCAGACCTACATCTGCAACGTGAATCACAAGCCCAGCAACACCAAGGTGGACAAGAGAGTTGAGCCCAAATCTTGTGACAAA |
| Ab11 | TTGGGCACCCAGACCTACATCTGCAACGTGAATCACAAGCCCAGCAACACCAAGGTGGACAAGAGAGTTGAGCCCAAATCTTGTGACAAA |
| Ab12 | TTGGGCACCCAGACCTACATCTGCAACGTGAATCACAAGCCCAGCAACACCAAGGTGGACAAGAGAGTTGAGCCCAAATCTTGTGACAAA |
| Ab13 | TTGGGCACCCAGACCTACATCTGCAACGTGAATCACAAGCCCAGCAACACCAAGGTGGACAAGAGAGTTGAGCCCAAATCTTGTGACAAA |
| Ab14 | TTGGGCACCCAGACCTACATCTGCAACGTGAATCACAAGCCCAGCAACACCAAGGTGGACAAGAGAGTTGAGCCCAAATCTTGTGACAAA |

Figure 3I - Heavy Chain DNA Sequence

| Sequence Name | Constant Region |
|---|---|
| Ab1 | ACTCACACACATGCCCACCGTGCCCAGCACCTGAACTCCTGGGGGGACCGTCAGTCTTCCTCTTCCCCCCAAAACCCAAGGACACCCTCATG |
| Ab2 | ACTCACACACATGCCCACCGTGCCCAGCACCTGAACTCCTGGGGGGACCGTCAGTCTTCCTCTTCCCCCCAAAACCCAAGGACACCCTCATG |
| Ab3 | ACTCACACACATGCCCACCGTGCCCAGCACCTGAACTCCTGGGGGGACCGTCAGTCTTCCTCTTCCCCCCAAAACCCAAGGACACCCTCATG |
| Ab4 | ACTCACACACATGCCCACCGTGCCCAGCACCTGAACTCCTGGGGGGACCGTCAGTCTTCCTCTTCCCCCCAAAACCCAAGGACACCCTCATG |
| Ab5 | ACTCACACACATGCCCACCGTGCCCAGCACCTGAACTCCTGGGGGGACCGTCAGTCTTCCTCTTCCCCCCAAAACCCAAGGACACCCTCATG |
| Ab6 | ACTCACACACATGCCCACCGTGCCCAGCACCTGAACTCCTGGGGGGACCGTCAGTCTTCCTCTTCCCCCCAAAACCCAAGGACACCCTCATG |
| Ab7 | ACTCACACACATGCCCACCGTGCCCAGCACCTGAACTCCTGGGGGGACCGTCAGTCTTCCTCTTCCCCCCAAAACCCAAGGACACCCTCATG |
| Ab8 | ACTCACACACATGCCCACCGTGCCCAGCACCTGAACTCCTGGGGGGACCGTCAGTCTTCCTCTTCCCCCCAAAACCCAAGGACACCCTCATG |
| Ab9 | ACTCACACACATGCCCACCGTGCCCAGCACCTGAACTCCTGGGGGGACCGTCAGTCTTCCTCTTCCCCCCAAAACCCAAGGACACCCTCATG |
| Ab10 | ACTCACACACATGCCCACCGTGCCCAGCACCTGAACTCCTGGGGGGACCGTCAGTCTTCCTCTTCCCCCCAAAACCCAAGGACACCCTCATG |
| Ab11 | ACTCACACACATGCCCACCGTGCCCAGCACCTGAACTCCTGGGGGGACCGTCAGTCTTCCTCTTCCCCCCAAAACCCAAGGACACCCTCATG |
| Ab12 | ACTCACACACATGCCCACCGTGCCCAGCACCTGAACTCCTGGGGGGACCGTCAGTCTTCCTCTTCCCCCCAAAACCCAAGGACACCCTCATG |
| Ab13 | ACTCACACACATGCCCACCGTGCCCAGCACCTGAACTCCTGGGGGGACCGTCAGTCTTCCTCTTCCCCCCAAAACCCAAGGACACCCTCATG |
| Ab14 | ACTCACACACATGCCCACCGTGCCCAGCACCTGAACTCCTGGGGGGACCGTCAGTCTTCCTCTTCCCCCCAAAACCCAAGGACACCCTCATG |

Figure 3J - Heavy Chain DNA Sequence

| Sequence Name | Constant Region |
|---|---|
| Ab1 | ATCTCCCGGACCCCTGAGGTCACATGCGTGGTGGTGGACGTGAGCCACGAAGACCCTGAGGTCAAGTTCAACTGGTACGTGGACGGCGTG |
| Ab2 | ATCTCCCGGACCCCTGAGGTCACATGCGTGGTGGTGGACGTGAGCCACGAAGACCCTGAGGTCAAGTTCAACTGGTACGTGGACGGCGTG |
| Ab3 | ATCTCCCGGACCCCTGAGGTCACATGCGTGGTGGTGGACGTGAGCCACGAAGACCCTGAGGTCAAGTTCAACTGGTACGTGGACGGCGTG |
| Ab4 | ATCTCCCGGACCCCTGAGGTCACATGCGTGGTGGTGGACGTGAGCCACGAAGACCCTGAGGTCAAGTTCAACTGGTACGTGGACGGCGTG |
| Ab5 | ATCTCCCGGACCCCTGAGGTCACATGCGTGGTGGTGGACGTGAGCCACGAAGACCCTGAGGTCAAGTTCAACTGGTACGTGGACGGCGTG |
| Ab6 | ATCTCCCGGACCCCTGAGGTCACATGCGTGGTGGTGGACGTGAGCCACGAAGACCCTGAGGTCAAGTTCAACTGGTACGTGGACGGCGTG |
| Ab7 | ATCTCCCGGACCCCTGAGGTCACATGCGTGGTGGTGGACGTGAGCCACGAAGACCCTGAGGTCAAGTTCAACTGGTACGTGGACGGCGTG |
| Ab8 | ATCTCCCGGACCCCTGAGGTCACATGCGTGGTGGTGGACGTGAGCCACGAAGACCCTGAGGTCAAGTTCAACTGGTACGTGGACGGCGTG |
| Ab9 | ATCTCCCGGACCCCTGAGGTCACATGCGTGGTGGTGGACGTGAGCCACGAAGACCCTGAGGTCAAGTTCAACTGGTACGTGGACGGCGTG |
| Ab10 | ATCTCCCGGACCCCTGAGGTCACATGCGTGGTGGTGGACGTGAGCCACGAAGACCCTGAGGTCAAGTTCAACTGGTACGTGGACGGCGTG |
| Ab11 | ATCTCCCGGACCCCTGAGGTCACATGCGTGGTGGTGGACGTGAGCCACGAAGACCCTGAGGTCAAGTTCAACTGGTACGTGGACGGCGTG |
| Ab12 | ATCTCCCGGACCCCTGAGGTCACATGCGTGGTGGTGGACGTGAGCCACGAAGACCCTGAGGTCAAGTTCAACTGGTACGTGGACGGCGTG |
| Ab13 | ATCTCCCGGACCCCTGAGGTCACATGCGTGGTGGTGGACGTGAGCCACGAAGACCCTGAGGTCAAGTTCAACTGGTACGTGGACGGCGTG |
| Ab14 | ATCTCCCGGACCCCTGAGGTCACATGCGTGGTGGTGGACGTGAGCCACGAAGACCCTGAGGTCAAGTTCAACTGGTACGTGGACGGCGTG |

Figure 3K – Heavy Chain DNA Sequence

| Sequence Name | Constant Region |
|---|---|
| Ab1 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab2 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab3 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab4 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab5 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab6 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab7 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab8 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab9 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab10 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab11 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab12 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab13 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |
| Ab14 | GAGGTGCATAATGCCAAGACAAAGCCGCGGGAGGAGGAGCAGTACGCCAGCACGTACCGTGTGGTCAGCGTCCTCCTCACCGTCCTGCACCAGGAC |

Figure 3L – Heavy Chain DNA Sequence

| Sequence Name | Constant Region |
|---|---|
| Ab1 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab2 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab3 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab4 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab5 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab6 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab7 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab8 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab9 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab10 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab11 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab12 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab13 | TGGCTGAATGGCAAGGAGTACAAGTGCAAGGTCTCCAACAAAGCCCTCCCAGCCCCCATCGAGAAAACCATCTCCAAAGCCAAAGGGCAG |
| Ab14 | TGGCTGAATGGCAAGGAGTACAAGTGCAAGGTCTCCAACAAAGCCCTCCCAGCCCCCATCGAGAAAACCATCTCCAAAGCCAAAGGGCAG |

Figure 3M - Heavy Chain DNA Sequence

| Sequence Name | Constant Region |
|---|---|
| Ab1 | CCCCGAGAACCACAGGTGTACACCCTGCCCCCATCCCGGGAGGAGATGACCAAGAACCAGGTCAGCCTGACCTGCCTGGTCAAAGGCTTC |
| Ab2 | CCCCGAGAACCACAGGTGTACACCCTGCCCCCATCCCGGGAGGAGATGACCAAGAACCAGGTCAGCCTGACCTGCCTGGTCAAAGGCTTC |
| Ab3 | CCCCGAGAACCACAGGTGTACACCCTGCCCCCATCCCGGGAGGAGATGACCAAGAACCAGGTCAGCCTGACCTGCCTGGTCAAAGGCTTC |
| Ab4 | CCCCGAGAACCACAGGTGTACACCCTGCCCCCATCCCGGGAGGAGATGACCAAGAACCAGGTCAGCCTGACCTGCCTGGTCAAAGGCTTC |
| Ab5 | CCCCGAGAACCACAGGTGTACACCCTGCCCCCATCCCGGGAGGAGATGACCAAGAACCAGGTCAGCCTGACCTGCCTGGTCAAAGGCTTC |
| Ab6 | CCCCGAGAACCACAGGTGTACACCCTGCCCCCATCCCGGGAGGAGATGACCAAGAACCAGGTCAGCCTGACCTGCCTGGTCAAAGGCTTC |
| Ab7 | CCCCGAGAACCACAGGTGTACACCCTGCCCCCATCCCGGGAGGAGATGACCAAGAACCAGGTCAGCCTGACCTGCCTGGTCAAAGGCTTC |
| Ab8 | CCCCGAGAACCACAGGTGTACACCCTGCCCCCATCCCGGGAGGAGATGACCAAGAACCAGGTCAGCCTGACCTGCCTGGTCAAAGGCTTC |
| Ab9 | CCCCGAGAACCACAGGTGTACACCCTGCCCCCATCCCGGGAGGAGATGACCAAGAACCAGGTCAGCCTGACCTGCCTGGTCAAAGGCTTC |
| Ab10 | CCCCGAGAACCACAGGTGTACACCCTGCCCCCATCCCGGGAGGAGATGACCAAGAACCAGGTCAGCCTGACCTGCCTGGTCAAAGGCTTC |
| Ab11 | CCCCGAGAACCACAGGTGTACACCCTGCCCCCATCCCGGGAGGAGATGACCAAGAACCAGGTCAGCCTGACCTGCCTGGTCAAAGGCTTC |
| Ab12 | CCCCGAGAACCACAGGTGTACACCCTGCCCCCATCCCGGGAGGAGATGACCAAGAACCAGGTCAGCCTGACCTGCCTGGTCAAAGGCTTC |
| Ab13 | CCCCGAGAACCACAGGTGTACACCCTGCCCCCATCCCGGGAGGAGATGACCAAGAACCAGGTCAGCCTGACCTGCCTGGTCAAAGGCTTC |
| Ab14 | CCCCGAGAACCACAGGTGTACACCCTGCCCCCATCCCGGGAGGAGATGACCAAGAACCAGGTCAGCCTGACCTGCCTGGTCAAAGGCTTC |

Figure 3N - Heavy Chain DNA Sequence

| Sequence Name | Constant Region |
|---|---|
| Ab1 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab2 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab3 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab4 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab5 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab6 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab7 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab8 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab9 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab10 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab11 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab12 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab13 | TATCCCAGCGACATCGCCGTGGAGTGGGAGAGCAATGGGCAGCCGGAGAACAACTACAAGACCACGCCTCCCGTGCTGCTGGACTCCGACGGC |
| Ab14 | TATCCCAGCGACATCGCCGTGGAGTGGGAGAGCAATGGGCAGCCGGAGAACAACTACAAGACCACGCCTCCCGTGCTGCTGGACTCCGACGGC |

Figure 3O - Heavy Chain DNA Sequence

| Sequence Name | Constant Region | |
|---|---|---|
| Ab1  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 11) |
| Ab2  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 51) |
| Ab3  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 91) |
| Ab4  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 131) |
| Ab5  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 171) |
| Ab6  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 211) |
| Ab7  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 251) |
| Ab8  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 291) |
| Ab9  | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 331) |
| Ab10 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 371) |
| Ab11 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 411) |
| Ab12 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 451) |
| Ab13 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 491) |
| Ab14 | TCCTTCTTCCTCTACAGCAAGCTCACCGTGGACAAGAGCAGGTGGCAGCAGGGGAACGTCTTCTCATGCTCCGTGATGCATGAGGCTCTG | (SEQ ID NO: 531) |

Figure 3P - Heavy Chain DNA Sequence

| Sequence Name | Constant Region | |
|---|---|---|
| Ab1  | CACAACCACTACACGCAGAAGAGCCTCTCCCTGTCTCCGGGTAAATGA | (SEQ ID NO: 11) |
| Ab2  | CACAACCACTACACGCAGAAGAGCCTCTCCCTGTCTCCGGGTAAATGA | (SEQ ID NO: 51) |
| Ab3  | CACAACCACTACACGCAGAAGAGCCTCTCCCTGTCTCCGGGTAAATGA | (SEQ ID NO: 91) |
| Ab4  | CACAACCACTACACGCAGAAGAGCCTCTCCCTGTCTCCGGGTAAATGA | (SEQ ID NO: 131) |
| Ab5  | CACAACCACTACACGCAGAAGAGCCTCTCCCTGTCTCCGGGTAAATGA | (SEQ ID NO: 171) |
| Ab6  | CACAACCACTACACGCAGAAGAGCCTCTCCCTGTCTCCGGGTAAATGA | (SEQ ID NO: 211) |
| Ab7  | CACAACCACTACACGCAGAAGAGCCTCTCCCTGTCTCCGGGTAAATGA | (SEQ ID NO: 251) |
| Ab8  | CACAACCACTACACGCAGAAGAGCCTCTCCCTGTCTCCGGGTAAATGA | (SEQ ID NO: 291) |
| Ab9  | CACAACCACTACACGCAGAAGAGCCTCTCCCTGTCTCCGGGTAAATGA | (SEQ ID NO: 331) |
| Ab10 | CACAACCACTACACGCAGAAGAGCCTCTCCCTGTCTCCGGGTAAATGA | (SEQ ID NO: 371) |
| Ab11 | CACAACCACTACACGCAGAAGAGCCTCTCCCTGTCTCCGGGTAAATGA | (SEQ ID NO: 411) |
| Ab12 | CACAACCACTACACGCAGAAGAGCCTCTCCCTGTCTCCGGGTAAATGA | (SEQ ID NO: 451) |
| Ab13 | CACAACCACTACACGCAGAAGAGCCTCTCCCTGTCTCCGGGTAAATGA | (SEQ ID NO: 491) |
| Ab14 | CACAACCACTACACGCAGAAGAGCCTCTCCCTGTCTCCGGGTAAATGA | (SEQ ID NO: 531) |

Figure 4A - Light Chain DNA Sequence

| Sequence Name | FR1 |
|---|---|
| Ab1 | CAAGTGCTGACCCAGACTGCATCCCCGTGTCTGCAGCTGTGGGAAGCACAGTCACCATCAATTGC |
| Ab2 | CAAGTGCTGACCCAGTCTCCATCCTCCGTGTCTGTGTCTGCAGCTGTGGGAAGACAGAGTCACCATCAATTGC |
| Ab3 | CAAGTGCTGACCCAGTCTCCATCCTCCGTGTCTGTGTCTGCAGCTGTGGGAAGACAGAGTCACCATCAATTGC |
| Ab4 | CAAGTGCTGACCCAGTCTCCATCCTCCGTGTCTGTGTCTGCAGCTGTGGGAAGACAGAGTCACCATCAATTGC |
| Ab5 | CAAGTGCTGACCCAGTCTCCATCCTCCGTGTCTGTGTCTGCAGCTGTGGGAAGACAGAGTCACCATCAATTGC |
| Ab6 | CAAGTGCTGACCCAGTCTCCATCCTCCGTGTCTGTGTCTGCAGCTGTGGGAAGACAGAGTCACCATCAATTGC |
| Ab7 | CAAGTGCTGACCCAGACTGCATCCCCGTGTCTGTGTCTGCAGCTGTGGGAAGCACAGTCACCATCAATTGC |
| Ab8 | CAAGTGCTGACCCAGTCTCCATCCTCCGTGTCTGCAGCTGTGGGAAGACAGAGTCACCATCAATTGC |
| Ab9 | CAAGTGCTGACCCAGTCTCCATCCTCCGTGTCTGCAGCTGTGGGAAGACAGAGTCACCATCAATTGC |
| Ab10 | CAAGTGCTGACCCAGTCTCCATCCTCCGTGTCTGTGTCTGCAGCTGTGGGAAGACAGAGTCACCATCAATTGC |
| Ab11 | CAGGTGCTGACCCAGTCTCCATCCTCCGTGTCTGTGTCTGCAGCTGTGGGAAGACAGAGTCACCATCAATTGC |
| Ab12 | CAAGTGCTGACCCAGTCTCCATCCTCCGTGTCTGTGTCTGTAGCTGTGGGAAGACAGAGTCACCATCAATTGC |
| Ab13 | GCCATCGTGATGACCCAGAGTCTCCAGTCTTCCAAGTCTGTGTCCCTGTGGGAGACACAGTCACCATCAATTGC |
| Ab14 | CAAGTGCTGACCCAGTCTCCATCCTCCGTGTCTGTGTCTGCAGCTGTGGGAAGACAGAGTCACCATCAATTGC |

Figure 4B - Light Chain DNA Sequence

| Sequence Name | CDR1 | FR2 |
|---|---|---|
| Ab1 | CAGGCCAGTCAGAGTGTTTATGATAACAACTACCTAGCC | TGGTATCAGCAGCAGAAACCAGGGCAGCCTCCCAAGCAACTGATCTAT |
| Ab2 | CAGGCCAGTCAGAGTGTTTATGATAACAACTACCTAGCC | TGGTATCAGCAGCAGAAACCAGGGCAGCCTCCTAAGCAACTGATCTAT |
| Ab3 | CAGGCCAGTCAGAGTGTTTATGATAACAACTACCTAGCC | TGGTATCAGCAGCAGAAACCAGGGAAAGTTCCTAAGCAACTGATCTAT |
| Ab4 | CAGGCCAGTCAGAGTGTTTATCATAACACCTACCTGGCC | TGGTATCAGCAGCAGAAACCAGGCAGCCTCCCAAACAACTGATCTAT |
| Ab5 | CAGGCCAGTCAGAGTGTTTATCATAACAACTACCTGGCC | TGGTATCAGCAGCAGAAACCAGGGAAAGTTCCTAAGCAACTGATCTAT |
| Ab6 | CAGGCCAGTCAGAGTGTTTATCATAACAACTACCTGGCC | TGGTATCAGCAGCAGAAACCAGGGAAAGTTCCTAAGCAACTGATCTAT |
| Ab7 | CAGGCCAGTCAGAGTGTTTATAATTACAACTACCTTGCC | TGGTATCAGCAGCAGAAACCAGGGCAGCCTCCCAAGCAACTGATCTAT |
| Ab8 | CAGGCCAGTCAGAGTGTTTATAATTACAACTACCTTGCC | TGGTATCAGCAGCAGAAACCAGGGAAAGTTCCTAAGCAACTGATCTAT |
| Ab9 | CAGGCCAGTCAGAATGTTTATAATAACAACTACCTAGCC | TGGTATCAGCAGCAGAAACCAGGGCAGCCTCCCAAGCAACTGATCTAT |
| Ab10 | CAGGCCAGTCAGAATGTTTATAATAACAACTACCTAGCC | TGGTATCAGCAGCAGAAACCAGGGAAAGTTCCTAAGCAACTGATCTAT |
| Ab11 | CGGGCCAGTCAGAGTGTTTATTATAACAACTACCTAGCC | TGGTATCAGCAGCAGAAACCAGGGCAGCCTCCCAAGCAACTGATCTAT |
| Ab12 | CGGGCCAGTCAGAGTGTTTACTATAACAACTACCTAGCC | TGGTATCAGCAGCAGAAACCAGGGCAGCCTCCCAAGCAACTGATCTAT |
| Ab13 | CAGGCCAGTGAGAGTGTCTTTATAATAACAAGCCTTGCC | TGTTTCAGCAGCAGAAACCAGGGCAGCCTCCCAAGCGCCTTGATCTAT |
| Ab14 | CAGGCCAGTCAGAATGTTTACAATAACAACTACCTAGCC | TGGTATCAGCAGCAGAAACCAGGGAAAGTTCCTAAGCAACTGATCTAT |

Figure 4C - Light Chain DNA Sequence

| Sequence Name | CDR2 | FR3 |
|---|---|---|
| Ab1 | TCTACATCCACTCTGGCATCT | GGGGTCTCATGCGGTTCAAAGGCAGTGGATCTGGGACACAGTTCACTCTCACCA |
| Ab2 | TCTACATCCACTCTGGCATCT | GGGGTCCCCATCTCGTTTCAGTGGCAGTGGATCTGGACAGATTCACTCTCACCA |
| Ab3 | TCTACATCCACTCTGGCATCT | GGGGTCCCCATCTCGTTTCAGTGGCAGTGGATCTGGACACAGTTCACTCTCACCA |
| Ab4 | GATGCATCCACTCTGGCGTCT | GGGGTCCCCATCGCGGTTCAGCGCAGTGGATCTGGGACACAGTTCACTCTCACCA |
| Ab5 | GATGCATCCACTCTGGCATCT | GGGGTCCCCATCTCGTTTCAGTGGCAGTGGATCTGGGACACAGATTCACTCTCACCA |
| Ab6 | GATGCATCCACTCTGGCATCT | GGGGTCCCCATCTCGTTTCAGTGGCAGTGGATCTGGGACAGATTCACTCTCACCA |
| Ab7 | TCTACATCCACTCTGGCATCT | GGGGTCTCATGCGATTCAAAGGCAGTGGATCTGGGACACAGTTCACTCTCACCA |
| Ab8 | TCTACATCCACTCTGGCATCT | GGGGTCCCCATCTCGTTTCAGTGGCAGTGGATCTGGGACACAGTTCACTCTCACCA |
| Ab9 | TCTACGTCCACTCTGGCATCT | GGGGTCCCCATCTCATGCGATTCAGAGGCAGTGGATCTGGGACACAGTTCACTCTCACCA |
| Ab10 | TCTACATCCACTCTGGCATCT | GGGGTCCCCATCTCGTTTCAGTGGATCTGGATCTGGGACACAGATTCACTCTCACCA |
| Ab11 | TCTACATCCACTCTGGCATCT | GGGGTCTCATGCGGTTCAAAGGCAGTGGATCTGGGACACAGTTCACTCTCACCA |
| Ab12 | TCTACATCCACTCTGGCATCT | GGGGTCCCATCTCGTTTCAGTGGCAGTGGATCTGGGACACAGATTCACTCTCACCA |
| Ab13 | GATGCATCCAAACTGGCATCT | GGGGTCCCCATCGCGGTTCGTTTCAGTGGCGGTGGGTCTGGGACACAGTTCACTCTCACCA |
| Ab14 | TCTACATCCACTCTGGCATCT | GGGGTCCCCATCTCGTTTCAGTGGCAGTGGATCTGGGACACAGATTCACTCTCACCA |

Figure 4D - Light Chain DNA Sequence

| Sequence Name | FR3 | CDR3 |
|---|---|---|
| Ab1 | TCAGCGGACCTGGAGTGTGCCGATGCTGCCACTTACTACTGT | CTAGGCAGTTATGATTGTAGTAGTGGTGATTGTTTTGTT |
| Ab2 | TCAGCAGCCTGCAGCCTGAAGATGTTGCAACTTATTACTGT | CTAGGCAGTTATGATTGTAGTAGTGGTGATTGTTTTGTT |
| Ab3 | TCAGCAGCCTGCAGCCTGAAGATGTTGCAACTTATTACTGT | CTAGGCAGTTATGATTGTAGTAGTGGTGATTGTTTTGTT |
| Ab4 | TCAGCGGCGTGCAGTGTAACGATGCTGCCGCTTACTACTGT | CTGGGCAGTTATGATTGTACTAATAGTGGTGATTGTTTTGTT |
| Ab5 | TCAGCGGCCTGCAGTGCAGCCTGAAGATGTTGCAACTTATTACTGT | CTGGGCAGTTATGATTGTACTAATAGTGGTGATTGTTTTGTT |
| Ab6 | TCAGCAGCCTGCAGTGTGACGATGCTGCCACTTACTACTGT | CTGGGCAGTTATGATTGTACTAATAGTGGTGATTGTTTTGTT |
| Ab7 | TCAGCGACGTGCAGTGTGACGATGCTGCCACTTACTACTGT | CTAGGCAGTTATGACTGTAGTAGTGGTGATTGTTTTGTT |
| Ab8 | TCAGCAGCCTGCAGTGTGACGATGCTGCCACTTACTACTGT | CTAGGCAGTTATGATTGTAGTAGTGGTGATTGTTTTGTT |
| Ab9 | TCAGCGACGTGCAGTGTGACGATGCTGCCACTTACTACTGT | CTGGGCAGTTATGATTGTAGTCGTGGTGATTGTTTTGTT |
| Ab10 | TCAGCGACGTGCAGTGTGACGATGCTGCCACTTACTACTGT | CTGGGCAGTTATGATTGTAGTCGTGGTAATGGTGATTGTTTTGTT |
| Ab11 | TCAGCAGCCTGCAGTGTGACGATGCTGCCACTTACTACTGT | CTAGGCAGTTATGATTGTAGTAATGGTAATGGTGATTGTTTTGTT |
| Ab12 | TCAGCAGCCTGCAGTGTGACGATGCTGCCACTTACTACTGT | CTGGGCAGTTATGATTGTAGTAATGGTAATGGTGATTGTTTTGTT |
| Ab13 | TCAGTGGCGTGCAGCCTGCAGTGTGACGATGCTGCCACTTACTACTGT | GGAGGCTACAGAAGTGATAGTGTTGATGGTGTTGCT |
| Ab14 | TCAGCAGCCTGCAGCCTGAAGATGTTGCAACTTATTACTGT | CTGGGCAGTTATGATTGTAGTCGTGGTGATTGTTTTGTT |

Figure 4E - Light Chain DNA Sequence

| Sequence Name | FR4 | Constant Region |
|---|---|---|
| Ab1 | TTCGGCGGAGGGACCGAGGTGGTGGTCAAACGT | ACGGTGGCTGCACCATCTGTCTTCATCTTCCCGCCATCTGATGAGCAGTTG |
| Ab2 | TTCGGCGGAGGGACCGAGGTGGTGGTCAAACGT | ACGGTGGCTGCACCATCTGTCTTCATCTTCCCGCCATCTGATGAGCAGTTG |
| Ab3 | TTCGGCGGAGGGACCAAGGTGGAAATCAAACGT | ACGGTGGCTGCACCATCTGTCTTCATCTTCCCGCCATCTGATGAGCAGTTG |
| Ab4 | TTCGGCGGAGGGACCGAGGTGGTGGTCAAACGT | ACGGTGGCTGCACCATCTGTCTTCATCTTCCCGCCATCTGATGAGCAGTTG |
| Ab5 | TTCGGCGGAGGGACCAAGGTGGAAATCAAACGT | ACGGTGGCTGCACCATCTGTCTTCATCTTCCCGCCATCTGATGAGCAGTTG |
| Ab6 | TTCGGCGGAGGGACCGAGGTGGTGGTCAAACGT | ACGGTGGCTGCACCATCTGTCTTCATCTTCCCGCCATCTGATGAGCAGTTG |
| Ab7 | TTCGGCGGAGGGACCGAGGTGGTGGTCAAACGT | ACGGTGGCTGCACCATCTGTCTTCATCTTCCCGCCATCTGATGAGCAGTTG |
| Ab8 | TTCGGCGGAGGGACCAAGGTGGAAATCAAACGT | ACGGTGGCTGCACCATCTGTCTTCATCTTCCCGCCATCTGATGAGCAGTTG |
| Ab9 | TTCGGCCGGAGGGACCGAGGTGGTGGTCAAACGT | ACGGTGGCTGCACCATCTGTCTTCATCTTCCCGCCATCTGATGAGCAGTTG |
| Ab10 | TTCGGCGGAGGGACCAAGGTGGAAATCAAACGT | ACGGTGGCTGCACCATCTGTCTTCATCTTCCCGCCATCTGATGAGCAGTTG |
| Ab11 | TTCGGCGGAGGGACCGAGGTGGTGGTCAAACGT | ACGGTGGCTGCACCATCTGTCTTCATCTTCCCGCCATCTGATGAGCAGTTG |
| Ab12 | TTCGGCCGGAGGGACCGAGGTGGTGGTCAAACGT | ACGGTGGCTGCACCATCTGTCTTCATCTTCCCGCCATCTGATGAGCAGTTG |
| Ab13 | TTCGCCCGGAGGGACCGAGGTGGTGGTCAAACGT | ACGGTGGCTGCACCATCTGTCTTCATCTTCCCGCCATCTGATGAGCAGTTG |
| Ab14 | TTCGGCGGAGGGACCAAGGTGGAAATCAAACGT | ACGGTGGCTGCACCATCTGTCTTCATCTTCCCGCCATCTGATGAGCAGTTG |

Figure 4F - Light Chain DNA Sequence

| Sequence Name | Constant Region |
|---|---|
| Ab1 | AAATCTGGAACTGCCTCTGTTGTTGCCTGCTGAATAACTTCTATCCCAGAGAGGCCAAAGTACAGTGGAAGGTGGATAACGCCC |
| Ab2 | AAATCTGGAACTGCCTCTGTTGTTGTGCCTGCTGAATAACTTCTATCCCAGAGAGGCCAAAGTACAGTGGAAGGTGGATAACGCCC |
| Ab3 | AAATCTGGAACTGCCTCTGTTGTTGTGCCTGCTGAATAACTTCTATCCCAGAGAGGCCAAAGTACAGTGGAAGGTGGATAACGCCC |
| Ab4 | AAATCTGGAACTGCCTCTGTTGTTGTGCCTGCTGAATAACTTCTATCCCAGAGAGGCCAAAGTACAGTGGAAGGTGGATAACGCCC |
| Ab5 | AAATCTGGAACTGCCTCTGTTGTTGTGCCTGCTGAATAACTTCTATCCCAGAGAGGCCAAAGTACAGTGGAAGGTGGATAACGCCC |
| Ab6 | AAATCTGGAACTGCCTCTGTTGTTGTGCCTGCTGAATAACTTCTATCCCAGAGAGGCCAAAGTACAGTGGAAGGTGGATAACGCCC |
| Ab7 | AAATCTGGAACTGCCTCTGTTGTTGTGCCTGCTGAATAACTTCTATCCCAGAGAGGCCAAAGTACAGTGGAAGGTGGATAACGCCC |
| Ab8 | AAATCTGGAACTGCCTCTGTTGTTGTGCCTGCTGAATAACTTCTATCCCAGAGAGGCCAAAGTACAGTGGAAGGTGGATAACGCCC |
| Ab9 | AAATCTGGAACTGCCTCTGTTGTTGTGCCTGCTGAATAACTTCTATCCCAGAGAGGCCAAAGTACAGTGGAAGGTGGATAACGCCC |
| Ab10 | AAATCTGGAACTGCCTCTGTTGTTGTGCCTGCTGAATAACTTCTATCCCAGAGAGGCCAAAGTACAGTGGAAGGTGGATAACGCCC |
| Ab11 | AAATCTGGAACTGCCTCTGTTGTTGTGCCTGCTGAATAACTTCTATCCCAGAGAGGCCAAAGTACAGTGGAAGGTGGATAACGCCC |
| Ab12 | AAATCTGGAACTGCCTCTGTTGTTGTGCCTGCTGAATAACTTCTATCCCAGAGAGGCCAAAGTACAGTGGAAGGTGGATAACGCCC |
| Ab13 | AAATCTGGAACTGCCTCTGTTGTTGTGCCTGCTGAATAACTTCTATCCCAGAGAGGCCAAAGTACAGTGGAAGGTGGATAACGCCC |
| Ab14 | AAATCTGGAACTGCCTCTGTTGTTGTGCCTGCTGAATAACTTCTATCCCAGAGAGGCCAAAGTACAGTGGAAGGTGGATAACGCCC |

Figure 4G - Light Chain DNA Sequence

| Sequence Name | Constant Region |
|---|---|
| Ab1 | TCCAATCGGGTAACTCCCAGGAGAGTGTCACAGAGCAGGAGACAGCAAGGACAGCACCTACAGCCTCAGCAGCAGCACCCTGACGCTGAG |
| Ab2 | TCCAATCGGGTAACTCCCAGGAGAGTGTCACAGAGCAGGAGACAGCAAGGACAGCACCTACAGCCTCAGCAGCAGCACCCTGACGCTGAG |
| Ab3 | TCCAATCGGGTAACTCCCAGGAGAGTGTCACAGAGCAGGAGACAGCAAGGACAGCACCTACAGCCTCAGCAGCAGCACCCTGACGCTGAG |
| Ab4 | TCCAATCGGGTAACTCCCAGGAGAGTGTCACAGAGCAGGAGACAGCAAGGACAGCACCTACAGCCTCAGCAGCAGCACCCTGACGCTGAG |
| Ab5 | TCCAATCGGGTAACTCCCAGGAGAGTGTCACAGAGCAGGAGACAGCAAGGACAGCACCTACAGCCTCAGCAGCAGCACCCTGACGCTGAG |
| Ab6 | TCCAATCGGGTAACTCCCAGGAGAGTGTCACAGAGCAGGAGACAGCAAGGACAGCACCTACAGCCTCAGCAGCAGCACCCTGACGCTGAG |
| Ab7 | TCCAATCGGGTAACTCCCAGGAGAGTGTCACAGAGCAGGAGACAGCAAGGACAGCACCTACAGCCTCAGCAGCAGCACCCTGACGCTGAG |
| Ab8 | TCCAATCGGGTAACTCCCAGGAGAGTGTCACAGAGCAGGAGACAGCAAGGACAGCACCTACAGCCTCAGCAGCAGCACCCTGACGCTGAG |
| Ab9 | TCCAATCGGGTAACTCCCAGGAGAGTGTCACAGAGCAGGAGACAGCAAGGACAGCACCTACAGCCTCAGCAGCAGCACCCTGACGCTGAG |
| Ab10 | TCCAATCGGGTAACTCCCAGGAGAGTGTCACAGAGCAGGAGACAGCAAGGACAGCACCTACAGCCTCAGCAGCAGCACCCTGACGCTGAG |
| Ab11 | TCCAATCGGGTAACTCCCAGGAGAGTGTCACAGAGCAGGAGACAGCAAGGACAGCACCTACAGCCTCAGCAGCAGCACCCTGACGCTGAG |
| Ab12 | TCCAATCGGGTAACTCCCAGGAGAGTGTCACAGAGCAGGAGACAGCAAGGACAGCACCTACAGCCTCAGCAGCAGCACCCTGACGCTGAG |
| Ab13 | TCCAATCGGGTAACTCCCAGGAGAGTGTCACAGAGCAGGAGACAGCAAGGACAGCACCTACAGCCTCAGCAGCAGCACCCTGACGCTGAG |
| Ab14 | TCCAATCGGGTAACTCCCAGGAGAGTGTCACAGAGCAGGAGACAGCAAGGACAGCACCTACAGCCTCAGCAGCAGCACCCTGACGCTGAG |

Figure 4H - Light Chain DNA Sequence

| Sequence Name | Constant Region |
|---|---|
| Ab1 | CAAAGCAGACTACGAGAAAACACAAAGTCTACGCCTGCGAAGTCACCCATCAGGGCCTGAGCTCGCCCGTCACAAAGAGCTTCAAC |
| Ab2 | CAAAGCAGACTACGAGAAAACACAAAGTCTACGCCTGCGAAGTCACCCATCAGGGCCTGAGCTCGCCCGTCACAAAGAGCTTCAAC |
| Ab3 | CAAAGCAGACTACGAGAAAACACAAAGTCTACGCCTGCGAAGTCACCCATCAGGGCCTGAGCTCGCCCGTCACAAAGAGCTTCAAC |
| Ab4 | CAAAGCAGACTACGAGAAAACACAAAGTCTACGCCTGCGAAGTCACCCATCAGGGCCTGAGCTCGCCCGTCACAAAGAGCTTCAAC |
| Ab5 | CAAAGCAGACTACGAGAAAACACAAAGTCTACGCCTGCGAAGTCACCCATCAGGGCCTGAGCTCGCCCGTCACAAAGAGCTTCAAC |
| Ab6 | CAAAGCAGACTACGAGAAAACACAAAGTCTACGCCTGCGAAGTCACCCATCAGGGCCTGAGCTCGCCCGTCACAAAGAGCTTCAAC |
| Ab7 | CAAAGCAGACTACGAGAAAACACAAAGTCTACGCCTGCGAAGTCACCCATCAGGGCCTGAGCTCGCCCGTCACAAAGAGCTTCAAC |
| Ab8 | CAAAGCAGACTACGAGAAAACACAAAGTCTACGCCTGCGAAGTCACCCATCAGGGCCTGAGCTCGCCCGTCACAAAGAGCTTCAAC |
| Ab9 | CAAAGCAGACTACGAGAAAACACAAAGTCTACGCCTGCGAAGTCACCCATCAGGGCCTGAGCTCGCCCGTCACAAAGAGCTTCAAC |
| Ab10 | CAAAGCAGACTACGAGAAAACACAAAGTCTACGCCTGCGAAGTCACCCATCAGGGCCTGAGCTCGCCCGTCACAAAGAGCTTCAAC |
| Ab11 | CAAAGCAGACTACGAGAAAACACAAAGTCTACGCCTGCGAAGTCACCCATCAGGGCCTGAGCTCGCCCGTCACAAAGAGCTTCAAC |
| Ab12 | CAAAGCAGACTACGAGAAAACACAAAGTCTACGCCTGCGAAGTCACCCATCAGGGCCTGAGCTCGCCCGTCACAAAGAGCTTCAAC |
| Ab13 | CAAAGCAGACTACGAGAAAACACAAAGTCTACGCCTGCGAAGTCACCCATCAGGGCCTGAGCTCGCCCGTCACAAAGAGCTTCAAC |
| Ab14 | CAAAGCAGACTACGAGAAAACACAAAGTCTACGCCTGCGAAGTCACCCATCAGGGCCTGAGCTCGCCCGTCACAAAGAGCTTCAAC |

Figure 4I - Light Chain DNA Sequence

| Sequence Name | | |
|---|---|---|
| Ab1 | AGGGGAGAGAGTGTTAG | (SEQ ID NO: 31) |
| Ab2 | AGGGGAGAGAGTGTTAG | (SEQ ID NO: 71) |
| Ab3 | AGGGGAGAGAGTGTTAG | (SEQ ID NO: 111) |
| Ab4 | AGGGGAGAGAGTGTTAG | (SEQ ID NO: 151) |
| Ab5 | AGGGGAGAGAGTGTTAG | (SEQ ID NO: 191) |
| Ab6 | AGGGGAGAGAGTGTTAG | (SEQ ID NO: 231) |
| Ab7 | AGGGGAGAGAGTGTTAG | (SEQ ID NO: 271) |
| Ab8 | AGGGGAGAGAGTGTTAG | (SEQ ID NO: 311) |
| Ab9 | AGGGGAGAGAGTGTTAG | (SEQ ID NO: 351) |
| Ab10 | AGGGGAGAGAGTGTTAG | (SEQ ID NO: 391) |
| Ab11 | AGGGGAGAGAGTGTTAG | (SEQ ID NO: 431) |
| Ab12 | AGGGGAGAGAGTGTTAG | (SEQ ID NO: 471) |
| Ab13 | AGGGGAGAGAGTGTTAG | (SEQ ID NO: 511) |
| Ab14 | AGGGGAGAGAGTGTTAG | (SEQ ID NO: 551) |

Figure 5
Heavy Chain Protein Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-109 | 2 | 30-34 | 4 | 49-64 | 6 | 96-98 | 8 |
| Ab2 | 1-111 | 42 | 31-35 | 44 | 50-65 | 46 | 98-100 | 48 |
| Ab3 | 1-111 | 82 | 31-35 | 84 | 50-65 | 86 | 98-100 | 88 |
| Ab4 | 1-109 | 122 | 30-34 | 124 | 49-64 | 126 | 96-98 | 128 |
| Ab5 | 1-111 | 162 | 31-35 | 164 | 50-65 | 166 | 98-100 | 168 |
| Ab6 | 1-111 | 202 | 31-35 | 204 | 50-65 | 206 | 98-100 | 208 |
| Ab7 | 1-110 | 242 | 31-35 | 244 | 50-65 | 246 | 97-99 | 248 |
| Ab8 | 1-111 | 282 | 31-35 | 284 | 50-65 | 286 | 98-100 | 288 |
| Ab9 | 1-109 | 322 | 30-34 | 324 | 49-64 | 326 | 96-98 | 328 |
| Ab10 | 1-111 | 362 | 31-35 | 364 | 50-65 | 366 | 98-100 | 368 |
| Ab11 | 1-109 | 402 | 30-34 | 404 | 49-64 | 406 | 96-98 | 408 |
| Ab12 | 1-111 | 442 | 31-35 | 444 | 50-65 | 446 | 98-100 | 448 |
| Ab13 | 1-111 | 482 | 30-34 | 484 | 49-65 | 486 | 97-100 | 488 |
| Ab14 | 1-111 | 522 | 31-35 | 524 | 50-65 | 526 | 98-100 | 528 |

Figure 6
Heavy Chain Protein Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-29 | 3 | 35-48 | 5 | 65-95 | 7 | 99-109 | 9 | 110-439 | 10 |
| Ab2 | 1-30 | 43 | 36-49 | 45 | 66-97 | 47 | 101-111 | 49 | 112-441 | 50 |
| Ab3 | 1-30 | 83 | 36-49 | 85 | 66-97 | 87 | 101-111 | 89 | 112-441 | 90 |
| Ab4 | 1-29 | 123 | 35-48 | 125 | 65-95 | 127 | 99-109 | 129 | 110-439 | 130 |
| Ab5 | 1-30 | 163 | 36-49 | 165 | 66-97 | 167 | 101-111 | 169 | 112-441 | 170 |
| Ab6 | 1-30 | 203 | 36-49 | 205 | 66-97 | 207 | 101-111 | 209 | 112-441 | 210 |
| Ab7 | 1-30 | 243 | 36-49 | 245 | 66-96 | 247 | 100-110 | 249 | 111-440 | 250 |
| Ab8 | 1-30 | 283 | 36-49 | 285 | 66-97 | 287 | 101-111 | 289 | 112-441 | 290 |
| Ab9 | 1-29 | 323 | 35-48 | 325 | 65-95 | 327 | 99-109 | 329 | 110-439 | 330 |
| Ab10 | 1-30 | 363 | 36-49 | 365 | 66-97 | 367 | 101-111 | 369 | 112-441 | 370 |
| Ab11 | 1-29 | 403 | 35-48 | 405 | 65-95 | 407 | 99-109 | 409 | 110-439 | 410 |
| Ab12 | 1-30 | 443 | 36-49 | 445 | 66-97 | 447 | 101-111 | 449 | 112-441 | 450 |
| Ab13 | 1-29 | 483 | 35-48 | 485 | 66-96 | 487 | 101-111 | 489 | 112-441 | 490 |
| Ab14 | 1-30 | 523 | 36-49 | 525 | 66-97 | 527 | 101-111 | 529 | 112-441 | 530 |

Figure 7
Light Chain Protein Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-113 | 22 | 23-35 | 24 | 51-57 | 26 | 90-102 | 28 |
| Ab2 | 1-113 | 62 | 23-35 | 64 | 51-57 | 66 | 90-102 | 68 |
| Ab3 | 1-113 | 102 | 23-35 | 104 | 51-57 | 106 | 90-102 | 108 |
| Ab4 | 1-113 | 142 | 23-35 | 144 | 51-57 | 146 | 90-102 | 148 |
| Ab5 | 1-113 | 182 | 23-35 | 184 | 51-57 | 186 | 90-102 | 188 |
| Ab6 | 1-113 | 222 | 23-35 | 224 | 51-57 | 226 | 90-102 | 228 |
| Ab7 | 1-113 | 262 | 23-35 | 264 | 51-57 | 266 | 90-102 | 268 |
| Ab8 | 1-113 | 302 | 23-35 | 304 | 51-57 | 306 | 90-102 | 308 |
| Ab9 | 1-113 | 342 | 23-35 | 344 | 51-57 | 346 | 90-102 | 348 |
| Ab10 | 1-113 | 382 | 23-35 | 384 | 51-57 | 386 | 90-102 | 388 |
| Ab11 | 1-113 | 422 | 23-35 | 424 | 51-57 | 426 | 90-102 | 428 |
| Ab12 | 1-113 | 462 | 23-35 | 464 | 51-57 | 466 | 90-102 | 468 |
| Ab13 | 1-113 | 502 | 24-36 | 504 | 52-58 | 506 | 91-102 | 508 |
| Ab14 | 1-113 | 542 | 23-35 | 544 | 51-57 | 546 | 90-102 | 548 |

Figure 8
Light Chain Protein Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-22 | 23 | 36-50 | 25 | 58-89 | 27 | 103-113 | 29 | 114-219 | 30 |
| Ab2 | 1-22 | 63 | 36-50 | 65 | 58-89 | 67 | 103-113 | 69 | 114-219 | 70 |
| Ab3 | 1-22 | 103 | 36-50 | 105 | 58-89 | 107 | 103-113 | 109 | 114-219 | 110 |
| Ab4 | 1-22 | 143 | 36-50 | 145 | 58-89 | 147 | 103-113 | 149 | 114-219 | 150 |
| Ab5 | 1-22 | 183 | 36-50 | 185 | 58-89 | 187 | 103-113 | 189 | 114-219 | 190 |
| Ab6 | 1-22 | 223 | 36-50 | 225 | 58-89 | 227 | 103-113 | 229 | 114-219 | 230 |
| Ab7 | 1-22 | 263 | 36-50 | 265 | 58-89 | 267 | 103-113 | 269 | 114-219 | 270 |
| Ab8 | 1-22 | 303 | 36-50 | 305 | 58-89 | 307 | 103-113 | 309 | 114-219 | 310 |
| Ab9 | 1-22 | 343 | 36-50 | 345 | 58-89 | 347 | 103-113 | 349 | 114-219 | 350 |
| Ab10 | 1-22 | 383 | 36-50 | 385 | 58-89 | 387 | 103-113 | 389 | 114-219 | 390 |
| Ab11 | 1-22 | 423 | 36-50 | 425 | 58-89 | 427 | 103-113 | 429 | 114-219 | 430 |
| Ab12 | 1-22 | 463 | 36-50 | 465 | 58-89 | 467 | 103-113 | 469 | 114-219 | 470 |
| Ab13 | 1-23 | 503 | 37-51 | 505 | 59-90 | 507 | 103-113 | 509 | 114-219 | 510 |
| Ab14 | 1-22 | 543 | 36-50 | 545 | 58-89 | 547 | 103-113 | 549 | 114-219 | 550 |

Figure 9
Heavy Chain DNA Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-327 | 12 | 88-102 | 14 | 145-192 | 16 | 286-294 | 18 |
| Ab2 | 1-333 | 52 | 91-105 | 54 | 148-195 | 56 | 292-300 | 58 |
| Ab3 | 1-333 | 92 | 91-105 | 94 | 148-195 | 96 | 292-300 | 98 |
| Ab4 | 1-327 | 132 | 88-102 | 134 | 145-192 | 136 | 286-294 | 138 |
| Ab5 | 1-333 | 172 | 91-105 | 174 | 148-195 | 176 | 292-300 | 178 |
| Ab6 | 1-333 | 212 | 91-105 | 214 | 148-195 | 216 | 292-300 | 218 |
| Ab7 | 1-330 | 252 | 91-105 | 254 | 148-195 | 256 | 289-297 | 258 |
| Ab8 | 1-333 | 292 | 91-105 | 294 | 148-195 | 296 | 292-300 | 298 |
| Ab9 | 1-327 | 332 | 88-102 | 334 | 145-192 | 336 | 286-294 | 338 |
| Ab10 | 1-333 | 372 | 91-105 | 374 | 148-195 | 376 | 292-300 | 378 |
| Ab11 | 1-327 | 412 | 88-102 | 414 | 145-192 | 416 | 286-294 | 418 |
| Ab12 | 1-333 | 452 | 91-105 | 454 | 148-195 | 456 | 292-300 | 458 |
| Ab13 | 1-333 | 492 | 88-102 | 494 | 145-195 | 496 | 289-300 | 498 |
| Ab14 | 1-333 | 532 | 91-105 | 534 | 148-195 | 536 | 292-300 | 538 |

Figure 10
Heavy Chain DNA Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-87 | 13 | 103-144 | 15 | 193-285 | 17 | 295-327 | 19 | 328-1320 | 20 |
| Ab2 | 1-90 | 53 | 106-147 | 55 | 196-291 | 57 | 301-333 | 59 | 334-1326 | 60 |
| Ab3 | 1-90 | 93 | 106-147 | 95 | 196-291 | 97 | 301-333 | 99 | 334-1326 | 100 |
| Ab4 | 1-87 | 133 | 103-144 | 135 | 193-285 | 137 | 295-327 | 139 | 328-1320 | 140 |
| Ab5 | 1-90 | 173 | 106-147 | 175 | 196-291 | 177 | 301-333 | 179 | 334-1326 | 180 |
| Ab6 | 1-90 | 213 | 106-147 | 215 | 196-291 | 217 | 301-333 | 219 | 334-1326 | 220 |
| Ab7 | 1-90 | 253 | 106-147 | 255 | 196-288 | 257 | 298-330 | 259 | 331-1323 | 260 |
| Ab8 | 1-90 | 293 | 106-147 | 295 | 196-291 | 297 | 301-333 | 299 | 334-1326 | 300 |
| Ab9 | 1-87 | 333 | 103-144 | 335 | 193-285 | 337 | 295-327 | 339 | 328-1320 | 340 |
| Ab10 | 1-90 | 373 | 106-147 | 375 | 196-291 | 377 | 301-333 | 379 | 334-1326 | 380 |
| Ab11 | 1-87 | 413 | 103-144 | 415 | 193-285 | 417 | 295-327 | 419 | 328-1320 | 420 |
| Ab12 | 1-90 | 453 | 106-147 | 455 | 196-291 | 457 | 301-333 | 459 | 334-1326 | 460 |
| Ab13 | 1-87 | 493 | 103-144 | 495 | 196-288 | 497 | 301-333 | 499 | 334-1326 | 500 |
| Ab14 | 1-90 | 533 | 106-147 | 535 | 196-291 | 537 | 301-333 | 539 | 334-1326 | 540 |

Figure 11
Light Chain DNA Sequence Features

| Antibody | Variable Region Coordinates | SEQ ID NO: | CDR1 Coordinates | SEQ ID NO: | CDR2 Coordinates | SEQ ID NO: | CDR3 Coordinates | SEQ ID NO: |
|---|---|---|---|---|---|---|---|---|
| Ab1 | 1-339 | 32 | 67-105 | 34 | 151-171 | 36 | 268-306 | 38 |
| Ab2 | 1-339 | 72 | 67-105 | 74 | 151-171 | 76 | 268-306 | 78 |
| Ab3 | 1-339 | 112 | 67-105 | 114 | 151-171 | 116 | 268-306 | 118 |
| Ab4 | 1-339 | 152 | 67-105 | 154 | 151-171 | 156 | 268-306 | 158 |
| Ab5 | 1-339 | 192 | 67-105 | 194 | 151-171 | 196 | 268-306 | 198 |
| Ab6 | 1-339 | 232 | 67-105 | 234 | 151-171 | 236 | 268-306 | 238 |
| Ab7 | 1-339 | 272 | 67-105 | 274 | 151-171 | 276 | 268-306 | 278 |
| Ab8 | 1-339 | 312 | 67-105 | 314 | 151-171 | 316 | 268-306 | 318 |
| Ab9 | 1-339 | 352 | 67-105 | 354 | 151-171 | 356 | 268-306 | 358 |
| Ab10 | 1-339 | 392 | 67-105 | 394 | 151-171 | 396 | 268-306 | 398 |
| Ab11 | 1-339 | 432 | 67-105 | 434 | 151-171 | 436 | 268-306 | 438 |
| Ab12 | 1-339 | 472 | 67-105 | 474 | 151-171 | 476 | 268-306 | 478 |
| Ab13 | 1-339 | 512 | 70-108 | 514 | 154-174 | 516 | 271-306 | 518 |
| Ab14 | 1-339 | 552 | 67-105 | 554 | 151-171 | 556 | 268-306 | 558 |

Figure 12
Light Chain DNA Sequence Features

| Antibody | FR1 Coordinates | SEQ ID NO: | FR2 Coordinates | SEQ ID NO: | FR3 Coordinates | SEQ ID NO: | FR4 Coordinates | SEQ ID NO: | Constant Region Coordinates | SEQ ID NO: |
|---|---|---|---|---|---|---|---|---|---|---|
| Ab1 | 1-66 | 33 | 106-150 | 35 | 172-267 | 37 | 307-339 | 39 | 340-660 | 40 |
| Ab2 | 1-66 | 73 | 106-150 | 75 | 172-267 | 77 | 307-339 | 79 | 340-660 | 80 |
| Ab3 | 1-66 | 113 | 106-150 | 115 | 172-267 | 117 | 307-339 | 119 | 340-660 | 120 |
| Ab4 | 1-66 | 153 | 106-150 | 155 | 172-267 | 157 | 307-339 | 159 | 340-660 | 160 |
| Ab5 | 1-66 | 193 | 106-150 | 195 | 172-267 | 197 | 307-339 | 199 | 340-660 | 200 |
| Ab6 | 1-66 | 233 | 106-150 | 235 | 172-267 | 237 | 307-339 | 239 | 340-660 | 240 |
| Ab7 | 1-66 | 273 | 106-150 | 275 | 172-267 | 277 | 307-339 | 279 | 340-660 | 280 |
| Ab8 | 1-66 | 313 | 106-150 | 315 | 172-267 | 317 | 307-339 | 319 | 340-660 | 320 |
| Ab9 | 1-66 | 353 | 106-150 | 355 | 172-267 | 357 | 307-339 | 359 | 340-660 | 360 |
| Ab10 | 1-66 | 393 | 106-150 | 395 | 172-267 | 397 | 307-339 | 399 | 340-660 | 400 |
| Ab11 | 1-66 | 433 | 106-150 | 435 | 172-267 | 437 | 307-339 | 439 | 340-660 | 440 |
| Ab12 | 1-66 | 473 | 106-150 | 475 | 172-267 | 477 | 307-339 | 479 | 340-660 | 480 |
| Ab13 | 1-69 | 513 | 109-153 | 515 | 175-270 | 517 | 307-339 | 519 | 340-660 | 520 |
| Ab14 | 1-66 | 553 | 106-150 | 555 | 172-267 | 557 | 307-339 | 559 | 340-660 | 560 |

Median % change from baseline: migraine episodes per month

Median % change from baseline: migraine hours per month

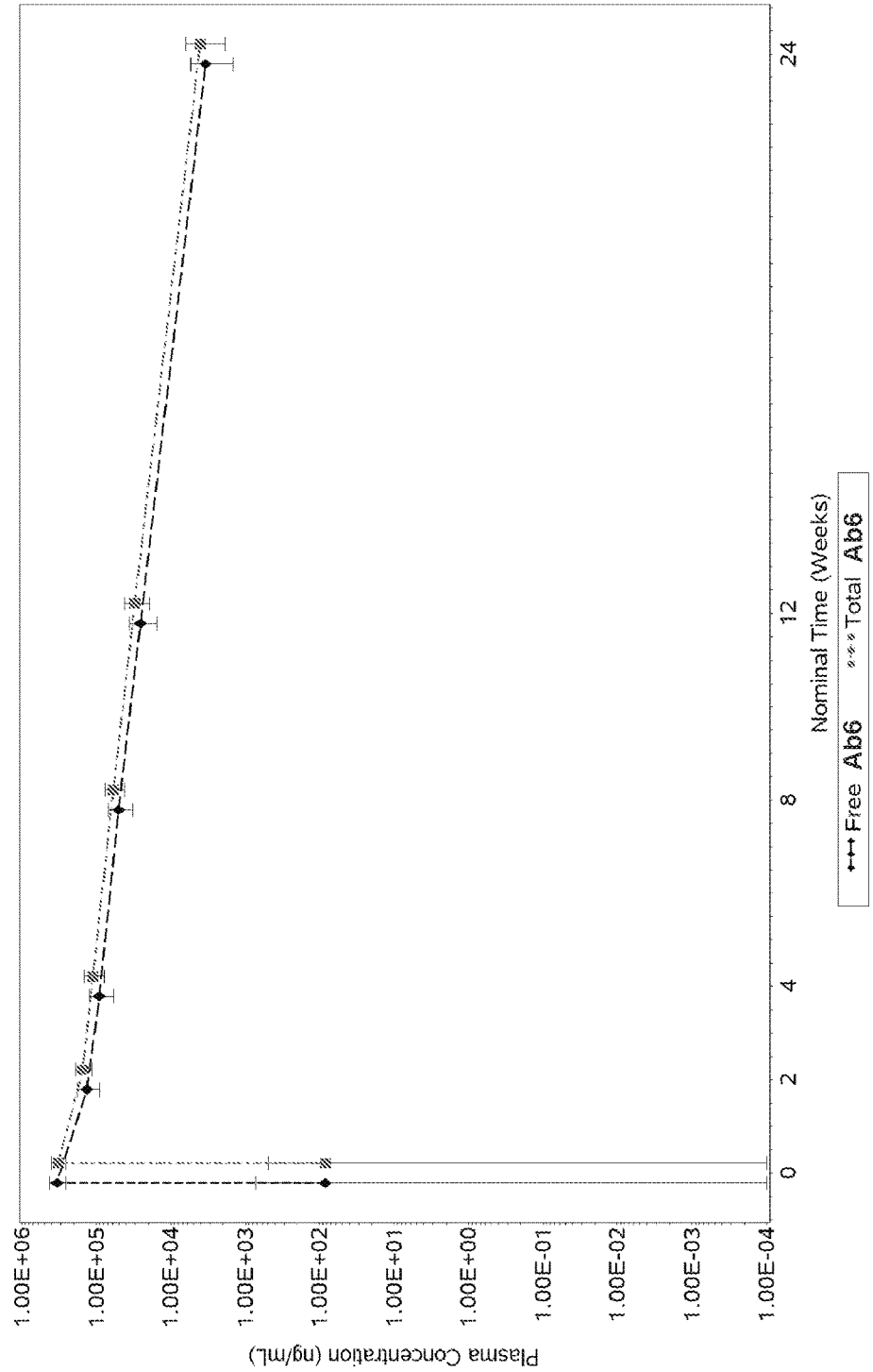
FIG. 20. PK Profile

FIG. 21. PK Parameters

Plasma Free Ab6*

|  | $C_{max}$ (µg/mL) | $AUC_{0-\infty}$ (mg*hr/mL) | Half-Life (Days) | Vz (L) | CL (mL/hr) |
|---|---|---|---|---|---|
| N | 81 | 78 | 78 | 78 | 78 |
| Mean | 336 | 219 | 31 | 5.2 | 5.0 |
| SD | 80 | 64 | 8 | 2.1 | 1.5 |

* - Following 1000 mg Ab6 IV single-dose

FIG. 34. Mean (±SD) Change from Baseline In Study Endpoints

| Endpoint | Weeks 1-4 | | Weeks 5-8 | | Weeks 9-12 | |
|---|---|---|---|---|---|---|
| | Placebo i.v. (n=82) | Ab6 1000mg i.v. (n=81) | Placebo i.v. (n=82) | Ab6 1000mg i.v. (n=81) | Placebo i.v. (n=82) | Ab6 1000mg i.v. (n=81) |
| Migraine Days | -3.9 (3.5) | -5.6 (3.3)[1] | -4.6 (3.6) | -5.6 (3.0)[2] | -4.6 (3.5) | -5.6 (4.0)[3] |
| Migraine Episodes | -3.0 (2.7) | -3.7 (2.4) | -3.7 (2.9) | -3.8 (2.2) | -3.7 (2.8) | -3.9 (2.6) |
| Migraine Hours | -33.7 (41.8) | -58.0 (49.1) | -36.1 (45.9) | -54.4 (48.3) | -37.1 (40.0) | -54.6 (60.5) |
| Average Migraine Severity[4] | -0.16 (0.58) | -0.31 (0.58) | -0.10 (0.54) | -0.16 (0.50) | -0.08 (0.54) | -0.11 (0.43) |
| Headache Frequency | -4.0 (3.8) | -5.6 (3.4) | -5.0 (3.7) | -5.3 (3.5) | -5.1 (3.7) | -5.9 (3.8) |
| HIT-6 score | -5.8 (7.8) | -10.2 (9.8) | -8.1 (8.9) | -9.9 (9.7) | -7.7 (9.0) | -10.1 (10.6) |
| MSQ RFP | 19.9 (23.8) | 29.3 (24.3) | 25.2 (24.8) | 28.8 (24.7) | 22.2 (23.1) | 28.5 (24.5) |
| MSQ RFR | 16.3 (23.2) | 21.1 (23.9) | 20.2 (22.1) | 20.9 (23.3) | 18.0 (20.5) | 21.4 (23.1) |
| MSQ EF | 19.4 (27.6) | 25.1 (28.3) | 21.2 (25.1) | 23.8 (25.8) | 21.1 (25.1) | 23.1 (26.8) |

[1] p<0.001; [2] p=0.03; [3] p=0.06; [4] Severity measured on a 4 point scale with 1 = mild and 4 = severe FIG. 36. Chronic migraine ≥ 50% responder rates FIG. 37. Chronic migraine ≥ 75% responder rates FIG. 38. Chronic migraine 100% responder rates

FIG. 39

| Subjects, n | Placebo 366 | 100 mg 356 | 300 mg 350 |
|---|---|---|---|
| Mean age, years (SD) | 39.6 (11.3) | 41.0 (11.7) | 41.0 (10.4) |
| Mean BMI, kg/m² (SD) | 27.0 (5.6) | 26.4 (5.0) | 26.3 (5.0) |
| Female, % | 89 | 86 | 90 |
| Mean years from migraine diagnosis | 17.0 | 18.3 | 19.0 |
| Mean duration of chronic migraine, years (SD) | 11.6 (10.9) | 11.6 (11.7) | 12.4 (11.2) |
| ≥1 prophylactic medication, n (%)* | 163 (44.5) | 161 (45.2) | 155 (44.3) |
| Mean migraine days/month (SD) | 16.2 (4.6) | 16.1 (4.6) | 16.1 (4.8) |
| Mean headache days/month (SD) | 20.6 (3.0) | 20.4 (3.1) | 20.4 (3.2) |

FIG. 40. Difference from placebo in change from baseline in mean migraine days (MMD) over months 1-3 by baseline subgroup FIG. 41. Difference from placebo in change from baseline in mean migraine days (MMD) over months 1-3 by baseline subgroup

|  | Month 1 | | | | Month 6 | | |
|---|---|---|---|---|---|---|---|
|  | Ab6 100 mg | Ab6 400 mg | Placebo | | Ab6 100 mg | Ab6 400 mg | Placebo |
| Baseline use | | | | | | | |
| 1-9 days/month, n | 37 | 49 | 49 | | 37 | 49 | 49 |
| ≥10 days/month, n | 264 | 265 | 260 | | 264 | 265 | 260 |
| ≥1 day/month, mean (SD) | 18.3 (9.05) | 18.4 (9.61) | 17.9 (8.60) | | 18.3 (9.05) | 18.4 (9.61) | 17.9 (8.60) |
| Post-baseline use, mean (SD) | | | | | | | |
| ≥1 day/month | 10.7 (9.39) | 10.2 (9.87) | 13.8 (9.52) | | 10.8 (11.18) | 8.6 (9.97) | 11.5 (10.16) |
| Change from baseline, mean (SD) | | | | | | | |
| ≥1 day/month | -7.8 (8.08) | -8.3 (7.64) | -4.5 (7.46) | | -8.1 (9.90) | -9.6 (9.92) | -7.0 (9.39) |
| 1-9 days/month | -1.5 (4.44) | -2.3 (4.34) | -1.0 (5.29) | | -0.8 (6.63) | -2.6 (4.57) | -1.3 (4.83) |
| ≥10 days/month | -8.7 (8.08) | -9.4 (7.62) | -5.1 (7.63) | | -8.9 (9.88) | -11.1 (10.10) | -7.9 (9.64) |
| Percent change from baseline, mean (SD) | | | | | | | |
| ≥1 day/month | -42.6 (39.98) | -47.0 (40.90) | -22.4 (52.02) | | -40.7 (60.66) | -52.9 (48.97) | -34.7 (58.48) |
| 1-9 days/month | -31.8 (67.95) | -47.3 (65.38) | -9.5 (100.52) | | 1.4 (132.84) | -45.0 (73.05) | -11.2 (108.44) |
| ≥10 days/month | -44.1 (34.24) | -47.0 (34.73) | -24.8 (36.17) | | -45.3 (44.91) | -54.5 (42.52) | -38.5 (44.63) |

FIG. 45.

FIG. 49. Summary of Acute Medication Days by Subgroups of Episodic Migraine Patients with Baseline Acute Medication Use

|  | Month 1 | | | Month 6 | | |
| --- | --- | --- | --- | --- | --- | --- |
|  | Ab6 100 mg | Ab6 400 mg | Placebo | Ab6 100 mg | Ab6 400 mg | Placebo |
| Baseline use |  |  |  |  |  |  |
| 1–9 days/month, n | 117 | 111 | 108 | 117 | 111 | 108 |
| ≥10 days/month, n | 42 | 41 | 44 | 42 | 41 | 44 |
| ≥1 day/month, mean (SD) | 7.5 (4.97) | 7.5 (4.58) | 7.8 (4.98) | 7.5 (4.97) | 7.5 (4.58) | 7.8 (4.98) |
| Post-baseline use, mean (SD) |  |  |  |  |  |  |
| ≥1 day/month | 4.3 (3.99) | 4.2 (4.45) | 5.7 (5.04) | 4.2 (5.87) | 3.5 (3.92) | 5.1 (5.19) |
| Change from baseline, mean (SD) |  |  |  |  |  |  |
| ≥1 day/month | -3.3 (4.14) | -3.2 (4.20) | -2.2 (4.68) | -2.8 (4.92) | -4.1 (4.60) | -2.3 (4.69) |
| 1–9 days/month | -2.0 (2.91) | -2.2 (3.57) | -1.3 (3.10) | -2.4 (3.11) | -2.7 (3.83) | -1.6 (3.52) |
| ≥10 days/month | -6.6 (5.11) | -5.8 (4.66) | -4.3 (6.82) | -4.0 (8.60) | -7.4 (4.60) | -4.1 (6.60) |
| Percent change from baseline, mean (SD) |  |  |  |  |  |  |
| ≥1 day/month | -36.9 (63.96) | -39.4 (77.71) | -22.4 (60.27) | -45.4 (62.28) | -50.9 (59.88) | -22.5 (95.61) |
| 1–9 days/month | -33.9 (72.22) | -37.0 (88.45) | -19.7 (64.62) | -50.1 (59.65) | -48.2 (68.26) | -18.2 (107.55) |
| ≥10 days/month | -45.1 (30.26) | -45.9 (34.95) | -29.1 (47.94) | -29.2 (69.14) | -57.2 (32.59) | -33.9 (52.53) |

```
SEQUENCE LISTING

Sequence total quantity: 567
SEQ ID NO: 1            moltype = AA  length = 439
FEATURE                 Location/Qualifiers
REGION                  1..439
                        note = Engineered antibody sequence
source                  1..439
                        mol_type = protein
                        organism = synthetic construct
SEQUENCE: 1
QSLEESGGRL VTPGTPLTLT CTVSGLDLSS YYMQWVRQAP GKGLEWIGVI GINDNTYYAS   60
WAKGRFTISR ASSTTVDLKM TSLTTEDTAT YFCARGDIWG PGTLVTVSSA STKGPSVFPL  120
APSSKSTSGG TAALGCLVKD YFPEPVTVSW NSGALTSGVH TFPAVLQSSG LYSLSSVVTV  180
PSSSLGTQTY ICNVNHKPSN TKVDKRVEPK SCDKTHTCPP CPAPELLGGP SVFLFPPKPK  240
DTLMISRTPE VTCVVVDVSH EDPEVKFNWY VDGVEVHNAK TKPREEQYAS TYRVVSVLTV  300
LHQDWLNGKE YKCKVSNKAL PAPIEKTISK AKGQPREPQV YTLPPSREEM TKNQVSLTCL  360
VKGFYPSDIA VEWESNGQPE NNYKTTPPVL DSDGSFFLYS KLTVDKSRWQ QGNVFSCSVM  420
HEALHNHYTQ KSLSLSPGK                                                439

SEQ ID NO: 2            moltype = AA  length = 109
FEATURE                 Location/Qualifiers
REGION                  1..109
                        note = Engineered antibody sequence
source                  1..109
                        mol_type = protein
                        organism = synthetic construct
SEQUENCE: 2
QSLEESGGRL VTPGTPLTLT CTVSGLDLSS YYMQWVRQAP GKGLEWIGVI GINDNTYYAS   60
WAKGRFTISR ASSTTVDLKM TSLTTEDTAT YFCARGDIWG PGTLVTVSS              109
```

```
SEQ ID NO: 3              moltype = AA   length = 29
FEATURE                   Location/Qualifiers
REGION                    1..29
                          note = Engineered antibody sequence
source                    1..29
                          mol_type = protein
                          organism = synthetic construct
SEQUENCE: 3
QSLEESGGRL VTPGTPLTLT CTVSGLDLS                                    29

SEQ ID NO: 4              moltype = AA   length = 5
FEATURE                   Location/Qualifiers
REGION                    1..5
                          note = Engineered antibody sequence
source                    1..5
                          mol_type = protein
                          organism = synthetic construct
SEQUENCE: 4
SYYMQ                                                              5

SEQ ID NO: 5              moltype = AA   length = 14
FEATURE                   Location/Qualifiers
REGION                    1..14
                          note = Engineered antibody sequence
source                    1..14
                          mol_type = protein
                          organism = synthetic construct
SEQUENCE: 5
WVRQAPGKGL EWIG                                                    14

SEQ ID NO: 6              moltype = AA   length = 16
FEATURE                   Location/Qualifiers
REGION                    1..16
                          note = Engineered antibody sequence
source                    1..16
                          mol_type = protein
                          organism = synthetic construct
SEQUENCE: 6
VIGINDNTYY ASWAKG                                                  16

SEQ ID NO: 7              moltype = AA   length = 31
FEATURE                   Location/Qualifiers
REGION                    1..31
                          note = Engineered antibody sequence
source                    1..31
                          mol_type = protein
                          organism = synthetic construct
SEQUENCE: 7
RFTISRASST TVDLKMTSLT TEDTATYFCA R                                 31

SEQ ID NO: 8              moltype =     length =
SEQUENCE: 8
000

SEQ ID NO: 9              moltype = AA   length = 11
FEATURE                   Location/Qualifiers
REGION                    1..11
                          note = Engineered antibody sequence
source                    1..11
                          mol_type = protein
                          organism = synthetic construct
SEQUENCE: 9
WGPGTLVTVS S                                                       11

SEQ ID NO: 10             moltype = AA   length = 330
FEATURE                   Location/Qualifiers
REGION                    1..330
                          note = Engineered antibody sequence
source                    1..330
                          mol_type = protein
                          organism = synthetic construct
SEQUENCE: 10
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330
```

```
SEQ ID NO: 11              moltype = DNA   length = 1320
FEATURE                    Location/Qualifiers
misc_feature               1..1320
                           note = Engineered antibody sequence
source                     1..1320
                           mol_type = other DNA
                           organism = synthetic construct
SEQUENCE: 11
cagtcgctgg aggagtccgg gggtcgcctg gtcacgcctg gacacccct gacactcacc   60
tgcacagtct ctggactcga cctcagtagc tactacatgc aatgggtccg ccaggctcca  120
gggaaggggc tggaatggat cggagtcatt ggtattaatg ataacacata ctacgcgagc  180
tgggcgaaag gccgattcac catctccaga gcctcgtcga ccacggtgga tctgaaaatg  240
accagtctga caaccgagga cacggccacc tatttctgtg ccagagggga catctgggcc  300
ccaggcaccc tcgtcaccgt ctcgagcgcc tccaccaagg gcccatcggt cttcccccta  360
gcaccctcct ccaagagcac ctctgggggc acagcggccc tgggctgcct ggtcaaggac  420
tacttccccg aaccggtgac ggtgtcgtgg aactcaggcg ccctgaccag cggcgtgcac  480
accttcccgg ctgtcctaca gtcctcagga ctctactccc tcagcagcgt ggtgaccgtg  540
ccctccagca gcttgggcac ccagacctac atctgcaacg tgaatcacaa gcccagcaac  600
accaaggtgg acaagagagt tgagcccaaa tcttgtgaca aaactcacac atgcccaccg  660
tgcccagcac ctgaactcct ggggggaccg tcagtcttcc tcttcccccc aaaacccaag  720
gacaccctca tgatctcccg gacccctgag gtcacatgcg tggtggtgga cgtgagccac  780
gaagaccctg aggtcaagtt caactggtac gtggacggcg tggaggtgca taatgccaag  840
acaaagccgc gggaggagca gtacgccagc acgtaccgtg tggtcagcgt cctcaccgtc  900
ctgcaccagg actggctgaa tggcaaggag tacaagtgca aggtctccaa caaagccctc  960
ccagccccca tcgagaaaac catctccaaa gccaaagggc agccccgaga accacaggtg 1020
tacaccctgc cccatcccg ggaggagatg accaagaacc aggtcagcct gacctgcctg 1080
gtcaaaggct tctatcccag cgacatcgcc gtggagtggg agagcaatgg gcagccggag 1140
aacaactaca agaccacgcc tcccgtgctg gactccgacg gctccttctt cctctacagc 1200
aagctcaccg tggacaagag caggtggcag caggggaacg tcttctcatg ctccgtgatg 1260
catgaggctc tgcacaacca ctacacgcag aagagcctct ccctgtctcc gggtaaatga 1320

SEQ ID NO: 12              moltype = DNA   length = 327
FEATURE                    Location/Qualifiers
misc_feature               1..327
                           note = Engineered antibody sequence
source                     1..327
                           mol_type = other DNA
                           organism = synthetic construct
SEQUENCE: 12
cagtcgctgg aggagtccgg gggtcgcctg gtcacgcctg gacacccct gacactcacc    60
tgcacagtct ctggactcga cctcagtagc tactacatgc aatgggtccg ccaggctcca  120
gggaaggggc tggaatggat cggagtcatt ggtattaatg ataacacata ctacgcgagc  180
tgggcgaaag gccgattcac catctccaga gcctcgtcga ccacggtgga tctgaaaatg  240
accagtctga caaccgagga cacggccacc tatttctgtg ccagagggga catctgggcc  300
ccaggcaccc tcgtcaccgt ctcgagc                                     327

SEQ ID NO: 13              moltype = DNA   length = 87
FEATURE                    Location/Qualifiers
misc_feature               1..87
                           note = Engineered antibody sequence
source                     1..87
                           mol_type = other DNA
                           organism = synthetic construct
SEQUENCE: 13
cagtcgctgg aggagtccgg gggtcgcctg gtcacgcctg gacacccct gacactcacc    60
tgcacagtct ctggactcga cctcagt                                      87

SEQ ID NO: 14              moltype = DNA   length = 15
FEATURE                    Location/Qualifiers
misc_feature               1..15
                           note = Engineered antibody sequence
source                     1..15
                           mol_type = other DNA
                           organism = synthetic construct
SEQUENCE: 14
agctactaca tgcaa                                                   15

SEQ ID NO: 15              moltype = DNA   length = 42
FEATURE                    Location/Qualifiers
misc_feature               1..42
                           note = Engineered antibody sequence
source                     1..42
                           mol_type = other DNA
                           organism = synthetic construct
SEQUENCE: 15
tgggtccgcc aggctccagg gaaggggctg gaatggatcg ga                     42

SEQ ID NO: 16              moltype = DNA   length = 48
```

| FEATURE | Location/Qualifiers |
|---|---|
| misc_feature | 1..48 |
| | note = Engineered antibody sequence |
| source | 1..48 |
| | mol_type = other DNA |
| | organism = synthetic construct |

SEQUENCE: 16
```
gtcattggta ttaatgataa cacatactac gcgagctggg cgaaaggc                 48
```

| SEQ ID NO: 17 | moltype = DNA  length = 93 |
|---|---|
| FEATURE | Location/Qualifiers |
| misc_feature | 1..93 |
| | note = Engineered antibody sequence |
| source | 1..93 |
| | mol_type = other DNA |
| | organism = synthetic construct |

SEQUENCE: 17
```
cgattcacca tctccagagc ctcgtcgacc acggtggatc tgaaaatgac cagtctgaca    60
accgaggaca cggccaccta tttctgtgcc aga                                 93
```

| SEQ ID NO: 18 | moltype =   length = |
|---|---|
SEQUENCE: 18
000

| SEQ ID NO: 19 | moltype = DNA  length = 33 |
|---|---|
| FEATURE | Location/Qualifiers |
| misc_feature | 1..33 |
| | note = Engineered antibody sequence |
| source | 1..33 |
| | mol_type = other DNA |
| | organism = synthetic construct |

SEQUENCE: 19
```
tggggcccag gcaccctcgt caccgtctcg agc                                 33
```

| SEQ ID NO: 20 | moltype = DNA  length = 993 |
|---|---|
| FEATURE | Location/Qualifiers |
| misc_feature | 1..993 |
| | note = Engineered antibody sequence |
| source | 1..993 |
| | mol_type = other DNA |
| | organism = synthetic construct |

SEQUENCE: 20
```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggga   360
ccgtcagtct tcctcttccc cccaaaaccc aaggacaccc tcatgatctc ccggacccct  420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag gcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993
```

| SEQ ID NO: 21 | moltype = AA  length = 219 |
|---|---|
| FEATURE | Location/Qualifiers |
| REGION | 1..219 |
| | note = Engineered antibody sequence |
| source | 1..219 |
| | mol_type = protein |
| | organism = synthetic construct |

SEQUENCE: 21
```
QVLTQTASPV SAAVGSTVTI NCQASQSVYD NNYLAWYQQK PGQPPKQLIY STSTLASGVS    60
SRFKGSGSGT QFTLTISDLE CADAATYYCL GSYDCSSGDC FVFGGGTEVV VKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

| SEQ ID NO: 22 | moltype = AA  length = 113 |
|---|---|
| FEATURE | Location/Qualifiers |
| REGION | 1..113 |
| | note = Engineered antibody sequence |
| source | 1..113 |
| | mol_type = protein |

```
                        organism = synthetic construct
SEQUENCE: 22
QVLTQTASPV SAAVGSTVTI NCQASQSVYD NNYLAWYQQK PGQPPKQLIY STSTLASGVS    60
SRFKGSGSGT QFTLTISDLE CADAATYYCL GSYDCSSGDC FVFGGGTEVV VKR          113

SEQ ID NO: 23           moltype = AA  length = 22
FEATURE                 Location/Qualifiers
REGION                  1..22
                        note = Engineered antibody sequence
source                  1..22
                        mol_type = protein
                        organism = synthetic construct
SEQUENCE: 23
QVLTQTASPV SAAVGSTVTI NC                                             22

SEQ ID NO: 24           moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 24
QASQSVYDNN YLA                                                       13

SEQ ID NO: 25           moltype = AA  length = 15
FEATURE                 Location/Qualifiers
REGION                  1..15
                        note = Engineered antibody sequence
source                  1..15
                        mol_type = protein
                        organism = synthetic construct
SEQUENCE: 25
WYQQKPGQPP KQLIY                                                     15

SEQ ID NO: 26           moltype = AA  length = 7
FEATURE                 Location/Qualifiers
REGION                  1..7
                        note = Engineered antibody sequence
source                  1..7
                        mol_type = protein
                        organism = synthetic construct
SEQUENCE: 26
STSTLAS                                                               7

SEQ ID NO: 27           moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 27
GVSSRFKGSG SGTQFTLTIS DLECADAATY YC                                  32

SEQ ID NO: 28           moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 28
LGSYDCSSGD CFV                                                       13

SEQ ID NO: 29           moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 29
FGGGTEVVVK R                                                         11

SEQ ID NO: 30           moltype = AA  length = 106
FEATURE                 Location/Qualifiers
REGION                  1..106
                        note = Engineered antibody sequence
```

```
source                          1..106
                                mol_type = protein
                                organism = synthetic construct
SEQUENCE: 30
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 31                   moltype = DNA   length = 660
FEATURE                         Location/Qualifiers
misc_feature                    1..660
                                note = Engineered antibody sequence
source                          1..660
                                mol_type = other DNA
                                organism = synthetic construct
SEQUENCE: 31
caagtgctga cccagactgc atccccgtg tctgcagctg tgggaagcac agtcaccatc    60
aattgccagg ccagtcagag tgtttatgat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacctggag   240
tgtgccgatg ctgccactta ctactgtcta ggcagttatg attgtagtag tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 32                   moltype = DNA   length = 339
FEATURE                         Location/Qualifiers
misc_feature                    1..339
                                note = Engineered antibody sequence
source                          1..339
                                mol_type = other DNA
                                organism = synthetic construct
SEQUENCE: 32
caagtgctga cccagactgc atccccgtg tctgcagctg tgggaagcac agtcaccatc    60
aattgccagg ccagtcagag tgtttatgat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacctggag   240
tgtgccgatg ctgccactta ctactgtcta ggcagttatg attgtagtag tggtgattgt   300
tttgttttcg gcggagggac cgaggtggtg gtcaaacgt                          339

SEQ ID NO: 33                   moltype = DNA   length = 66
FEATURE                         Location/Qualifiers
misc_feature                    1..66
                                note = Engineered antibody sequence
source                          1..66
                                mol_type = other DNA
                                organism = synthetic construct
SEQUENCE: 33
caagtgctga cccagactgc atccccgtg tctgcagctg tgggaagcac agtcaccatc    60
aattgc                                                              66

SEQ ID NO: 34                   moltype = DNA   length = 39
FEATURE                         Location/Qualifiers
misc_feature                    1..39
                                note = Engineered antibody sequence
source                          1..39
                                mol_type = other DNA
                                organism = synthetic construct
SEQUENCE: 34
caggccagtc agagtgttta tgataacaac tacctagcc                          39

SEQ ID NO: 35                   moltype = DNA   length = 45
FEATURE                         Location/Qualifiers
misc_feature                    1..45
                                note = Engineered antibody sequence
source                          1..45
                                mol_type = other DNA
                                organism = synthetic construct
SEQUENCE: 35
tggtatcagc agaaaccagg gcagcctccc aagcaactga tctat                   45

SEQ ID NO: 36                   moltype = DNA   length = 21
FEATURE                         Location/Qualifiers
misc_feature                    1..21
                                note = Engineered antibody sequence
source                          1..21
                                mol_type = other DNA
```

```
                        organism = synthetic construct
SEQUENCE: 36
tctacatcca ctctggcatc t                                              21

SEQ ID NO: 37           moltype = DNA   length = 96
FEATURE                 Location/Qualifiers
misc_feature            1..96
                        note = Engineered antibody sequence
source                  1..96
                        mol_type = other DNA
                        organism = synthetic construct
SEQUENCE: 37
ggggtctcat cgcggttcaa aggcagtgga tctgggacac agttcactct caccatcagc    60
gacctggagt gtgccgatgc tgccacttac tactgt                              96

SEQ ID NO: 38           moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 38
ctaggcagtt atgattgtag tagtggtgat tgttttgtt                           39

SEQ ID NO: 39           moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 39
ttcggcggag ggaccgaggt ggtggtcaaa cgt                                 33

SEQ ID NO: 40           moltype = DNA   length = 321
FEATURE                 Location/Qualifiers
misc_feature            1..321
                        note = Engineered antibody sequence
source                  1..321
                        mol_type = other DNA
                        organism = synthetic construct
SEQUENCE: 40
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 41           moltype = AA   length = 441
FEATURE                 Location/Qualifiers
REGION                  1..441
                        note = Engineered antibody sequence
source                  1..441
                        mol_type = protein
                        organism = synthetic construct
SEQUENCE: 41
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKRVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 42           moltype = AA   length = 111
FEATURE                 Location/Qualifiers
REGION                  1..111
                        note = Engineered antibody sequence
source                  1..111
                        mol_type = protein
                        organism = synthetic construct
SEQUENCE: 42
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS S            111

SEQ ID NO: 43           moltype = AA   length = 30
```

```
FEATURE                 Location/Qualifiers
REGION                  1..30
                        note = Engineered antibody sequence
source                  1..30
                        mol_type = protein
                        organism = synthetic construct
SEQUENCE: 43
EVQLVESGGG LVQPGGSLRL SCAVSGLDLS                                    30

SEQ ID NO: 44           moltype = AA   length = 5
FEATURE                 Location/Qualifiers
REGION                  1..5
                        note = Engineered antibody sequence
source                  1..5
                        mol_type = protein
                        organism = synthetic construct
SEQUENCE: 44
SYYMQ                                                               5

SEQ ID NO: 45           moltype = AA   length = 14
FEATURE                 Location/Qualifiers
REGION                  1..14
                        note = Engineered antibody sequence
source                  1..14
                        mol_type = protein
                        organism = synthetic construct
SEQUENCE: 45
WVRQAPGKGL EWVG                                                     14

SEQ ID NO: 46           moltype = AA   length = 16
FEATURE                 Location/Qualifiers
REGION                  1..16
                        note = Engineered antibody sequence
source                  1..16
                        mol_type = protein
                        organism = synthetic construct
SEQUENCE: 46
VIGINDNTYY ASWAKG                                                   16

SEQ ID NO: 47           moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 47
RFTISRDNSK TTVYLQMNSL RAEDTAVYFC AR                                 32

SEQ ID NO: 48           moltype =     length =
SEQUENCE: 48
000

SEQ ID NO: 49           moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 49
WGQGTLVTVS S                                                        11

SEQ ID NO: 50           moltype = AA   length = 330
FEATURE                 Location/Qualifiers
REGION                  1..330
                        note = Engineered antibody sequence
source                  1..330
                        mol_type = protein
                        organism = synthetic construct
SEQUENCE: 50
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 51           moltype = DNA   length = 1326
```

| FEATURE | Location/Qualifiers |
|---|---|
| misc_feature | 1..1326 |
| | note = Engineered antibody sequence |
| source | 1..1326 |
| | mol_type = other DNA |
| | organism = synthetic construct |

SEQUENCE: 51

```
gaggtgcagc ttgtggagtc tggggggaggc ttggtccagc ctgggggggtc cctgagactc   60
tcctgtgcag tctctggact cgacctcagt agctactaca tgcaatgggt ccgtcaggct  120
ccagggaagg ggctggagtg ggtcggagtc attggtatca atgataacac atactacgca  180
agctgggcga aaggccgatt caccatctcc agagacaatt ccaagaccac ggtgtatctt  240
caaatgaaca gcctgagagc tgaggacact gctgtgtatt tctgtgctag aggggacatc  300
tggggccaag ggaccctcgt caccgtctcg agcgcctcca ccaagggccc atcggtcttc  360
cccctggcac cctcctccaa gagcacctct gggggcacag cggccctggg ctgcctggtc  420
aaggactact tccccgaacc ggtgacggtg tcgtggaact caggcgccct gaccagcggc  480
gtgcacacct tcccggctgt cctacagtcc tcaggactct actccctcag cagcgtggtg  540
accgtgccct ccagcagctt gggcacccag acctacatct gcaacgtgaa tcacaagccc  600
agcaacacca aggtggacaa gagagttgag cccaaatctt gtgacaaaac tcacacatgc  660
ccaccgtgcc cagcacctga actcctgggg ggaccgtcag tcttcctctt cccccccaaa  720
cccaaggaca ccctcatgat ctcccggacc cctgaggtca catgcgtggt ggtggacgtg  780
agccacgaag accctgaggt caagttcaac tggtacgtgg acggcgtgga ggtgcataat  840
gccaagacaa agccgcggga ggagcagtac gccagcacgt accgtgtggt cagcgtcctc  900
accgtcctgc accaggactg gctgaatggc aaggagtaca agtgcaaggt ctccaacaaa  960
gccctcccag ccccatcga gaaaaccatc tccaaagcca aagggcagcc ccgagaacca 1020
caggtgtaca ccctgccccc atcccgggag gagatgacca gaaccaggt cagcctgacc 1080
tgcctggtca aaggcttcta tcccagcgac atcgccgtg agtgggagag caatgggcag 1140
ccggagaaca actacaagac cacgcctccc gtgctggact ccgacggctc cttcttcctc 1200
tacagcaagc tcaccgtgga caagagcagg tggcagcagg ggaacgtctt ctcatgctcc 1260
gtgatgcatg aggctctgca caaccactac acgcagaaga gcctctccct gtctccgggt 1320
aaatga                                                             1326
```

| SEQ ID NO: 52 | moltype = DNA   length = 333 |
|---|---|
| FEATURE | Location/Qualifiers |
| misc_feature | 1..333 |
| | note = Engineered antibody sequence |
| source | 1..333 |
| | mol_type = other DNA |
| | organism = synthetic construct |

SEQUENCE: 52

```
gaggtgcagc ttgtggagtc tggggggaggc ttggtccagc ctgggggggtc cctgagactc   60
tcctgtgcag tctctggact cgacctcagt agctactaca tgcaatgggt ccgtcaggct  120
ccagggaagg ggctggagtg ggtcggagtc attggtatca atgataacac atactacgcg  180
agctgggcga aaggccgatt caccatctcc agagacaatt ccaagaccac ggtgtatctt  240
caaatgaaca gcctgagagc tgaggacact gctgtgtatt tctgtgctag aggggacatc  300
tggggccaag ggaccctcgt caccgtctcg agc                                333
```

| SEQ ID NO: 53 | moltype = DNA   length = 90 |
|---|---|
| FEATURE | Location/Qualifiers |
| misc_feature | 1..90 |
| | note = Engineered antibody sequence |
| source | 1..90 |
| | mol_type = other DNA |
| | organism = synthetic construct |

SEQUENCE: 53

```
gaggtgcagc ttgtggagtc tggggggaggc ttggtccagc ctgggggggtc cctgagactc   60
tcctgtgcag tctctggact cgacctcagt                                     90
```

| SEQ ID NO: 54 | moltype = DNA   length = 15 |
|---|---|
| FEATURE | Location/Qualifiers |
| misc_feature | 1..15 |
| | note = Engineered antibody sequence |
| source | 1..15 |
| | mol_type = other DNA |
| | organism = synthetic construct |

SEQUENCE: 54

```
agctactaca tgcaa                                                     15
```

| SEQ ID NO: 55 | moltype = DNA   length = 42 |
|---|---|
| FEATURE | Location/Qualifiers |
| misc_feature | 1..42 |
| | note = Engineered antibody sequence |
| source | 1..42 |
| | mol_type = other DNA |
| | organism = synthetic construct |

SEQUENCE: 55

```
tgggtccgtc aggctccagg gaaggggctg gagtgggtcg ga                       42
```

| SEQ ID NO: 56 | moltype = DNA   length = 48 |
|---|---|
| FEATURE | Location/Qualifiers |

```
misc_feature            1..48
                        note = Engineered antibody sequence
source                  1..48
                        mol_type = other DNA
                        organism = synthetic construct
SEQUENCE: 56
gtcattggta tcaatgataa cacatactac gcgagctggg cgaaaggc                48

SEQ ID NO: 57           moltype = DNA  length = 96
FEATURE                 Location/Qualifiers
misc_feature            1..96
                        note = Engineered antibody sequence
source                  1..96
                        mol_type = other DNA
                        organism = synthetic construct
SEQUENCE: 57
cgattcacca tctccagaga caattccaag accacggtgt atcttcaaat gaacagcctg    60
agagctgagg acactgctgt gtatttctgt gctaga                             96

SEQ ID NO: 58           moltype =   length =
SEQUENCE: 58
000

SEQ ID NO: 59           moltype = DNA  length = 33
FEATURE                 Location/Qualifiers
misc_feature            1..33
                        note = Engineered antibody sequence
source                  1..33
                        mol_type = other DNA
                        organism = synthetic construct
SEQUENCE: 59
tggggccaag ggaccctcgt caccgtctcg agc                                33

SEQ ID NO: 60           moltype = DNA  length = 993
FEATURE                 Location/Qualifiers
misc_feature            1..993
                        note = Engineered antibody sequence
source                  1..993
                        mol_type = other DNA
                        organism = synthetic construct
SEQUENCE: 60
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

SEQ ID NO: 61           moltype = AA  length = 219
FEATURE                 Location/Qualifiers
REGION                  1..219
                        note = Engineered antibody sequence
source                  1..219
                        mol_type = protein
                        organism = synthetic construct
SEQUENCE: 61
QVLTQSPSSL SASVGDRVTI NCQASQSVYD NNYLAWYQQK PGKVPKQLIY STSTLASGVP    60
SRFSGSGSGT DFTLTISSLQ PEDVATYYCL GSYDCSSGDC FVFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 62           moltype = AA  length = 113
FEATURE                 Location/Qualifiers
REGION                  1..113
                        note = Engineered antibody sequence
source                  1..113
                        mol_type = protein
                        organism = synthetic construct
```

```
SEQUENCE: 62
QVLTQSPSSL SASVGDRVTI NCQASQSVYD NNYLAWYQQK PGKVPKQLIY STSTLASGVP    60
SRFSGSGSGT DFTLTISSLQ PEDVATYYCL GSYDCSSGDC FVFGGGTKVE IKR          113

SEQ ID NO: 63              moltype = AA   length = 22
FEATURE                    Location/Qualifiers
REGION                     1..22
                           note = Engineered antibody sequence
source                     1..22
                           mol_type = protein
                           organism = synthetic construct
SEQUENCE: 63
QVLTQSPSSL SASVGDRVTI NC                                            22

SEQ ID NO: 64              moltype = AA   length = 13
FEATURE                    Location/Qualifiers
REGION                     1..13
                           note = Engineered antibody sequence
source                     1..13
                           mol_type = protein
                           organism = synthetic construct
SEQUENCE: 64
QASQSVYDNN YLA                                                      13

SEQ ID NO: 65              moltype = AA   length = 15
FEATURE                    Location/Qualifiers
REGION                     1..15
                           note = Engineered antibody sequence
source                     1..15
                           mol_type = protein
                           organism = synthetic construct
SEQUENCE: 65
WYQQKPGKVP KQLIY                                                    15

SEQ ID NO: 66              moltype = AA   length = 7
FEATURE                    Location/Qualifiers
REGION                     1..7
                           note = Engineered antibody sequence
source                     1..7
                           mol_type = protein
                           organism = synthetic construct
SEQUENCE: 66
STSTLAS                                                             7

SEQ ID NO: 67              moltype = AA   length = 32
FEATURE                    Location/Qualifiers
REGION                     1..32
                           note = Engineered antibody sequence
source                     1..32
                           mol_type = protein
                           organism = synthetic construct
SEQUENCE: 67
GVPSRFSGSG SGTDFTLTIS SLQPEDVATY YC                                 32

SEQ ID NO: 68              moltype = AA   length = 13
FEATURE                    Location/Qualifiers
REGION                     1..13
                           note = Engineered antibody sequence
source                     1..13
                           mol_type = protein
                           organism = synthetic construct
SEQUENCE: 68
LGSYDCSSGD CFV                                                      13

SEQ ID NO: 69              moltype = AA   length = 11
FEATURE                    Location/Qualifiers
REGION                     1..11
                           note = Engineered antibody sequence
source                     1..11
                           mol_type = protein
                           organism = synthetic construct
SEQUENCE: 69
FGGGTKVEIK R                                                        11

SEQ ID NO: 70              moltype = AA   length = 106
FEATURE                    Location/Qualifiers
REGION                     1..106
                           note = Engineered antibody sequence
source                     1..106
```

```
                    mol_type = protein
                    organism = synthetic construct
SEQUENCE: 70
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 71           moltype = DNA   length = 660
FEATURE                 Location/Qualifiers
misc_feature            1..660
                        note = Engineered antibody sequence
source                  1..660
                        mol_type = other DNA
                        organism = synthetic construct
SEQUENCE: 71
caagtgctga cccagtctcc atcctccctg tctgcatctg taggagacag agtcaccatc    60
aattgccagg ccagtcagag tgtttatgat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtcta ggcagttatg attgtagtag tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 72           moltype = DNA   length = 339
FEATURE                 Location/Qualifiers
misc_feature            1..339
                        note = Engineered antibody sequence
source                  1..339
                        mol_type = other DNA
                        organism = synthetic construct
SEQUENCE: 72
caagtgctga cccagtctcc atcctccctg tctgcatctg taggagacag agtcaccatc    60
aattgccagg ccagtcagag tgtttatgat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtcta ggcagttatg attgtagtag tggtgattgt   300
tttgttttcg gcggaggaac caaggtggaa atcaaacgt                          339

SEQ ID NO: 73           moltype = DNA   length = 66
FEATURE                 Location/Qualifiers
misc_feature            1..66
                        note = Engineered antibody sequence
source                  1..66
                        mol_type = other DNA
                        organism = synthetic construct
SEQUENCE: 73
caagtgctga cccagtctcc atcctccctg tctgcatctg taggagacag agtcaccatc    60
aattgc                                                              66

SEQ ID NO: 74           moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 74
caggccagtc agagtgttta tgataacaac tacctagcc                           39

SEQ ID NO: 75           moltype = DNA   length = 45
FEATURE                 Location/Qualifiers
misc_feature            1..45
                        note = Engineered antibody sequence
source                  1..45
                        mol_type = other DNA
                        organism = synthetic construct
SEQUENCE: 75
tggtatcagc agaaaccagg gaaagttcct aagcaactga tctat                    45

SEQ ID NO: 76           moltype = DNA   length = 21
FEATURE                 Location/Qualifiers
misc_feature            1..21
                        note = Engineered antibody sequence
source                  1..21
                        mol_type = other DNA
                        organism = synthetic construct
```

```
SEQUENCE: 76
tctacatcca ctctggcatc t                                              21

SEQ ID NO: 77           moltype = DNA   length = 96
FEATURE                 Location/Qualifiers
misc_feature            1..96
                        note = Engineered antibody sequence
source                  1..96
                        mol_type = other DNA
                        organism = synthetic construct
SEQUENCE: 77
ggggtcccat ctcgtttcag tggcagtgga tctgggacag atttcactct caccatcagc    60
agcctgcagc ctgaagatgt tgcaacttat tactgt                              96

SEQ ID NO: 78           moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 78
ctaggcagtt atgattgtag tagtggtgat tgttttgtt                           39

SEQ ID NO: 79           moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 79
ttcggcggag gaaccaaggt ggaaatcaaa cgt                                 33

SEQ ID NO: 80           moltype = DNA   length = 321
FEATURE                 Location/Qualifiers
misc_feature            1..321
                        note = Engineered antibody sequence
source                  1..321
                        mol_type = other DNA
                        organism = synthetic construct
SEQUENCE: 80
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 81           moltype = AA   length = 441
FEATURE                 Location/Qualifiers
REGION                  1..441
                        note = Engineered antibody sequence
source                  1..441
                        mol_type = protein
                        organism = synthetic construct
SEQUENCE: 81
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDARVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 82           moltype = AA   length = 111
FEATURE                 Location/Qualifiers
REGION                  1..111
                        note = Engineered antibody sequence
source                  1..111
                        mol_type = protein
                        organism = synthetic construct
SEQUENCE: 82
EVQLVESGGG LVQPGGSLRL SCAVSGLDLS SYYMQWVRQA PGKGLEWVGV IGINDNTYYA    60
SWAKGRFTIS RDNSKTTVYL QMNSLRAEDT AVYFCARGDI WGQGTLVTVS S            111

SEQ ID NO: 83           moltype = AA   length = 30
FEATURE                 Location/Qualifiers
```

```
REGION                  1..30
                        note = Engineered antibody sequence
source                  1..30
                        mol_type = protein
                        organism = synthetic construct
SEQUENCE: 83
EVQLVESGGG LVQPGGSLRL SCAVSGLDLS                                    30

SEQ ID NO: 84           moltype = AA  length = 5
FEATURE                 Location/Qualifiers
REGION                  1..5
                        note = Engineered antibody sequence
source                  1..5
                        mol_type = protein
                        organism = synthetic construct
SEQUENCE: 84
SYYMQ                                                                5

SEQ ID NO: 85           moltype = AA  length = 14
FEATURE                 Location/Qualifiers
REGION                  1..14
                        note = Engineered antibody sequence
source                  1..14
                        mol_type = protein
                        organism = synthetic construct
SEQUENCE: 85
WVRQAPGKGL EWVG                                                     14

SEQ ID NO: 86           moltype = AA  length = 16
FEATURE                 Location/Qualifiers
REGION                  1..16
                        note = Engineered antibody sequence
source                  1..16
                        mol_type = protein
                        organism = synthetic construct
SEQUENCE: 86
VIGINDNTYY ASWAKG                                                   16

SEQ ID NO: 87           moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 87
RFTISRDNSK TTVYLQMNSL RAEDTAVYFC AR                                 32

SEQ ID NO: 88           moltype =    length =
SEQUENCE: 88
000

SEQ ID NO: 89           moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 89
WGQGTLVTVS S                                                        11

SEQ ID NO: 90           moltype = AA  length = 330
FEATURE                 Location/Qualifiers
REGION                  1..330
                        note = Engineered antibody sequence
source                  1..330
                        mol_type = protein
                        organism = synthetic construct
SEQUENCE: 90
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDARVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 91           moltype = DNA  length = 1326
FEATURE                 Location/Qualifiers
```

```
misc_feature                1..1326
                            note = Engineered antibody sequence
source                      1..1326
                            mol_type = other DNA
                            organism = synthetic construct
SEQUENCE: 91
gaggtgcagc ttgtggagtc tgggggaggc ttggtccagc ctgggggtc cctgagactc    60
tcctgtgcag tctctggact cgacctcagt agctactaca tgcaatgggt ccgtcaggct   120
ccagggaagg ggctggagtg ggtcggagtc attggtatca atgataacac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag gaccctcgt caccgtctcg agcgcctcca ccaagggccc atcggtcttc    360
cccctggcac cctcctccaa gagcacctct ggggcacaca cggccctggg ctgcctggtc   420
aaggactact tccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacgc gagagttgag cccaaatctt gtgacaaaac tcacacatgc   660
ccaccgtgcc cagcacctga actcctgggg gaccgtcag tcttcctctt cccccaaaa    720
cccaaggaca ccctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca aagggcagcc ccgagaacca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg ggaacgtctt ctcatgctcc  1260
gtgatgcatg aggctctgca caaccactac acgcagaaga gcctctccct gtctccgggt  1320
aaatga                                                             1326

SEQ ID NO: 92               moltype = DNA  length = 333
FEATURE                     Location/Qualifiers
misc_feature                1..333
                            note = Engineered antibody sequence
source                      1..333
                            mol_type = other DNA
                            organism = synthetic construct
SEQUENCE: 92
gaggtgcagc ttgtggagtc tgggggaggc ttggtccagc ctgggggtc cctgagactc    60
tcctgtgcag tctctggact cgacctcagt agctactaca tgcaatgggt ccgtcaggct   120
ccagggaagg ggctggagtg ggtcggagtc attggtatca atgataacac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag gaccctcgt caccgtctcg agc                                 333

SEQ ID NO: 93               moltype = DNA  length = 90
FEATURE                     Location/Qualifiers
misc_feature                1..90
                            note = Engineered antibody sequence
source                      1..90
                            mol_type = other DNA
                            organism = synthetic construct
SEQUENCE: 93
gaggtgcagc ttgtggagtc tgggggaggc ttggtccagc ctgggggtc cctgagactc    60
tcctgtgcag tctctggact cgacctcagt                                    90

SEQ ID NO: 94               moltype = DNA  length = 15
FEATURE                     Location/Qualifiers
misc_feature                1..15
                            note = Engineered antibody sequence
source                      1..15
                            mol_type = other DNA
                            organism = synthetic construct
SEQUENCE: 94
agctactaca tgcaa                                                    15

SEQ ID NO: 95               moltype = DNA  length = 42
FEATURE                     Location/Qualifiers
misc_feature                1..42
                            note = Engineered antibody sequence
source                      1..42
                            mol_type = other DNA
                            organism = synthetic construct
SEQUENCE: 95
tgggtccgtc aggctccagg gaaggggctg gagtgggtcg ga                      42

SEQ ID NO: 96               moltype = DNA  length = 48
FEATURE                     Location/Qualifiers
misc_feature                1..48
```

|   |   |   |
|---|---|---|
| source | 1..48 note = Engineered antibody sequence mol_type = other DNA organism = synthetic construct | |
| SEQUENCE: 96 | | |
| gtcattggta tcaatgataa cacatactac gcgagctggg cgaaaggc | | 48 |

| | | |
|---|---|---|
| SEQ ID NO: 97 | moltype = DNA length = 96 | |
| FEATURE | Location/Qualifiers | |
| misc_feature | 1..96 note = Engineered antibody sequence | |
| source | 1..96 mol_type = other DNA organism = synthetic construct | |
| SEQUENCE: 97 | | |
| cgattcacca tctccagaga caattccaag accacggtgt atcttcaaat gaacagcctg | | 60 |
| agagctgagg acactgctgt gtatttctgt gctaga | | 96 |

| | | |
|---|---|---|
| SEQ ID NO: 98 | moltype = length = | |
| SEQUENCE: 98 | | |
| 000 | | |

| | | |
|---|---|---|
| SEQ ID NO: 99 | moltype = DNA length = 33 | |
| FEATURE | Location/Qualifiers | |
| misc_feature | 1..33 note = Engineered antibody sequence | |
| source | 1..33 mol_type = other DNA organism = synthetic construct | |
| SEQUENCE: 99 | | |
| tggggccaag ggaccctcgt caccgtctcg agc | | 33 |

| | | |
|---|---|---|
| SEQ ID NO: 100 | moltype = DNA length = 993 | |
| FEATURE | Location/Qualifiers | |
| misc_feature | 1..993 note = Engineered antibody sequence | |
| source | 1..993 mol_type = other DNA organism = synthetic construct | |
| SEQUENCE: 100 | | |
| gcctccacca agggcccatc ggtcttcccc ctggcaccct cctccaagag cacctctggg | | 60 |
| ggcacagcgg ccctgggctg cctggtcaag gactacttcc ccgaaccggt gacggtgtcg | | 120 |
| tggaactcag gcgccctgac cagcggcgtg cacaccttcc cggctgtcct acagtcctca | | 180 |
| ggactctact ccctcagcag cgtggtgacc gtgccctcca gcagcttggg cacccagacc | | 240 |
| tacatctgca acgtgaatca caagcccagc aacaccaagg tggacgcgag agttgagccc | | 300 |
| aaatcttgtg acaaaactca cacatgccca ccgtgcccag cacctgaact cctggggga | | 360 |
| ccgtcagtct tcctcttccc cccaaaaccc aaggacaccc tcatgatctc ccggacccct | | 420 |
| gaggtcacat gcgtggtggt ggacgtgagc cacgaagacc ctgaggtcaa gttcaactgg | | 480 |
| tacgtggacg gcgtggaggt gcataatgcc aagacaaagc cgcgggagga gcagtacgcc | | 540 |
| agcacgtacc gtgtggtcag cgtcctcacc gtcctgcacc aggactggct gaatggcaag | | 600 |
| gagtacaagt gcaaggtctc caacaaagcc ctcccagccc ccatcgagaa aaccatctcc | | 660 |
| aaagccaaag ggcagccccg agaaccacag gtgtacaccc tgcccccatc ccgggaggag | | 720 |
| atgaccaaga accaggtcag cctgacctgc ctggtcaaag gcttctatcc cagcgacatc | | 780 |
| gccgtggagt gggagagcaa tgggcagccg gagaacaact acaagaccac gcctcccgtg | | 840 |
| ctggactccg acggctcctt cttcctctac agcaagctca ccgtggacaa gagcaggtgg | | 900 |
| cagcagggga acgtcttctc atgctccgtg atgcatgagg ctctgcacaa ccactacacg | | 960 |
| cagaagagcc tctccctgtc tccgggtaaa tga | | 993 |

| | | |
|---|---|---|
| SEQ ID NO: 101 | moltype = AA length = 219 | |
| FEATURE | Location/Qualifiers | |
| REGION | 1..219 note = Engineered antibody sequence | |
| source | 1..219 mol_type = protein organism = synthetic construct | |
| SEQUENCE: 101 | | |
| QVLTQSPSSL SASVGDRVTI NCQASQSVYD NNYLAWYQQK PGKVPKQLIY STSTLASGVP | | 60 |
| SRFSGSGSGT DFTLTISSLQ PEDVATYYCL GSYDCSSGDC FVFGGGTKVE IKRTVAAPSV | | 120 |
| FIFPPSDEQL KSGTASVVCL LNNFYPREAK VQWKVDNALQ SGNSQESVTE QDSKDSTYSL | | 180 |
| SSTLTLSKAD YEKHKVYACE VTHQGLSSPV TKSFNRGEC | | 219 |

| | | |
|---|---|---|
| SEQ ID NO: 102 | moltype = AA length = 113 | |
| FEATURE | Location/Qualifiers | |
| REGION | 1..113 note = Engineered antibody sequence | |
| source | 1..113 mol_type = protein organism = synthetic construct | |
| SEQUENCE: 102 | | |

```
QVLTQSPSSL SASVGDRVTI NCQASQSVYD NNYLAWYQQK PGKVPKQLIY STSTLASGVP    60
SRFSGSGSGT DFTLTISSLQ PEDVATYYCL GSYDCSSGDC FVFGGGTKVE IKR          113

SEQ ID NO: 103          moltype = AA  length = 22
FEATURE                 Location/Qualifiers
REGION                  1..22
                        note = Engineered antibody sequence
source                  1..22
                        mol_type = protein
                        organism = synthetic construct
SEQUENCE: 103
QVLTQSPSSL SASVGDRVTI NC                                            22

SEQ ID NO: 104          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 104
QASQSVYDNN YLA                                                      13

SEQ ID NO: 105          moltype = AA  length = 15
FEATURE                 Location/Qualifiers
REGION                  1..15
                        note = Engineered antibody sequence
source                  1..15
                        mol_type = protein
                        organism = synthetic construct
SEQUENCE: 105
WYQQKPGKVP KQLIY                                                    15

SEQ ID NO: 106          moltype = AA  length = 7
FEATURE                 Location/Qualifiers
REGION                  1..7
                        note = Engineered antibody sequence
source                  1..7
                        mol_type = protein
                        organism = synthetic construct
SEQUENCE: 106
STSTLAS                                                             7

SEQ ID NO: 107          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 107
GVPSRFSGSG SGTDFTLTIS SLQPEDVATY YC                                 32

SEQ ID NO: 108          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 108
LGSYDCSSGD CFV                                                      13

SEQ ID NO: 109          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 109
FGGGTKVEIK R                                                        11

SEQ ID NO: 110          moltype = AA  length = 106
FEATURE                 Location/Qualifiers
REGION                  1..106
                        note = Engineered antibody sequence
source                  1..106
                        mol_type = protein
```

```
                        organism = synthetic construct
SEQUENCE: 110
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 111          moltype = DNA  length = 660
FEATURE                 Location/Qualifiers
misc_feature            1..660
                        note = Engineered antibody sequence
source                  1..660
                        mol_type = other DNA
                        organism = synthetic construct
SEQUENCE: 111
caagtgctga cccagtctcc atcctccctg tctgcatctg taggagacag agtcaccatc    60
aattgccagg ccagtcagag tgtttatgat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtcta ggcagttata attgtagtag tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 112          moltype = DNA  length = 339
FEATURE                 Location/Qualifiers
misc_feature            1..339
                        note = Engineered antibody sequence
source                  1..339
                        mol_type = other DNA
                        organism = synthetic construct
SEQUENCE: 112
caagtgctga cccagtctcc atcctccctg tctgcatctg taggagacag agtcaccatc    60
aattgccagg ccagtcagag tgtttatgat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtcta ggcagttatg attgtagtag tggtgattgt   300
tttgttttcg gcggaggaac caaggtggaa atcaaacgt                          339

SEQ ID NO: 113          moltype = DNA  length = 66
FEATURE                 Location/Qualifiers
misc_feature            1..66
                        note = Engineered antibody sequence
source                  1..66
                        mol_type = other DNA
                        organism = synthetic construct
SEQUENCE: 113
caagtgctga cccagtctcc atcctccctg tctgcatctg taggagacag agtcaccatc    60
aattgc                                                              66

SEQ ID NO: 114          moltype = DNA  length = 39
FEATURE                 Location/Qualifiers
misc_feature            1..39
                        note = Engineered antibody sequence
source                  1..39
                        mol_type = other DNA
                        organism = synthetic construct
SEQUENCE: 114
caggccagtc agagtgttta tgataacaac tacctagcc                           39

SEQ ID NO: 115          moltype = DNA  length = 45
FEATURE                 Location/Qualifiers
misc_feature            1..45
                        note = Engineered antibody sequence
source                  1..45
                        mol_type = other DNA
                        organism = synthetic construct
SEQUENCE: 115
tggtatcagc agaaaccagg gaaagttcct aagcaactga tctat                    45

SEQ ID NO: 116          moltype = DNA  length = 21
FEATURE                 Location/Qualifiers
misc_feature            1..21
                        note = Engineered antibody sequence
source                  1..21
                        mol_type = other DNA
                        organism = synthetic construct
SEQUENCE: 116
```
tctacatcca ctctggcatc t                                                    21

SEQ ID NO: 117         moltype = DNA   length = 96
FEATURE                Location/Qualifiers
misc_feature           1..96
                       note = Engineered antibody sequence
source                 1..96
                       mol_type = other DNA
                       organism = synthetic construct
SEQUENCE: 117
ggggtcccat ctcgtttcag tggcagtgga tctgggacag atttcactct caccatcagc     60
agcctgcagc ctgaagatgt tgcaacttat tactgt                                96

SEQ ID NO: 118         moltype = DNA   length = 39
FEATURE                Location/Qualifiers
misc_feature           1..39
                       note = Engineered antibody sequence
source                 1..39
                       mol_type = other DNA
                       organism = synthetic construct
SEQUENCE: 118
ctaggcagtt atgattgtag tagtggtgat tgttttgtt                              39

SEQ ID NO: 119         moltype = DNA   length = 33
FEATURE                Location/Qualifiers
misc_feature           1..33
                       note = Engineered antibody sequence
source                 1..33
                       mol_type = other DNA
                       organism = synthetic construct
SEQUENCE: 119
ttcggcggag gaaccaaggt ggaaatcaaa cgt                                    33

SEQ ID NO: 120         moltype = DNA   length = 321
FEATURE                Location/Qualifiers
misc_feature           1..321
                       note = Engineered antibody sequence
source                 1..321
                       mol_type = other DNA
                       organism = synthetic construct
SEQUENCE: 120
acggtggctg caccatctgt cttcatcttc ccgccatctg atgagcagtt gaaatctgga     60
actgcctctg ttgtgtgcct gctgaataac ttctatccca gagaggccaa agtacagtgg    120
aaggtggata acgccctcca atcgggtaac tcccaggaga gtgtcacaga gcaggacagc    180
aaggacagca cctacagcct cagcagcacc ctgacgctga gcaaagcaga ctacgagaaa    240
cacaaagtct acgcctgcga agtcacccat caggggctga gctcgcccgt cacaaagagc    300
ttcaacaggg gagagtgtta g                                               321

SEQ ID NO: 121         moltype = AA    length = 439
FEATURE                Location/Qualifiers
REGION                 1..439
                       note = Engineered antibody sequence
source                 1..439
                       mol_type = protein
                       organism = synthetic construct
SEQUENCE: 121
QSLEESGGRL VTPGTPLTLT CSVSGIDLSG YYMNWVRQAP GKGLEWIGVI GINGATYYAS     60
WAKGRFTISK TSSTTVDLKM TSLTTEDTAT YFCARGDIWG PGTLVTVSSA STKGPSVFPL    120
APSSKSTSGG TAALGCLVKD YFPEPVTVSW NSGALTSGVH TFPAVLQSSG LYSLSSVVTV    180
PSSSLGTQTY ICNVNHKPSN TKVDKRVEPK SCDKTHTCPP CPAPELLGGP SVFLFPPKPK    240
DTLMISRTPE VTCVVVDVSH EDPEVKFNWY VDGVEVHNAK TKPREEQYAS TYRVVSVLTV    300
LHQDWLNGKE YKCKVSNKAL PAPIEKTISK AKGQPREPQV YTLPPSREEM TKNQVSLTCL    360
VKGFYPSDIA VEWESNGQPE NNYKTTPPVL DSDGSFFLYS KLTVDKSRWQ QGNVFSCSVM    420
HEALHNHYTQ KSLSLSPGK                                                 439

SEQ ID NO: 122         moltype = AA    length = 109
FEATURE                Location/Qualifiers
REGION                 1..109
                       note = Engineered antibody sequence
source                 1..109
                       mol_type = protein
                       organism = synthetic construct
SEQUENCE: 122
QSLEESGGRL VTPGTPLTLT CSVSGIDLSG YYMNWVRQAP GKGLEWIGVI GINGATYYAS     60
WAKGRFTISK TSSTTVDLKM TSLTTEDTAT YFCARGDIWG PGTLVTVSS               109

SEQ ID NO: 123         moltype = AA    length = 29
FEATURE                Location/Qualifiers
REGION                 1..29

```
                        note = Engineered antibody sequence
source                  1..29
                        mol_type = protein
                        organism = synthetic construct
SEQUENCE: 123
QSLEESGGRL VTPGTPLTLT CSVSGIDLS                                       29

SEQ ID NO: 124          moltype = AA   length = 5
FEATURE                 Location/Qualifiers
REGION                  1..5
                        note = Engineered antibody sequence
source                  1..5
                        mol_type = protein
                        organism = synthetic construct
SEQUENCE: 124
GYYMN                                                                  5

SEQ ID NO: 125          moltype = AA   length = 14
FEATURE                 Location/Qualifiers
REGION                  1..14
                        note = Engineered antibody sequence
source                  1..14
                        mol_type = protein
                        organism = synthetic construct
SEQUENCE: 125
WVRQAPGKGL EWIG                                                       14

SEQ ID NO: 126          moltype = AA   length = 16
FEATURE                 Location/Qualifiers
REGION                  1..16
                        note = Engineered antibody sequence
source                  1..16
                        mol_type = protein
                        organism = synthetic construct
SEQUENCE: 126
VIGINGATYY ASWAKG                                                     16

SEQ ID NO: 127          moltype = AA   length = 31
FEATURE                 Location/Qualifiers
REGION                  1..31
                        note = Engineered antibody sequence
source                  1..31
                        mol_type = protein
                        organism = synthetic construct
SEQUENCE: 127
RFTISKTSST TVDLKMTSLT TEDTATYFCA R                                    31

SEQ ID NO: 128          moltype =      length =
SEQUENCE: 128
000

SEQ ID NO: 129          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 129
WGPGTLVTVS S                                                          11

SEQ ID NO: 130          moltype = AA   length = 330
FEATURE                 Location/Qualifiers
REGION                  1..330
                        note = Engineered antibody sequence
source                  1..330
                        mol_type = protein
                        organism = synthetic construct
SEQUENCE: 130
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYA     180
STYRVVSVLT VLHQDWLNGK EYKCKVSNKA LPAPIEKTIS KAKGQPREPQ VYTLPPSREE     240
MTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                     330

SEQ ID NO: 131          moltype = DNA  length = 1320
FEATURE                 Location/Qualifiers
misc_feature            1..1320
```

```
                        note = Engineered antibody sequence
source                  1..1320
                        mol_type = other DNA
                        organism = synthetic construct
SEQUENCE: 131
cagtcgctgg aggagtccgg gggtcgcctg gtcacgcctg gacacccct gacactcacc    60
tgttccgtct ctggcatcga cctcagtggc tactacatga actgggtccg ccaggctcca   120
gggaaggggc tggaatggat cggagtcatt ggtattaatg gtgccacata ctacgcgagc   180
tgggcgaaag gccgattcac catctccaaa acctcgtcga ccacggtgga tctgaaaatg   240
accagtctga caaccgagga cacgccacc tatttctgtg ccagagggga catctggggc    300
ccgggcaccc tcgtcaccgt ctcgagcgcc tccaccaagg gcccatcggt cttccccctg   360
gcaccctcct ccaagagcac ctctgggggc acagcggccc tgggctgcct ggtcaaggac   420
tacttccccg aaccggtgac ggtgtcgtgg aactcaggcg ccctgaccag cggcgtgcac   480
accttcccgg ctgtcctaca gtcctcagga ctctactcc tcagcagcgt ggtgaccgtg    540
ccctccagca gcttgggcac ccagacctac atctgcaacg tgaatcacaa gcccagcaac   600
accaaggtgg acaagagagt tgagcccaaa tcttgtgaca aaactcacac atgcccaccg   660
tgcccagcac ctgaactcct ggggggaccg tcagtcttcc tcttcccccc aaaacccaag   720
gacaccctca tgatctcccg gacccctgag gtcacatgcg tggtggtgga cgtgagccac   780
gaagaccctg aggtcaagtt caactggtac gtggacggcg tggaggtgca taatgccaag   840
acaaagccgc gggaggagca gtacgccagc acgtaccgtg tggtcagcgt cctcaccgtc   900
ctgcaccagg actggctgaa tggcaaggag tacaagtgca aggtctccaa caaagccctc   960
ccagccccca tcgagaaaac catctccaaa gccaaagggc agccccgaga accacaggtg  1020
tacaccctgc ccccatcccg ggaggagatg accaagaacc aggtcagcct gacctgcctg  1080
gtcaaaggct tctatcccag cgacatcgcc gtggagtggg agagcaatgg gcagccggag  1140
aacaactaca agaccacgcc tcccgtgctg gactccgacg gctccttctt cctctacagc  1200
aagctcaccg tggacaagag caggtggcag caggggaacg tcttctcatg ctccgtgatg  1260
catgaggctc tgcacaacca ctacacgcag aagagcctct ccctgtctcc gggtaaatga  1320

SEQ ID NO: 132         moltype = DNA   length = 327
FEATURE                Location/Qualifiers
misc_feature           1..327
                       note = Engineered antibody sequence
source                 1..327
                       mol_type = other DNA
                       organism = synthetic construct
SEQUENCE: 132
cagtcgctgg aggagtccgg gggtcgcctg gtcacgcctg gacacccct gacactcacc    60
tgttccgtct ctggcatcga cctcagtggc tactacatga actgggtccg ccaggctcca   120
gggaaggggc tggaatggat cggagtcatt ggtattaatg gtgccacata ctacgcgagc   180
tgggcgaaag gccgattcac catctccaaa acctcgtcga ccacggtgga tctgaaaatg   240
accagtctga caaccgagga cacgccacc tatttctgtg ccagagggga catctggggc    300
ccgggcaccc tcgtcaccgt ctcgagc                                       327

SEQ ID NO: 133         moltype = DNA   length = 87
FEATURE                Location/Qualifiers
misc_feature           1..87
                       note = Engineered antibody sequence
source                 1..87
                       mol_type = other DNA
                       organism = synthetic construct
SEQUENCE: 133
cagtcgctgg aggagtccgg gggtcgcctg gtcacgcctg gacacccct gacactcacc    60
tgttccgtct ctggcatcga cctcagt                                       87

SEQ ID NO: 134         moltype = DNA   length = 15
FEATURE                Location/Qualifiers
misc_feature           1..15
                       note = Engineered antibody sequence
source                 1..15
                       mol_type = other DNA
                       organism = synthetic construct
SEQUENCE: 134
ggctactaca tgaac                                                    15

SEQ ID NO: 135         moltype = DNA   length = 42
FEATURE                Location/Qualifiers
misc_feature           1..42
                       note = Engineered antibody sequence
source                 1..42
                       mol_type = other DNA
                       organism = synthetic construct
SEQUENCE: 135
tgggtccgcc aggctccagg gaaggggctg gaatggatcg ga                      42

SEQ ID NO: 136         moltype = DNA   length = 48
FEATURE                Location/Qualifiers
misc_feature           1..48
                       note = Engineered antibody sequence
source                 1..48
```

```
                              mol_type = other DNA
                              organism = synthetic construct
SEQUENCE: 136
gtcattggta ttaatggtgc cacatactac gcgagctggg cgaaaggc                    48

SEQ ID NO: 137           moltype = DNA  length = 93
FEATURE                  Location/Qualifiers
misc_feature             1..93
                         note = Engineered antibody sequence
source                   1..93
                         mol_type = other DNA
                         organism = synthetic construct
SEQUENCE: 137
cgattcacca tctccaaaac ctcgtcgacc acggtggatc tgaaaatgac cagtctgaca       60
accgaggaca cggccaccta tttctgtgcc aga                                    93

SEQ ID NO: 138           moltype =    length =
SEQUENCE: 138
000

SEQ ID NO: 139           moltype = DNA  length = 33
FEATURE                  Location/Qualifiers
misc_feature             1..33
                         note = Engineered antibody sequence
source                   1..33
                         mol_type = other DNA
                         organism = synthetic construct
SEQUENCE: 139
tggggcccgg gcaccctcgt caccgtctcg agc                                    33

SEQ ID NO: 140           moltype = DNA  length = 993
FEATURE                  Location/Qualifiers
misc_feature             1..993
                         note = Engineered antibody sequence
source                   1..993
                         mol_type = other DNA
                         organism = synthetic construct
SEQUENCE: 140
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagaa agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggaccccc      420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacgcc      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag ggcagccccg agaaccacag gtgtacaccc tgcccccatc ccgggaggag      720
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa tga                                   993

SEQ ID NO: 141           moltype = AA  length = 219
FEATURE                  Location/Qualifiers
REGION                   1..219
                         note = Engineered antibody sequence
source                   1..219
                         mol_type = protein
                         organism = synthetic construct
SEQUENCE: 141
QVLTQTPSPV SAAVGSTVTI NCQASQSVYH NTYLAWYQQK PGQPPKQLIY DASTLASGVP       60
SRFSGSGSGT QFTLTISGVQ CNDAAAYYCL GSYDCTNGDC FVFGGGTEVV VKRTVAAPSV      120
FIFPPSDEQL KSGTASVVCL LNNFYPREAK VQWKVDNALQ SGNSQESVTE QDSKDSTYSL      180
SSTLTLSKAD YEKHKVYACE VTHQGLSSPV TKSFNRGEC                             219

SEQ ID NO: 142           moltype = AA  length = 113
FEATURE                  Location/Qualifiers
REGION                   1..113
                         note = Engineered antibody sequence
source                   1..113
                         mol_type = protein
                         organism = synthetic construct
SEQUENCE: 142
QVLTQTPSPV SAAVGSTVTI NCQASQSVYH NTYLAWYQQK PGQPPKQLIY DASTLASGVP       60
SRFSGSGSGT QFTLTISGVQ CNDAAAYYCL GSYDCTNGDC FVFGGGTEVV VKR             113
```

```
SEQ ID NO: 143          moltype = AA  length = 22
FEATURE                 Location/Qualifiers
REGION                  1..22
                        note = Engineered antibody sequence
source                  1..22
                        mol_type = protein
                        organism = synthetic construct
SEQUENCE: 143
QVLTQTPSPV SAAVGSTVTI NC                                              22

SEQ ID NO: 144          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 144
QASQSVYHNT YLA                                                        13

SEQ ID NO: 145          moltype = AA  length = 15
FEATURE                 Location/Qualifiers
REGION                  1..15
                        note = Engineered antibody sequence
source                  1..15
                        mol_type = protein
                        organism = synthetic construct
SEQUENCE: 145
WYQQKPGQPP KQLIY                                                      15

SEQ ID NO: 146          moltype = AA  length = 7
FEATURE                 Location/Qualifiers
REGION                  1..7
                        note = Engineered antibody sequence
source                  1..7
                        mol_type = protein
                        organism = synthetic construct
SEQUENCE: 146
DASTLAS                                                               7

SEQ ID NO: 147          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 147
GVPSRFSGSG SGTQFTLTIS GVQCNDAAAY YC                                   32

SEQ ID NO: 148          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 148
LGSYDCTNGD CFV                                                        13

SEQ ID NO: 149          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 149
FGGGTEVVVK R                                                          11

SEQ ID NO: 150          moltype = AA  length = 106
FEATURE                 Location/Qualifiers
REGION                  1..106
                        note = Engineered antibody sequence
source                  1..106
                        mol_type = protein
                        organism = synthetic construct
SEQUENCE: 150
```

TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

```
SEQ ID NO: 151          moltype = DNA   length = 660
FEATURE                 Location/Qualifiers
misc_feature            1..660
                        note = Engineered antibody sequence
source                  1..660
                        mol_type = other DNA
                        organism = synthetic construct
SEQUENCE: 151
caagtgctga cccagactcc atccccgtg tctgcagctg tgggaagcac agtcaccatc      60
aattgccagg ccagtcagag tgtttatcat aacacctacc tggcctggta tcagcagaaa   120
ccagggcagc ctcccaaaca actgatctat gatgcatcca ctctggcgtc tggggtccca   180
tcgcggttca gcggcagtgg atctgggaca cagttcactc tcaccatcag cggcgtgcag   240
tgtaacgatg ctgccgctta ctactgtctg ggcagttatg attgtactaa tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 152          moltype = DNA   length = 339
FEATURE                 Location/Qualifiers
misc_feature            1..339
                        note = Engineered antibody sequence
source                  1..339
                        mol_type = other DNA
                        organism = synthetic construct
SEQUENCE: 152
caagtgctga cccagactcc atccccgtg tctgcagctg tgggaagcac agtcaccatc      60
aattgccagg ccagtcagag tgtttatcat aacacctacc tggcctggta tcagcagaaa   120
ccagggcagc ctcccaaaca actgatctat gatgcatcca ctctggcgtc tggggtccca   180
tcgcggttca gcggcagtgg atctgggaca cagttcactc tcaccatcag cggcgtgcag   240
tgtaacgatg ctgccgctta ctactgtctg ggcagttatg attgtactaa tggtgattgt   300
tttgttttcg gcggagggac cgaggtggtg gtcaaacgt                          339

SEQ ID NO: 153          moltype = DNA   length = 66
FEATURE                 Location/Qualifiers
misc_feature            1..66
                        note = Engineered antibody sequence
source                  1..66
                        mol_type = other DNA
                        organism = synthetic construct
SEQUENCE: 153
caagtgctga cccagactcc atccccgtg tctgcagctg tgggaagcac agtcaccatc      60
aattgc                                                                66

SEQ ID NO: 154          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 154
caggccagtc agagtgttta tcataacacc tacctggcc                            39

SEQ ID NO: 155          moltype = DNA   length = 45
FEATURE                 Location/Qualifiers
misc_feature            1..45
                        note = Engineered antibody sequence
source                  1..45
                        mol_type = other DNA
                        organism = synthetic construct
SEQUENCE: 155
tggtatcagc agaaaccagg gcagcctccc aaacaactga tctat                     45

SEQ ID NO: 156          moltype = DNA   length = 21
FEATURE                 Location/Qualifiers
misc_feature            1..21
                        note = Engineered antibody sequence
source                  1..21
                        mol_type = other DNA
                        organism = synthetic construct
SEQUENCE: 156
gatgcatcca ctctggcgtc t                                               21
```

| SEQ ID NO: 157 | moltype = DNA   length = 96 |
| --- | --- |
| FEATURE | Location/Qualifiers |
| misc_feature | 1..96 |
| | note = Engineered antibody sequence |
| source | 1..96 |
| | mol_type = other DNA |
| | organism = synthetic construct |

SEQUENCE: 157
```
ggggtcccat cgcggttcag cggcagtgga tctgggacac agttcactct caccatcagc    60
ggcgtgcagt gtaacgatgc tgccgcttac tactgt                              96
```

| SEQ ID NO: 158 | moltype = DNA   length = 39 |
| --- | --- |
| FEATURE | Location/Qualifiers |
| misc_feature | 1..39 |
| | note = Engineered antibody sequence |
| source | 1..39 |
| | mol_type = other DNA |
| | organism = synthetic construct |

SEQUENCE: 158
```
ctgggcagtt atgattgtac taatggtgat tgttttgtt                           39
```

| SEQ ID NO: 159 | moltype = DNA   length = 33 |
| --- | --- |
| FEATURE | Location/Qualifiers |
| misc_feature | 1..33 |
| | note = Engineered antibody sequence |
| source | 1..33 |
| | mol_type = other DNA |
| | organism = synthetic construct |

SEQUENCE: 159
```
ttcggcggag ggaccgaggt ggtggtcaaa cgt                                 33
```

| SEQ ID NO: 160 | moltype = DNA   length = 321 |
| --- | --- |
| FEATURE | Location/Qualifiers |
| misc_feature | 1..321 |
| | note = Engineered antibody sequence |
| source | 1..321 |
| | mol_type = other DNA |
| | organism = synthetic construct |

SEQUENCE: 160
```
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321
```

| SEQ ID NO: 161 | moltype = AA   length = 441 |
| --- | --- |
| FEATURE | Location/Qualifiers |
| REGION | 1..441 |
| | note = Engineered antibody sequence |
| source | 1..441 |
| | mol_type = protein |
| | organism = synthetic construct |

SEQUENCE: 161
```
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKRVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441
```

| SEQ ID NO: 162 | moltype = AA   length = 111 |
| --- | --- |
| FEATURE | Location/Qualifiers |
| REGION | 1..111 |
| | note = Engineered antibody sequence |
| source | 1..111 |
| | mol_type = protein |
| | organism = synthetic construct |

SEQUENCE: 162
```
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS S            111
```

| SEQ ID NO: 163 | moltype = AA   length = 30 |
| --- | --- |
| FEATURE | Location/Qualifiers |
| REGION | 1..30 |
| | note = Engineered antibody sequence |
| source | 1..30 |

```
                        mol_type = protein
                        organism = synthetic construct
SEQUENCE: 163
EVQLVESGGG LVQPGGSLRL SCAVSGIDLS                              30

SEQ ID NO: 164          moltype = AA   length = 5
FEATURE                 Location/Qualifiers
REGION                  1..5
                        note = Engineered antibody sequence
source                  1..5
                        mol_type = protein
                        organism = synthetic construct
SEQUENCE: 164
GYYMN                                                         5

SEQ ID NO: 165          moltype = AA   length = 14
FEATURE                 Location/Qualifiers
REGION                  1..14
                        note = Engineered antibody sequence
source                  1..14
                        mol_type = protein
                        organism = synthetic construct
SEQUENCE: 165
WVRQAPGKGL EWVG                                               14

SEQ ID NO: 166          moltype = AA   length = 16
FEATURE                 Location/Qualifiers
REGION                  1..16
                        note = Engineered antibody sequence
source                  1..16
                        mol_type = protein
                        organism = synthetic construct
SEQUENCE: 166
VIGINGATYY ASWAKG                                             16

SEQ ID NO: 167          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 167
RFTISRDNSK TTVYLQMNSL RAEDTAVYFC AR                           32

SEQ ID NO: 168          moltype =      length =
SEQUENCE: 168
000

SEQ ID NO: 169          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 169
WGQGTLVTVS S                                                  11

SEQ ID NO: 170          moltype = AA   length = 330
FEATURE                 Location/Qualifiers
REGION                  1..330
                        note = Engineered antibody sequence
source                  1..330
                        mol_type = protein
                        organism = synthetic construct
SEQUENCE: 170
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 171          moltype = DNA  length = 1326
FEATURE                 Location/Qualifiers
misc_feature            1..1326
                        note = Engineered antibody sequence
source                  1..1326
```

```
                        mol_type = other DNA
                        organism = synthetic construct
SEQUENCE: 171
gaggtgcagc ttgtggagtc tgggggaggc ttggtccagc ctgggggtc cctgagactc    60
tcctgtgcag tctctggaat cgacctcagt ggctactaca tgaactggtc ccgtcaggct   120
ccagggaagg ggctggagtg ggtcggagtc attggtatta atggtgccac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag ggaccctcgt caccgtctcg agcgcctcca caagggccc atcggtcttc    360
cccctggcac cctcctccaa gagcacctct gggggcacag cggccctggg ctgcctggtc   420
aaggactact ccccgaacc ggtgacggtg tcgtggaact caggcgccct gaccagcggc    480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacaa gagagttgag cccaaatctt gtgacaaaac tcacacatgc   660
ccaccgtgcc cagcacctga actcctgggg ggaccgtcag tcttcctctt cccccccaaaa  720
cccaaggaca ccctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag ccccatcga gaaaaccatc tccaaagcca aagggcagcc ccgagaacca   1020
caggtgtaca ccctgcccc atcccgggag gagatgacca gaaccaggt cagcctgacc    1080
tgcctggtca aaggcttcta tcccagcgac atcgccgttg aggagagcaa tgggcagccg   1140
gagaacaact acaagaccac acgcctccc gtgctggact ccgacggctc cttcttcctc    1200
tacagcaagc tcaccgtgga caagagcagg tggcagcagg gaacgtcttc tcatgctcc   1260
gtgatgcatg aggctctgca caaccactac acgcagaaga gcctctccct gtctccgggt   1320
aaatga                                                             1326

SEQ ID NO: 172          moltype = DNA   length = 333
FEATURE                 Location/Qualifiers
misc_feature            1..333
                        note = Engineered antibody sequence
source                  1..333
                        mol_type = other DNA
                        organism = synthetic construct
SEQUENCE: 172
gaggtgcagc ttgtggagtc tgggggaggc ttggtccagc ctgggggtc cctgagactc    60
tcctgtgcag tctctggaat cgacctcagt ggctactaca tgaactgggt ccgtcaggct   120
ccagggaagg ggctggagtg ggtcggagtc attggtatta atggtgccac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag ggaccctcgt caccgtctcg agc                                333

SEQ ID NO: 173          moltype = DNA   length = 90
FEATURE                 Location/Qualifiers
misc_feature            1..90
                        note = Engineered antibody sequence
source                  1..90
                        mol_type = other DNA
                        organism = synthetic construct
SEQUENCE: 173
gaggtgcagc ttgtggagtc tgggggaggc ttggtccagc ctgggggtc cctgagactc    60
tcctgtgcag tctctggaat cgacctcagt                                    90

SEQ ID NO: 174          moltype = DNA   length = 15
FEATURE                 Location/Qualifiers
misc_feature            1..15
                        note = Engineered antibody sequence
source                  1..15
                        mol_type = other DNA
                        organism = synthetic construct
SEQUENCE: 174
ggctactaca tgaac                                                    15

SEQ ID NO: 175          moltype = DNA   length = 42
FEATURE                 Location/Qualifiers
misc_feature            1..42
                        note = Engineered antibody sequence
source                  1..42
                        mol_type = other DNA
                        organism = synthetic construct
SEQUENCE: 175
tgggtccgtc aggctccagg gaaggggctg gagtgggtcg ga                      42

SEQ ID NO: 176          moltype = DNA   length = 48
FEATURE                 Location/Qualifiers
misc_feature            1..48
                        note = Engineered antibody sequence
source                  1..48
                        mol_type = other DNA
```

```
                            organism = synthetic construct
SEQUENCE: 176
gtcattggta ttaatggtgc cacatactac gcgagctggg cgaaaggc                    48

SEQ ID NO: 177           moltype = DNA  length = 96
FEATURE                  Location/Qualifiers
misc_feature             1..96
                         note = Engineered antibody sequence
source                   1..96
                         mol_type = other DNA
                         organism = synthetic construct
SEQUENCE: 177
cgattcacca tctccagaga caattccaag accacggtgt atcttcaaat gaacagcctg        60
agagctgagg acactgctgt gtatttctgt gctaga                                  96

SEQ ID NO: 178           moltype =    length =
SEQUENCE: 178
000

SEQ ID NO: 179           moltype = DNA  length = 33
FEATURE                  Location/Qualifiers
misc_feature             1..33
                         note = Engineered antibody sequence
source                   1..33
                         mol_type = other DNA
                         organism = synthetic construct
SEQUENCE: 179
tggggccaag ggaccctcgt caccgtctcg agc                                     33

SEQ ID NO: 180           moltype = DNA  length = 993
FEATURE                  Location/Qualifiers
misc_feature             1..993
                         note = Engineered antibody sequence
source                   1..993
                         mol_type = other DNA
                         organism = synthetic construct
SEQUENCE: 180
gcctccacca agggcccatc ggtcttcccc ctggcaccct cctccaagag cacctctggg        60
ggcacagcgg ccctgggctg cctggtcaag gactacttcc ccgaaccggt gacggtgtcg       120
tggaactcag gcgccctgac cagcggcgtg cacaccttcc cggctgtcct acagtcctca       180
ggactctact ccctcagcag cgtggtgacc gtgccctcca gcagcttggg cacccagacc       240
tacatctgca acgtgaatca caagcccagc aacaccaagg tggacaagag agttgagccc       300
aaatcttgtg acaaaactca cacatgccca ccgtgcccag cacctgaact cctggggggga      360
ccgtcagtct tcctcttccc cccaaaaccc aaggacaccc tcatgatctc ccggacccct       420
gaggtcacat gcgtggtggt ggacgtgagc cacgaagacc ctgaggtcaa gttcaactgg       480
tacgtggacg gcgtggaggt gcataatgcc aagacaaagc cgcgggagga gcagtacgcc       540
agcacgtacc gtgtggtcag cgtcctcacc gtcctgcacc aggactggct gaatggcaag       600
gagtacaagt gcaaggtctc caacaaagcc ctcccagccc ccatcgagaa aaccatctcc       660
aaagccaaag gcagccccg agaaccacag gtgtacaccc tgcccccatc ccgggaggag        720
atgaccaaga accaggtcag cctgacctgc ctggtcaaag gcttctatcc cagcgacatc       780
gccgtggagt gggagagcaa tgggcagccg gagaacaact acaagaccac gcctcccgtg       840
ctggactccg acggctcctt cttcctctac agcaagctca ccgtggacaa gagcaggtgg       900
cagcagggga acgtcttctc atgctccgtg atgcatgagg ctctgcacaa ccactacacg       960
cagaagagcc tctccctgtc tccgggtaaa tga                                    993

SEQ ID NO: 181           moltype = AA  length = 219
FEATURE                  Location/Qualifiers
REGION                   1..219
                         note = Engineered antibody sequence
source                   1..219
                         mol_type = protein
                         organism = synthetic construct
SEQUENCE: 181
QVLTQSPSSL SASVGDRVTI NCQASQSVYH NTYLAWYQQK PGKVPKQLIY DASTLASGVP        60
SRFSGSGSGT DFTLTISSLQ PEDVATYYCL GSYDCTNGDC FVFGGGTKVE IKRTVAAPSV       120
FIFPPSDEQL KSGTASVVCL LNNFYPREAK VQWKVDNALQ SGNSQESVTE QDSKDSTYSL       180
SSTLTLSKAD YEKHKVYACE VTHQGLSSPV TKSFNRGEC                              219

SEQ ID NO: 182           moltype = AA  length = 113
FEATURE                  Location/Qualifiers
REGION                   1..113
                         note = Engineered antibody sequence
source                   1..113
                         mol_type = protein
                         organism = synthetic construct
SEQUENCE: 182
QVLTQSPSSL SASVGDRVTI NCQASQSVYH NTYLAWYQQK PGKVPKQLIY DASTLASGVP        60
SRFSGSGSGT DFTLTISSLQ PEDVATYYCL GSYDCTNGDC FVFGGGTKVE IKR              113
```

```
SEQ ID NO: 183          moltype = AA  length = 22
FEATURE                 Location/Qualifiers
REGION                  1..22
                        note = Engineered antibody sequence
source                  1..22
                        mol_type = protein
                        organism = synthetic construct
SEQUENCE: 183
QVLTQSPSSL SASVGDRVTI NC                                           22

SEQ ID NO: 184          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 184
QASQSVYHNT YLA                                                     13

SEQ ID NO: 185          moltype = AA  length = 15
FEATURE                 Location/Qualifiers
REGION                  1..15
                        note = Engineered antibody sequence
source                  1..15
                        mol_type = protein
                        organism = synthetic construct
SEQUENCE: 185
WYQQKPGKVP KQLIY                                                   15

SEQ ID NO: 186          moltype = AA  length = 7
FEATURE                 Location/Qualifiers
REGION                  1..7
                        note = Engineered antibody sequence
source                  1..7
                        mol_type = protein
                        organism = synthetic construct
SEQUENCE: 186
DASTLAS                                                             7

SEQ ID NO: 187          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 187
GVPSRFSGSG SGTDFTLTIS SLQPEDVATY YC                                32

SEQ ID NO: 188          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 188
LGSYDCTNGD CFV                                                     13

SEQ ID NO: 189          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 189
FGGGTKVEIK R                                                       11

SEQ ID NO: 190          moltype = AA  length = 106
FEATURE                 Location/Qualifiers
REGION                  1..106
                        note = Engineered antibody sequence
source                  1..106
                        mol_type = protein
                        organism = synthetic construct
SEQUENCE: 190
TVAAPSVFIF PPSDEQLKSG TASVVCLLNN FYPREAKVQW KVDNALQSGN SQESVTEQDS   60
```

KDSTYSLSST LTLSKADYEK HKVYACEVTH QGLSSPVTKS FNRGEC                106

SEQ ID NO: 191          moltype = DNA   length = 660
FEATURE                 Location/Qualifiers
misc_feature            1..660
                        note = Engineered antibody sequence
source                  1..660
                        mol_type = other DNA
                        organism = synthetic construct
SEQUENCE: 191
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cctgaagatg   240
cctgaagatg ttgcaactta ttactgtctg ggcagttatg attgtactaa tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 192          moltype = DNA   length = 339
FEATURE                 Location/Qualifiers
misc_feature            1..339
                        note = Engineered antibody sequence
source                  1..339
                        mol_type = other DNA
                        organism = synthetic construct
SEQUENCE: 192
caagtgctga cccagtctcc atcctccctg tctgcatctg taggagacag agtcaccatc    60
aattgccagg ccagtcagag tgtttatcat aacacctacc tggcctggta tcagcagaaa   120
ccagggaaag ttcctaagca actgatctat gatgcatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtactaa tggtgattgt   300
tttgttttcg gcggaggaac caaggtggaa atcaaacgt                          339

SEQ ID NO: 193          moltype = DNA   length = 66
FEATURE                 Location/Qualifiers
misc_feature            1..66
                        note = Engineered antibody sequence
source                  1..66
                        mol_type = other DNA
                        organism = synthetic construct
SEQUENCE: 193
caagtgctga cccagtctcc atcctccctg tctgcatctg taggagacag agtcaccatc    60
aattgc                                                               66

SEQ ID NO: 194          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 194
caggccagtc agagtgttta tcataacacc tacctggcc                           39

SEQ ID NO: 195          moltype = DNA   length = 45
FEATURE                 Location/Qualifiers
misc_feature            1..45
                        note = Engineered antibody sequence
source                  1..45
                        mol_type = other DNA
                        organism = synthetic construct
SEQUENCE: 195
tggtatcagc agaaaccagg gaaagttcct aagcaactga tctat                    45

SEQ ID NO: 196          moltype = DNA   length = 21
FEATURE                 Location/Qualifiers
misc_feature            1..21
                        note = Engineered antibody sequence
source                  1..21
                        mol_type = other DNA
                        organism = synthetic construct
SEQUENCE: 196
gatgcatcca ctctggcatc t                                              21

SEQ ID NO: 197          moltype = DNA   length = 96

```
FEATURE                 Location/Qualifiers
misc_feature            1..96
                        note = Engineered antibody sequence
source                  1..96
                        mol_type = other DNA
                        organism = synthetic construct
SEQUENCE: 197
ggggtcccat ctcgtttcag tggcagtgga tctgggacag atttcactct caccatcagc    60
agcctgcagc ctgaagatgt tgcaacttat tactgt                              96

SEQ ID NO: 198          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 198
ctgggcagtt atgattgtac taatggtgat tgttttgtt                           39

SEQ ID NO: 199          moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 199
ttcggcggag gaaccaaggt ggaaatcaaa cgt                                 33

SEQ ID NO: 200          moltype = DNA   length = 321
FEATURE                 Location/Qualifiers
misc_feature            1..321
                        note = Engineered antibody sequence
source                  1..321
                        mol_type = other DNA
                        organism = synthetic construct
SEQUENCE: 200
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 201          moltype = AA   length = 441
FEATURE                 Location/Qualifiers
REGION                  1..441
                        note = Engineered antibody sequence
source                  1..441
                        mol_type = protein
                        organism = synthetic construct
SEQUENCE: 201
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDARVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 202          moltype = AA   length = 111
FEATURE                 Location/Qualifiers
REGION                  1..111
                        note = Engineered antibody sequence
source                  1..111
                        mol_type = protein
                        organism = synthetic construct
SEQUENCE: 202
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS S            111

SEQ ID NO: 203          moltype = AA   length = 30
FEATURE                 Location/Qualifiers
REGION                  1..30
                        note = Engineered antibody sequence
source                  1..30
                        mol_type = protein
```

```
                              organism = synthetic construct
SEQUENCE: 203
EVQLVESGGG LVQPGGSLRL SCAVSGIDLS                                                30

SEQ ID NO: 204          moltype = AA  length = 5
FEATURE                 Location/Qualifiers
REGION                  1..5
                        note = Engineered antibody sequence
source                  1..5
                        mol_type = protein
                        organism = synthetic construct
SEQUENCE: 204
GYYMN                                                                            5

SEQ ID NO: 205          moltype = AA  length = 14
FEATURE                 Location/Qualifiers
REGION                  1..14
                        note = Engineered antibody sequence
source                  1..14
                        mol_type = protein
                        organism = synthetic construct
SEQUENCE: 205
WVRQAPGKGL EWVG                                                                 14

SEQ ID NO: 206          moltype = AA  length = 16
FEATURE                 Location/Qualifiers
REGION                  1..16
                        note = Engineered antibody sequence
source                  1..16
                        mol_type = protein
                        organism = synthetic construct
SEQUENCE: 206
VIGINGATYY ASWAKG                                                               16

SEQ ID NO: 207          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 207
RFTISRDNSK TTVYLQMNSL RAEDTAVYFC AR                                             32

SEQ ID NO: 208          moltype =   length =
SEQUENCE: 208
000

SEQ ID NO: 209          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 209
WGQGTLVTVS S                                                                    11

SEQ ID NO: 210          moltype = AA  length = 330
FEATURE                 Location/Qualifiers
REGION                  1..330
                        note = Engineered antibody sequence
source                  1..330
                        mol_type = protein
                        organism = synthetic construct
SEQUENCE: 210
ASTKGPSVFP LAPSSKSTSG GTAALGCLVK DYFPEPVTVS WNSGALTSGV HTFPAVLQSS               60
GLYSLSSVVT VPSSSLGTQT YICNVNHKPS NTKVDKRVEP KSCDKTHTCP PCPAPELLGG              120
PSVFLFPPKP KDTLMISRTP EVTCVVVDVS HEDPEVKFNW YVDGVEVHNA KTKPREEQYA              180
STYRVVSVLT VLHQDWLNGK EYKCKVSNKA LPAPIEKTIS KAKGQPREPQ VYTLPPSREE              240
MTKNQVSLTC LVKGFYPSDI AVEWESNGQP ENNYKTTPPV LDSDGSFFLY SKLTVDKSRW              300
QQGNVFSCSV MHEALHNHYT QKSLSLSPGK                                               330

SEQ ID NO: 211          moltype = DNA  length = 1326
FEATURE                 Location/Qualifiers
misc_feature            1..1326
                        note = Engineered antibody sequence
source                  1..1326
                        mol_type = other DNA
```

```
                        organism = synthetic construct
SEQUENCE: 211
gaggtgcagc ttgtggagtc tgggggaggc ttggtccagc ctgggggtc cctgagactc    60
tcctgtgcag tctctggaat cgacctcagt ggctactaca tgaactgggt ccgtcaggct   120
ccagggaagg ggctggagtg ggtcggagtc attggtatta atggtgccac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag ggaccctcgt caccgtctcg agcgcctcca ccaagggccc atcggtcttc   360
cccctggcac cctcctccaa gagcacctct ggggcacag cggccctggg ctgcctggtc    420
aaggactact ccccgaacc ggtgacggtg tcgtggaact caggcgccct gaccagcggc    480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacgc gagagttgag cccaaatctt gtgacaaaac tcacacatgc   660
ccaccgtgcc cagcacctga actcctgggg gaccgtcagt cttcctcttc cccccaaaa    720
cccaaggaca ccctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca aagggcagcc ccgagaacca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg ggaacgtctt ctcatgctcc  1260
gtgatgcatg aggctctgca caaccactac acgcagaaga gcctctccct gtctccgggt  1320
aaatga                                                              1326

SEQ ID NO: 212          moltype = DNA  length = 333
FEATURE                 Location/Qualifiers
misc_feature            1..333
                        note = Engineered antibody sequence
source                  1..333
                        mol_type = other DNA
                        organism = synthetic construct
SEQUENCE: 212
gaggtgcagc ttgtggagtc tgggggaggc ttggtccagc ctgggggtc cctgagactc    60
tcctgtgcag tctctggaat cgacctcagt ggctactaca tgaactgggt ccgtcaggct   120
ccagggaagg ggctggagtg ggtcggagtc attggtatta atggtgccac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag ggaccctcgt caccgtctcg agc                                333

SEQ ID NO: 213          moltype = DNA  length = 90
FEATURE                 Location/Qualifiers
misc_feature            1..90
                        note = Engineered antibody sequence
source                  1..90
                        mol_type = other DNA
                        organism = synthetic construct
SEQUENCE: 213
gaggtgcagc ttgtggagtc tgggggaggc ttggtccagc ctgggggtc cctgagactc    60
tcctgtgcag tctctggaat cgacctcagt                                    90

SEQ ID NO: 214          moltype = DNA  length = 15
FEATURE                 Location/Qualifiers
misc_feature            1..15
                        note = Engineered antibody sequence
source                  1..15
                        mol_type = other DNA
                        organism = synthetic construct
SEQUENCE: 214
ggctactaca tgaac                                                    15

SEQ ID NO: 215          moltype = DNA  length = 42
FEATURE                 Location/Qualifiers
misc_feature            1..42
                        note = Engineered antibody sequence
source                  1..42
                        mol_type = other DNA
                        organism = synthetic construct
SEQUENCE: 215
tgggtccgtc aggctccagg gaaggggctg gagtgggtcg ga                      42

SEQ ID NO: 216          moltype = DNA  length = 48
FEATURE                 Location/Qualifiers
misc_feature            1..48
                        note = Engineered antibody sequence
source                  1..48
                        mol_type = other DNA
                        organism = synthetic construct
```

| SEQUENCE: 216 | | |
|---|---|---|
| gtcattggta ttaatggtgc cacatactac gcgagctggg cgaaaggc | | 48 |

| SEQ ID NO: 217 | moltype = DNA  length = 96 |
|---|---|
| FEATURE | Location/Qualifiers |
| misc_feature | 1..96 |
| | note = Engineered antibody sequence |
| source | 1..96 |
| | mol_type = other DNA |
| | organism = synthetic construct |

| SEQUENCE: 217 | | |
|---|---|---|
| cgattcacca tctccagaga caattccaag accacggtgt atcttcaaat gaacagcctg | | 60 |
| agagctgagg acactgctgt gtatttctgt gctaga | | 96 |

| SEQ ID NO: 218 | moltype =   length = |
|---|---|
| SEQUENCE: 218 | |
| 000 | |

| SEQ ID NO: 219 | moltype = DNA  length = 33 |
|---|---|
| FEATURE | Location/Qualifiers |
| misc_feature | 1..33 |
| | note = Engineered antibody sequence |
| source | 1..33 |
| | mol_type = other DNA |
| | organism = synthetic construct |

| SEQUENCE: 219 | | |
|---|---|---|
| tggggccaag ggaccctcgt caccgtctcg agc | | 33 |

| SEQ ID NO: 220 | moltype = DNA  length = 993 |
|---|---|
| FEATURE | Location/Qualifiers |
| misc_feature | 1..993 |
| | note = Engineered antibody sequence |
| source | 1..993 |
| | mol_type = other DNA |
| | organism = synthetic construct |

| SEQUENCE: 220 | | |
|---|---|---|
| gcctccacca agggcccatc ggtcttcccc ctggcaccct cctccaagag cacctctggg | | 60 |
| ggcacagcgg ccctgggctg cctggtcaag gactacttcc ccgaaccggt gacggtgtcg | | 120 |
| tggaactcag gcgccctgac cagcggcgtg cacaccttcc cggctgtcct acagtcctca | | 180 |
| ggactctact ccctcagcag cgtggtgacc gtgccctcca gcagcttggg cacccagacc | | 240 |
| tacatctgca acgtgaatca caagcccagc aacaccaagg tggacgcgag agttgagccc | | 300 |
| aaatcttgtg acaaaactca cacatgccca ccgtgcccag cacctgaact cctgggggga | | 360 |
| ccgtcagtct tcctcttccc cccaaaaccc aaggacaccc tcatgatctc ccggacccct | | 420 |
| gaggtcacat gcgtggtggt ggacgtgagc cacgaagacc ctgaggtcaa gttcaactgg | | 480 |
| tacgtggacg gcgtggaggt gcataatgcc aagacaaagc cgcgggagga gcagtacgcc | | 540 |
| agcacgtacc gtgtggtcag cgtcctcacc gtcctgcacc aggactggct gaatggcaag | | 600 |
| gagtacaagt gcaaggtctc caacaaagcc ctcccagccc ccatcgagaa aaccatctca | | 660 |
| aaagccaaag ggcagccccg agaaccacag gtgtacaccc tgcccccatc ccgggaggag | | 720 |
| atgaccaaga accaggtcag cctgacctgc ctggtcaaag gcttctatcc cagcgacatc | | 780 |
| gccgtggagt gggagagcaa tgggcagccg gagaacaact acaagaccac gcctcccgtg | | 840 |
| ctggactccg acggctcctt cttcctctac agcaagctca ccgtggacaa gagcaggtgg | | 900 |
| cagcagggga acgtcttctc atgctccgtg atgcatgagg ctctgcacaa ccactacacg | | 960 |
| cagaagagcc tctccctgtc tccgggtaaa tga | | 993 |

| SEQ ID NO: 221 | moltype = AA  length = 219 |
|---|---|
| FEATURE | Location/Qualifiers |
| REGION | 1..219 |
| | note = Engineered antibody sequence |
| source | 1..219 |
| | mol_type = protein |
| | organism = synthetic construct |

| SEQUENCE: 221 | | |
|---|---|---|
| QVLTQSPSSL SASVGDRVTI NCQASQSVYH NTYLAWYQQK PGKVPKQLIY DASTLASGVP | | 60 |
| SRFSGSGSGT DFTLTISSLQ PEDVATYYCL GSYDCTNGDC FVFGGGTKVE IKRTVAAPSV | | 120 |
| FIFPPSDEQL KSGTASVVCL LNNFYPREAK VQWKVDNALQ SGNSQESVTE QDSKDSTYSL | | 180 |
| SSTLTLSKAD YEKHKVYACE VTHQGLSSPV TKSFNRGEC | | 219 |

| SEQ ID NO: 222 | moltype = AA  length = 113 |
|---|---|
| FEATURE | Location/Qualifiers |
| REGION | 1..113 |
| | note = Engineered antibody sequence |
| source | 1..113 |
| | mol_type = protein |
| | organism = synthetic construct |

| SEQUENCE: 222 | | |
|---|---|---|
| QVLTQSPSSL SASVGDRVTI NCQASQSVYH NTYLAWYQQK PGKVPKQLIY DASTLASGVP | | 60 |
| SRFSGSGSGT DFTLTISSLQ PEDVATYYCL GSYDCTNGDC FVFGGGTKVE IKR | | 113 |

| SEQ ID NO: 223 | moltype = AA  length = 22 |
|---|---|

```
FEATURE                 Location/Qualifiers
REGION                  1..22
                        note = Engineered antibody sequence
source                  1..22
                        mol_type = protein
                        organism = synthetic construct
SEQUENCE: 223
QVLTQSPSSL SASVGDRVTI NC                                              22

SEQ ID NO: 224          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 224
QASQSVYHNT YLA                                                        13

SEQ ID NO: 225          moltype = AA  length = 15
FEATURE                 Location/Qualifiers
REGION                  1..15
                        note = Engineered antibody sequence
source                  1..15
                        mol_type = protein
                        organism = synthetic construct
SEQUENCE: 225
WYQQKPGKVP KQLIY                                                      15

SEQ ID NO: 226          moltype = AA  length = 7
FEATURE                 Location/Qualifiers
REGION                  1..7
                        note = Engineered antibody sequence
source                  1..7
                        mol_type = protein
                        organism = synthetic construct
SEQUENCE: 226
DASTLAS                                                                7

SEQ ID NO: 227          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 227
GVPSRFSGSG SGTDFTLTIS SLQPEDVATY YC                                   32

SEQ ID NO: 228          moltype = AA  length = 13
FEATURE                 Location/Qualifiers
REGION                  1..13
                        note = Engineered antibody sequence
source                  1..13
                        mol_type = protein
                        organism = synthetic construct
SEQUENCE: 228
LGSYDCTNGD CFV                                                        13

SEQ ID NO: 229          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 229
FGGGTKVEIK R                                                          11

SEQ ID NO: 230          moltype = AA  length = 106
FEATURE                 Location/Qualifiers
REGION                  1..106
                        note = Engineered antibody sequence
source                  1..106
                        mol_type = protein
                        organism = synthetic construct
SEQUENCE: 230
TVAAPSVFIF PPSDEQLKSG TASVVCLLNN FYPREAKVQW KVDNALQSGN SQESVTEQDS     60
KDSTYSLSST LTLSKADYEK HKVYACEVTH QGLSSPVTKS FNRGEC                   106
```

```
SEQ ID NO: 231           moltype = DNA   length = 660
FEATURE                  Location/Qualifiers
misc_feature             1..660
                         note = Engineered antibody sequence
source                   1..660
                         mol_type = other DNA
                         organism = synthetic construct
SEQUENCE: 231
caagtgctga cccagtctcc atcctccctg tctgcatctg taggagacag agtcaccatc   60
aattgccagg ccagtcagag tgtttatcat aacacctacc tggcctggta tcagcagaaa  120
ccagggaaag ttcctaagca actgatctat gatgcatcca ctctggcatc tggggtccca  180
tctcgtttca gtggcagtgg atctgggaca gatttcactc tcaccatcag cagcctgcag  240
cctgaagatg ttgcaactta ttactgtctg ggcagttatg attgtactaa tggtgattgt  300
tttgttttcg gcggaggaac caaggtggaa atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttag  660

SEQ ID NO: 232           moltype = DNA   length = 339
FEATURE                  Location/Qualifiers
misc_feature             1..339
                         note = Engineered antibody sequence
source                   1..339
                         mol_type = other DNA
                         organism = synthetic construct
SEQUENCE: 232
caagtgctga cccagtctcc atcctccctg tctgcatctg taggagacag agtcaccatc   60
aattgccagg ccagtcagag tgtttatcat aacacctacc tggcctggta tcagcagaaa  120
ccagggaaag ttcctaagca actgatctat gatgcatcca ctctggcatc tggggtccca  180
tctcgtttca gtggcagtgg atctgggaca gatttcactc tcaccatcag cagcctgcag  240
cctgaagatg ttgcaactta ttactgtctg ggcagttatg attgtactaa tggtgattgt  300
tttgttttcg gcggaggaac caaggtggaa atcaaacgt                         339

SEQ ID NO: 233           moltype = DNA   length = 66
FEATURE                  Location/Qualifiers
misc_feature             1..66
                         note = Engineered antibody sequence
source                   1..66
                         mol_type = other DNA
                         organism = synthetic construct
SEQUENCE: 233
caagtgctga cccagtctcc atcctccctg tctgcatctg taggagacag agtcaccatc   60
aattgc                                                              66

SEQ ID NO: 234           moltype = DNA   length = 39
FEATURE                  Location/Qualifiers
misc_feature             1..39
                         note = Engineered antibody sequence
source                   1..39
                         mol_type = other DNA
                         organism = synthetic construct
SEQUENCE: 234
caggccagtc agagtgttta tcataacacc tacctggcc                          39

SEQ ID NO: 235           moltype = DNA   length = 45
FEATURE                  Location/Qualifiers
misc_feature             1..45
                         note = Engineered antibody sequence
source                   1..45
                         mol_type = other DNA
                         organism = synthetic construct
SEQUENCE: 235
tggtatcagc agaaaccagg gaaagttcct aagcaactga tctat                   45

SEQ ID NO: 236           moltype = DNA   length = 21
FEATURE                  Location/Qualifiers
misc_feature             1..21
                         note = Engineered antibody sequence
source                   1..21
                         mol_type = other DNA
                         organism = synthetic construct
SEQUENCE: 236
gatgcatcca ctctggcatc t                                             21

SEQ ID NO: 237           moltype = DNA   length = 96
FEATURE                  Location/Qualifiers
```

```
misc_feature            1..96
                        note = Engineered antibody sequence
source                  1..96
                        mol_type = other DNA
                        organism = synthetic construct
SEQUENCE: 237
ggggtcccat ctcgtttcag tggcagtgga tctgggacag atttcactct caccatcagc    60
agcctgcagc ctgaagatgt tgcaacttat tactgt                              96

SEQ ID NO: 238          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 238
ctgggcagtt atgattgtac taatggtgat tgttttgtt                            39

SEQ ID NO: 239          moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 239
ttcggcggag gaaccaaggt ggaaatcaaa cgt                                  33

SEQ ID NO: 240          moltype = DNA   length = 321
FEATURE                 Location/Qualifiers
misc_feature            1..321
                        note = Engineered antibody sequence
source                  1..321
                        mol_type = other DNA
                        organism = synthetic construct
SEQUENCE: 240
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 241          moltype = AA    length = 440
FEATURE                 Location/Qualifiers
REGION                  1..440
                        note = Engineered antibody sequence
source                  1..440
                        mol_type = protein
                        organism = synthetic construct
SEQUENCE: 241
QEQLKESGGR LVTPGTSLTL TCTVSGIDLS NHYMQWVRQA PGKGLEWIGV VGINGRTYYA    60
SWAKGRFTIS RTSSTTVDLK MTRLTTEDTA TYFCARGDIW GPGTLVTVSS ASTKGPSVFP   120
LAPSSKSTSG GTAALGCLVK DYFPEPVTVS WNSGALTSGV HTFPAVLQSS GLYSLSSVVT   180
VPSSSLGTQT YICNVNHKPS NTKVDKRVEP KSCDKTHTCP PCPAPELLGG PSVFLFPPKP   240
KDTLMISRTP EVTCVVVDVS HEDPEVKFNW YVDGVEVHNA KTKPREEQYA STYRVVSVLT   300
VLHQDWLNGK EYKCKVSNKA LPAPIEKTIS KAKGQPREPQ VYTLPPSREE MTKNQVSLTC   360
LVKGFYPSDI AVEWESNGQP ENNYKTTPPV LDSDGSFFLY SKLTVDKSRW QQGNVFSCSV   420
MHEALHNHYT QKSLSLSPGK                                               440

SEQ ID NO: 242          moltype = AA    length = 110
FEATURE                 Location/Qualifiers
REGION                  1..110
                        note = Engineered antibody sequence
source                  1..110
                        mol_type = protein
                        organism = synthetic construct
SEQUENCE: 242
QEQLKESGGR LVTPGTSLTL TCTVSGIDLS NHYMQWVRQA PGKGLEWIGV VGINGRTYYA    60
SWAKGRFTIS RTSSTTVDLK MTRLTTEDTA TYFCARGDIW GPGTLVTVSS               110

SEQ ID NO: 243          moltype = AA    length = 30
FEATURE                 Location/Qualifiers
REGION                  1..30
                        note = Engineered antibody sequence
source                  1..30
                        mol_type = protein
                        organism = synthetic construct
```

```
SEQUENCE: 243
QEQLKESGGR LVTPGTSLTL TCTVSGIDLS                                          30

SEQ ID NO: 244          moltype = AA  length = 5
FEATURE                 Location/Qualifiers
REGION                  1..5
                        note = Engineered antibody sequence
source                  1..5
                        mol_type = protein
                        organism = synthetic construct
SEQUENCE: 244
NHYMQ                                                                      5

SEQ ID NO: 245          moltype = AA  length = 14
FEATURE                 Location/Qualifiers
REGION                  1..14
                        note = Engineered antibody sequence
source                  1..14
                        mol_type = protein
                        organism = synthetic construct
SEQUENCE: 245
WVRQAPGKGL EWIG                                                           14

SEQ ID NO: 246          moltype = AA  length = 16
FEATURE                 Location/Qualifiers
REGION                  1..16
                        note = Engineered antibody sequence
source                  1..16
                        mol_type = protein
                        organism = synthetic construct
SEQUENCE: 246
VVGINGRTYY ASWAKG                                                         16

SEQ ID NO: 247          moltype = AA  length = 31
FEATURE                 Location/Qualifiers
REGION                  1..31
                        note = Engineered antibody sequence
source                  1..31
                        mol_type = protein
                        organism = synthetic construct
SEQUENCE: 247
RFTISRTSST TVDLKMTRLT TEDTATYFCA R                                        31

SEQ ID NO: 248          moltype =    length =
SEQUENCE: 248
000

SEQ ID NO: 249          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 249
WGPGTLVTVS S                                                              11

SEQ ID NO: 250          moltype = AA  length = 330
FEATURE                 Location/Qualifiers
REGION                  1..330
                        note = Engineered antibody sequence
source                  1..330
                        mol_type = protein
                        organism = synthetic construct
SEQUENCE: 250
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKRVEP KSCDKTHTCP PCPAPELLGG         120
PSVFLFPPKP KDTLMISRTP EVTCVVVDVS HEDPEVKFNW YVDGVEVHNA KTKPREEQYA         180
STYRVVSVLT VLHQDWLNGK EYKCKVSNKA LPAPIEKTIS KAKGQPREPQ VYTLPPSREE         240
MTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                          330

SEQ ID NO: 251          moltype = DNA  length = 1323
FEATURE                 Location/Qualifiers
misc_feature            1..1323
                        note = Engineered antibody sequence
source                  1..1323
                        mol_type = other DNA
                        organism = synthetic construct
```

```
SEQUENCE: 251
caggagcagc tgaaggagtc cgggggtcgc ctggtcacgc ctgggacatc cctgacactc    60
acctgcaccg tctctggaat cgacctcagt aaccactaca tgcaatgggt ccgccaggct   120
ccagggaagg ggctggagtg gatcggagtc gttggtatta atggtcgcac atactacgcg   180
agctgggcga aaggccgatt caccatctcc agaacctcgt cgaccacggt ggatctgaaa   240
atgaccaggc tgacaaccga ggacacggcc acctatttct gtgccagagg ggacatctgg   300
ggcccaggca ccctggtcac cgtctcgagc gcctccacca agggcccatc ggtcttcccc   360
ctggcaccct cctccaagag cacctctggg ggcacagcgg ccctgggctg cctggtcaag   420
gactacttcc ccgaaccggt gacggtgtcg tggaactcag gcgccctgac cagcggcgtg   480
cacaccttcc cggctgtcct acagtcctca ggactctact ccctcagcag cgtggtgacc   540
gtgccctcca gcagcttggg cacccagacc tacatctgca acgtgaatca caagcccagc   600
aacaccaagg tggacaagag agttgagccc aaatcttgtg acaaaactca cacatgccca   660
ccgtgcccag cacctgaact cctggggggga ccgtcagtct tcctcttccc cccaaaaccc   720
aaggacaccc tcatgatctc ccggacccct gaggtcacat gcgtggtggt ggacgtgagc   780
cacgaagacc ctgaggtcaa gttcaactgg tacgtggacg gcgtggaggt gcataatgcc   840
aagacaaagc cgcgggagga gcagtacggc agcacgtacc gtgtggtcag cgtcctcacc   900
gtcctgcacc aggactggct gaatggcaag gagtacaagt gcaaggtctc caacaaagcc   960
ctcccagccc ccatcgagaa aaccatctcc aaagccaaag ggcagccccg agaaccacag  1020
gtgtacaccc tgcccccatc ccgggaggag atgaccaaga accaggtcag cctgacctgc  1080
ctggtcaaag gcttctatcc cagcgacatc gccgtggagt gggagagcaa tgggcagccg  1140
gagaacaact acaagaccac gcctcccgtg ctggactccg acggctcctt cttcctctac  1200
agcaagctca ccgtggacaa gagcaggtgg cagcagggga acgtcttctc atgctccgtg  1260
atgcatgagg ctctgcacaa ccactacacg cagaagagcc tctccctgtc tccgggtaaa  1320
tga                                                                1323

SEQ ID NO: 252          moltype = DNA  length = 330
FEATURE                 Location/Qualifiers
misc_feature            1..330
                        note = Engineered antibody sequence
source                  1..330
                        mol_type = other DNA
                        organism = synthetic construct
SEQUENCE: 252
caggagcagc tgaaggagtc cgggggtcgc ctggtcacgc ctgggacatc cctgacactc    60
acctgcaccg tctctggaat cgacctcagt aaccactaca tgcaatgggt ccgccaggct   120
ccagggaagg ggctggagtg gatcggagtc gttggtatta atggtcgcac atactacgcg   180
agctgggcga aaggccgatt caccatctcc agaacctcgt cgaccacggt ggatctgaaa   240
atgaccaggc tgacaaccga ggacacggcc acctatttct gtgccagagg ggacatctgg   300
ggcccaggca ccctggtcac cgtctcgagc                                    330

SEQ ID NO: 253          moltype = DNA  length = 90
FEATURE                 Location/Qualifiers
misc_feature            1..90
                        note = Engineered antibody sequence
source                  1..90
                        mol_type = other DNA
                        organism = synthetic construct
SEQUENCE: 253
caggagcagc tgaaggagtc cgggggtcgc ctggtcacgc ctgggacatc cctgacactc    60
acctgcaccg tctctggaat cgacctcagt                                    90

SEQ ID NO: 254          moltype = DNA  length = 15
FEATURE                 Location/Qualifiers
misc_feature            1..15
                        note = Engineered antibody sequence
source                  1..15
                        mol_type = other DNA
                        organism = synthetic construct
SEQUENCE: 254
aaccactaca tgcaa                                                    15

SEQ ID NO: 255          moltype = DNA  length = 42
FEATURE                 Location/Qualifiers
misc_feature            1..42
                        note = Engineered antibody sequence
source                  1..42
                        mol_type = other DNA
                        organism = synthetic construct
SEQUENCE: 255
tgggtccgcc aggctccagg gaaggggctg gagtggatcg ga                      42

SEQ ID NO: 256          moltype = DNA  length = 48
FEATURE                 Location/Qualifiers
misc_feature            1..48
                        note = Engineered antibody sequence
source                  1..48
                        mol_type = other DNA
                        organism = synthetic construct
SEQUENCE: 256
```

```
gtcgttggta ttaatggtcg cacatactac gcgagctggg cgaaaggc                         48

SEQ ID NO: 257          moltype = DNA  length = 93
FEATURE                 Location/Qualifiers
misc_feature            1..93
                        note = Engineered antibody sequence
source                  1..93
                        mol_type = other DNA
                        organism = synthetic construct
SEQUENCE: 257
cgattcacca tctccagaac ctcgtcgacc acggtggatc tgaaaatgac caggctgaca           60
accgaggaca cggccaccta tttctgtgcc aga                                        93

SEQ ID NO: 258          moltype =      length =
SEQUENCE: 258
000

SEQ ID NO: 259          moltype = DNA  length = 33
FEATURE                 Location/Qualifiers
misc_feature            1..33
                        note = Engineered antibody sequence
source                  1..33
                        mol_type = other DNA
                        organism = synthetic construct
SEQUENCE: 259
tggggcccag gcaccctggt caccgtctcg agc                                        33

SEQ ID NO: 260          moltype = DNA  length = 993
FEATURE                 Location/Qualifiers
misc_feature            1..993
                        note = Engineered antibody sequence
source                  1..993
                        mol_type = other DNA
                        organism = synthetic construct
SEQUENCE: 260
gcctccacca agggcccatc ggtcttcccc ctggcaccct cctccaagag cacctctggg           60
ggcacagcgg ccctgggctg cctggtcaag gactacttcc ccgaaccggt gacggtgtcg          120
tggaactcag gcgccctgac cagcggcgtg cacaccttcc cggctgtcct acagtcctca          180
ggactctact ccctcagcag cgtggtgacc gtgccctcca gcagcttggg cacccagacc          240
tacatctgca acgtgaatca caagcccagc aacaccaagg tggacaagag agttgagccc          300
aaatcttgtg acaaaactca cacatgccca ccgtgcccag cacctgaact cctgggggga          360
ccgtcagtct tcctcttccc cccaaaaccc aaggacaccc tcatgatctc ccggacccct          420
gaggtcacat gcgtggtggt ggacgtgagc cacgaagacc ctgaggtcaa gttcaactgg          480
tacgtggacg gcgtggaggt gcataatgcc aagacaaagc cgcggggagga gcagtacgcc          540
agcacgtacc gtgtggtcag cgtcctcacc gtcctgcacc aggactggct gaatggcaag          600
gagtacaagt gcaaggtctc caacaaagcc ctcccagccc ccatcgagaa aaccatctcc          660
aaagccaaag ggcagccccg agaaccacag gtgtacaccc tgcccccatc ccgggaggag          720
atgaccaaga accaggtcag cctgacctgc ctggtcaaag gcttctatcc cagcgacatc          780
gccgtggagt gggagagcaa tgggcagccg gagaacaact acaagaccac gcctcccgtg          840
ctggactccg acggctcctt cttcctctac agcaagctca ccgtggacaa gagcaggtgg          900
cagcagggga acgtcttctc atgctccgtg atgcatgagg ctctgcacaa ccactacacg          960
cagaagagcc tctccctgtc tccgggtaaa tga                                       993

SEQ ID NO: 261          moltype = AA   length = 219
FEATURE                 Location/Qualifiers
REGION                  1..219
                        note = Engineered antibody sequence
source                  1..219
                        mol_type = protein
                        organism = synthetic construct
SEQUENCE: 261
QVLTQTASPV SAAVGSTVTI NCQASQSVYN YNYLAWYQQK PGQPPKQLIY STSTLASGVS           60
SRFKGSGSGT QFTLTISDVQ CDDAATYYCL GSYDCSTGDC FVFGGGTEVV VKRTVAAPSV          120
FIFPPSDEQL KSGTASVVCL LNNFYPREAK VQWKVDNALQ SGNSQESVTE QDSKDSTYSL          180
SSTLTLSKAD YEKHKVYACE VTHQGLSSPV TKSFNRGEC                                 219

SEQ ID NO: 262          moltype = AA   length = 113
FEATURE                 Location/Qualifiers
REGION                  1..113
                        note = Engineered antibody sequence
source                  1..113
                        mol_type = protein
                        organism = synthetic construct
SEQUENCE: 262
QVLTQTASPV SAAVGSTVTI NCQASQSVYN YNYLAWYQQK PGQPPKQLIY STSTLASGVS           60
SRFKGSGSGT QFTLTISDVQ CDDAATYYCL GSYDCSTGDC FVFGGGTEVV VKR                 113

SEQ ID NO: 263          moltype = AA   length = 22
FEATURE                 Location/Qualifiers
```

```
REGION                    1..22
                          note = Engineered antibody sequence
source                    1..22
                          mol_type = protein
                          organism = synthetic construct
SEQUENCE: 263
QVLTQTASPV SAAVGSTVTI NC                                              22

SEQ ID NO: 264            moltype = AA  length = 13
FEATURE                   Location/Qualifiers
REGION                    1..13
                          note = Engineered antibody sequence
source                    1..13
                          mol_type = protein
                          organism = synthetic construct
SEQUENCE: 264
QASQSVYNYN YLA                                                        13

SEQ ID NO: 265            moltype = AA  length = 15
FEATURE                   Location/Qualifiers
REGION                    1..15
                          note = Engineered antibody sequence
source                    1..15
                          mol_type = protein
                          organism = synthetic construct
SEQUENCE: 265
WYQQKPGQPP KQLIY                                                      15

SEQ ID NO: 266            moltype = AA  length = 7
FEATURE                   Location/Qualifiers
REGION                    1..7
                          note = Engineered antibody sequence
source                    1..7
                          mol_type = protein
                          organism = synthetic construct
SEQUENCE: 266
STSTLAS                                                                7

SEQ ID NO: 267            moltype = AA  length = 32
FEATURE                   Location/Qualifiers
REGION                    1..32
                          note = Engineered antibody sequence
source                    1..32
                          mol_type = protein
                          organism = synthetic construct
SEQUENCE: 267
GVSSRFKGSG SGTQFTLTIS DVQCDDAATY YC                                   32

SEQ ID NO: 268            moltype = AA  length = 13
FEATURE                   Location/Qualifiers
REGION                    1..13
                          note = Engineered antibody sequence
source                    1..13
                          mol_type = protein
                          organism = synthetic construct
SEQUENCE: 268
LGSYDCSTGD CFV                                                        13

SEQ ID NO: 269            moltype = AA  length = 11
FEATURE                   Location/Qualifiers
REGION                    1..11
                          note = Engineered antibody sequence
source                    1..11
                          mol_type = protein
                          organism = synthetic construct
SEQUENCE: 269
FGGGTEVVVK R                                                          11

SEQ ID NO: 270            moltype = AA  length = 106
FEATURE                   Location/Qualifiers
REGION                    1..106
                          note = Engineered antibody sequence
source                    1..106
                          mol_type = protein
                          organism = synthetic construct
SEQUENCE: 270
TVAAPSVFIF PPSDEQLKSG TASVVCLLNN FYPREAKVQW KVDNALQSGN SQESVTEQDS     60
KDSTYSLSST LTLSKADYEK HKVYACEVTH QGLSSPVTKS FNRGEC                   106
```

```
SEQ ID NO: 271            moltype = DNA    length = 660
FEATURE                   Location/Qualifiers
misc_feature              1..660
                          note = Engineered antibody sequence
source                    1..660
                          mol_type = other DNA
                          organism = synthetic construct
SEQUENCE: 271
caagtgctga cccagactgc atccccgtg tctgcagctg tgggaagcac agtcaccatc    60
aattgccagg ccagtcagag tgtttataat tacaactacc ttgcctggta tcagcagaaa   120
ccagggcagc ctcccaagca actgatctat tctacatcca ctctggcatc tggggtctca   180
tcgcgattca aaggcagtgg atctgggaca cagttcactc tcaccatcag cgacgtgcag   240
tgtgacgatg ctgccactta ctactgtcta ggcagttatg actgtagtac tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact ctatcccag agaggccaaa gtacagtgga aggtggataa cgccctccaa    480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 272            moltype = DNA    length = 339
FEATURE                   Location/Qualifiers
misc_feature              1..339
                          note = Engineered antibody sequence
source                    1..339
                          mol_type = other DNA
                          organism = synthetic construct
SEQUENCE: 272
caagtgctga cccagactgc atccccgtg tctgcagctg tgggaagcac agtcaccatc    60
aattgccagg ccagtcagag tgtttataat tacaactacc ttgcctggta tcagcagaaa   120
ccagggcagc ctcccaagca actgatctat tctacatcca ctctggcatc tggggtctca   180
tcgcgattca aaggcagtgg atctgggaca cagttcactc tcaccatcag cgacgtgcag   240
tgtgacgatg ctgccactta ctactgtcta ggcagttatg actgtagtac tggtgattgt   300
tttgttttcg gcggagggac cgaggtggtg gtcaaacgt                          339

SEQ ID NO: 273            moltype = DNA    length = 66
FEATURE                   Location/Qualifiers
misc_feature              1..66
                          note = Engineered antibody sequence
source                    1..66
                          mol_type = other DNA
                          organism = synthetic construct
SEQUENCE: 273
caagtgctga cccagactgc atccccgtg tctgcagctg tgggaagcac agtcaccatc    60
aattgc                                                              66

SEQ ID NO: 274            moltype = DNA    length = 39
FEATURE                   Location/Qualifiers
misc_feature              1..39
                          note = Engineered antibody sequence
source                    1..39
                          mol_type = other DNA
                          organism = synthetic construct
SEQUENCE: 274
caggccagtc agagtgttta taattacaac taccttgcc                          39

SEQ ID NO: 275            moltype = DNA    length = 45
FEATURE                   Location/Qualifiers
misc_feature              1..45
                          note = Engineered antibody sequence
source                    1..45
                          mol_type = other DNA
                          organism = synthetic construct
SEQUENCE: 275
tggtatcagc agaaaccagg gcagcctccc aagcaactga tctat                   45

SEQ ID NO: 276            moltype = DNA    length = 21
FEATURE                   Location/Qualifiers
misc_feature              1..21
                          note = Engineered antibody sequence
source                    1..21
                          mol_type = other DNA
                          organism = synthetic construct
SEQUENCE: 276
tctacatcca ctctggcatc t                                             21

SEQ ID NO: 277            moltype = DNA    length = 96
FEATURE                   Location/Qualifiers
misc_feature              1..96
```

```
                          note = Engineered antibody sequence
source                    1..96
                          mol_type = other DNA
                          organism = synthetic construct
SEQUENCE: 277
ggggtctcat cgcgattcaa aggcagtgga tctgggacac agttcactct caccatcagc    60
gacgtgcagt gtgacgatgc tgccacttac tactgt                              96

SEQ ID NO: 278            moltype = DNA  length = 39
FEATURE                   Location/Qualifiers
misc_feature              1..39
                          note = Engineered antibody sequence
source                    1..39
                          mol_type = other DNA
                          organism = synthetic construct
SEQUENCE: 278
ctaggcagtt atgactgtag tactggtgat tgttttgtt                            39

SEQ ID NO: 279            moltype = DNA  length = 33
FEATURE                   Location/Qualifiers
misc_feature              1..33
                          note = Engineered antibody sequence
source                    1..33
                          mol_type = other DNA
                          organism = synthetic construct
SEQUENCE: 279
ttcggcggag ggaccgaggt ggtggtcaaa cgt                                  33

SEQ ID NO: 280            moltype = DNA  length = 321
FEATURE                   Location/Qualifiers
misc_feature              1..321
                          note = Engineered antibody sequence
source                    1..321
                          mol_type = other DNA
                          organism = synthetic construct
SEQUENCE: 280
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 281            moltype = AA  length = 441
FEATURE                   Location/Qualifiers
REGION                    1..441
                          note = Engineered antibody sequence
source                    1..441
                          mol_type = protein
                          organism = synthetic construct
SEQUENCE: 281
EVQLVESGGG LVQPGGSLRL SCAVSGIDLS NHYMQWVRQA PGKGLEWVGV VGINGRTYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKRVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 282            moltype = AA  length = 111
FEATURE                   Location/Qualifiers
REGION                    1..111
                          note = Engineered antibody sequence
source                    1..111
                          mol_type = protein
                          organism = synthetic construct
SEQUENCE: 282
EVQLVESGGG LVQPGGSLRL SCAVSGIDLS NHYMQWVRQA PGKGLEWVGV VGINGRTYYA    60
SWAKGRFTIS RDNSKTTVYL QMNSLRAEDT AVYFCARGDI WGQGTLVTVS S            111

SEQ ID NO: 283            moltype = AA  length = 30
FEATURE                   Location/Qualifiers
REGION                    1..30
                          note = Engineered antibody sequence
source                    1..30
                          mol_type = protein
                          organism = synthetic construct
SEQUENCE: 283
```

```
EVQLVESGGG LVQPGGSLRL SCAVSGIDLS                                    30

SEQ ID NO: 284         moltype = AA   length = 5
FEATURE                Location/Qualifiers
REGION                 1..5
                       note = Engineered antibody sequence
source                 1..5
                       mol_type = protein
                       organism = synthetic construct
SEQUENCE: 284
NHYMQ                                                                5

SEQ ID NO: 285         moltype = AA   length = 14
FEATURE                Location/Qualifiers
REGION                 1..14
                       note = Engineered antibody sequence
source                 1..14
                       mol_type = protein
                       organism = synthetic construct
SEQUENCE: 285
WVRQAPGKGL EWVG                                                     14

SEQ ID NO: 286         moltype = AA   length = 16
FEATURE                Location/Qualifiers
REGION                 1..16
                       note = Engineered antibody sequence
source                 1..16
                       mol_type = protein
                       organism = synthetic construct
SEQUENCE: 286
VVGINGRTYY ASWAKG                                                   16

SEQ ID NO: 287         moltype = AA   length = 32
FEATURE                Location/Qualifiers
REGION                 1..32
                       note = Engineered antibody sequence
source                 1..32
                       mol_type = protein
                       organism = synthetic construct
SEQUENCE: 287
RFTISRDNSK TTVYLQMNSL RAEDTAVYFC AR                                 32

SEQ ID NO: 288         moltype =     length =
SEQUENCE: 288
000

SEQ ID NO: 289         moltype = AA   length = 11
FEATURE                Location/Qualifiers
REGION                 1..11
                       note = Engineered antibody sequence
source                 1..11
                       mol_type = protein
                       organism = synthetic construct
SEQUENCE: 289
WGQGTLVTVS S                                                        11

SEQ ID NO: 290         moltype = AA   length = 330
FEATURE                Location/Qualifiers
REGION                 1..330
                       note = Engineered antibody sequence
source                 1..330
                       mol_type = protein
                       organism = synthetic construct
SEQUENCE: 290
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 291         moltype = DNA   length = 1326
FEATURE                Location/Qualifiers
misc_feature           1..1326
                       note = Engineered antibody sequence
source                 1..1326
                       mol_type = other DNA
                       organism = synthetic construct
SEQUENCE: 291
```

```
gaggtgcagc ttgtggagtc tgggggaggc ttggtccagc ctgggggtc cctgagactc    60
tcctgtgcag tctctggaat cgacctcagt aaccactaca tgcaatgggt ccgtcaggct   120
ccagggaagg ggctggagtg ggtcggagtc gttggtatca atggtcgcac atactacgcg   180
agctgggcga aaggccgatt caccatctcc agagacaatt ccaagaccac ggtgtatctt   240
caaatgaaca gcctgagagc tgaggacact gctgtgtatt tctgtgctag agggacatc    300
tggggccaag ggaccctcgt caccgtctcg agcgcctcca ccaagggccc atcggtcttc   360
cccctggcac cctcctccaa gagcacctcg gggggcacag cggccctggg ctgcctggtc   420
aaggactact tccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacaa gagagttgag cccaaatctt gtgacaaaac tcacacatgc   660
ccaccgtgcc cagcacctga actcctgggg ggaccgtcag tcttcctctt ccccccaaaa   720
cccaaggaca cctctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca aagggcagcc ccgagaacca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg gaacgtcttc tcatgctcc   1260
gtgatgcatg aggctctgca caaccactac acgcagaaga cctctcct gtctccgggt   1320
aaatga                                                              1326

SEQ ID NO: 292          moltype = DNA   length = 333
FEATURE                 Location/Qualifiers
misc_feature            1..333
                        note = Engineered antibody sequence
source                  1..333
                        mol_type = other DNA
                        organism = synthetic construct
SEQUENCE: 292
gaggtgcagc ttgtggagtc tgggggaggc ttggtccagc ctgggggtc cctgagactc    60
tcctgtgcag tctctggaat cgacctcagt aaccactaca tgcaatgggt ccgtcaggct   120
ccagggaagg ggctggagtg ggtcggagtc gttggtatca atggtcgcac atactacgcg   180
agctgggcga aaggccgatt caccatctcc agagacaatt ccaagaccac ggtgtatctt   240
caaatgaaca gcctgagagc tgaggacact gctgtgtatt tctgtgctag agggacatc    300
tggggccaag ggaccctcgt caccgtctcg agc                                333

SEQ ID NO: 293          moltype = DNA   length = 90
FEATURE                 Location/Qualifiers
misc_feature            1..90
                        note = Engineered antibody sequence
source                  1..90
                        mol_type = other DNA
                        organism = synthetic construct
SEQUENCE: 293
gaggtgcagc ttgtggagtc tgggggaggc ttggtccagc ctgggggtc cctgagactc    60
tcctgtgcag tctctggaat cgacctcagt                                    90

SEQ ID NO: 294          moltype = DNA   length = 15
FEATURE                 Location/Qualifiers
misc_feature            1..15
                        note = Engineered antibody sequence
source                  1..15
                        mol_type = other DNA
                        organism = synthetic construct
SEQUENCE: 294
aaccactaca tgcaa                                                    15

SEQ ID NO: 295          moltype = DNA   length = 42
FEATURE                 Location/Qualifiers
misc_feature            1..42
                        note = Engineered antibody sequence
source                  1..42
                        mol_type = other DNA
                        organism = synthetic construct
SEQUENCE: 295
tgggtccgtc aggctccagg gaaggggctg gagtgggtcg ga                      42

SEQ ID NO: 296          moltype = DNA   length = 48
FEATURE                 Location/Qualifiers
misc_feature            1..48
                        note = Engineered antibody sequence
source                  1..48
                        mol_type = other DNA
                        organism = synthetic construct
SEQUENCE: 296
gtcgttggta tcaatggtcg cacatactac gcgagctggg cgaaaggc                48
```

```
SEQ ID NO: 297          moltype = DNA  length = 96
FEATURE                 Location/Qualifiers
misc_feature            1..96
                        note = Engineered antibody sequence
source                  1..96
                        mol_type = other DNA
                        organism = synthetic construct
SEQUENCE: 297
cgattcacca tctccagaga caattccaag accacggtgt atcttcaaat gaacagcctg    60
agagctgagg acactgctgt gtatttctgt gctaga                              96

SEQ ID NO: 298          moltype =   length =
SEQUENCE: 298
000

SEQ ID NO: 299          moltype = DNA  length = 33
FEATURE                 Location/Qualifiers
misc_feature            1..33
                        note = Engineered antibody sequence
source                  1..33
                        mol_type = other DNA
                        organism = synthetic construct
SEQUENCE: 299
tggggccaag ggaccctcgt caccgtctcg agc                                 33

SEQ ID NO: 300          moltype = DNA  length = 993
FEATURE                 Location/Qualifiers
misc_feature            1..993
                        note = Engineered antibody sequence
source                  1..993
                        mol_type = other DNA
                        organism = synthetic construct
SEQUENCE: 300
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

SEQ ID NO: 301          moltype = AA  length = 219
FEATURE                 Location/Qualifiers
REGION                  1..219
                        note = Engineered antibody sequence
source                  1..219
                        mol_type = protein
                        organism = synthetic construct
SEQUENCE: 301
QVLTQSPSSL SASVGDRVTI NCQASQSVYN YNYLAWYQQK PGKVPKQLIY STSTLASGVP    60
SRFSGSGSGT DFTLTISSLQ PEDVATYYCL GSYDCSTGDC FVFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 302          moltype = AA  length = 113
FEATURE                 Location/Qualifiers
REGION                  1..113
                        note = Engineered antibody sequence
source                  1..113
                        mol_type = protein
                        organism = synthetic construct
SEQUENCE: 302
QVLTQSPSSL SASVGDRVTI NCQASQSVYN YNYLAWYQQK PGKVPKQLIY STSTLASGVP    60
SRFSGSGSGT DFTLTISSLQ PEDVATYYCL GSYDCSTGDC FVFGGGTKVE IKR          113

SEQ ID NO: 303          moltype = AA  length = 22
FEATURE                 Location/Qualifiers
REGION                  1..22
```

```
                        note = Engineered antibody sequence
source                  1..22
                        mol_type = protein
                        organism = synthetic construct
SEQUENCE: 303
QVLTQSPSSL SASVGDRVTI NC                                                   22

SEQ ID NO: 304          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 304
QASQSVYNYN YLA                                                             13

SEQ ID NO: 305          moltype = AA   length = 15
FEATURE                 Location/Qualifiers
REGION                  1..15
                        note = Engineered antibody sequence
source                  1..15
                        mol_type = protein
                        organism = synthetic construct
SEQUENCE: 305
WYQQKPGKVP KQLIY                                                           15

SEQ ID NO: 306          moltype = AA   length = 7
FEATURE                 Location/Qualifiers
REGION                  1..7
                        note = Engineered antibody sequence
source                  1..7
                        mol_type = protein
                        organism = synthetic construct
SEQUENCE: 306
STSTLAS                                                                     7

SEQ ID NO: 307          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 307
GVPSRFSGSG SGTDFTLTIS SLQPEDVATY YC                                        32

SEQ ID NO: 308          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 308
LGSYDCSTGD CFV                                                             13

SEQ ID NO: 309          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 309
FGGGTKVEIK R                                                               11

SEQ ID NO: 310          moltype = AA   length = 106
FEATURE                 Location/Qualifiers
REGION                  1..106
                        note = Engineered antibody sequence
source                  1..106
                        mol_type = protein
                        organism = synthetic construct
SEQUENCE: 310
TVAAPSVFIF PPSDEQLKSG TASVVCLLNN FYPREAKVQW KVDNALQSGN SQESVTEQDS          60
KDSTYSLSST LTLSKADYEK HKVYACEVTH QGLSSPVTKS FNRGEC                        106

SEQ ID NO: 311          moltype = DNA   length = 660
```

```
FEATURE                     Location/Qualifiers
misc_feature                1..660
                            note = Engineered antibody sequence
source                      1..660
                            mol_type = other DNA
                            organism = synthetic construct
SEQUENCE: 311
caagtgctga cccagtctcc atcctccctg tctgcatctg taggagacag agtcaccatc   60
aattgccagg ccagtcagag tgtttacaat tacaactacc ttgcctggta tcagcagaaa  120
ccagggaaag ttcctaagca actgatctat tctacatcca ctctggcatc tggggtccca  180
tctcgtttca gtggcagtgg atctgggaca gatttcactc tcaccatcag cagcctgcag  240
cctgaagatt ttgcaactta ttactgtctg ggcagttatg attgtagtac tggtgattgt  300
tttgttttcg gcggaggaac caaggtggaa atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgttag  660

SEQ ID NO: 312              moltype = DNA   length = 339
FEATURE                     Location/Qualifiers
misc_feature                1..339
                            note = Engineered antibody sequence
source                      1..339
                            mol_type = other DNA
                            organism = synthetic construct
SEQUENCE: 312
caagtgctga cccagtctcc atcctccctg tctgcatctg taggagacag agtcaccatc   60
aattgccagg ccagtcagag tgtttacaat tacaactacc ttgcctggta tcagcagaaa  120
ccagggaaag ttcctaagca actgatctat tctacatcca ctctggcatc tggggtccca  180
tctcgtttca gtggcagtgg atctgggaca gatttcactc tcaccatcag cagcctgcag  240
cctgaagatt ttgcaactta ttactgtctg ggcagttatg attgtagtac tggtgattgt  300
tttgttttcg gcggaggaac caaggtggaa atcaaacgt                         339

SEQ ID NO: 313              moltype = DNA   length = 66
FEATURE                     Location/Qualifiers
misc_feature                1..66
                            note = Engineered antibody sequence
source                      1..66
                            mol_type = other DNA
                            organism = synthetic construct
SEQUENCE: 313
caagtgctga cccagtctcc atcctccctg tctgcatctg taggagacag agtcaccatc   60
aattgc                                                              66

SEQ ID NO: 314              moltype = DNA   length = 39
FEATURE                     Location/Qualifiers
misc_feature                1..39
                            note = Engineered antibody sequence
source                      1..39
                            mol_type = other DNA
                            organism = synthetic construct
SEQUENCE: 314
caggccagtc agagtgttta caattacaac taccttgcc                          39

SEQ ID NO: 315              moltype = DNA   length = 45
FEATURE                     Location/Qualifiers
misc_feature                1..45
                            note = Engineered antibody sequence
source                      1..45
                            mol_type = other DNA
                            organism = synthetic construct
SEQUENCE: 315
tggtatcagc agaaaccagg gaaagttcct aagcaactga tctat                   45

SEQ ID NO: 316              moltype = DNA   length = 21
FEATURE                     Location/Qualifiers
misc_feature                1..21
                            note = Engineered antibody sequence
source                      1..21
                            mol_type = other DNA
                            organism = synthetic construct
SEQUENCE: 316
tctacatcca ctctggcatc t                                             21

SEQ ID NO: 317              moltype = DNA   length = 96
FEATURE                     Location/Qualifiers
misc_feature                1..96
                            note = Engineered antibody sequence
```

```
source                   1..96
                         mol_type = other DNA
                         organism = synthetic construct
SEQUENCE: 317
ggggtcccat ctcgtttcag tggcagtgga tctgggacag atttcactct caccatcagc    60
agcctgcagc ctgaagatgt tgcaacttat tactgt                              96

SEQ ID NO: 318           moltype = DNA   length = 39
FEATURE                  Location/Qualifiers
misc_feature             1..39
                         note = Engineered antibody sequence
source                   1..39
                         mol_type = other DNA
                         organism = synthetic construct
SEQUENCE: 318
ctgggcagtt atgattgtag tactggtgat tgttttgtt                           39

SEQ ID NO: 319           moltype = DNA   length = 33
FEATURE                  Location/Qualifiers
misc_feature             1..33
                         note = Engineered antibody sequence
source                   1..33
                         mol_type = other DNA
                         organism = synthetic construct
SEQUENCE: 319
ttcggcggag gaaccaaggt ggaaatcaaa cgt                                 33

SEQ ID NO: 320           moltype = DNA   length = 321
FEATURE                  Location/Qualifiers
misc_feature             1..321
                         note = Engineered antibody sequence
source                   1..321
                         mol_type = other DNA
                         organism = synthetic construct
SEQUENCE: 320
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 321           moltype = AA   length = 439
FEATURE                  Location/Qualifiers
REGION                   1..439
                         note = Engineered antibody sequence
source                   1..439
                         mol_type = protein
                         organism = synthetic construct
SEQUENCE: 321
QSLEESGGRL VTPGTPLTLT CTVSGIGLSS YYMQWVRQSP GRGLEWIGVI GSDGKTYYAT    60
WAKGRFTISK TSSTTVDLRM ASLTTEDTAT YFCTRGDIWG PGTLVTVSSA STKGPSVFPL   120
APSSKSTSGG TAALGCLVKD YFPEPVTVSW NSGALTSGVH TFPAVLQSSG LYSLSSVVTV   180
PSSSLGTQTY ICNVNHKPSN TKVDKRVEPK SCDKTHTCPP CPAPELLGGP SVFLFPPKPK   240
DTLMISRTPE VTCVVVDVSH EDPEVKFNWY VDGVEVHNAK TKPREEQYAS TYRVVSVLTV   300
LHQDWLNGKE YKCKVSNKAL PAPIEKTISK AKGQPREPQV YTLPPSREEM TKNQVSLTCL   360
VKGFYPSDIA VEWESNGQPE NNYKTTPPVL DSDGSFFLYS KLTVDKSRWQ QGNVFSCSVM   420
HEALHNHYTQ KSLSLSPGK                                                439

SEQ ID NO: 322           moltype = AA   length = 109
FEATURE                  Location/Qualifiers
REGION                   1..109
                         note = Engineered antibody sequence
source                   1..109
                         mol_type = protein
                         organism = synthetic construct
SEQUENCE: 322
QSLEESGGRL VTPGTPLTLT CTVSGIGLSS YYMQWVRQSP GRGLEWIGVI GSDGKTYYAT    60
WAKGRFTISK TSSTTVDLRM ASLTTEDTAT YFCTRGDIWG PGTLVTVSS               109

SEQ ID NO: 323           moltype = AA   length = 29
FEATURE                  Location/Qualifiers
REGION                   1..29
                         note = Engineered antibody sequence
source                   1..29
                         mol_type = protein
                         organism = synthetic construct
SEQUENCE: 323
QSLEESGGRL VTPGTPLTLT CTVSGIGLS                                      29
```

```
SEQ ID NO: 324           moltype = AA  length = 5
FEATURE                  Location/Qualifiers
REGION                   1..5
                         note = Engineered antibody sequence
source                   1..5
                         mol_type = protein
                         organism = synthetic construct
SEQUENCE: 324
SYYMQ                                                                      5

SEQ ID NO: 325           moltype = AA  length = 14
FEATURE                  Location/Qualifiers
REGION                   1..14
                         note = Engineered antibody sequence
source                   1..14
                         mol_type = protein
                         organism = synthetic construct
SEQUENCE: 325
WVRQSPGRGL EWIG                                                           14

SEQ ID NO: 326           moltype = AA  length = 16
FEATURE                  Location/Qualifiers
REGION                   1..16
                         note = Engineered antibody sequence
source                   1..16
                         mol_type = protein
                         organism = synthetic construct
SEQUENCE: 326
VIGSDGKTYY ATWAKG                                                         16

SEQ ID NO: 327           moltype = AA  length = 31
FEATURE                  Location/Qualifiers
REGION                   1..31
                         note = Engineered antibody sequence
source                   1..31
                         mol_type = protein
                         organism = synthetic construct
SEQUENCE: 327
RFTISKTSST TVDLRMASLT TEDTATYFCT R                                        31

SEQ ID NO: 328           moltype =     length =
SEQUENCE: 328
000

SEQ ID NO: 329           moltype = AA  length = 11
FEATURE                  Location/Qualifiers
REGION                   1..11
                         note = Engineered antibody sequence
source                   1..11
                         mol_type = protein
                         organism = synthetic construct
SEQUENCE: 329
WGPGTLVTVS S                                                              11

SEQ ID NO: 330           moltype = AA  length = 330
FEATURE                  Location/Qualifiers
REGION                   1..330
                         note = Engineered antibody sequence
source                   1..330
                         mol_type = protein
                         organism = synthetic construct
SEQUENCE: 330
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKRVEP KSCDKTHTCP PCPAPELLGG         120
PSVFLFPPKP KDTLMISRTP EVTCVVVDVS HEDPEVKFNW YVDGVEVHNA KTKPREEQYA         180
STYRVVSVLT VLHQDWLNGK EYKCKVSNKA LPAPIEKTIS KAKGQPREPQ VYTLPPSREE         240
MTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                         330

SEQ ID NO: 331           moltype = DNA  length = 1320
FEATURE                  Location/Qualifiers
misc_feature             1..1320
                         note = Engineered antibody sequence
source                   1..1320
                         mol_type = other DNA
                         organism = synthetic construct
SEQUENCE: 331
cagtcgctgg aggagtccgg gggtcgcctg gtcacgcctg ggacacccct gacactcacc          60
```

```
tgcacagtct ctggaatcgg cctcagtagc tactacatgc agtgggtccg ccagtctcca    120
gggaggggc tggaatggat cggagtcatt ggtagtgatg gtaagacata ctacgcgacc     180
tgggcgaaag gccgattcac catctccaag acctcgtcga ccacggtgga tctgagaatg    240
gccagtctga caaccgagga cacggccacc tatttctgta ccagagggga catctggggc    300
ccggggaccc tcgtcaccgt ctcgagcgcc tccaccaagg gcccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccg ctgtcctaca gtcctcagga ctctactccc tcagcagcgt ggtgaccgtg     540
ccctccagca gcttgggcac ccagacctac atctgcaacg tgaatcacaa gcccagcaac    600
accaaggtgg acaagagagt tgagcccaaa tcttgtgaca aaactcacac atgcccaccg    660
tgcccagcac ctgaactcct ggggggaccg tcagtcttcc tcttcccccc aaaacccaag    720
gacaccctca tgatctcccg acccctgag gtcacatgcg tggtggtgga cgtgagccac     780
gaagaccctg aggtcaagtt caactggtac gtggacggcg tggaggtgca taatgccaag    840
acaaagccgc gggaggagca gtacgccagc acgtaccgtg tggtcagcgt cctcaccgtc    900
ctgcaccagg actggctgaa tggcaaggag tacaagtgca aggtctccaa caaagccctc    960
ccagccccca tcgagaaaac catctccaaa gccaaagggc agccccgaga accacaggtg    1020
tacaccctgc cccatcccg ggaggagatg accaagaacc aggtcagcct gacctgcctg     1080
gtcaaaggct tctatcccag cgacatcgcc gtggagtggg agagcaatgg gcagccggag    1140
aacaactaca agaccacgcc tcccgtgctg gactccgacg gctccttctt cctctacagc    1200
aagctcaccg tggacaagag caggtggcag caggggaacg tcttctcatg ctccgtgatg    1260
catgaggctc tgcacaacca ctacacgcag aagagcctct ccctgtctcc gggtaaatga    1320

SEQ ID NO: 332           moltype = DNA   length = 327
FEATURE                  Location/Qualifiers
misc_feature             1..327
                         note = Engineered antibody sequence
source                   1..327
                         mol_type = other DNA
                         organism = synthetic construct
SEQUENCE: 332
cagtcgctgg aggagtccgg gggtcgcctg gtcacgcctg gacacccct gacactcacc      60
tgcacagtct ctggaatcgg cctcagtagc tactacatgc agtgggtccg ccagtctcca    120
gggaggggc tggaatggat cggagtcatt ggtagtgatg gtaagacata ctacgcgacc     180
tgggcgaaag gccgattcac catctccaag acctcgtcga ccacggtgga tctgagaatg    240
gccagtctga caaccgagga cacggccacc tatttctgta ccagagggga catctggggc    300
ccggggaccc tcgtcaccgt ctcgagc                                        327

SEQ ID NO: 333           moltype = DNA   length = 87
FEATURE                  Location/Qualifiers
misc_feature             1..87
                         note = Engineered antibody sequence
source                   1..87
                         mol_type = other DNA
                         organism = synthetic construct
SEQUENCE: 333
cagtcgctgg aggagtccgg gggtcgcctg gtcacgcctg gacacccct gacactcacc      60
tgcacagtct ctggaatcgg cctcagt                                         87

SEQ ID NO: 334           moltype = DNA   length = 15
FEATURE                  Location/Qualifiers
misc_feature             1..15
                         note = Engineered antibody sequence
source                   1..15
                         mol_type = other DNA
                         organism = synthetic construct
SEQUENCE: 334
agctactaca tgcag                                                      15

SEQ ID NO: 335           moltype = DNA   length = 42
FEATURE                  Location/Qualifiers
misc_feature             1..42
                         note = Engineered antibody sequence
source                   1..42
                         mol_type = other DNA
                         organism = synthetic construct
SEQUENCE: 335
tgggtccgcc agtctccagg gaggggctg gaatggatcg ga                         42

SEQ ID NO: 336           moltype = DNA   length = 48
FEATURE                  Location/Qualifiers
misc_feature             1..48
                         note = Engineered antibody sequence
source                   1..48
                         mol_type = other DNA
                         organism = synthetic construct
SEQUENCE: 336
gtcattggta gtgatggtaa gacatactac gcgacctggg cgaaaggc                  48

SEQ ID NO: 337           moltype = DNA   length = 93
```

```
FEATURE              Location/Qualifiers
misc_feature         1..93
                     note = Engineered antibody sequence
source               1..93
                     mol_type = other DNA
                     organism = synthetic construct
SEQUENCE: 337
cgattcacca tctccaagac ctcgtcgacc acggtggatc tgagaatggc cagtctgaca    60
accgaggaca cggccaccta tttctgtacc aga                                 93

SEQ ID NO: 338       moltype =     length =
SEQUENCE: 338
000

SEQ ID NO: 339       moltype = DNA  length = 33
FEATURE              Location/Qualifiers
misc_feature         1..33
                     note = Engineered antibody sequence
source               1..33
                     mol_type = other DNA
                     organism = synthetic construct
SEQUENCE: 339
tggggcccgg ggaccctcgt caccgtctcg agc                                 33

SEQ ID NO: 340       moltype = DNA  length = 993
FEATURE              Location/Qualifiers
misc_feature         1..993
                     note = Engineered antibody sequence
source               1..993
                     mol_type = other DNA
                     organism = synthetic construct
SEQUENCE: 340
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

SEQ ID NO: 341       moltype = AA  length = 219
FEATURE              Location/Qualifiers
REGION               1..219
                     note = Engineered antibody sequence
source               1..219
                     mol_type = protein
                     organism = synthetic construct
SEQUENCE: 341
QVLTQTPSPV SAAVGSTVTI NCQASQNVYN NNYLAWYQQK PGQPPKQLIY STSTLASGVS    60
SRFRGSGSGT QFTLTISDVQ CDDAATYYCL GSYDCSRGDC FVFGGGTEVV KRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 342       moltype = AA  length = 113
FEATURE              Location/Qualifiers
REGION               1..113
                     note = Engineered antibody sequence
source               1..113
                     mol_type = protein
                     organism = synthetic construct
SEQUENCE: 342
QVLTQTPSPV SAAVGSTVTI NCQASQNVYN NNYLAWYQQK PGQPPKQLIY STSTLASGVS    60
SRFRGSGSGT QFTLTISDVQ CDDAATYYCL GSYDCSRGDC FVFGGGTEVV KR           113

SEQ ID NO: 343       moltype = AA  length = 22
FEATURE              Location/Qualifiers
REGION               1..22
                     note = Engineered antibody sequence
source               1..22
```

```
                        mol_type = protein
                        organism = synthetic construct
SEQUENCE: 343
QVLTQTPSPV SAAVGSTVTI NC                                              22

SEQ ID NO: 344          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 344
QASQNVYNNN YLA                                                        13

SEQ ID NO: 345          moltype = AA   length = 15
FEATURE                 Location/Qualifiers
REGION                  1..15
                        note = Engineered antibody sequence
source                  1..15
                        mol_type = protein
                        organism = synthetic construct
SEQUENCE: 345
WYQQKPGQPP KQLIY                                                      15

SEQ ID NO: 346          moltype = AA   length = 7
FEATURE                 Location/Qualifiers
REGION                  1..7
                        note = Engineered antibody sequence
source                  1..7
                        mol_type = protein
                        organism = synthetic construct
SEQUENCE: 346
STSTLAS                                                                7

SEQ ID NO: 347          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 347
GVSSRFRGSG SGTQFTLTIS DVQCDDAATY YC                                   32

SEQ ID NO: 348          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 348
LGSYDCSRGD CFV                                                        13

SEQ ID NO: 349          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 349
FGGGTEVVVK R                                                          11

SEQ ID NO: 350          moltype = AA   length = 106
FEATURE                 Location/Qualifiers
REGION                  1..106
                        note = Engineered antibody sequence
source                  1..106
                        mol_type = protein
                        organism = synthetic construct
SEQUENCE: 350
TVAAPSVFIF PPSDEQLKSG TASVVCLLNN FYPREAKVQW KVDNALQSGN SQESVTEQDS      60
KDSTYSLSST LTLSKADYEK HKVYACEVTH QGLSSPVTKS FNRGEC                   106

SEQ ID NO: 351          moltype = DNA   length = 660
FEATURE                 Location/Qualifiers
misc_feature            1..660
```

```
                        note = Engineered antibody sequence
source                  1..660
                        mol_type = other DNA
                        organism = synthetic construct
SEQUENCE: 351
caagtgctga cccagactcc atccccgtg tctgcagctg tgggaagcac agtcaccatc    60
aattgccagg ccagtcagaa tgtttataat aacaactacc tagcctggta tcagcagaaa   120
ccagggcagc ctcccaagca actgatctat tctacgtcca ctctggcatc tggggtctca   180
tcgcgattca gaggcagtgg atctgggaca cagttcactc tcaccatcag cgacgtgcag   240
tgtgacgatg ctgccactta ctactgtcta ggcagttatg attgtagtcg tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 352           moltype = DNA   length = 339
FEATURE                  Location/Qualifiers
misc_feature             1..339
                         note = Engineered antibody sequence
source                   1..339
                         mol_type = other DNA
                         organism = synthetic construct
SEQUENCE: 352
caagtgctga cccagactcc atccccgtg tctgcagctg tgggaagcac agtcaccatc    60
aattgccagg ccagtcagaa tgtttataat aacaactacc tagcctggta tcagcagaaa   120
ccagggcagc ctcccaagca actgatctat tctacgtcca ctctggcatc tggggtctca   180
tcgcgattca gaggcagtgg atctgggaca cagttcactc tcaccatcag cgacgtgcag   240
tgtgacgatg ctgccactta ctactgtcta ggcagttatg attgtagtcg tggtgattgt   300
tttgttttcg gcggagggac cgaggtggtg gtcaaacgt                          339

SEQ ID NO: 353           moltype = DNA   length = 66
FEATURE                  Location/Qualifiers
misc_feature             1..66
                         note = Engineered antibody sequence
source                   1..66
                         mol_type = other DNA
                         organism = synthetic construct
SEQUENCE: 353
caagtgctga cccagactcc atccccgtg tctgcagctg tgggaagcac agtcaccatc    60
aattgc                                                              66

SEQ ID NO: 354           moltype = DNA   length = 39
FEATURE                  Location/Qualifiers
misc_feature             1..39
                         note = Engineered antibody sequence
source                   1..39
                         mol_type = other DNA
                         organism = synthetic construct
SEQUENCE: 354
caggccagtc agaatgttta taataacaac tacctagcc                          39

SEQ ID NO: 355           moltype = DNA   length = 45
FEATURE                  Location/Qualifiers
misc_feature             1..45
                         note = Engineered antibody sequence
source                   1..45
                         mol_type = other DNA
                         organism = synthetic construct
SEQUENCE: 355
tggtatcagc agaaaccagg gcagcctccc aagcaactga tctat                   45

SEQ ID NO: 356           moltype = DNA   length = 21
FEATURE                  Location/Qualifiers
misc_feature             1..21
                         note = Engineered antibody sequence
source                   1..21
                         mol_type = other DNA
                         organism = synthetic construct
SEQUENCE: 356
tctacgtcca ctctggcatc t                                             21

SEQ ID NO: 357           moltype = DNA   length = 96
FEATURE                  Location/Qualifiers
misc_feature             1..96
                         note = Engineered antibody sequence
source                   1..96
                         mol_type = other DNA
```

```
                        organism = synthetic construct
SEQUENCE: 357
ggggtctcat cgcgattcag aggcagtgga tctgggacac agttcactct caccatcagc     60
gacgtgcagt gtgacgatgc tgccacttac tactgt                              96

SEQ ID NO: 358           moltype = DNA   length = 39
FEATURE                  Location/Qualifiers
misc_feature             1..39
                         note = Engineered antibody sequence
source                   1..39
                         mol_type = other DNA
                         organism = synthetic construct
SEQUENCE: 358
ctaggcagtt atgattgtag tcgtggtgat tgttttgtt                            39

SEQ ID NO: 359           moltype = DNA   length = 33
FEATURE                  Location/Qualifiers
misc_feature             1..33
                         note = Engineered antibody sequence
source                   1..33
                         mol_type = other DNA
                         organism = synthetic construct
SEQUENCE: 359
ttcggcggag ggaccgaggt ggtggtcaaa cgt                                  33

SEQ ID NO: 360           moltype = DNA   length = 321
FEATURE                  Location/Qualifiers
misc_feature             1..321
                         note = Engineered antibody sequence
source                   1..321
                         mol_type = other DNA
                         organism = synthetic construct
SEQUENCE: 360
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgcctccaa atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 361           moltype = AA   length = 441
FEATURE                  Location/Qualifiers
REGION                   1..441
                         note = Engineered antibody sequence
source                   1..441
                         mol_type = protein
                         organism = synthetic construct
SEQUENCE: 361
EVQLVESGGG LVQPGGSLRL SCAVSGIGLS SYYMQWVRQA PGKGLEWVGV IGSDGKTYYA    60
TWAKGRFTIS RDNSKTTVYL QMNSLRAEDT AVYFCTRGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDKRVE PKSCDTHTC PPCPAPELLG GPSVFLFPPK    240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 362           moltype = AA   length = 111
FEATURE                  Location/Qualifiers
REGION                   1..111
                         note = Engineered antibody sequence
source                   1..111
                         mol_type = protein
                         organism = synthetic construct
SEQUENCE: 362
EVQLVESGGG LVQPGGSLRL SCAVSGIGLS SYYMQWVRQA PGKGLEWVGV IGSDGKTYYA    60
TWAKGRFTIS RDNSKTTVYL QMNSLRAEDT AVYFCTRGDI WGQGTLVTVS S            111

SEQ ID NO: 363           moltype = AA   length = 30
FEATURE                  Location/Qualifiers
REGION                   1..30
                         note = Engineered antibody sequence
source                   1..30
                         mol_type = protein
                         organism = synthetic construct
SEQUENCE: 363
EVQLVESGGG LVQPGGSLRL SCAVSGIGLS                                     30

SEQ ID NO: 364           moltype = AA   length = 5
```

```
FEATURE                 Location/Qualifiers
REGION                  1..5
                        note = Engineered antibody sequence
source                  1..5
                        mol_type = protein
                        organism = synthetic construct
SEQUENCE: 364
SYYMQ                                                                    5

SEQ ID NO: 365          moltype = AA  length = 14
FEATURE                 Location/Qualifiers
REGION                  1..14
                        note = Engineered antibody sequence
source                  1..14
                        mol_type = protein
                        organism = synthetic construct
SEQUENCE: 365
WVRQAPGKGL EWVG                                                         14

SEQ ID NO: 366          moltype = AA  length = 16
FEATURE                 Location/Qualifiers
REGION                  1..16
                        note = Engineered antibody sequence
source                  1..16
                        mol_type = protein
                        organism = synthetic construct
SEQUENCE: 366
VIGSDGKTYY ATWAKG                                                       16

SEQ ID NO: 367          moltype = AA  length = 32
FEATURE                 Location/Qualifiers
REGION                  1..32
                        note = Engineered antibody sequence
source                  1..32
                        mol_type = protein
                        organism = synthetic construct
SEQUENCE: 367
RFTISRDNSK TTVYLQMNSL RAEDTAVYFC TR                                     32

SEQ ID NO: 368          moltype =    length =
SEQUENCE: 368
000

SEQ ID NO: 369          moltype = AA  length = 11
FEATURE                 Location/Qualifiers
REGION                  1..11
                        note = Engineered antibody sequence
source                  1..11
                        mol_type = protein
                        organism = synthetic construct
SEQUENCE: 369
WGQGTLVTVS S                                                            11

SEQ ID NO: 370          moltype = AA  length = 330
FEATURE                 Location/Qualifiers
REGION                  1..330
                        note = Engineered antibody sequence
source                  1..330
                        mol_type = protein
                        organism = synthetic construct
SEQUENCE: 370
ASTKGPSVFP LAPSSKSTSG GTAALGCLVK DYFPEPVTVS WNSGALTSGV HTFPAVLQSS        60
GLYSLSSVVT VPSSSLGTQT YICNVNHKPS NTKVDKRVEP KSCDKTHTCP PCPAPELLGG       120
PSVFLFPPKP KDTLMISRTP EVTCVVVDVS HEDPEVKFNW YVDGVEVHNA KTKPREEQYA       180
STYRVVSVLT VLHQDWLNGK EYKCKVSNKA LPAPIEKTIS KAKGQPREPQ VYTLPPSREE       240
MTKNQVSLTC LVKGFYPSDI AVEWESNGQP ENNYKTTPPV LDSDGSFFLY SKLTVDKSRW       300
QQGNVFSCSV MHEALHNHYT QKSLSLSPGK                                        330

SEQ ID NO: 371          moltype = DNA  length = 1326
FEATURE                 Location/Qualifiers
misc_feature            1..1326
                        note = Engineered antibody sequence
source                  1..1326
                        mol_type = other DNA
                        organism = synthetic construct
SEQUENCE: 371
gaggtgcagc ttgtggagtc tgggggaggc ttggtccagc ctgggggtc cctgagactc         60
tcctgtgcag tctctggaat cggcctcagt agctactaca tgcaatgggt ccgtcaggct       120
ccagggaagg ggctggagtg ggtcggagtc attggtagtg atggtaagac atactacgcg       180
```

```
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agcgcctcca ccaagggccc atcggtcttc   360
cccctggcac cctcctccaa gagcacctct ggggcacag cggccctggg ctgcctggtc    420
aaggactact tccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacaa gagagttgag cccaaatctt gtgacaaaac tcacacatgc   660
ccaccgtgcc cagcacctga actcctgggg gaccgtcagt cttcctcttc cccccaaaa    720
cccaaggaca ccctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag ccccccatcga gaaaaccatc tccaaagcca aagggcagcc ccgagaacca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc  1260
gtgatgcatg aggctctgca caaccactac acgcagaaga gcctctccct gtctccgggt  1320
aaatga                                                              1326

SEQ ID NO: 372             moltype = DNA   length = 333
FEATURE                    Location/Qualifiers
misc_feature               1..333
                           note = Engineered antibody sequence
source                     1..333
                           mol_type = other DNA
                           organism = synthetic construct
SEQUENCE: 372
gaggtgcagc ttgtggagtc tgggggaggc ttggtccagc ctggggggtc cctgagactc    60
tcctgtgcag tctctggaat cggcctcagt agctactaca tgcaatgggt ccgtcaggct   120
ccagggaagg ggctggagtg gtcggagtc attggtagtg atggtaagac atactacgcg   180
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agc                                333

SEQ ID NO: 373             moltype = DNA   length = 90
FEATURE                    Location/Qualifiers
misc_feature               1..90
                           note = Engineered antibody sequence
source                     1..90
                           mol_type = other DNA
                           organism = synthetic construct
SEQUENCE: 373
gaggtgcagc ttgtggagtc tgggggaggc ttggtccagc ctggggggtc cctgagactc    60
tcctgtgcag tctctggaat cggcctcagt                                    90

SEQ ID NO: 374             moltype = DNA   length = 15
FEATURE                    Location/Qualifiers
misc_feature               1..15
                           note = Engineered antibody sequence
source                     1..15
                           mol_type = other DNA
                           organism = synthetic construct
SEQUENCE: 374
agctactaca tgcaa                                                    15

SEQ ID NO: 375             moltype = DNA   length = 42
FEATURE                    Location/Qualifiers
misc_feature               1..42
                           note = Engineered antibody sequence
source                     1..42
                           mol_type = other DNA
                           organism = synthetic construct
SEQUENCE: 375
tgggtccgtc aggctccagg gaaggggctg gagtgggtcg ga                      42

SEQ ID NO: 376             moltype = DNA   length = 48
FEATURE                    Location/Qualifiers
misc_feature               1..48
                           note = Engineered antibody sequence
source                     1..48
                           mol_type = other DNA
                           organism = synthetic construct
SEQUENCE: 376
gtcattggta gtgatggtaa gacatactac gcgacctggg cgaaaggc                48

SEQ ID NO: 377             moltype = DNA   length = 96
FEATURE                    Location/Qualifiers
```

```
misc_feature           1..96
                       note = Engineered antibody sequence
source                 1..96
                       mol_type = other DNA
                       organism = synthetic construct
SEQUENCE: 377
cgattcacca tctccagaga caattccaag accacggtgt atcttcaaat gaacagcctg    60
agagctgagg acactgctgt gtatttctgt accaga                              96

SEQ ID NO: 378         moltype =   length =
SEQUENCE: 378
000

SEQ ID NO: 379         moltype = DNA   length = 33
FEATURE                Location/Qualifiers
misc_feature           1..33
                       note = Engineered antibody sequence
source                 1..33
                       mol_type = other DNA
                       organism = synthetic construct
SEQUENCE: 379
tggggccaag ggaccctcgt caccgtctcg agc                                 33

SEQ ID NO: 380         moltype = DNA   length = 993
FEATURE                Location/Qualifiers
misc_feature           1..993
                       note = Engineered antibody sequence
source                 1..993
                       mol_type = other DNA
                       organism = synthetic construct
SEQUENCE: 380
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcggggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

SEQ ID NO: 381         moltype = AA    length = 219
FEATURE                Location/Qualifiers
REGION                 1..219
                       note = Engineered antibody sequence
source                 1..219
                       mol_type = protein
                       organism = synthetic construct
SEQUENCE: 381
QVLTQSPSSL SASVGDRVTI NCQASQNVYN NNYLAWYQQK PGKVPKQLIY STSTLASGVP    60
SRFSGSGSGT DFTLTISSLQ PEDVATYYCL GSYDCSRGDC FVFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 382         moltype = AA    length = 113
FEATURE                Location/Qualifiers
REGION                 1..113
                       note = Engineered antibody sequence
source                 1..113
                       mol_type = protein
                       organism = synthetic construct
SEQUENCE: 382
QVLTQSPSSL SASVGDRVTI NCQASQNVYN NNYLAWYQQK PGKVPKQLIY STSTLASGVP    60
SRFSGSGSGT DFTLTISSLQ PEDVATYYCL GSYDCSRGDC FVFGGGTKVE IKR          113

SEQ ID NO: 383         moltype = AA    length = 22
FEATURE                Location/Qualifiers
REGION                 1..22
                       note = Engineered antibody sequence
source                 1..22
                       mol_type = protein
```

```
                                  organism = synthetic construct
SEQUENCE: 383
QVLTQSPSSL SASVGDRVTI NC                                              22

SEQ ID NO: 384           moltype = AA  length = 13
FEATURE                  Location/Qualifiers
REGION                   1..13
                         note = Engineered antibody sequence
source                   1..13
                         mol_type = protein
                         organism = synthetic construct
SEQUENCE: 384
QASQNVYNNN YLA                                                        13

SEQ ID NO: 385           moltype = AA  length = 15
FEATURE                  Location/Qualifiers
REGION                   1..15
                         note = Engineered antibody sequence
source                   1..15
                         mol_type = protein
                         organism = synthetic construct
SEQUENCE: 385
WYQQKPGKVP KQLIY                                                      15

SEQ ID NO: 386           moltype = AA  length = 7
FEATURE                  Location/Qualifiers
REGION                   1..7
                         note = Engineered antibody sequence
source                   1..7
                         mol_type = protein
                         organism = synthetic construct
SEQUENCE: 386
STSTLAS                                                                7

SEQ ID NO: 387           moltype = AA  length = 32
FEATURE                  Location/Qualifiers
REGION                   1..32
                         note = Engineered antibody sequence
source                   1..32
                         mol_type = protein
                         organism = synthetic construct
SEQUENCE: 387
GVPSRFSGSG SGTDFTLTIS SLQPEDVATY YC                                   32

SEQ ID NO: 388           moltype = AA  length = 13
FEATURE                  Location/Qualifiers
REGION                   1..13
                         note = Engineered antibody sequence
source                   1..13
                         mol_type = protein
                         organism = synthetic construct
SEQUENCE: 388
LGSYDCSRGD CFV                                                        13

SEQ ID NO: 389           moltype = AA  length = 11
FEATURE                  Location/Qualifiers
REGION                   1..11
                         note = Engineered antibody sequence
source                   1..11
                         mol_type = protein
                         organism = synthetic construct
SEQUENCE: 389
FGGGTKVEIK R                                                          11

SEQ ID NO: 390           moltype = AA  length = 106
FEATURE                  Location/Qualifiers
REGION                   1..106
                         note = Engineered antibody sequence
source                   1..106
                         mol_type = protein
                         organism = synthetic construct
SEQUENCE: 390
TVAAPSVFIF PPSDEQLKSG TASVVCLLNN FYPREAKVQW KVDNALQSGN SQESVTEQDS     60
KDSTYSLSST LTLSKADYEK HKVYACEVTH QGLSSPVTKS FNRGEC                   106

SEQ ID NO: 391           moltype = DNA  length = 660
FEATURE                  Location/Qualifiers
misc_feature             1..660
                         note = Engineered antibody sequence
```

```
                        source              1..660
                                            mol_type = other DNA
                                            organism = synthetic construct
SEQUENCE: 391
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 392         moltype = DNA   length = 339
FEATURE                Location/Qualifiers
misc_feature           1..339
                       note = Engineered antibody sequence
source                 1..339
                       mol_type = other DNA
                       organism = synthetic construct
SEQUENCE: 392
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgt                          339

SEQ ID NO: 393         moltype = DNA   length = 66
FEATURE                Location/Qualifiers
misc_feature           1..66
                       note = Engineered antibody sequence
source                 1..66
                       mol_type = other DNA
                       organism = synthetic construct
SEQUENCE: 393
caagtgctga cccagtctcc atcctccctg tctgcatctg taggagacag agtcaccatc    60
aattgc                                                               66

SEQ ID NO: 394         moltype = DNA   length = 39
FEATURE                Location/Qualifiers
misc_feature           1..39
                       note = Engineered antibody sequence
source                 1..39
                       mol_type = other DNA
                       organism = synthetic construct
SEQUENCE: 394
caggccagtc agaatgttta caataacaac tacctagcc                           39

SEQ ID NO: 395         moltype = DNA   length = 45
FEATURE                Location/Qualifiers
misc_feature           1..45
                       note = Engineered antibody sequence
source                 1..45
                       mol_type = other DNA
                       organism = synthetic construct
SEQUENCE: 395
tggtatcagc agaaaccagg gaaagttcct aagcaactga tctat                    45

SEQ ID NO: 396         moltype = DNA   length = 21
FEATURE                Location/Qualifiers
misc_feature           1..21
                       note = Engineered antibody sequence
source                 1..21
                       mol_type = other DNA
                       organism = synthetic construct
SEQUENCE: 396
tctacatcca ctctggcatc t                                              21

SEQ ID NO: 397         moltype = DNA   length = 96
FEATURE                Location/Qualifiers
misc_feature           1..96
                       note = Engineered antibody sequence
source                 1..96
                       mol_type = other DNA
                       organism = synthetic construct
```

```
SEQUENCE: 397
ggggtcccat ctcgtttcag tggcagtgga tctgggacag atttcactct caccatcagc    60
agcctgcagc ctgaagatgt tgcaacttat tactgt                              96

SEQ ID NO: 398          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 398
ctgggcagtt atgattgtag tcgtggtgat tgttttgtt                            39

SEQ ID NO: 399          moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 399
ttcggcggag gaaccaaggt ggaaatcaaa cgt                                  33

SEQ ID NO: 400          moltype = DNA   length = 321
FEATURE                 Location/Qualifiers
misc_feature            1..321
                        note = Engineered antibody sequence
source                  1..321
                        mol_type = other DNA
                        organism = synthetic construct
SEQUENCE: 400
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                              321

SEQ ID NO: 401          moltype = AA    length = 439
FEATURE                 Location/Qualifiers
REGION                  1..439
                        note = Engineered antibody sequence
source                  1..439
                        mol_type = protein
                        organism = synthetic construct
SEQUENCE: 401
QSLEESGGRL VTPGGSLTLT CTVSGIDVTN YYMQWVRQAP GKGLEWIGVI GVNGKRYYAS     60
WAKGRFTISK TSSTTVDLKM TSLTTEDTAT YFCARGDIWG PGTLVTVSSA STKGPSVFPL    120
APSSKSTSGG TAALGCLVKD YFPEPVTVSW NSGALTSGVH TFPAVLQSSG LYSLSSVVTV    180
PSSSLGTQTY ICNVNHKPSN TKVDKRVEPK SCDKTHTCPP CPAPELLGGP SVFLFPPKPK    240
DTLMISRTPE VTCVVVDVSH EDPEVKFNWY VDGVEVHNAK TKPREEQYAS TYRVVSVLTV    300
LHQDWLNGKE YKCKVSNKAL PAPIEKTISK AKGQPREPQV YTLPPSREEM TKNQVSLTCL    360
VKGFYPSDIA VEWESNGQPE NNYKTTPPVL DSDGSFFLYS KLTVDKSRWQ QGNVFSCSVM    420
HEALHNHYTQ KSLSLSPGK                                                 439

SEQ ID NO: 402          moltype = AA    length = 109
FEATURE                 Location/Qualifiers
REGION                  1..109
                        note = Engineered antibody sequence
source                  1..109
                        mol_type = protein
                        organism = synthetic construct
SEQUENCE: 402
QSLEESGGRL VTPGGSLTLT CTVSGIDVTN YYMQWVRQAP GKGLEWIGVI GVNGKRYYAS     60
WAKGRFTISK TSSTTVDLKM TSLTTEDTAT YFCARGDIWG PGTLVTVSS                109

SEQ ID NO: 403          moltype = AA    length = 29
FEATURE                 Location/Qualifiers
REGION                  1..29
                        note = Engineered antibody sequence
source                  1..29
                        mol_type = protein
                        organism = synthetic construct
SEQUENCE: 403
QSLEESGGRL VTPGGSLTLT CTVSGIDVT                                       29

SEQ ID NO: 404          moltype = AA    length = 5
FEATURE                 Location/Qualifiers
```

| | | |
|---|---|---|
| REGION | 1..5 | |
| | note = Engineered antibody sequence | |
| source | 1..5 | |
| | mol_type = protein | |
| | organism = synthetic construct | |

SEQUENCE: 404
NYYMQ                                                                    5

| | | |
|---|---|---|
| SEQ ID NO: 405 | moltype = AA  length = 14 | |
| FEATURE | Location/Qualifiers | |
| REGION | 1..14 | |
| | note = Engineered antibody sequence | |
| source | 1..14 | |
| | mol_type = protein | |
| | organism = synthetic construct | |

SEQUENCE: 405
WVRQAPGKGL EWIG                                                          14

| | | |
|---|---|---|
| SEQ ID NO: 406 | moltype = AA  length = 16 | |
| FEATURE | Location/Qualifiers | |
| REGION | 1..16 | |
| | note = Engineered antibody sequence | |
| source | 1..16 | |
| | mol_type = protein | |
| | organism = synthetic construct | |

SEQUENCE: 406
VIGVNGKRYY ASWAKG                                                        16

| | | |
|---|---|---|
| SEQ ID NO: 407 | moltype = AA  length = 31 | |
| FEATURE | Location/Qualifiers | |
| REGION | 1..31 | |
| | note = Engineered antibody sequence | |
| source | 1..31 | |
| | mol_type = protein | |
| | organism = synthetic construct | |

SEQUENCE: 407
RFTISKTSST TVDLKMTSLT TEDTATYFCA R                                       31

| | | |
|---|---|---|
| SEQ ID NO: 408 | moltype =   length = | |
| SEQUENCE: 408 | | |
| 000 | | |

| | | |
|---|---|---|
| SEQ ID NO: 409 | moltype = AA  length = 11 | |
| FEATURE | Location/Qualifiers | |
| REGION | 1..11 | |
| | note = Engineered antibody sequence | |
| source | 1..11 | |
| | mol_type = protein | |
| | organism = synthetic construct | |

SEQUENCE: 409
WGPGTLVTVS S                                                             11

| | | |
|---|---|---|
| SEQ ID NO: 410 | moltype = AA  length = 330 | |
| FEATURE | Location/Qualifiers | |
| REGION | 1..330 | |
| | note = Engineered antibody sequence | |
| source | 1..330 | |
| | mol_type = protein | |
| | organism = synthetic construct | |

SEQUENCE: 410
ASTKGPSVFP LAPSSKSTSG GTAALGCLVK DYFPEPVTVS WNSGALTSGV HTFPAVLQSS      60
GLYSLSSVVT VPSSSLGTQT YICNVNHKPS NTKVDKRVEP KSCDKTHTCP PCPAPELLGG     120
PSVFLFPPKP KDTLMISRTP EVTCVVVDVS HEDPEVKFNW YVDGVEVHNA KTKPREEQYA     180
STYRVVSVLT VLHQDWLNGK EYKCKVSNKA LPAPIEKTIS KAKGQPREPQ VYTLPPSREE     240
MTKNQVSLTC LVKGFYPSDI AVEWESNGQP ENNYKTTPPV LDSDGSFFLY SKLTVDKSRW     300
QQGNVFSCSV MHEALHNHYT QKSLSLSPGK                                      330

| | | |
|---|---|---|
| SEQ ID NO: 411 | moltype = DNA  length = 1320 | |
| FEATURE | Location/Qualifiers | |
| misc_feature | 1..1320 | |
| | note = Engineered antibody sequence | |
| source | 1..1320 | |
| | mol_type = other DNA | |
| | organism = synthetic construct | |

SEQUENCE: 411
cagtcgctgg aggagtccgg gggtcgcctg gtcacgcctg gaggatccct gacactcacc      60
tgcacagtct ctggaatcga cgtcactaac tactatatgc aatgggtccg ccaggctcca     120
gggaaggggc tggaatggat cggagtcatt ggtgtgaatg gtaagagata ctacgcgagc     180
tgggcgaaag gccgattcac catctccaaa acctcgtcga ccacggtgga tctgaaaatg     240

```
accagtctga caaccgagga cacggccacc tatttctgtg ccagaggcga catctggggc    300
ccggggaccc tcgtcaccgt ctcgagcgca tccaccaagg gcccatcggt cttccccctg    360
gcaccctcct ccaagagcac ctctgggggc acagcggccc tgggctgcct ggtcaaggac    420
tacttccccg aaccggtgac ggtgtcgtgg aactcaggcg ccctgaccag cggcgtgcac    480
accttcccgg ctgtcctaca gtcctcagga ctctactccc tcagcagcgt ggtgaccgtg    540
ccctccagca gcttgggcac ccagacctac atctgcaacg tgaatcacaa gcccagcaac    600
accaaggtgg acaagagagt tgagcccaaa tcttgtgaca aaactcacac atgcccaccg    660
tgcccagcac ctgaactcct ggggggaccg tcagtcttcc tcttccccc aaaacccaag     720
gacaccctca tgatctcccg gacccctgag gtcacatgcg tggtggtgga cgtgagccac    780
gaagaccctg aggtcaagtt caactggtac gtggacggcg tggaggtgca taatgccaag    840
acaaagccgc gggaggagca gtacgccagc acgtaccgtg tggtcagcgt cctcaccgtc    900
ctgcaccagg actggctgaa tggcaaggag tacaagtgca aggtctccaa caaagccctc    960
ccagccccca tcgagaaaac catctccaaa gccaaagggc agccccgaga accacaggtg   1020
tacaccctgc ccccatcccg ggaggagatg accaagaacc aggtcagcct gacctgcctg   1080
gtcaaaggct tctatcccag cgacatcgcc gtggagtggg agagcaatgg gcagccggag   1140
aacaactaca agaccacgcc tcccgtgctg gactccgacg gctccttctt cctctacagc   1200
aagctcaccg tggacaagag caggtggcag caggggaacg tcttctcatg ctccgtgatg   1260
catgaggctc tgcacaacca ctacacgcag aagagcctct ccctgtctcc gggtaaatga   1320

SEQ ID NO: 412          moltype = DNA   length = 327
FEATURE                 Location/Qualifiers
misc_feature            1..327
                        note = Engineered antibody sequence
source                  1..327
                        mol_type = other DNA
                        organism = synthetic construct
SEQUENCE: 412
cagtcgctgg aggagtccgg gggtcgcctg gtcacgcctg gaggatccct gacactcacc     60
tgcacagtct ctggaatcga cgtcactaac tactatatgc aatgggtccg ccaggctcca    120
gggaaggggc tggaatggat cggagtcatt ggtgtgaatg gtaagagata ctacgcgagc    180
tgggcgaaag gccgattcac catctccaaa acctcgtcga ccacggtgga tctgaaaatg    240
accagtctga caaccgagga cacggccacc tatttctgtg ccagaggcga catctggggc    300
ccggggaccc tcgtcaccgt ctcgagc                                        327

SEQ ID NO: 413          moltype = DNA   length = 87
FEATURE                 Location/Qualifiers
misc_feature            1..87
                        note = Engineered antibody sequence
source                  1..87
                        mol_type = other DNA
                        organism = synthetic construct
SEQUENCE: 413
cagtcgctgg aggagtccgg gggtcgcctg gtcacgcctg gaggatccct gacactcacc     60
tgcacagtct ctggaatcga cgtcact                                         87

SEQ ID NO: 414          moltype = DNA   length = 15
FEATURE                 Location/Qualifiers
misc_feature            1..15
                        note = Engineered antibody sequence
source                  1..15
                        mol_type = other DNA
                        organism = synthetic construct
SEQUENCE: 414
aactactata tgcaa                                                      15

SEQ ID NO: 415          moltype = DNA   length = 42
FEATURE                 Location/Qualifiers
misc_feature            1..42
                        note = Engineered antibody sequence
source                  1..42
                        mol_type = other DNA
                        organism = synthetic construct
SEQUENCE: 415
tgggtccgcc aggctccagg gaaggggctg gaatggatcg ga                        42

SEQ ID NO: 416          moltype = DNA   length = 48
FEATURE                 Location/Qualifiers
misc_feature            1..48
                        note = Engineered antibody sequence
source                  1..48
                        mol_type = other DNA
                        organism = synthetic construct
SEQUENCE: 416
gtcattggtg tgaatggtaa gagatactac gcgagctggg cgaaaggc                  48

SEQ ID NO: 417          moltype = DNA   length = 93
FEATURE                 Location/Qualifiers
misc_feature            1..93
                        note = Engineered antibody sequence
```

```
source                      1..93
                            mol_type = other DNA
                            organism = synthetic construct
SEQUENCE: 417
cgattcacca tctccaaaac ctcgtcgacc acggtggatc tgaaaatgac cagtctgaca      60
accgaggaca cggccaccta tttctgtgcc aga                                   93

SEQ ID NO: 418              moltype =    length =
SEQUENCE: 418
000

SEQ ID NO: 419              moltype = DNA   length = 33
FEATURE                     Location/Qualifiers
misc_feature                1..33
                            note = Engineered antibody sequence
source                      1..33
                            mol_type = other DNA
                            organism = synthetic construct
SEQUENCE: 419
tggggcccgg ggaccctcgt caccgtctcg agc                                   33

SEQ ID NO: 420              moltype = DNA   length = 993
FEATURE                     Location/Qualifiers
misc_feature                1..993
                            note = Engineered antibody sequence
source                      1..993
                            mol_type = other DNA
                            organism = synthetic construct
SEQUENCE: 420
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctggggggga    360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacgcc     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggaggag     720
atgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa tga                                  993

SEQ ID NO: 421              moltype = AA   length = 219
FEATURE                     Location/Qualifiers
REGION                      1..219
                            note = Engineered antibody sequence
source                      1..219
                            mol_type = protein
                            organism = synthetic construct
SEQUENCE: 421
QVLTQTASPV SPAVGSTVTI NCRASQSVYY NNYLAWYQQK PGQPPKQLIY STSTLASGVS      60
SRFKGSGSGT QFTLTISDVQ CDDAATYYCL GSYDCSNGDC FVFGGGTEVV VKRTVAAPSV     120
FIFPPSDEQL KSGTASVVCL LNNFYPREAK VQWKVDNALQ SGNSQESVTE QDSKDSTYSL     180
SSTLTLSKAD YEKHKVYACE VTHQGLSSPV TKSFNRGEC                            219

SEQ ID NO: 422              moltype = AA   length = 113
FEATURE                     Location/Qualifiers
REGION                      1..113
                            note = Engineered antibody sequence
source                      1..113
                            mol_type = protein
                            organism = synthetic construct
SEQUENCE: 422
QVLTQTASPV SPAVGSTVTI NCRASQSVYY NNYLAWYQQK PGQPPKQLIY STSTLASGVS      60
SRFKGSGSGT QFTLTISDVQ CDDAATYYCL GSYDCSNGDC FVFGGGTEVV VKR            113

SEQ ID NO: 423              moltype = AA   length = 22
FEATURE                     Location/Qualifiers
REGION                      1..22
                            note = Engineered antibody sequence
source                      1..22
                            mol_type = protein
                            organism = synthetic construct
SEQUENCE: 423
```

```
QVLTQTASPV SPAVGSTVTI NC                                             22

SEQ ID NO: 424          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 424
RASQSVYYNN YLA                                                       13

SEQ ID NO: 425          moltype = AA   length = 15
FEATURE                 Location/Qualifiers
REGION                  1..15
                        note = Engineered antibody sequence
source                  1..15
                        mol_type = protein
                        organism = synthetic construct
SEQUENCE: 425
WYQQKPGQPP KQLIY                                                     15

SEQ ID NO: 426          moltype = AA   length = 7
FEATURE                 Location/Qualifiers
REGION                  1..7
                        note = Engineered antibody sequence
source                  1..7
                        mol_type = protein
                        organism = synthetic construct
SEQUENCE: 426
STSTLAS                                                              7

SEQ ID NO: 427          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 427
GVSSRFKGSG SGTQFTLTIS DVQCDDAATY YC                                  32

SEQ ID NO: 428          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 428
LGSYDCSNGD CFV                                                       13

SEQ ID NO: 429          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 429
FGGGTEVVVK R                                                         11

SEQ ID NO: 430          moltype = AA   length = 106
FEATURE                 Location/Qualifiers
REGION                  1..106
                        note = Engineered antibody sequence
source                  1..106
                        mol_type = protein
                        organism = synthetic construct
SEQUENCE: 430
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                   106

SEQ ID NO: 431          moltype = DNA   length = 660
FEATURE                 Location/Qualifiers
misc_feature            1..660
                        note = Engineered antibody sequence
source                  1..660
                        mol_type = other DNA
```

```
                        organism = synthetic construct
SEQUENCE: 431
caggtgctga cccagactgc atccccgtg tctccagctg tgggaagcac agtcaccatc    60
aattgccggg ccagtcagag tgtttattat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacgtgcag   240
tgtgacgatg ctgccactta ctactgtcta ggcagttatg attgtagtaa tggtgattgt   300
tttgttttcg gcggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct caacaggggg agagtgttag   660

SEQ ID NO: 432             moltype = DNA   length = 339
FEATURE                    Location/Qualifiers
misc_feature               1..339
                           note = Engineered antibody sequence
source                     1..339
                           mol_type = other DNA
                           organism = synthetic construct
SEQUENCE: 432
caggtgctga cccagactgc atccccgtg tctccagctg tgggaagcac agtcaccatc    60
aattgccggg ccagtcagag tgtttattat aacaactacc tagcctggta tcagcagaaa   120
ccagggcagc ctcccaagca actgatctat tctacatcca ctctggcatc tggggtctca   180
tcgcggttca aaggcagtgg atctgggaca cagttcactc tcaccatcag cgacgtgcag   240
tgtgacgatg ctgccactta ctactgtcta ggcagttatg attgtagtaa tggtgattgt   300
tttgttttcg gcggagggac cgaggtggtg gtcaaacgt                         339

SEQ ID NO: 433             moltype = DNA   length = 66
FEATURE                    Location/Qualifiers
misc_feature               1..66
                           note = Engineered antibody sequence
source                     1..66
                           mol_type = other DNA
                           organism = synthetic construct
SEQUENCE: 433
caggtgctga cccagactgc atccccgtg tctccagctg tgggaagcac agtcaccatc    60
aattgc                                                              66

SEQ ID NO: 434             moltype = DNA   length = 39
FEATURE                    Location/Qualifiers
misc_feature               1..39
                           note = Engineered antibody sequence
source                     1..39
                           mol_type = other DNA
                           organism = synthetic construct
SEQUENCE: 434
cgggccagtc agagtgttta ttataacaac tacctagcc                          39

SEQ ID NO: 435             moltype = DNA   length = 45
FEATURE                    Location/Qualifiers
misc_feature               1..45
                           note = Engineered antibody sequence
source                     1..45
                           mol_type = other DNA
                           organism = synthetic construct
SEQUENCE: 435
tggtatcagc agaaaccagg gcagcctccc aagcaactga tctat                   45

SEQ ID NO: 436             moltype = DNA   length = 21
FEATURE                    Location/Qualifiers
misc_feature               1..21
                           note = Engineered antibody sequence
source                     1..21
                           mol_type = other DNA
                           organism = synthetic construct
SEQUENCE: 436
tctacatcca ctctggcatc t                                             21

SEQ ID NO: 437             moltype = DNA   length = 96
FEATURE                    Location/Qualifiers
misc_feature               1..96
                           note = Engineered antibody sequence
source                     1..96
                           mol_type = other DNA
                           organism = synthetic construct
SEQUENCE: 437
ggggtctcat cgcggttcaa aggcagtgga tctgggacac agttcactct caccatcagc    60
```

```
gacgtgcagt gtgacgatgc tgccacttac tactgt                                 96

SEQ ID NO: 438           moltype = DNA  length = 39
FEATURE                  Location/Qualifiers
misc_feature             1..39
                         note = Engineered antibody sequence
source                   1..39
                         mol_type = other DNA
                         organism = synthetic construct
SEQUENCE: 438
ctaggcagtt atgattgtag taatggtgat tgttttgtt                              39

SEQ ID NO: 439           moltype = DNA  length = 33
FEATURE                  Location/Qualifiers
misc_feature             1..33
                         note = Engineered antibody sequence
source                   1..33
                         mol_type = other DNA
                         organism = synthetic construct
SEQUENCE: 439
ttcggcggag ggaccgaggt ggtggtcaaa cgt                                    33

SEQ ID NO: 440           moltype = DNA  length = 321
FEATURE                  Location/Qualifiers
misc_feature             1..321
                         note = Engineered antibody sequence
source                   1..321
                         mol_type = other DNA
                         organism = synthetic construct
SEQUENCE: 440
acggtggctg caccatctgt cttcatcttc ccgccatctg atgagcagtt gaaatctgga       60
actgcctctg ttgtgtgcct gctgaataac ttctatccca gagaggccaa agtacagtgg      120
aaggtggata acgccctcca atcgggtaac tcccaggaga gtgtcacaga gcaggacagc      180
aaggacagca cctacagcct cagcagcacc ctgacgctga gcaaagcaga ctacgagaaa      240
cacaaagtct acgcctgcga agtcacccat cagggcctga gctcgcccgt cacaaagagc      300
ttcaacaggg gagagtgtta g                                                321

SEQ ID NO: 441           moltype = AA  length = 441
FEATURE                  Location/Qualifiers
REGION                   1..441
                         note = Engineered antibody sequence
source                   1..441
                         mol_type = protein
                         organism = synthetic construct
SEQUENCE: 441
EVQLVESGGG LVQPGGSLRL SCAVSGIDVT NYYMQWVRQA PGKGLEWVGV IGVNGKRYYA       60
SWAKGRFTIS RDNSKTTVYL QMNSLRAEDT AVYFCARGDI WGQGTLVTVS SASTKGPSVF      120
PLAPSSKSTS GGTAALGCLV KDYFPEPVTV SWNSGALTSG VHTFPAVLQS SGLYSLSSVV      180
TVPSSSLGTQ TYICNVNHKP SNTKVDKRVE PKSCDKTHTC PPCPAPELLG GPSVFLFPPK      240
PKDTLMISRT PEVTCVVVDV SHEDPEVKFN WYVDGVEVHN AKTKPREEQY ASTYRVVSVL      300
TVLHQDWLNG KEYKCKVSNK ALPAPIEKTI SKAKGQPREP QVYTLPPSRE EMTKNQVSLT      360
CLVKGFYPSD IAVEWESNGQ PENNYKTTPP VLDSDGSFFL YSKLTVDKSR WQQGNVFSCS      420
VMHEALHNHY TQKSLSLSPG K                                                441

SEQ ID NO: 442           moltype = AA  length = 111
FEATURE                  Location/Qualifiers
REGION                   1..111
                         note = Engineered antibody sequence
source                   1..111
                         mol_type = protein
                         organism = synthetic construct
SEQUENCE: 442
EVQLVESGGG LVQPGGSLRL SCAVSGIDVT NYYMQWVRQA PGKGLEWVGV IGVNGKRYYA       60
SWAKGRFTIS RDNSKTTVYL QMNSLRAEDT AVYFCARGDI WGQGTLVTVS S               111

SEQ ID NO: 443           moltype = AA  length = 30
FEATURE                  Location/Qualifiers
REGION                   1..30
                         note = Engineered antibody sequence
source                   1..30
                         mol_type = protein
                         organism = synthetic construct
SEQUENCE: 443
EVQLVESGGG LVQPGGSLRL SCAVSGIDVT                                        30

SEQ ID NO: 444           moltype = AA  length = 5
FEATURE                  Location/Qualifiers
REGION                   1..5
                         note = Engineered antibody sequence
```

| source | 1..5 |
| --- | --- |
| | mol_type = protein |
| | organism = synthetic construct |

SEQUENCE: 444
NYYMQ                                                                5

| SEQ ID NO: 445 | moltype = AA   length = 14 |
| --- | --- |
| FEATURE | Location/Qualifiers |
| REGION | 1..14 |
| | note = Engineered antibody sequence |
| source | 1..14 |
| | mol_type = protein |
| | organism = synthetic construct |

SEQUENCE: 445
WVRQAPGKGL EWVG                                                     14

| SEQ ID NO: 446 | moltype = AA   length = 16 |
| --- | --- |
| FEATURE | Location/Qualifiers |
| REGION | 1..16 |
| | note = Engineered antibody sequence |
| source | 1..16 |
| | mol_type = protein |
| | organism = synthetic construct |

SEQUENCE: 446
VIGVNGKRYY ASWAKG                                                   16

| SEQ ID NO: 447 | moltype = AA   length = 32 |
| --- | --- |
| FEATURE | Location/Qualifiers |
| REGION | 1..32 |
| | note = Engineered antibody sequence |
| source | 1..32 |
| | mol_type = protein |
| | organism = synthetic construct |

SEQUENCE: 447
RFTISRDNSK TTVYLQMNSL RAEDTAVYFC AR                                  32

| SEQ ID NO: 448 | moltype =    length = |
| --- | --- |

SEQUENCE: 448
000

| SEQ ID NO: 449 | moltype = AA   length = 11 |
| --- | --- |
| FEATURE | Location/Qualifiers |
| REGION | 1..11 |
| | note = Engineered antibody sequence |
| source | 1..11 |
| | mol_type = protein |
| | organism = synthetic construct |

SEQUENCE: 449
WGQGTLVTVS S                                                        11

| SEQ ID NO: 450 | moltype = AA   length = 330 |
| --- | --- |
| FEATURE | Location/Qualifiers |
| REGION | 1..330 |
| | note = Engineered antibody sequence |
| source | 1..330 |
| | mol_type = protein |
| | organism = synthetic construct |

SEQUENCE: 450
ASTKGPSVFP LAPSSKSTSG GTAALGCLVK DYFPEPVTVS WNSGALTSGV HTFPAVLQSS     60
GLYSLSSVVT VPSSSLGTQT YICNVNHKPS NTKVDKRVEP KSCDKTHTCP PCPAPELLGG    120
PSVFLFPPKP KDTLMISRTP EVTCVVVDVS HEDPEVKFNW YVDGVEVHNA KTKPREEQYA    180
STYRVVSVLT VLHQDWLNGK EYKCKVSNKA LPAPIEKTIS KAKGQPREPQ VYTLPPSREE    240
MTKNQVSLTC LVKGFYPSDI AVEWESNGQP ENNYKTTPPV LDSDGSFFLY SKLTVDKSRW    300
QQGNVFSCSV MHEALHNHYT QKSLSLSPGK                                    330

| SEQ ID NO: 451 | moltype = DNA   length = 1326 |
| --- | --- |
| FEATURE | Location/Qualifiers |
| misc_feature | 1..1326 |
| | note = Engineered antibody sequence |
| source | 1..1326 |
| | mol_type = other DNA |
| | organism = synthetic construct |

SEQUENCE: 451
gaggtgcagc ttgtggagtc tgggggaggc ttggtccagc ctggggggtc cctgagactc     60
tcctgtgcag tctctggaat cgacgtcact aactactaca tgcaatgggt ccgtcaggct    120
ccagggaagg ggctgagtg gtcggagtc attgtgtga atggtaagag atactacgcg      180
agctgggcga aaggccgatt caccatctcc agagacaatt ccaagaccac ggtgtatctt    240
caaatgaaca gcctgagagc tgaggacact gctgtgtatt tctgtgccag aggggacatc    300
tggggccaag gaccctcgt caccgtctcg agcgcctcca ccaagggccc atcggtcttc     360

```
cccctggcac cctcctccaa gagcacctct gggggcacag cggccctggg ctgcctggtc    420
aaggactact tccccgaacc ggtgacggtg tcgtggaact caggcgccct gaccagcggc    480
gtgcacacct tccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga actcctgggg gaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac gccagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca aagggcagcc ccgagaacca   1020
caggtgtaca ccctgccccc atcccggag gagatgacca gaaccaggt cagcctgacc   1080
tgcctggtca aaggcttcta tcccagcgac atcgccgtgg agtgggagag caatgggcag   1140
ccggagaaca actacaagac cacgcctccc gtgctgtact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                                1326

SEQ ID NO: 452         moltype = DNA  length = 333
FEATURE                Location/Qualifiers
misc_feature           1..333
                       note = Engineered antibody sequence
source                 1..333
                       mol_type = other DNA
                       organism = synthetic construct
SEQUENCE: 452
gaggtgcagc ttgtggagtc tgggggaggc ttggtccagc ctggggggtc cctgagactc     60
tcctgtgcag tctctggaat cgacgtcact aactactaca tgcaatgggt ccgtcaggct    120
ccagggaagg ggctggagtg ggtcggagtc attggtgtga atggtaagag atactacgcg    180
agctgggcga aggccgatt caccatctcc agagacaatt ccaagaccac ggtgtatctt    240
caaatgaaca gcctgagagc tgaggacact gctgtgtatt tctgtgccag aggggacatc    300
tggggccaag ggaccctcgt caccgtctcg agc                                 333

SEQ ID NO: 453         moltype = DNA  length = 90
FEATURE                Location/Qualifiers
misc_feature           1..90
                       note = Engineered antibody sequence
source                 1..90
                       mol_type = other DNA
                       organism = synthetic construct
SEQUENCE: 453
gaggtgcagc ttgtggagtc tgggggaggc ttggtccagc ctggggggtc cctgagactc     60
tcctgtgcag tctctggaat cgacgtcact                                      90

SEQ ID NO: 454         moltype = DNA  length = 15
FEATURE                Location/Qualifiers
misc_feature           1..15
                       note = Engineered antibody sequence
source                 1..15
                       mol_type = other DNA
                       organism = synthetic construct
SEQUENCE: 454
aactactaca tgcaa                                                      15

SEQ ID NO: 455         moltype = DNA  length = 42
FEATURE                Location/Qualifiers
misc_feature           1..42
                       note = Engineered antibody sequence
source                 1..42
                       mol_type = other DNA
                       organism = synthetic construct
SEQUENCE: 455
tgggtccgtc aggctccagg gaaggggctg gagtgggtcg ga                        42

SEQ ID NO: 456         moltype = DNA  length = 48
FEATURE                Location/Qualifiers
misc_feature           1..48
                       note = Engineered antibody sequence
source                 1..48
                       mol_type = other DNA
                       organism = synthetic construct
SEQUENCE: 456
gtcattggtg tgaatggtaa gagatactac gcgagctggg cgaaaggc                  48

SEQ ID NO: 457         moltype = DNA  length = 96
FEATURE                Location/Qualifiers
misc_feature           1..96
                       note = Engineered antibody sequence
source                 1..96
```

```
                        mol_type = other DNA
                        organism = synthetic construct
SEQUENCE: 457
cgattcacca tctccagaga caattccaag accacggtgt atcttcaaat gaacagcctg    60
agagctgagg acactgctgt gtatttctgt gccaga                              96

SEQ ID NO: 458          moltype =    length =
SEQUENCE: 458
000

SEQ ID NO: 459          moltype = DNA   length = 33
FEATURE                 Location/Qualifiers
misc_feature            1..33
                        note = Engineered antibody sequence
source                  1..33
                        mol_type = other DNA
                        organism = synthetic construct
SEQUENCE: 459
tggggccaag ggaccctcgt caccgtctcg agc                                 33

SEQ ID NO: 460          moltype = DNA   length = 993
FEATURE                 Location/Qualifiers
misc_feature            1..993
                        note = Engineered antibody sequence
source                  1..993
                        mol_type = other DNA
                        organism = synthetic construct
SEQUENCE: 460
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctggggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993

SEQ ID NO: 461          moltype = AA   length = 219
FEATURE                 Location/Qualifiers
REGION                  1..219
                        note = Engineered antibody sequence
source                  1..219
                        mol_type = protein
                        organism = synthetic construct
SEQUENCE: 461
QVLTQSPSSL SASVGDRVTI NCRASQSVYY NNYLAWYQQK PGKVPKQLIY STSTLASGVP    60
SRFSGSGSGT DFTLTISSLQ PEDVATYYCL GSYDCSNGDC FVFGGGTKVE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 462          moltype = AA   length = 113
FEATURE                 Location/Qualifiers
REGION                  1..113
                        note = Engineered antibody sequence
source                  1..113
                        mol_type = protein
                        organism = synthetic construct
SEQUENCE: 462
QVLTQSPSSL SASVGDRVTI NCRASQSVYY NNYLAWYQQK PGKVPKQLIY STSTLASGVP    60
SRFSGSGSGT DFTLTISSLQ PEDVATYYCL GSYDCSNGDC FVFGGGTKVE IKR          113

SEQ ID NO: 463          moltype = AA   length = 22
FEATURE                 Location/Qualifiers
REGION                  1..22
                        note = Engineered antibody sequence
source                  1..22
                        mol_type = protein
                        organism = synthetic construct
SEQUENCE: 463
QVLTQSPSSL SASVGDRVTI NC                                             22
```

| | | |
|---|---|---|
| SEQ ID NO: 464 | moltype = AA  length = 13 | |
| FEATURE | Location/Qualifiers | |
| REGION | 1..13 | |
| | note = Engineered antibody sequence | |
| source | 1..13 | |
| | mol_type = protein | |
| | organism = synthetic construct | |
| SEQUENCE: 464 | | |
| RASQSVYYNN YLA | | 13 |
| | | |
| SEQ ID NO: 465 | moltype = AA  length = 15 | |
| FEATURE | Location/Qualifiers | |
| REGION | 1..15 | |
| | note = Engineered antibody sequence | |
| source | 1..15 | |
| | mol_type = protein | |
| | organism = synthetic construct | |
| SEQUENCE: 465 | | |
| WYQQKPGKVP KQLIY | | 15 |
| | | |
| SEQ ID NO: 466 | moltype = AA  length = 7 | |
| FEATURE | Location/Qualifiers | |
| REGION | 1..7 | |
| | note = Engineered antibody sequence | |
| source | 1..7 | |
| | mol_type = protein | |
| | organism = synthetic construct | |
| SEQUENCE: 466 | | |
| STSTLAS | | 7 |
| | | |
| SEQ ID NO: 467 | moltype = AA  length = 32 | |
| FEATURE | Location/Qualifiers | |
| REGION | 1..32 | |
| | note = Engineered antibody sequence | |
| source | 1..32 | |
| | mol_type = protein | |
| | organism = synthetic construct | |
| SEQUENCE: 467 | | |
| GVPSRFSGSG SGTDFTLTIS SLQPEDVATY YC | | 32 |
| | | |
| SEQ ID NO: 468 | moltype = AA  length = 13 | |
| FEATURE | Location/Qualifiers | |
| REGION | 1..13 | |
| | note = Engineered antibody sequence | |
| source | 1..13 | |
| | mol_type = protein | |
| | organism = synthetic construct | |
| SEQUENCE: 468 | | |
| LGSYDCSNGD CFV | | 13 |
| | | |
| SEQ ID NO: 469 | moltype = AA  length = 11 | |
| FEATURE | Location/Qualifiers | |
| REGION | 1..11 | |
| | note = Engineered antibody sequence | |
| source | 1..11 | |
| | mol_type = protein | |
| | organism = synthetic construct | |
| SEQUENCE: 469 | | |
| FGGGTKVEIK R | | 11 |
| | | |
| SEQ ID NO: 470 | moltype = AA  length = 106 | |
| FEATURE | Location/Qualifiers | |
| REGION | 1..106 | |
| | note = Engineered antibody sequence | |
| source | 1..106 | |
| | mol_type = protein | |
| | organism = synthetic construct | |
| SEQUENCE: 470 | | |
| TVAAPSVFIF PPSDEQLKSG TASVVCLLNN FYPREAKVQW KVDNALQSGN SQESVTEQDS | | 60 |
| KDSTYSLSST LTLSKADYEK HKVYACEVTH QGLSSPVTKS FNRGEC | | 106 |
| | | |
| SEQ ID NO: 471 | moltype = DNA  length = 660 | |
| FEATURE | Location/Qualifiers | |
| misc_feature | 1..660 | |
| | note = Engineered antibody sequence | |
| source | 1..660 | |
| | mol_type = other DNA | |
| | organism = synthetic construct | |

-continued

```
SEQUENCE: 471
caagtgctga cccagtctcc atcctccctg tctgcatctg taggagacag agtcaccatc     60
aattgccggg ccagtcagag tgtttactat aacaactacc tagcctggta tcagcagaaa    120
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtagtaa tggtgattgt    300
tttgttttcg gcggaggaac caaggtggaa atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660

SEQ ID NO: 472             moltype = DNA  length = 339
FEATURE                    Location/Qualifiers
misc_feature               1..339
                           note = Engineered antibody sequence
source                     1..339
                           mol_type = other DNA
                           organism = synthetic construct
SEQUENCE: 472
caagtgctga cccagtctcc atcctccctg tctgcatctg taggagacag agtcaccatc     60
aattgccggg ccagtcagag tgtttactat aacaactacc tagcctggta tcagcagaaa    120
ccagggaaag ttcctaagca actgatctat tctacatcca ctctggcatc tggggtccca    180
tctcgtttca gtggcagtgg atctgggaca gatttcactc tcaccatcag cagcctgcag    240
cctgaagatg ttgcaactta ttactgtctg ggcagttatg attgtagtaa tggtgattgt    300
tttgttttcg gcggaggaac caaggtggaa atcaaacgt                           339

SEQ ID NO: 473             moltype = DNA  length = 66
FEATURE                    Location/Qualifiers
misc_feature               1..66
                           note = Engineered antibody sequence
source                     1..66
                           mol_type = other DNA
                           organism = synthetic construct
SEQUENCE: 473
caagtgctga cccagtctcc atcctccctg tctgcatctg taggagacag agtcaccatc     60
aattgc                                                                66

SEQ ID NO: 474             moltype = DNA  length = 39
FEATURE                    Location/Qualifiers
misc_feature               1..39
                           note = Engineered antibody sequence
source                     1..39
                           mol_type = other DNA
                           organism = synthetic construct
SEQUENCE: 474
cgggccagtc agagtgttta ctataacaac tacctagcc                            39

SEQ ID NO: 475             moltype = DNA  length = 45
FEATURE                    Location/Qualifiers
misc_feature               1..45
                           note = Engineered antibody sequence
source                     1..45
                           mol_type = other DNA
                           organism = synthetic construct
SEQUENCE: 475
tggtatcagc agaaaccagg gaaagttcct aagcaactga tctat                     45

SEQ ID NO: 476             moltype = DNA  length = 21
FEATURE                    Location/Qualifiers
misc_feature               1..21
                           note = Engineered antibody sequence
source                     1..21
                           mol_type = other DNA
                           organism = synthetic construct
SEQUENCE: 476
tctacatcca ctctggcatc t                                               21

SEQ ID NO: 477             moltype = DNA  length = 96
FEATURE                    Location/Qualifiers
misc_feature               1..96
                           note = Engineered antibody sequence
source                     1..96
                           mol_type = other DNA
                           organism = synthetic construct
SEQUENCE: 477
ggggtcccat ctcgtttcag tggcagtgga tctgggacag atttcactct caccatcagc     60
agcctgcagc ctgaagatgt tgcaacttat tactgt                               96
```

```
SEQ ID NO: 478            moltype = DNA  length = 39
FEATURE                   Location/Qualifiers
misc_feature              1..39
                          note = Engineered antibody sequence
source                    1..39
                          mol_type = other DNA
                          organism = synthetic construct
SEQUENCE: 478
ctgggcagtt atgattgtag taatggtgat tgttttgtt                              39

SEQ ID NO: 479            moltype = DNA  length = 33
FEATURE                   Location/Qualifiers
misc_feature              1..33
                          note = Engineered antibody sequence
source                    1..33
                          mol_type = other DNA
                          organism = synthetic construct
SEQUENCE: 479
ttcggcggag gaaccaaggt ggaaatcaaa cgt                                    33

SEQ ID NO: 480            moltype = DNA  length = 321
FEATURE                   Location/Qualifiers
misc_feature              1..321
                          note = Engineered antibody sequence
source                    1..321
                          mol_type = other DNA
                          organism = synthetic construct
SEQUENCE: 480
acggtggctg caccatctgt cttcatcttc ccgccatctg atgagcagtt gaaatctgga        60
actgcctctg ttgtgtgcct gctgaataac ttctatccca gagaggccaa agtacagtgg       120
aaggtggata acgccctcca atcgggtaac tcccaggaga gtgtcacaga gcaggacagc       180
aaggacagca cctacagcct cagcagcacc ctgacgctga gcaaagcaga ctacgagaaa       240
cacaaagtct acgcctgcga agtcacccat cagggcctga gctcgcccgt cacaaagagc       300
ttcaacaggg gagagtgtta g                                                321

SEQ ID NO: 481            moltype = AA  length = 441
FEATURE                   Location/Qualifiers
REGION                    1..441
                          note = Engineered antibody sequence
source                    1..441
                          mol_type = protein
                          organism = synthetic construct
SEQUENCE: 481
QSVEESGGGL VQPEGSLTLT CTASGFDFSS NAMWWVRQAP GKGLEWIGCI YNGDGSTYYA        60
SWVNGRFSIS KTSSTTVTLQ LNSLTVADTA TYYCARDLDL WGPGTLVTVS SASTKGPSVF       120
PLAPSSKSTS GGTAALGCLV KDYFPEPVTV SWNSGALTSG VHTFPAVLQS SGLYSLSSVV       180
TVPSSSLGTQ TYICNVNHKP SNTKVDKRVE PKSCDKTHTC PPCPAPELLG GPSVFLFPPK       240
PKDTLMISRT PEVTCVVVDV SHEDPEVKFN WYVDGVEVHN AKTKPREEQY ASTYRVVSVL       300
TVLHQDWLNG KEYKCKVSNK ALPAPIEKTI SKAKGQPREP QVYTLPPSRE EMTKNQVSLT       360
CLVKGFYPSD IAVEWESNGQ PENNYKTTPP VLDSDGSFFL YSKLTVDKSR WQQGNVFSCS       420
VMHEALHNHY TQKSLSLSPG K                                                441

SEQ ID NO: 482            moltype = AA  length = 111
FEATURE                   Location/Qualifiers
REGION                    1..111
                          note = Engineered antibody sequence
source                    1..111
                          mol_type = protein
                          organism = synthetic construct
SEQUENCE: 482
QSVEESGGGL VQPEGSLTLT CTASGFDFSS NAMWWVRQAP GKGLEWIGCI YNGDGSTYYA        60
SWVNGRFSIS KTSSTTVTLQ LNSLTVADTA TYYCARDLDL WGPGTLVTVS S                111

SEQ ID NO: 483            moltype = AA  length = 29
FEATURE                   Location/Qualifiers
REGION                    1..29
                          note = Engineered antibody sequence
source                    1..29
                          mol_type = protein
                          organism = synthetic construct
SEQUENCE: 483
QSVEESGGGL VQPEGSLTLT CTASGFDFS                                         29

SEQ ID NO: 484            moltype = AA  length = 5
FEATURE                   Location/Qualifiers
REGION                    1..5
                          note = Engineered antibody sequence
source                    1..5
```

-continued

```
                          mol_type = protein
                          organism = synthetic construct
SEQUENCE: 484
SNAMW                                                                      5

SEQ ID NO: 485            moltype = AA   length = 14
FEATURE                   Location/Qualifiers
REGION                    1..14
                          note = Engineered antibody sequence
source                    1..14
                          mol_type = protein
                          organism = synthetic construct
SEQUENCE: 485
WVRQAPGKGL EWIG                                                           14

SEQ ID NO: 486            moltype = AA   length = 17
FEATURE                   Location/Qualifiers
REGION                    1..17
                          note = Engineered antibody sequence
source                    1..17
                          mol_type = protein
                          organism = synthetic construct
SEQUENCE: 486
CIYNGDGSTY YASWVNG                                                        17

SEQ ID NO: 487            moltype = AA   length = 31
FEATURE                   Location/Qualifiers
REGION                    1..31
                          note = Engineered antibody sequence
source                    1..31
                          mol_type = protein
                          organism = synthetic construct
SEQUENCE: 487
RFSISKTSST TVTLQLNSLT VADTATYYCA R                                        31

SEQ ID NO: 488            moltype = AA   length = 4
FEATURE                   Location/Qualifiers
REGION                    1..4
                          note = Engineered antibody sequence
source                    1..4
                          mol_type = protein
                          organism = synthetic construct
SEQUENCE: 488
DLDL                                                                       4

SEQ ID NO: 489            moltype = AA   length = 11
FEATURE                   Location/Qualifiers
REGION                    1..11
                          note = Engineered antibody sequence
source                    1..11
                          mol_type = protein
                          organism = synthetic construct
SEQUENCE: 489
WGPGTLVTVS S                                                              11

SEQ ID NO: 490            moltype = AA   length = 330
FEATURE                   Location/Qualifiers
REGION                    1..330
                          note = Engineered antibody sequence
source                    1..330
                          mol_type = protein
                          organism = synthetic construct
SEQUENCE: 490
ASTKGPSVFP LAPSSKSTSG GTAALGCLVK DYFPEPVTVS WNSGALTSGV HTFPAVLQSS          60
GLYSLSSVVT VPSSSLGTQT YICNVNHKPS NTKVDKRVEP KSCDKTHTCP PCPAPELLGG         120
PSVFLFPPKP KDTLMISRTP EVTCVVVDVS HEDPEVKFNW YVDGVEVHNA KTKPREEQYA         180
STYRVVSVLT VLHQDWLNGK EYKCKVSNKA LPAPIEKTIS KAKGQPREPQ VYTLPPSREE         240
MTKNQVSLTC LVKGFYPSDI AVEWESNGQP ENNYKTTPPV LDSDGSFFLY SKLTVDKSRW         300
QQGNVFSCSV MHEALHNHYT QKSLSLSPGK                                         330

SEQ ID NO: 491            moltype = DNA   length = 1326
FEATURE                   Location/Qualifiers
misc_feature              1..1326
                          note = Engineered antibody sequence
source                    1..1326
                          mol_type = other DNA
                          organism = synthetic construct
SEQUENCE: 491
cagtcggtgg aggagtccgg gggaggcctg gtccagcctg aggatccct gacactcacc          60
```

```
tgcacagcct ctggattcga cttcagtagc aatgcaatgt ggtgggtccg ccaggctcca    120
gggaaggggc tggagtggat cggatgcatt tacaatggtg atggcagcac atactacgcg    180
agctgggtga atgccgatt ctccatctcc aaaacctcgt cgaccacggt gactctgcaa     240
ctgaatagtc tgacagtcgc ggacacggcc acgtattatt gtgcgagaga tcttgacttg    300
tggggcccgg gcaccctcgt caccgtctcg agcgcctcca ccaagggccc atcggtcttc    360
cccctggcac cctcctccaa gagcacctct gggggcacag cggccctggg ctgcctggtc    420
aaggactact ccccgaacc ggtgacggtg tcgtggaact caggcgccct gaccagcggc     480
gtgcacacct tcccggctgt cctacagtcc tcaggactct actccctcag cagcgtggtg    540
accgtgccct ccagcagctt gggcacccag acctacatct gcaacgtgaa tcacaagccc    600
agcaacacca aggtggacaa gagagttgag cccaaatctt gtgacaaaac tcacacatgc    660
ccaccgtgcc cagcacctga actcctgggg ggaccgtcag tcttcctctt ccccccaaaa    720
cccaaggaca cctcatgat ctcccggacc cctgaggtca catgcgtggt ggtggacgtg     780
agccacgaag accctgaggt caagttcaac tggtacgtgg acggcgtgga ggtgcataat    840
gccaagacaa agccgcggga ggaggagtac cagcagcag acccgtgtgt cagcgtcctc    900
accgtcctgc accaggactg gctgaatggc aaggagtaca agtgcaaggt ctccaacaaa    960
gccctcccag ccccatcga gaaaaccatc tccaaagcca aagggcagcc ccgagaacca   1020
caggtgtaca ccctgccccc atcccgggag gagatgacca gaaccaggt cagcctgacc    1080
tgcctggtca aaggcttcta tcccagcgac atcgccgttg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                             1326

SEQ ID NO: 492          moltype = DNA   length = 333
FEATURE                 Location/Qualifiers
misc_feature            1..333
                        note = Engineered antibody sequence
source                  1..333
                        mol_type = other DNA
                        organism = synthetic construct
SEQUENCE: 492
cagtcggtgg aggagtccgg gggaggcctg gtccagcctg agggatccct gacactcacc     60
tgcacagcct ctggattcga cttcagtagc aatgcaatgt ggtgggtccg ccaggctcca    120
gggaaggggc tggagtggat cggatgcatt tacaatggtg atggcagcac atactacgcg    180
agctgggtga atgccgatt ctccatctcc aaaacctcgt cgaccacggt gactctgcaa     240
ctgaatagtc tgacagtcgc ggacacggcc acgtattatt gtgcgagaga tcttgacttg    300
tggggcccgg gcaccctcgt caccgtctcg agc                                 333

SEQ ID NO: 493          moltype = DNA   length = 87
FEATURE                 Location/Qualifiers
misc_feature            1..87
                        note = Engineered antibody sequence
source                  1..87
                        mol_type = other DNA
                        organism = synthetic construct
SEQUENCE: 493
cagtcggtgg aggagtccgg gggaggcctg gtccagcctg agggatccct gacactcacc     60
tgcacagcct ctggattcga cttcagt                                        87

SEQ ID NO: 494          moltype = DNA   length = 15
FEATURE                 Location/Qualifiers
misc_feature            1..15
                        note = Engineered antibody sequence
source                  1..15
                        mol_type = other DNA
                        organism = synthetic construct
SEQUENCE: 494
agcaatgcaa tgtgg                                                     15

SEQ ID NO: 495          moltype = DNA   length = 42
FEATURE                 Location/Qualifiers
misc_feature            1..42
                        note = Engineered antibody sequence
source                  1..42
                        mol_type = other DNA
                        organism = synthetic construct
SEQUENCE: 495
tgggtccgcc aggctccagg gaaggggctg gagtggatcg ga                       42

SEQ ID NO: 496          moltype = DNA   length = 51
FEATURE                 Location/Qualifiers
misc_feature            1..51
                        note = Engineered antibody sequence
source                  1..51
                        mol_type = other DNA
                        organism = synthetic construct
SEQUENCE: 496
tgcatttaca atggtgatgg cagcacatac tacgcgagct gggtgaatgg c              51
```

| SEQ ID NO: 497 | moltype = DNA length = 93 |
| FEATURE | Location/Qualifiers |
| misc_feature | 1..93 |
| | note = Engineered antibody sequence |
| source | 1..93 |
| | mol_type = other DNA |
| | organism = synthetic construct |

SEQUENCE: 497
```
cgattctcca tctccaaaac ctcgtcgacc acggtgactc tgcaactgaa tagtctgaca    60
gtcgcggaca cggccacgta ttattgtgcg aga                                 93
```

| SEQ ID NO: 498 | moltype = DNA length = 12 |
| FEATURE | Location/Qualifiers |
| misc_feature | 1..12 |
| | note = Engineered antibody sequence |
| source | 1..12 |
| | mol_type = other DNA |
| | organism = synthetic construct |

SEQUENCE: 498
```
gatcttgact tg                                                        12
```

| SEQ ID NO: 499 | moltype = DNA length = 33 |
| FEATURE | Location/Qualifiers |
| misc_feature | 1..33 |
| | note = Engineered antibody sequence |
| source | 1..33 |
| | mol_type = other DNA |
| | organism = synthetic construct |

SEQUENCE: 499
```
tggggcccgg gcaccctcgt caccgtctcg agc                                 33
```

| SEQ ID NO: 500 | moltype = DNA length = 993 |
| FEATURE | Location/Qualifiers |
| misc_feature | 1..993 |
| | note = Engineered antibody sequence |
| source | 1..993 |
| | mol_type = other DNA |
| | organism = synthetic construct |

SEQUENCE: 500
```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagag agttgagccc   300
aaatcttgtg acaaaactca cacatgccca ccgtgcccag cacctgaact cctgggggga   360
ccgtcagtct tcctcttccc cccaaaaccc aaggacaccc tcatgatctc ccggacccct   420
gaggtcacat gcgtggtggt ggacgtgagc cacgaagacc ctgaggtcaa gttcaactgg   480
tacgtggacg gcgtggaggt gcataatgcc aagacaaagc cgcgggagga gcagtacgcc   540
agcacgtacc gtgtggtcag cgtcctcacc gtcctgcacc aggactggct gaatggcaag   600
gagtacaagt gcaaggtctc caacaaagcc ctcccagccc ccatcgagaa aaccatctcc   660
aaagccaaag ggcagccccg agaaccacag gtgtacaccc tgcccccatc ccgggaggag   720
atgaccaaga accaggtcag cctgacctgc ctggtcaaag gcttctatcc cagcgacatc   780
gccgtggagt gggagagcaa tgggcagccg gagaacaact acaagaccac gcctcccgtg   840
ctggactccg acggctcctt cttcctctac agcaagctca ccgtggacaa gagcaggtgg   900
cagcagggga acgtcttctc atgctccgtg atgcatgagg ctctgcacaa ccactacacg   960
cagaagagcc tctccctgtc tccgggtaaa tga                                993
```

| SEQ ID NO: 501 | moltype = AA length = 219 |
| FEATURE | Location/Qualifiers |
| REGION | 1..219 |
| | note = Engineered antibody sequence |
| source | 1..219 |
| | mol_type = protein |
| | organism = synthetic construct |

SEQUENCE: 501
```
AIVMTQTPSS KSVPVGDTVT INCQASESLY NNNALAWFQQ KPGQPPKRLI YDASKLASGV    60
PSRFSGGGSG TQFTLTISGV QCDDAATYYC GGYRSDSVDG VAFAGGTEVV VKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219
```

| SEQ ID NO: 502 | moltype = AA length = 113 |
| FEATURE | Location/Qualifiers |
| REGION | 1..113 |
| | note = Engineered antibody sequence |
| source | 1..113 |
| | mol_type = protein |
| | organism = synthetic construct |

SEQUENCE: 502
```
AIVMTQTPSS KSVPVGDTVT INCQASESLY NNNALAWFQQ KPGQPPKRLI YDASKLASGV    60
```

```
PSRFSGGGSG TQFTLTISGV QCDDAATYYC GGYRSDSVDG VAFAGGTEVV VKR          113

SEQ ID NO: 503          moltype = AA   length = 23
FEATURE                 Location/Qualifiers
REGION                  1..23
                        note = Engineered antibody sequence
source                  1..23
                        mol_type = protein
                        organism = synthetic construct
SEQUENCE: 503
AIVMTQTPSS KSVPVGDTVT INC                                          23

SEQ ID NO: 504          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 504
QASESLYNNN ALA                                                     13

SEQ ID NO: 505          moltype = AA   length = 15
FEATURE                 Location/Qualifiers
REGION                  1..15
                        note = Engineered antibody sequence
source                  1..15
                        mol_type = protein
                        organism = synthetic construct
SEQUENCE: 505
WFQQKPGQPP KRLIY                                                   15

SEQ ID NO: 506          moltype = AA   length = 7
FEATURE                 Location/Qualifiers
REGION                  1..7
                        note = Engineered antibody sequence
source                  1..7
                        mol_type = protein
                        organism = synthetic construct
SEQUENCE: 506
DASKLAS                                                            7

SEQ ID NO: 507          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 507
GVPSRFSGGG SGTQFTLTIS GVQCDDAATY YC                                32

SEQ ID NO: 508          moltype = AA   length = 12
FEATURE                 Location/Qualifiers
REGION                  1..12
                        note = Engineered antibody sequence
source                  1..12
                        mol_type = protein
                        organism = synthetic construct
SEQUENCE: 508
GGYRSDSVDG VA                                                      12

SEQ ID NO: 509          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 509
FAGGTEVVVK R                                                       11

SEQ ID NO: 510          moltype = AA   length = 106
FEATURE                 Location/Qualifiers
REGION                  1..106
                        note = Engineered antibody sequence
source                  1..106
                        mol_type = protein
                        organism = synthetic construct
```

```
SEQUENCE: 510
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 511          moltype = DNA   length = 660
FEATURE                 Location/Qualifiers
misc_feature            1..660
                        note = Engineered antibody sequence
source                  1..660
                        mol_type = other DNA
                        organism = synthetic construct
SEQUENCE: 511
gccatcgtga tgacccagac tccatcttcc aagtctgtcc ctgtgggaga cacagtcacc    60
atcaattgcc aggccagtga gagtctttat aataacaacg ccttggcctg gtttcagcag   120
aaaccagggc agcctcccaa gcgcctgatc tatgatgcat ccaaactggc atctggggtc   180
ccatcgcggt tcagtggcgg tgggtctggg acacagttca ctctcaccat cagtggcgtg   240
cagtgtgacg atgctgccac ttactactgt ggaggctaca gaagtgatag tgttgatggt   300
gttgctttcg ccggagggac cgaggtggtg gtcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 512          moltype = DNA   length = 339
FEATURE                 Location/Qualifiers
misc_feature            1..339
                        note = Engineered antibody sequence
source                  1..339
                        mol_type = other DNA
                        organism = synthetic construct
SEQUENCE: 512
gccatcgtga tgacccagac tccatcttcc aagtctgtcc ctgtgggaga cacagtcacc    60
atcaattgcc aggccagtga gagtctttat aataacaacg ccttggcctg gtttcagcag   120
aaaccagggc agcctcccaa gcgcctgatc tatgatgcat ccaaactggc atctggggtc   180
ccatcgcggt tcagtggcgg tgggtctggg acacagttca ctctcaccat cagtggcgtg   240
cagtgtgacg atgctgccac ttactactgt ggaggctaca gaagtgatag tgttgatggt   300
gttgctttcg ccggagggac cgaggtggtg gtcaaacgt                          339

SEQ ID NO: 513          moltype = DNA   length = 69
FEATURE                 Location/Qualifiers
misc_feature            1..69
                        note = Engineered antibody sequence
source                  1..69
                        mol_type = other DNA
                        organism = synthetic construct
SEQUENCE: 513
gccatcgtga tgacccagac tccatcttcc aagtctgtcc ctgtgggaga cacagtcacc    60
atcaattgc                                                            69

SEQ ID NO: 514          moltype = DNA   length = 39
FEATURE                 Location/Qualifiers
misc_feature            1..39
                        note = Engineered antibody sequence
source                  1..39
                        mol_type = other DNA
                        organism = synthetic construct
SEQUENCE: 514
caggccagtg agagtcttta taataacaac gccttggcc                           39

SEQ ID NO: 515          moltype = DNA   length = 45
FEATURE                 Location/Qualifiers
misc_feature            1..45
                        note = Engineered antibody sequence
source                  1..45
                        mol_type = other DNA
                        organism = synthetic construct
SEQUENCE: 515
tggtttcagc agaaaccagg gcagcctccc aagcgcctga tctat                    45

SEQ ID NO: 516          moltype = DNA   length = 21
FEATURE                 Location/Qualifiers
misc_feature            1..21
                        note = Engineered antibody sequence
source                  1..21
                        mol_type = other DNA
                        organism = synthetic construct
SEQUENCE: 516
gatgcatcca aactggcatc t                                              21
```

```
SEQ ID NO: 517          moltype = DNA  length = 96
FEATURE                 Location/Qualifiers
misc_feature            1..96
                        note = Engineered antibody sequence
source                  1..96
                        mol_type = other DNA
                        organism = synthetic construct
SEQUENCE: 517
ggggtcccat cgcggttcag tggcggtggg tctgggacac agttcactct caccatcagt    60
ggcgtgcagt gtgacgatgc tgccacttac tactgt                              96

SEQ ID NO: 518          moltype = DNA  length = 36
FEATURE                 Location/Qualifiers
misc_feature            1..36
                        note = Engineered antibody sequence
source                  1..36
                        mol_type = other DNA
                        organism = synthetic construct
SEQUENCE: 518
ggaggctaca gaagtgatag tgttgatggt gttgct                              36

SEQ ID NO: 519          moltype = DNA  length = 33
FEATURE                 Location/Qualifiers
misc_feature            1..33
                        note = Engineered antibody sequence
source                  1..33
                        mol_type = other DNA
                        organism = synthetic construct
SEQUENCE: 519
ttcgccggag ggaccgaggt ggtggtcaaa cgt                                 33

SEQ ID NO: 520          moltype = DNA  length = 321
FEATURE                 Location/Qualifiers
misc_feature            1..321
                        note = Engineered antibody sequence
source                  1..321
                        mol_type = other DNA
                        organism = synthetic construct
SEQUENCE: 520
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 521          moltype = AA  length = 441
FEATURE                 Location/Qualifiers
REGION                  1..441
                        note = Engineered antibody sequence
source                  1..441
                        mol_type = protein
                        organism = synthetic construct
SEQUENCE: 521
EVQLVESGGG LVQPGGSLRL SCAVSGIGLS SYYMQWVRQA PGKGLEWVGV IGSDGKTYYA    60
TWAKGRFTIS RDNSKTTVYL QMNSLRAEDT AVYFCTRGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDARVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG K                                             441

SEQ ID NO: 522          moltype = AA  length = 111
FEATURE                 Location/Qualifiers
REGION                  1..111
                        note = Engineered antibody sequence
source                  1..111
                        mol_type = protein
                        organism = synthetic construct
SEQUENCE: 522
EVQLVESGGG LVQPGGSLRL SCAVSGIGLS SYYMQWVRQA PGKGLEWVGV IGSDGKTYYA    60
TWAKGRFTIS RDNSKTTVYL QMNSLRAEDT AVYFCTRGDI WGQGTLVTVS S            111

SEQ ID NO: 523          moltype = AA  length = 30
FEATURE                 Location/Qualifiers
REGION                  1..30
                        note = Engineered antibody sequence
```

```
source                      1..30
                            mol_type = protein
                            organism = synthetic construct
SEQUENCE: 523
EVQLVESGGG LVQPGGSLRL SCAVSGIGLS                                    30

SEQ ID NO: 524              moltype = AA   length = 5
FEATURE                     Location/Qualifiers
REGION                      1..5
                            note = Engineered antibody sequence
source                      1..5
                            mol_type = protein
                            organism = synthetic construct
SEQUENCE: 524
SYYMQ                                                                5

SEQ ID NO: 525              moltype = AA   length = 14
FEATURE                     Location/Qualifiers
REGION                      1..14
                            note = Engineered antibody sequence
source                      1..14
                            mol_type = protein
                            organism = synthetic construct
SEQUENCE: 525
WVRQAPGKGL EWVG                                                     14

SEQ ID NO: 526              moltype = AA   length = 16
FEATURE                     Location/Qualifiers
REGION                      1..16
                            note = Engineered antibody sequence
source                      1..16
                            mol_type = protein
                            organism = synthetic construct
SEQUENCE: 526
VIGSDGKTYY ATWAKG                                                   16

SEQ ID NO: 527              moltype = AA   length = 32
FEATURE                     Location/Qualifiers
REGION                      1..32
                            note = Engineered antibody sequence
source                      1..32
                            mol_type = protein
                            organism = synthetic construct
SEQUENCE: 527
RFTISRDNSK TTVYLQMNSL RAEDTAVYFC TR                                 32

SEQ ID NO: 528              moltype =    length =
SEQUENCE: 528
000

SEQ ID NO: 529              moltype = AA   length = 11
FEATURE                     Location/Qualifiers
REGION                      1..11
                            note = Engineered antibody sequence
source                      1..11
                            mol_type = protein
                            organism = synthetic construct
SEQUENCE: 529
WGQGTLVTVS S                                                        11

SEQ ID NO: 530              moltype = AA   length = 330
FEATURE                     Location/Qualifiers
REGION                      1..330
                            note = Engineered antibody sequence
source                      1..330
                            mol_type = protein
                            organism = synthetic construct
SEQUENCE: 530
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDARVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 531              moltype = DNA   length = 1326
FEATURE                     Location/Qualifiers
misc_feature                1..1326
                            note = Engineered antibody sequence
```

| | | |
|---|---|---|
| source | 1..1326<br>mol_type = other DNA<br>organism = synthetic construct | |

SEQUENCE: 531

```
gaggtgcagc ttgtggagtc tgggggaggc ttggtccagc ctgggggtc cctgagactc    60
tcctgtgcag tctctggaat cggcctcagt agctactaca tgcaatgggt ccgtcaggct   120
ccagggaagg ggctggagtg ggtcggagtc attggtagtg atggtaagac atactacgcg   180
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agcgcctcca ccaagggccc atcggtcttc   360
cccctggcac cctcctccaa gagcacctcg gggggcacag cggccctggg ctgcctggtc   420
aaggactact ccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacgc gagagttgag cccaaatctt gtgacaaaac tcacacatgc   660
ccaccgtgcc cagcacctga actcctgggg ggaccgtcag tcttcctctt ccccccaaaa   720
cccaaggaca ccctcatgat ctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca aagggcagcc ccgagaacca  1020
caggtgtaca ccctgccccc atcccgggag gagatgacca agaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg ggaacgtctt ctcatgctcc  1260
gtgatgcatg aggctctgca caaccactac acgcagaaga gcctctccct gtctccgggt  1320
aaatga                                                              1326
```

| | | |
|---|---|---|
| SEQ ID NO: 532<br>FEATURE<br>misc_feature<br>source | moltype = DNA   length = 333<br>Location/Qualifiers<br>1..333<br>note = Engineered antibody sequence<br>1..333<br>mol_type = other DNA<br>organism = synthetic construct | |

SEQUENCE: 532

```
gaggtgcagc ttgtggagtc tgggggaggc ttggtccagc ctgggggtc cctgagactc    60
tcctgtgcag tctctggaat cggcctcagt agctactaca tgcaatgggt ccgtcaggct   120
ccagggaagg ggctggagtg ggtcggagtc attggtagtg atggtaagac atactacgcg   180
acctgggcga aaggccgatt caccatctcc agagacaatt ccaagaccac ggtgtatctt   240
caaatgaaca gcctgagagc tgaggacact gctgtgtatt tctgtaccag aggggacatc   300
tggggccaag ggaccctcgt caccgtctcg agc                                333
```

| | | |
|---|---|---|
| SEQ ID NO: 533<br>FEATURE<br>misc_feature<br>source | moltype = DNA   length = 90<br>Location/Qualifiers<br>1..90<br>note = Engineered antibody sequence<br>1..90<br>mol_type = other DNA<br>organism = synthetic construct | |

SEQUENCE: 533

```
gaggtgcagc ttgtggagtc tgggggaggc ttggtccagc ctgggggtc cctgagactc    60
tcctgtgcag tctctggaat cggcctcagt                                    90
```

| | | |
|---|---|---|
| SEQ ID NO: 534<br>FEATURE<br>misc_feature<br>source | moltype = DNA   length = 15<br>Location/Qualifiers<br>1..15<br>note = Engineered antibody sequence<br>1..15<br>mol_type = other DNA<br>organism = synthetic construct | |

SEQUENCE: 534

```
agctactaca tgcaa                                                     15
```

| | | |
|---|---|---|
| SEQ ID NO: 535<br>FEATURE<br>misc_feature<br>source | moltype = DNA   length = 42<br>Location/Qualifiers<br>1..42<br>note = Engineered antibody sequence<br>1..42<br>mol_type = other DNA<br>organism = synthetic construct | |

SEQUENCE: 535

```
tgggtccgtc aggctccagg gaaggggctg gagtgggtcg ga                       42
```

| | | |
|---|---|---|
| SEQ ID NO: 536<br>FEATURE<br>misc_feature<br>source | moltype = DNA   length = 48<br>Location/Qualifiers<br>1..48<br>note = Engineered antibody sequence<br>1..48 | |

```
                              mol_type = other DNA
                              organism = synthetic construct
SEQUENCE: 536
gtcattggta gtgatggtaa gacatactac gcgacctggg cgaaaggc                   48

SEQ ID NO: 537            moltype = DNA  length = 96
FEATURE                   Location/Qualifiers
misc_feature              1..96
                          note = Engineered antibody sequence
source                    1..96
                          mol_type = other DNA
                          organism = synthetic construct
SEQUENCE: 537
cgattcacca tctccagaga caattccaag accacggtgt atcttcaaat gaacagcctg       60
agagctgagg acactgctgt gtatttctgt accaga                                96

SEQ ID NO: 538            moltype =   length =
SEQUENCE: 538
000

SEQ ID NO: 539            moltype = DNA  length = 33
FEATURE                   Location/Qualifiers
misc_feature              1..33
                          note = Engineered antibody sequence
source                    1..33
                          mol_type = other DNA
                          organism = synthetic construct
SEQUENCE: 539
tggggccaag ggaccctcgt caccgtctcg agc                                   33

SEQ ID NO: 540            moltype = DNA  length = 993
FEATURE                   Location/Qualifiers
misc_feature              1..993
                          note = Engineered antibody sequence
source                    1..993
                          mol_type = other DNA
                          organism = synthetic construct
SEQUENCE: 540
gcctccacca agggcccatc ggtcttcccc ctggcaccct cctccaagag cacctctggg       60
ggcacagcgg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacgcgca gttgagccc       300
aaatcttgtg acaaaactca cacatgccca ccgtgcccag cacctgaact cctgggggga      360
ccgtcagtct tcctcttccc cccaaaaccc aaggacaccc tcatgatctc ccggaccct       420
gaggtcacat gcgtggtggt ggacgtgagc cacgaagacc ctgaggtcaa gttcaactgg      480
tacgtggacg gcgtggaggt gcataatgcc aagacaaagc cgcgggagga gcagtacgcc      540
agcacgtacc gtgtggtcag cgtcctcacc gtcctgcacc aggactggct gaatggcaag      600
gagtacaagt gcaaggtctc caacaaagcc ctcccagccc ccatcgagaa aaccatctcc      660
aaagccaaag gcagccccg agaaccacag gtgtacaccc tgcccccatc ccgggaggag      720
atgaccaaga accaggtcag cctgacctgc ctggtcaaag gcttctatcc cagcgacatc      780
gccgtggagt gggagagcaa tgggcagccg gagaacaact acaagaccac gcctcccgtg      840
ctggactccg acggctcctt cttcctctac agcaagctca ccgtggacaa gagcaggtgg      900
cagcagggga acgtcttctc atgctccgtg atgcatgagg ctctgcacaa ccactacacg      960
cagaagagcc tctccctgtc tccgggtaaa tga                                   993

SEQ ID NO: 541            moltype = AA  length = 219
FEATURE                   Location/Qualifiers
REGION                    1..219
                          note = Engineered antibody sequence
source                    1..219
                          mol_type = protein
                          organism = synthetic construct
SEQUENCE: 541
QVLTQSPSSL SASVGDRVTI NCQASQNVYN NNYLAWYQQK PGKVPKQLIY STSTLASGVP       60
SRFSGSGSGT DFTLTISSLQ PEDVATYYCL GSYDCSRGDC FVFGGGTKVE IKRTVAAPSV      120
FIFPPSDEQL KSGTASVVCL LNNFYPREAK VQWKVDNALQ SGNSQESVTE QDSKDSTYSL      180
SSTLTLSKAD YEKHKVYACE VTHQGLSSPV TKSFNRGEC                             219

SEQ ID NO: 542            moltype = AA  length = 113
FEATURE                   Location/Qualifiers
REGION                    1..113
                          note = Engineered antibody sequence
source                    1..113
                          mol_type = protein
                          organism = synthetic construct
SEQUENCE: 542
QVLTQSPSSL SASVGDRVTI NCQASQNVYN NNYLAWYQQK PGKVPKQLIY STSTLASGVP       60
SRFSGSGSGT DFTLTISSLQ PEDVATYYCL GSYDCSRGDC FVFGGGTKVE IKR             113
```

```
SEQ ID NO: 543          moltype = AA   length = 22
FEATURE                 Location/Qualifiers
REGION                  1..22
                        note = Engineered antibody sequence
source                  1..22
                        mol_type = protein
                        organism = synthetic construct
SEQUENCE: 543
QVLTQSPSSL SASVGDRVTI NC                                              22

SEQ ID NO: 544          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 544
QASQNVYNNN YLA                                                        13

SEQ ID NO: 545          moltype = AA   length = 15
FEATURE                 Location/Qualifiers
REGION                  1..15
                        note = Engineered antibody sequence
source                  1..15
                        mol_type = protein
                        organism = synthetic construct
SEQUENCE: 545
WYQQKPGKVP KQLIY                                                      15

SEQ ID NO: 546          moltype = AA   length = 7
FEATURE                 Location/Qualifiers
REGION                  1..7
                        note = Engineered antibody sequence
source                  1..7
                        mol_type = protein
                        organism = synthetic construct
SEQUENCE: 546
STSTLAS                                                                7

SEQ ID NO: 547          moltype = AA   length = 32
FEATURE                 Location/Qualifiers
REGION                  1..32
                        note = Engineered antibody sequence
source                  1..32
                        mol_type = protein
                        organism = synthetic construct
SEQUENCE: 547
GVPSRFSGSG SGTDFTLTIS SLQPEDVATY YC                                   32

SEQ ID NO: 548          moltype = AA   length = 13
FEATURE                 Location/Qualifiers
REGION                  1..13
                        note = Engineered antibody sequence
source                  1..13
                        mol_type = protein
                        organism = synthetic construct
SEQUENCE: 548
LGSYDCSRGD CFV                                                        13

SEQ ID NO: 549          moltype = AA   length = 11
FEATURE                 Location/Qualifiers
REGION                  1..11
                        note = Engineered antibody sequence
source                  1..11
                        mol_type = protein
                        organism = synthetic construct
SEQUENCE: 549
FGGGTKVEIK R                                                          11

SEQ ID NO: 550          moltype = AA   length = 106
FEATURE                 Location/Qualifiers
REGION                  1..106
                        note = Engineered antibody sequence
source                  1..106
                        mol_type = protein
                        organism = synthetic construct
SEQUENCE: 550
```

```
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 551              moltype = DNA   length = 660
FEATURE                     Location/Qualifiers
misc_feature                1..660
                            note = Engineered antibody sequence
source                      1..660
                            mol_type = other DNA
                            organism = synthetic construct
SEQUENCE: 551
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660

SEQ ID NO: 552              moltype = DNA   length = 339
FEATURE                     Location/Qualifiers
misc_feature                1..339
                            note = Engineered antibody sequence
source                      1..339
                            mol_type = other DNA
                            organism = synthetic construct
SEQUENCE: 552
caagtgctga cccagtctcc atcctccctg tctgcatctg taggagacag agtcaccatc    60
aattgccagg ccagtcagaa tgtttacaat aacaactacc tagcctggta tcagcagaaa   120
ccagggaaag ttcctaagca actgatctat tctacatcca ctctggcatc tggggtccca   180
tctcgtttca gtggcagtgg atctgggaca gatttcactc tcaccatcag cagcctgcag   240
cctgaagatg ttgcaactta ttactgtctg ggcagttatg attgtagtcg tggtgattgt   300
tttgttttcg gcggaggaac caaggtggaa atcaaacgt                          339

SEQ ID NO: 553              moltype = DNA   length = 66
FEATURE                     Location/Qualifiers
misc_feature                1..66
                            note = Engineered antibody sequence
source                      1..66
                            mol_type = other DNA
                            organism = synthetic construct
SEQUENCE: 553
caagtgctga cccagtctcc atcctccctg tctgcatctg taggagacag agtcaccatc    60
aattgc                                                               66

SEQ ID NO: 554              moltype = DNA   length = 39
FEATURE                     Location/Qualifiers
misc_feature                1..39
                            note = Engineered antibody sequence
source                      1..39
                            mol_type = other DNA
                            organism = synthetic construct
SEQUENCE: 554
caggccagtc agaatgttta caataacaac tacctagcc                           39

SEQ ID NO: 555              moltype = DNA   length = 45
FEATURE                     Location/Qualifiers
misc_feature                1..45
                            note = Engineered antibody sequence
source                      1..45
                            mol_type = other DNA
                            organism = synthetic construct
SEQUENCE: 555
tggtatcagc agaaaccagg gaaagttcct aagcaactga tctat                    45

SEQ ID NO: 556              moltype = DNA   length = 21
FEATURE                     Location/Qualifiers
misc_feature                1..21
                            note = Engineered antibody sequence
source                      1..21
                            mol_type = other DNA
                            organism = synthetic construct
SEQUENCE: 556
tctacatcca ctctggcatc t                                              21
```

```
SEQ ID NO: 557            moltype = DNA   length = 96
FEATURE                   Location/Qualifiers
misc_feature              1..96
                          note = Engineered antibody sequence
source                    1..96
                          mol_type = other DNA
                          organism = synthetic construct
SEQUENCE: 557
ggggtcccat ctcgtttcag tggcagtgga tctgggacag atttcactct caccatcagc    60
agcctgcagc ctgaagatgt tgcaacttat tactgt                              96

SEQ ID NO: 558            moltype = DNA   length = 39
FEATURE                   Location/Qualifiers
misc_feature              1..39
                          note = Engineered antibody sequence
source                    1..39
                          mol_type = other DNA
                          organism = synthetic construct
SEQUENCE: 558
ctgggcagtt atgattgtag tcgtggtgat tgttttgtt                           39

SEQ ID NO: 559            moltype = DNA   length = 33
FEATURE                   Location/Qualifiers
misc_feature              1..33
                          note = Engineered antibody sequence
source                    1..33
                          mol_type = other DNA
                          organism = synthetic construct
SEQUENCE: 559
ttcggcggag gaaccaaggt ggaaatcaaa cgt                                 33

SEQ ID NO: 560            moltype = DNA   length = 321
FEATURE                   Location/Qualifiers
misc_feature              1..321
                          note = Engineered antibody sequence
source                    1..321
                          mol_type = other DNA
                          organism = synthetic construct
SEQUENCE: 560
acggtggctg caccatctgt cttcatcttc ccgccatctg atgagcagtt gaaatctgga    60
actgcctctg ttgtgtgcct gctgaataac ttctatccca gagaggccaa agtacagtgg   120
aaggtggata acgccctcca atcgggtaac tcccaggaga gtgtcacaga gcaggacagc   180
aaggacagca cctacagcct cagcagcacc ctgacgctga gcaaagcaga ctacgagaaa   240
cacaaagtct acgcctgcga agtcacccat cagggcctga gctcgcccgt cacaaagagc   300
ttcaacaggg gagagtgtta g                                             321

SEQ ID NO: 561            moltype = AA   length = 37
FEATURE                   Location/Qualifiers
REGION                    1..37
                          note = C-term amidated
source                    1..37
                          mol_type = protein
                          organism = Homo sapiens
SEQUENCE: 561
ACDTATCVTH RLAGLLSRSG GVVKNNFVPT NVGSKAF                             37

SEQ ID NO: 562            moltype = AA   length = 37
FEATURE                   Location/Qualifiers
REGION                    1..37
                          note = C-term amidated
source                    1..37
                          mol_type = protein
                          organism = Homo sapiens
SEQUENCE: 562
ACNTATCVTH RLAGLLSRSG GMVKSNFVPT NVGSKAF                             37

SEQ ID NO: 563            moltype = AA   length = 106
FEATURE                   Location/Qualifiers
source                    1..106
                          mol_type = protein
                          organism = Homo sapiens
SEQUENCE: 563
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                  106

SEQ ID NO: 564            moltype = AA   length = 330
FEATURE                   Location/Qualifiers
REGION                    1..330
                          note = Engineered antibody sequence
```

```
                        source          1..330
                                        mol_type = protein
                                        organism = synthetic construct
SEQUENCE: 564
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 565          moltype = AA   length = 329
FEATURE                 Location/Qualifiers
REGION                  1..329
                        note = Engineered antibody sequence
source                  1..329
                        mol_type = protein
                        organism = synthetic construct
SEQUENCE: 565
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYA   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 566          moltype = AA   length = 440
FEATURE                 Location/Qualifiers
REGION                  1..440
                        note = Engineered antibody sequence
source                  1..440
                        mol_type = protein
                        organism = synthetic construct
SEQUENCE: 566
EVQLVESGGG LVQPGGSLRL SCAVSGIDLS GYYMNWVRQA PGKGLEWVGV IGINGATYYA    60
SWAKGRFTIS RDNSKTTVYL QMNSLRAEDT AVYFCARGDI WGQGTLVTVS SASTKGPSVF   120
PLAPSSKSTS GGTAALGCLV KDYFPEPVTV SWNSGALTSG VHTFPAVLQS SGLYSLSSVV   180
TVPSSSLGTQ TYICNVNHKP SNTKVDARVE PKSCDKTHTC PPCPAPELLG GPSVFLFPPK   240
PKDTLMISRT PEVTCVVVDV SHEDPEVKFN WYVDGVEVHN AKTKPREEQY ASTYRVVSVL   300
TVLHQDWLNG KEYKCKVSNK ALPAPIEKTI SKAKGQPREP QVYTLPPSRE EMTKNQVSLT   360
CLVKGFYPSD IAVEWESNGQ PENNYKTTPP VLDSDGSFFL YSKLTVDKSR WQQGNVFSCS   420
VMHEALHNHY TQKSLSLSPG                                              440

SEQ ID NO: 567          moltype = DNA   length = 1323
FEATURE                 Location/Qualifiers
misc_feature            1..1323
                        note = Engineered antibody sequence
source                  1..1323
                        mol_type = other DNA
                        organism = synthetic construct
SEQUENCE: 567
gaggtgcagc ttgtggagtc tgggggaggc ttggtccagc ctggggggtc cctgagactc    60
tcctgtgcag tctctggaat cgacctcagt ggctactaca tgaactgggt ccgtcaggct   120
ccagggaagg gctgagagtg gtcggagtc attggtatta atggtgccac atactacgcg   180
agctgggcga aaggccgatt caccatctcc agagacaatt ccaagaccac ggtgtatctt   240
caaatgaaca gcctgagagc tgaggacact gctgtgtatt tctgtgctag aggggacatc   300
tggggccaag ggaccctcgt caccgtctcg agcgcctcca ccaagggccc atcggtcttc   360
cccctggcac cctcctccaa gagcacctcg ggggggcacag cggccctggg ctgcctggtc   420
aaggactact tccccgaacc ggtgacggtg tcgtggaact caggcgccct gaccagcggc   480
gtgcacacct tcccggctgt cctacagtcc tcaggactct actccctcag cagcgtggtg   540
accgtgccct ccagcagctt gggcacccag acctacatct gcaacgtgaa tcacaagccc   600
agcaacacca aggtggacgc gagagttgag cccaaatctt gtgacaaaac tcacacatgc   660
ccaccgtgcc cagcacctga actcctgggg ggaccgtcag tcttcctctt ccccccaaaa   720
cccaaggaca cctctcatga tctcccggacc cctgaggtca catgcgtggt ggtggacgtg   780
agccacgaag accctgaggt caagttcaac tggtacgtgg acggcgtgga ggtgcataat   840
gccaagacaa agccgcggga ggagcagtac gccagcacgt accgtgtggt cagcgtcctc   900
accgtcctgc accaggactg gctgaatggc aaggagtaca agtgcaaggt ctccaacaaa   960
gccctcccag cccccatcga gaaaaccatc tccaaagcca aagggcagcc ccgagaacca  1020
caggtgtaca cctgccccc atccgggag gagatgacca gaaccaggt cagcctgacc  1080
tgcctggtca aaggcttcta tcccagcgac atcgccgtgg agtgggagag caatgggcag  1140
ccggagaaca actacaagac cacgcctccc gtgctggact ccgacggctc cttcttcctc  1200
tacagcaagc tcaccgtgga caagagcagg tggcagcagg gaacgtcttc tcatgctcc  1260
gtgatgcatg aggctctgca caaccactac acgcagaaga gcctctccct gtctccgggt  1320
tga                                                                1323
```

ACUTE TREATMENT AND RAPID TREATMENT OF HEADACHE USING ANTI-CGRP ANTIBODIES

RELATED APPLICATIONS

This application is a divisional of U.S. patent application Ser. No. 18/173,116 filed Feb. 23, 2023, which is a divisional of U.S. patent application Ser. No. 16/736,925, filed Jan. 8, 2020, which claims priority to Provisional Appl. No. 62/872,989, filed Jul. 11, 2019, Provisional Appl. No. 62/842,162, filed May 2, 2019, and Provisional Appl. No. 62/789,828, filed Jan. 8, 2019, the disclosures of each of which are hereby incorporated by reference in their entireties,

REFERENCE TO AN ELECTRONIC SEQUENCE LISTING

The contents of the electronic sequence listing (11432570008603.xml; Size: 771,659 bytes; and Date of Creation: Mar. 18, 2024) is herein incorporated by reference in its entirety.

BACKGROUND

Field

This invention pertains to methods of acute treatment of headache disorders, such as migraine, using antibodies and fragments thereof (including Fab fragments) that specifically bind to human Calcitonin Gene Related Peptide (hereinafter "CGRP"). The invention also pertains to rapid treatment of headache, e.g., chronic migraine, using antibodies and fragments thereof (including Fab fragments) that specifically bind to human Calcitonin Gene Related Peptide (hereinafter "CGRP").

Description of Related Art

Calcitonin Gene Related Peptide (CGRP) is produced as a multifunctional neuropeptide of 37 amino acids in length. Two forms of CGRP, the CGRP-alpha and CGRP-beta forms, exist in humans and have similar activities. CGRP-alpha and CGRP-beta differ by three amino acids in humans, and are derived from different genes. CGRP is released from numerous tissues such as trigeminal nerves, which when activated release neuropeptides within the meninges, mediating neurogenic inflammation that is characterized by vasodilation, vessel leakage, and mast-cell degradation. Durham, P. L., *New Eng. J. Med.*, 350 (11):1073-75 (2004). Biological effects of CGRP are mediated via the CGRP receptor (CGRP-R), which consists of a seven-transmembrane component, in conjunction with receptor-associated membrane protein (RAMP). CGRP-R further requires the activity of the receptor component protein (RCP), which is essential for an efficient coupling to adenylate cyclase through G proteins and the production of cAMP. Doods, H., *Curr. Op. Invest. Drugs*, 2(9):1261-68 (2001).

Migraines are neurovascular disorder affecting approximately 10% of the adult population in the U.S., and are typically accompanied by intense headaches. CGRP is believed to play a prominent role in the development of migraines. In fact several companies, i.e., Amgen, Eli Lilly, Teva and Alder Biopharmaceuticals (recently acquired by Lundbeck A/S) have developed anti-CGRP and anti-CGRP-R antibodies for use in treating or preventing migraine headaches. The present assignee has previously filed patent applications related to anti-CGRP antibodies and uses thereof including published PCT Application WO/2012/162243 filed May 21, 2012 entitled "ANTI-CGRP COMPOSITIONS AND USE THEREOF", published PCT Application WO/2012/162257 filed May 21, 2012, entitled "USE OF ANTI-CGRP ANTIBODIES AND ANTIBODY FRAGMENTS TO PREVENT OR INHIBIT PHOTOPHOBIA OR LIGHT AVERSION IN SUBJECTS IN NEED THEREOF, ESPECIALLY MIGRAINE SUFFERERS" published PCT Application WO/2012/162253, filed May 21, 2012, entitled "USE OF ANTI-CGRP OR ANTI-CGRP-R ANTIBODIES OR ANTIBODY FRAGMENTS TO TREAT OR PREVENT CHRONIC AND ACUTE FORMS OF DIARRHEA" and published PCT Application WO/2015/003122, filed Jul. 3, 2014, entitled "REGULATION OF GLUCOSE METABOLISM USING ANTI-CGRP ANTIBODIES" all of which applications are incorporated by reference in their entirety.

BRIEF SUMMARY

The present disclosure provides methods of acute treatment of headache, comprising administering to a patient in need an effective amount of at least one anti-CGRP antibody or antibody fragment or an anti-CGRP-R antibody or antibody fragment or one or more formulations comprising said antibody or antibody fragment as disclosed herein. Said antibody may be administered while said patient has a headache. Said antibody administration may be initiated within 1-6 hours of the onset of said headache. Said headache may comprise migraine, e.g., episodic migraine or chronic migraine. Said headache may comprise medication overuse headache. Said anti-CGRP antibody or antibody fragment optionally comprises any one of Ab1-Ab14 or a Fab fragment thereof, such as Ab6 or a Fab fragment thereof, e.g., having the light chain CDR 1, 2, and 3 polypeptide sequences of SEQ ID NO: 224; SEQ ID NO: 226; and SEQ ID NO: 228, respectively and the heavy chain CDR 1, 2, and 3 polypeptide sequences of SEQ ID NO: 204; SEQ ID NO: 206; and SEQ ID NO: 208; or having the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively. Said anti-CGRP antibody may comprise the variable light chain polypeptide of SEQ ID NO: 222 and the variable heavy chain polypeptide of SEQ ID NO: 202. Said anti-CGRP antibody may comprise the variable light chain polypeptide encoded by SEQ ID NO: 232 and the variable heavy chain polypeptide encoded by SEQ ID NO: 212. Said anti-CGRP antibody may comprise the light chain polypeptide of SEQ ID NO: 221 and the heavy chain polypeptide of SEQ ID NO: 201 or SEQ ID NO: 566. Said anti-CGRP antibody may comprise the light chain polypeptide encoded by SEQ ID NO: 231 and the heavy chain polypeptide encoded by SEQ ID NO: 211 or SEQ ID NO: 567. Said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells. Said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions. Any of the aforementioned anti-CGRP antibodies or antibody fragments, preferably Ab6, may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The administered dosage of said antibody may be between about 100 mg and about 300 mg, such as about 100 mg, about 300 mg, 100 mg, or 300 mg. The dosage may be administered by different means, e.g., intravenously, e.g., in a saline solution such as 0.9% sodium chloride in a suitable volume, such as 100 mL.

Said patient may exhibit less than 25 headache days per month, less than 20 headache days per month, less than 15 headache days per month, or less than 10 headache days per month. For example, said patient may exhibit less than 14 headache days, less than headache 13 days, less than headache 12 days, less than headache 11 days, less than 10 headache days, less than 9 headache days, less than 8 headache days, less than 7 headache days, or less than 6 headache days per month. Said patient may exhibit between 2-15 headache days, e.g., 3-14 headache days, 4-13 headache days, 5-12 headache days, 6-11 headache days, or 7-10 headache days/month.

Said patient may exhibit less than 10 migraines per month, such as between 1-9 migraines per month, such as between 2-8 migraines per month, between 3-7 migraine per month, between 4-6 migraine per month, or about 5 migraines per month. Said patient may exhibit fewer than 1 migraine per month on average, e.g., on average one migraine every 2 months, one every 3 months, one every 4 or 6 months, or intermediate values such as 2 every 3 months, etc. Said migraine may be diagnosed in accord with the ICHD-3 guidelines.

In exemplary embodiments, said headache may comprise medication overuse headache. Said medication overuse headache may be determined based on meeting the following criteria: (a) headache occurring on 15 or more days/month in a patient with a pre-existing headache disorder; and (b) overuse for more than 3 months of one or more drugs that can be taken for acute and/or symptomatic treatment of headache.

Said overuse may comprise use of an ergot alkoid (e.g., ergotamine) on 10 or more days/month, use of a triptan on 10 or more days/month, use of one or more non-opioid analgesics (such as paracetamol (acetaminophen), acetylsalicylic acid (aspirin), another NSAID, or another non-opioid analgesic) on 15 or more days/month, use of one or more combination-analgesics (as further described below) on 10 or more days/month, use of one or more opioids on 10 or more days/month, or use of a combination of two or more drug classes (as further described below) on 10 or more days/month.

In the methods herein, said triptan may include, without limitation thereto, any one of or any combination of triptans such as sumatriptan, zolmitriptan, naratriptan, rizatriptan, eletriptan, almotriptan, and frovatriptan, among others.

Said medication overuse headache may comprise ergotamine-overuse headache, triptan-overuse headache, non-opioid analgesic-overuse headache, opioid-overuse headache, combination-analgesic-overuse headache, medication-overuse headache attributed to multiple drug classes not individually overused, medication-overuse headache attributed to unspecified or unverified overuse of multiple drug classes, or medication-overuse headache attributed to other medication.

Said non-opioid analgesic-overuse headache may comprise paracetamol (acetaminophen)-overuse headache, non-steroidal anti-inflammatory drug (NSAID)-overuse headache such as acetylsalicylic acid (aspirin)-overuse headache or ibuprofen-overuse headache, or another non-opioid analgesic-overuse headache.

Said ergotamine-overuse headache may comprise headache occurring on 15 or more days/month in a patient with a pre-existing primary headache and developing as a consequence of regular use of an ergot alkaloid such as ergotamine on 10 or more days/month for more than 3 months.

In the methods herein, said ergot alkaloid may comprise ergotamine, nicergoline, methysergide, or dihydroergotamine, or may comprise an ergot derivative.

Said triptan-overuse headache may comprise headache occurring on 15 or more days/month in a patient with a pre-existing primary headache and developing as a consequence of regular use of one or more triptans on 10 or more days/month for more than 3 months.

Said non-opioid analgesic-overuse headache may comprise headache occurring on 15 or more days/month in a patient with a pre-existing primary headache and developing as a consequence of regular use of one or more non-opioid analgesics (such as paracetamol (acetaminophen), acetylsalicylic acid (aspirin), ibuprofen, another NSAID, or another non-opioid analgesic) on 15 or more days/month for more than 3 months.

In the methods herein, said NSAID may comprise any NSAID or combination thereof, including without limitation thereto, ibuprofen, naproxen, or indomethacin.

Said combination-analgesic-overuse headache may comprise headache occurring on 15 or more days/month developing as a consequence of regular use of one or more combination-analgesics on 10 or more days/month for more than 3 months. In the context of medication overuse headache, the term combination-analgesic refers to formulations combining drugs of two or more classes, each with analgesic effects (for example, paracetamol and codeine) or analgesics in combination with agents acting as adjuvants (for example, caffeine). Commonly overused combination-analgesics combine non-opioid analgesics with at least one opioid, barbiturate such as butalbital and/or caffeine. In exemplary embodiments, the combination-analgesic overuse-headache is due to the combination of acetaminophen, aspirin, and caffeine, e.g., EXCEDRIN® or EXCEDRIN MIGRAINE®. Other known combination analgesics comprise an analgesic in combination with at least one non-analgesic, e.g., with a vasoconstrictor drug such as pseudoephedrine for sinus-related preparations, antihistamine drug used to treat allergy sufferers, etc.

Said opioid-overuse headache may comprise headache occurring on 15 or more days/month in a patient with a pre-existing primary headache and developing as a consequence of regular use of one or more opioids 10 or more days/month for more than 3 months.

Said medication-overuse headache attributed to multiple drug classes not individually overused may comprise headache occurring on 15 or more days/month in a patient with a pre-existing primary headache and developing as a result of regular intake of any combination of ergotamine, triptans, non-opioid analgesics and/or opioids on a total of at least 10 days/month for more than 3 months without overuse of any single drug or drug class alone.

In the methods herein, said opioid may be any one or any combination of opioid drugs, including without limitation thereto, oxycodone, tramadol, butorphanol, morphine, codeine, hydrocodone, thebaine, oripavine, mixed opium alkaloids such as papaveretum, diacetylmorphine, nicomorphine, dipropanoylmorphine, diacetyldihydromorphine, acetylpropionylmorphine, desomorphine, methyldesorphine, dibenzoylmorphine, ethylmorphine, heterocodeine, buprenorphine, etorphine, hydromorphone, oxymorphone, fentanyl, alphamethylfentanyl, alfentanil, sufentanil, remifentanil, carfentanyl, ohmefentanyl, pethidine (meperidine), ketobemidone, MPPP, allylprodine, prodine, PEPAP, promedol, diphenylpropylamine, propoxyphene, dextropropoxyphene, dextromoramide, bezitramide, piritramide, among others.

Said medication-overuse headache attributed to unspecified or unverified overuse of multiple drug classes may comprise headache occurring on 15 or more days/month in a patient with a pre-existing primary headache and developing as a result of regular intake of any combination of ergotamine, triptans, non-opioid analgesics and/or opioids on at least 10 days/month for more than 3 months, wherein the identity, quantity and/or pattern of use or overuse of these classes of drug is not reliably established.

Said medication-overuse headache attributed to other medication may comprise headache occurring on 15 or more days/month in a patient with a pre-existing primary headache and developing as a result of regular intake of one or more medications other than those described above, taken for acute or symptomatic treatment of headache, on at least 10 days/month for more than 3 months.

The amount and duration of medication use may be determined utilizing known methods, such as the usage reported by the patient or a relative, a diary, medical records, drug purchase history, prescription fulfilment, biomarkers of medication use, incidence of medication toxicity, incidence of medication overdose, and/or other indicators of a patient's medication use.

The present disclosure provides methods of treating or preventing probable medication overuse headache, comprising administering to a patient in need an effective amount of an anti-CGRP antibody or anti-CGRP antibody fragment or one or more formulations comprising said anti-CGRP antibody or anti-CGRP antibody fragment as disclosed herein. Said anti-CGRP antibody optionally comprises any one of Ab1-Ab14, such as Ab6, e.g., having the light chain CDR 1, 2, and 3 polypeptide sequences of SEQ ID NO: 224; SEQ ID NO: 226; and SEQ ID NO: 228, respectively and the heavy chain CDR 1, 2, and 3 polypeptide sequences of SEQ ID NO: 204; SEQ ID NO: 206; and SEQ ID NO: 208; or having the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively. Said anti-CGRP antibody may comprise the variable light chain polypeptide of SEQ ID NO: 222 and the variable heavy chain polypeptide of SEQ ID NO: 202. Said anti-CGRP antibody may comprise the variable light chain polypeptide encoded by SEQ ID NO: 232 and the variable heavy chain polypeptide encoded by SEQ ID NO: 212. Said anti-CGRP antibody may comprise the light chain polypeptide of SEQ ID NO: 221 and the heavy chain polypeptide of SEQ ID NO: 201 or SEQ ID NO: 566. Said anti-CGRP antibody may comprise the light chain polypeptide encoded by SEQ ID NO: 231 and the heavy chain polypeptide encoded by SEQ ID NO: 211 or SEQ ID NO: 567. Said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells. Said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions. Any of the aforementioned anti-CGRP antibodies or antibody fragments, preferably Ab6, may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The administered dosage of said antibody may be between about 100 mg and about 300 mg, such as about 100 mg, about 300 mg, 100 mg, or 300 mg. The dosage may be administered by different means, e.g., intravenously, e.g., in a saline solution such as 0.9% sodium chloride in a suitable volume, such as 100 mL. Probable medication overuse headache refers to criteria (a) and (b) not being entirely fulfilled, e.g., having at least 80% or at least 90% of the specified number of headache days and/or medication use days per month, and/or over a shorter time period such as at least 2 months, optionally in the absence of another ICHD-3 diagnosis.

Said medication-overuse headache (such as ergotamine-overuse headache, triptan-overuse headache, non-opioid analgesic-overuse headache, opioid-overuse headache, combination-analgesic-overuse headache, medication-overuse headache attributed to multiple drug classes not individually overused, medication-overuse headache attributed to unspecified or unverified overuse of multiple drug classes, or medication-overuse headache attributed to other medication) may be diagnosed according to the third edition of the International Classification of Headache Disorders (ICHD-3). See Headache Classification Committee of the International Headache Society (IHS), The International Classification of Headache Disorders, 3rd edition, Cephalalgia. 2018 January; 38(1):1-211, which is hereby incorporated by reference in its entirety.

Herein, the criterion that a headache occurs "as a consequence of" over use of a medication or medications refers to the apparent association between the medication(s) overuse and the headache, e.g., that the medication(s) overuse and headache are present at the above-specified frequency such that causation may be presumed.

The present disclosure also provides methods of treating chronic migraine, comprising intravenously administering to a patient in need thereof a first dosage comprising between about 100 mg and about 300 mg of an anti-CGRP antibody, wherein said anti-CGRP antibody preferably comprises the light chain polypeptide of SEQ ID NO: 221 and the heavy chain polypeptide of SEQ ID NO: 201 or 566, wherein in the first 24 hours after administration of said first dosage the patient exhibits at least a 50% reduction in migraine prevalence.

In another aspect, the disclosure provides methods of treating chronic migraine, comprising intravenously administering to a patient in need thereof a first dosage comprising between about 100 mg and about 300 mg of an anti-CGRP antibody, wherein said anti-CGRP antibody preferably comprises the light chain polypeptide of SEQ ID NO: 221 and the heavy chain polypeptide of SEQ ID NO: 201 or 566, wherein on the first day following the day of administration the patient exhibits at least a 50% reduction in migraine prevalence.

In some exemplary embodiments the dosage, e.g., the first dosage, of said anti-CGRP antibody may be 100 mg.

In other exemplary embodiments the dosage, e.g., the first dosage, of said anti-CGRP antibody may be 300 mg.

The method may further comprise intravenously administering 100 mg of said anti-CGRP antibody every 10-14 weeks, preferably every 11-13 weeks, more preferably every 12 weeks.

The method may further comprise intravenously administering 300 mg of said anti-CGRP antibody every 10-14 weeks, preferably every 11-13 weeks, more preferably every 12 weeks.

The antibody may be provided or administered in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8.

Prior to said first dosage, the patient may exhibit between about 10 and about 22 migraine days per month, such as between about 13 and about 19 migraine days per month, such as about 16 migraine days per month.

Prior to said first dosage, the patient may exhibit between about 14 and about 27 headache days per month, such as between about 17 and about 24 headache days per month, such as about 20 or about 21 headache days per month.

Said patient may have been diagnosed with migraine at least 10 years prior to said first dosage, such as at least 15 years prior to said first dosage, such as at least 18 or at least 19 years prior to said first dosage.

Said patient may have been diagnosed with chronic migraine at least 5 years prior to said first dosage, such as at least 8 years prior to said first dosage, such as at least 11 or at least 12 years prior to said first dosage.

The patient may have a headache when administered said first dosage.

The patient may have a migraine, such as a migraine with aura, when administered said first dosage.

Said patient may have a reduction in the number of migraine days by at least 50% in the one month period after being administered said first dose relative to the baseline number of migraine days experienced by that patient prior to said first dose.

Said patient may have a reduction in the number of migraine days by at least 75% in the one month period after being administered said first dose relative to the baseline number of migraine days experienced by that patient prior to said first dose.

Said patient may have a reduction in the number of migraine days by 100% in the one month period after being administered said first dose relative to the baseline number of migraine days experienced by that patient prior to said first dose.

Said patient may have a reduction in the number of migraine days by at least 50% in the 12 week period after being administered said first dose relative to the baseline number of migraine days experienced by that patient prior to said first dose.

Said patient may have a reduction in the number of migraine days by at least 75% in the 12 week period after being administered said first dose relative to the baseline number of migraine days experienced by that patient prior to said first dose.

Said patient may have a reduction in the number of migraine days by 100% in the 12 week period after being administered said first dose relative to the baseline number of migraine days experienced by that patient prior to said first dose.

The method may further comprise administering, e.g., intravenously, a second dose of said anti-CGRP antibody to said patient within about 10-14 weeks, preferably 11-13 weeks, more preferably about 12 weeks or about 3 months, after said first dose.

Said first dose may comprise about 100 mg, about 125 mg, about 150 mg, about 175 mg, about 200 mg, about 225 mg, about 250 mg, about 275 mg, or about 300 mg of said anti-CGRP antibody.

Said patient may be a chronic migraine patient or episodic migraine patient at risk of developing medication overuse headache. Said patient may use acute headache medication on at least 1, 2, 3, 4, 5, 6, 7, 8, 9, or 10 day(s) per month. Said patient may use acute headache medication on at least 10 days per month. Optionally said acute medication use is determined over a baseline period of at least 28 days. Said acute medication use may be reported by the patient, a caregiver, or based on records. Said acute medication may comprise use of ergot alkaloids, triptans, non-opioid analgesics, acetaminophen, aspirin, NSAIDs, non-opioid analgesics, combination-analgesics, or opioids.

Prior to said administration, the patient may exhibit between about 15 and about 30 migraine days per month, such as between about 16 and about 28 migraine days per month, such as between about 17 and about 26 migraine days per month, such as about 16 migraine days per month.

Prior to said administration, the patient may exhibit between about 15 and about 27 headache days per month, such as between about 17 and about 24 headache days per month, such as about 20 or about 21 headache days per month.

Said patient may have been diagnosed with migraine at least 10 years prior to said administration, such as at least 15 years prior to said administration, such as at least 18 or at least 19 years prior to said administration.

Said patient may have been diagnosed with chronic migraine at least 5 years prior to said administration, such as at least 8 years prior to said administration, such as at least 11 or at least 12 years prior to said administration.

Said patient may have a reduction in the number of migraine days by at least 50% in the one month period after being administered said antibody relative to the baseline number of migraine days experienced by that patient prior to said administration.

Said patient may have a reduction in the number of migraine days by at least 75% in the one month period after being administered said antibody relative to the baseline number of migraine days experienced by that patient prior to said administration.

Said patient may have a reduction in the number of migraine days by 100% in the one month period after being administered said antibody relative to the baseline number of migraine days experienced by that patient prior to said administration.

Said patient may have a reduction in the number of migraine days by at least 50% in the 12 week period after being administered said antibody relative to the baseline number of migraine days experienced by that patient prior to said administration.

Said patient may have a reduction in the number of migraine days by at least 75% in the 12 week period after being administered said antibody relative to the baseline number of migraine days experienced by that patient prior to said administration.

Said patient may have a reduction in the number of migraine days by 100% in the 12 week period after being administered said antibody relative to the baseline number of migraine days experienced by that patient prior to said administration.

The method may further comprise administering, e.g., intravenously, a second dose of said anti-CGRP antibody to said patient within about 10-14 weeks, preferably 11-13 weeks, more preferably about 12 weeks or about 3 months, after said administration.

Said administration may comprise about 100 mg, about 125 mg, about 150 mg, about 175 mg, about 200 mg, about 225 mg, about 250 mg, about 275 mg, or about 300 mg of said anti-CGRP antibody.

Said anti-CGRP antibody may be aglycosylated or if glycosylated only may contain only mannose residues.

Said anti-CGRP antibody may consist of the light chain polypeptide of SEQ ID NO: 221 and the heavy chain polypeptide of SEQ ID NO: 201 or SEQ ID NO: 566. Said anti-CGRP antibody may consist of the light chain polypeptide encoded by SEQ ID NO: 231 and the heavy chain polypeptide encoded by SEQ ID NO: 211 or SEQ ID NO: 567.

In some embodiments, said anti-human CGRP antibody or antibody fragment comprises the variable light chain of SEQ ID NO: 222 and/or the variable heavy chain of SEQ ID NO: 202. In some embodiments, said anti-human CGRP antibody or antibody fragment comprises the variable light chain encoded by SEQ ID NO: 232 and/or the variable heavy chain encoded by SEQ ID NO: 212.

In some embodiments, said anti-human CGRP antibody or antibody fragment comprises the light chain of SEQ ID NO: 221 and/or the heavy chain of SEQ ID NO: 201 or SEQ ID NO: 566. In some embodiments, said anti-human CGRP antibody or antibody fragment comprises the light chain encoded by SEQ ID NO: 231 and/or the heavy chain encoded by SEQ ID NO: 211 or SEQ ID NO: 567.

In some embodiments, said anti-CGRP antibody may comprise the antibody expression product isolated from recombinant cells which express nucleic acid sequences encoding the VL polypeptide of SEQ ID NO: 222 and the VH polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells.

In some embodiments, said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions.

In some embodiments any of the aforementioned anti-CGRP antibodies or antibody fragments may be comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8. The antibody or fragment may be administered by different means, e.g., intravenously, e.g., in a saline solution such as 0.9% sodium chloride in a suitable volume, such as 100 mL.

In some embodiments, about 100 mg, about 125 mg, about 150 mg, about 175 mg, about 200 mg, about 225 mg, about 250 mg, about 275 mg, or about 300 mg of said anti-CGRP antibody or antibody fragment is administered, e.g., intravenously.

In other embodiments, about 100 mg of said anti-CGRP antibody or antibody fragment is administered.

In other embodiments, about 300 mg of said anti-CGRP antibody or antibody fragment is administered, e.g., intravenously.

In exemplary embodiments, the anti-human CGRP antibody or antibody fragment is administered, e.g., intravenously at a frequency which is at most every 10-14 weeks, preferably every 11-13 weeks, more preferably every 3 months or every 12 weeks, wherein the antibody dosage is administered in a single formulation or divided into different formulations which are administered at a frequency of approximately every 10-14 weeks, preferably every 11-13 weeks, more preferably every 3 months or every 12 weeks. The phrase "the antibody dosage is administered in a single formulation or divided into different formulations" refers to the administration of the recited amount of antibody within a relatively short period of time, e.g., within a period of several hours, e.g., 1 to 8 hours, about one day, within about two days, or within about one week, which may be by the same or different routes (e.g., i.v., i.m., and/or s.c.), sites of administration. The term "different formulations" in this context refers to antibody dosages that are administered at different times and/or at different sites and/or different routes, irrespective of whether the dosages are the same or different with respect to the chemical composition of the pharmaceutical formulation in with each dosage is administered; for example, the concentration, excipients, carriers, pH, and the like may be the same or different between the different administered dosages.

In other exemplary embodiments, the anti-human CGRP antibody or antibody fragment dosage is administered in a single formulation or divided into different formulations which are administered at a frequency of approximately every 8 weeks or every 2 months.

In other exemplary embodiments, the anti-human CGRP antibody or antibody fragment dosage is administered in a single formulation or divided into different formulations which are administered at a frequency of approximately every 10-14 weeks, preferably every 11-13 weeks, more preferably every 12 weeks or every 3 months.

In other exemplary embodiments, the anti-human CGRP antibody or antibody fragment dosage is administered in a single formulation or divided into different formulations which are administered at a frequency of approximately every 16 weeks or every 4 months.

In other exemplary embodiments, the anti-human CGRP antibody or antibody fragment dosage is administered in a single formulation or divided into different formulations which are administered at a frequency of approximately every 20 weeks or every 5 months.

In other exemplary embodiments, the anti-human CGRP antibody or antibody fragment dosage is administered in a single formulation or divided into different formulations which are administered at a frequency of approximately every 24 weeks or every 6 months.

In other exemplary embodiments, the anti-human CGRP antibody or antibody fragment dosage is administered in a single formulation or divided into different formulations which are administered at a frequency of approximately every 28 weeks or every 7 months.

In other exemplary embodiments, the anti-human CGRP antibody or antibody fragment dosage is administered in a single formulation or divided into different formulations which are administered at a frequency of approximately every 32 weeks or every 8 months.

In other exemplary embodiments, the anti-human CGRP antibody or antibody fragment dosage is administered in a single formulation or divided into different formulations which are administered at a frequency of approximately every 36 weeks or every 9 months.

In other exemplary embodiments, the anti-human CGRP antibody or antibody fragment dosage is administered in a single formulation or divided into different formulations which are administered at a frequency of approximately every 40 weeks or every 8 months.

In other exemplary embodiments, the anti-human CGRP antibody or antibody fragment dosage is administered in a single formulation or divided into different formulations which are administered at a frequency of approximately every 44 weeks or every 9 months.

In other exemplary embodiments, the anti-human CGRP antibody or antibody fragment dosage is administered in a single formulation or divided into different formulations which are administered at a frequency of approximately every 48 weeks or every 10 months.

In other exemplary embodiments, the anti-human CGRP antibody or antibody fragment dosage is administered in a single formulation or divided into different formulations which are administered at a frequency of approximately every 52 weeks or every 11 months.

In other exemplary embodiments, the anti-human CGRP antibody or antibody fragment dosage is administered in a single formulation or divided into different formulations which are administered at a frequency of approximately every 56 weeks or every 12 months.

In other exemplary embodiments, the anti-human CGRP antibody or antibody fragment dosage is administered in a single formulation or divided into different formulations which are administered at a frequency of approximately every 15-18 months.

In other exemplary embodiments, the anti-human CGRP antibody or antibody fragment dosage is administered in a single formulation or divided into different formulations which are administered at a frequency of approximately every 18-21 months.

In other exemplary embodiments, the anti-human CGRP antibody dosage or antibody fragment used in the afore-mentioned methods is administered in a single formulation or divided into different formulations which are administered at a frequency of approximately every 2 years.

In other exemplary embodiments, the anti-human CGRP antibody used in the afore-mentioned methods is administered systemically.

In other exemplary embodiments, the anti-human CGRP antibody or antibody fragment used in the afore-mentioned methods is administered by a mode of administration is selected from intravenous, intramuscular, intravenous, intrathecal, intracranial, topical, intranasal, and oral. In a preferred embodiment, the anti-human CGRP antibody or antibody fragment used in the afore-mentioned methods is administered intravenously.

In other exemplary embodiments, the anti-human CGRP antibody used in the afore-mentioned methods has an in vivo half-life of at least 10 days.

In other exemplary embodiments, the anti-human CGRP antibody has an in vivo half-life of at least 15 days.

In other exemplary embodiments, the anti-human CGRP antibody used in the afore-mentioned methods has an in vivo half-life of at least 20 days.

In other exemplary embodiments, the anti-human CGRP antibody used in the afore-mentioned methods has an in vivo half-life of at least 20-30 days.

In other exemplary embodiments, the anti-human CGRP antibody is administered at a dosage of between about 100 mg and about 300 mg has an in vivo half-life of ±20% of at least about (284±44 hours).

In other exemplary embodiments, the anti-human CGRP antibody used in the afore-mentioned methods binds to human α- and β-CGRP.

In other exemplary embodiments, the administered anti-human CGRP antibody dosage results in the inhibition of vasodilation induced by topically applied capsaicin at least 30 days after antibody administration.

In other exemplary embodiments, the administered anti-human CGRP antibody dosage results in the inhibition of vasodilation induced by topically applied capsaicin at least 60 days after antibody administration.

In other exemplary embodiments, the administered anti-human CGRP antibody dosage results in inhibition of vasodilation induced by topically applied capsaicin at least 90 days after antibody administration.

In other exemplary embodiments, the administered anti-human CGRP antibody dosage results in the inhibition of vasodilation induced by topically applied capsaicin at least 120 days after antibody administration.

In other exemplary embodiments, the administered anti-human CGRP antibody dosage results in the inhibition of vasodilation induced by topically applied capsaicin at least 150 days after antibody administration.

In other exemplary embodiments, the administered anti-human CGRP antibody dosage results in the inhibition of vasodilation induced by topically applied capsaicin at least 180 days after antibody administration.

In other exemplary embodiments, the administered anti-human CGRP antibody dosage results in the inhibition of vasodilation induced by topically applied capsaicin more than 180 days after antibody administration.

In other exemplary embodiments, the administered anti-human CGRP antibody dosage results in sustained pharmacodynamic (PK) activity, within 5% of the maximal response (Imax) (as compared to lower antibody doses).

In other exemplary embodiments, the administered anti-human CGRP antibody dosage results in sustained pharmacodynamic (PK) activity which is maintained for at least 2-3 months after antibody administration, wherein PK analysis of the anti-human CGRP antibody is derived from plasma concentrations.

In other exemplary embodiments, the administered anti-human CGRP antibody dosage is between about 100 mg and about 300 mg or more which is administered no more frequently than every 2 months.

The present invention is additionally directed to the use of specific antibodies and fragments thereof having binding specificity for CGRP, in particular antibodies having desired epitopic specificity, high affinity or avidity and/or functional properties. A preferred embodiment of the invention is directed to usage of chimeric or humanized antibodies and fragments thereof (including Fab fragments) capable of binding to CGRP and/or inhibiting the biological activities mediated by the binding of CGRP to the CGRP receptor ("CGRP-R") e.g., wherein such antibodies optionally are derived from recombinant cells engineered to express same, optionally yeast or mammalian cells, further optionally *Pichia pastoris* and CHO cells.

In another preferred embodiment of the invention, full length antibodies and Fab fragments thereof are contemplated that inhibit the CGRP-alpha-, CGRP-beta-, and rat CGRP-driven production of cAMP. In a further preferred embodiment of the invention, full length and Fab fragments thereof are contemplated that reduce vasodilation in a recipient following administration.

The invention also contemplates usage of conjugates of anti-CGRP antibodies and binding fragments thereof conjugated to one or more functional or detectable moieties. The invention also contemplates usage of chimeric or humanized anti-CGRP or anti-CGRP/CGRP-R complex antibodies and binding fragments thereof. In one embodiment, binding fragments include, but are not limited to, Fab, Fab', F(ab')$_2$, Fv, scFv fragments, SMIPs (small molecule immunopharmaceuticals), camelbodies, nanobodies, and IgNAR.

BRIEF DESCRIPTION OF THE SEVERAL VIEWS OF THE DRAWINGS

FIGS. 1A-1F provide the polypeptide sequences of the full-length heavy chain for antibodies Ab1-Ab14 with their framework regions (FR), complementarity determining regions (CDRs), and constant region sequences delimited.

FIGS. 2A-2D provide the polypeptide sequences of the full-length light chain for antibodies Ab1-Ab14 with their framework regions (FR), complementarity determining regions (CDRs), and constant region sequences delimited.

FIGS. 3A-3P provide exemplary polynucleotide sequences encoding the full-length heavy chain for antibodies Ab1-Ab14 with their framework regions (FR), complementarity determining regions (CDRs), and constant region coding sequences delimited.

FIGS. 4A-4I provide exemplary polynucleotide sequences encoding the full-length light chain for antibodies Ab1-Ab14 with their framework regions (FR), complementarity determining regions (CDRs), and constant region coding sequences delimited.

FIG. 5 provides the polypeptide sequence coordinates within the full-length heavy chain polypeptide sequences of antibodies Ab1-Ab14 of sequence features including the variable region and complementarity determining regions (CDRs), and the SEQ ID NO of each individual feature.

FIG. 6 provides the polypeptide sequence coordinates within the full-length heavy chain polypeptide sequences of antibodies Ab1-Ab14 of sequence features including the framework regions (FRs) and constant region, and the SEQ ID NO of each individual feature.

FIG. 7 provides the polypeptide sequence coordinates within the full-length light chain polypeptide sequences of antibodies Ab1-Ab14 of sequence features including the variable region and complementarity determining regions (CDRs), and the SEQ ID NO of each individual feature.

FIG. 8 provides the polypeptide sequence coordinates within the full-length light chain polypeptide sequences of antibodies Ab1-Ab14 of sequence features including the framework regions (FRs) and constant region, and the SEQ ID NO of each individual feature.

FIG. 9 provides the polynucleotide sequence coordinates within the exemplary polynucleotide sequences encoding the full-length heavy chain polypeptide sequences of antibodies Ab1-Ab14 of sequence features including the variable region and complementarity determining regions (CDRs), and the SEQ ID NO of each individual feature.

FIG. 10 provides the polynucleotide sequence coordinates within the exemplary polynucleotide sequences encoding the full-length heavy chain polypeptide sequences of antibodies Ab1-Ab14 of sequence features including the framework regions (FRs) and constant region, and the SEQ ID NO of each individual feature.

FIG. 11 provides the polynucleotide sequence coordinates within the exemplary polynucleotide sequences encoding the full-length light chain polypeptide sequences of antibodies Ab1-Ab14 of sequence features including the variable region and complementarity determining regions (CDRs), and the SEQ ID NO of each individual feature.

FIG. 12 provides the polynucleotide sequence coordinates within the exemplary polynucleotide sequences encoding the full-length light chain polypeptide sequences of antibodies Ab1-Ab14 of sequence features including the framework regions (FRs) and constant region, and the SEQ ID NO of each individual feature.

FIG. 20 contains the pharmacokinetic (PK) profile for Ab6 administered intravenously at a single dosage of 1000 mg.

FIG. 21 contains plasma-free pharmacokinetic (PK) parameters N (number of patients), mean, and standard deviation (SD) for a single 1000 mg intravenous dosage of Ab6. The parameters shown in the table and the units are $C_{max}$ (μg/mL), $AUC_{0-\infty}$ (mg*hr/mL), half-life (days), $V_z$ (L) and $C_L$ (mL/hr).

FIG. 34 summarizes the change from baseline in measured attributes for the placebo and treatment groups in the study described in Example 2.

FIG. 39 summarizes the characteristics of patients in each treatment group in the clinical trial described in Example 3. * According to the American Academy of Neurology/American Headache Society guidelines for migraine preventative treatment (medications identified by clinical review of coded medical data); SD, standard deviation; BMI, body mass index.

FIG. 45. Summary of Acute Medication Days by Subgroups of Chronic Migraine Patients with Baseline Acute Medication Use.

FIG. 49. Summary of Acute Medication Days by Subgroups of Episodic Migraine Patients with Baseline Acute Medication Use.

DETAILED DESCRIPTION

Figure 13:
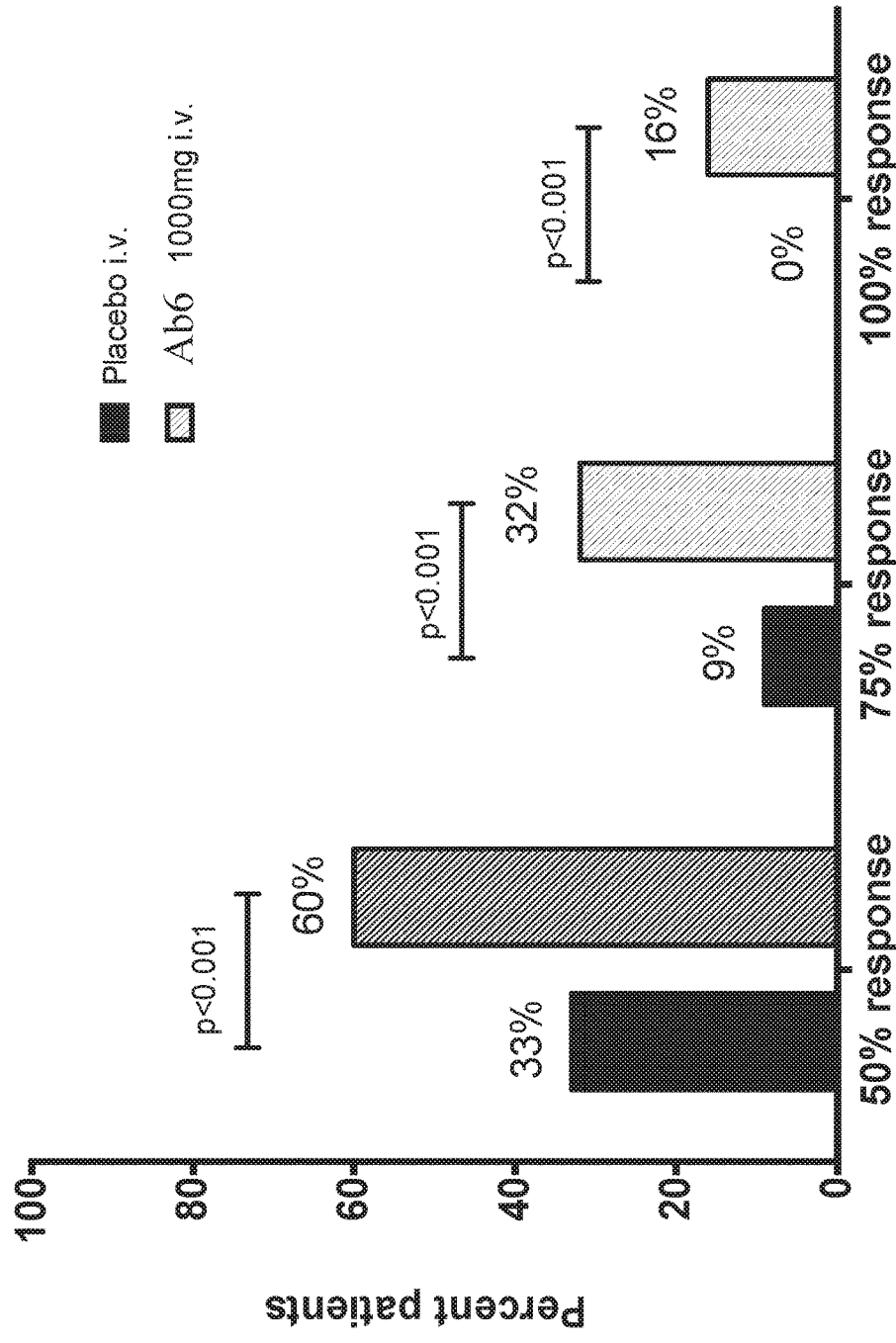
FIG. 13 shows the number of subjects in a human clinical trial described in Example 2 who were either treated with Ab6 (treatment group) or placebo groups who showed a 50, 75 or 100% reduction in migraines at each monitoring point throughout the period. The right bar in each group corresponds to patients receiving 1000 mg Ab6 and the left bar in each group corresponds to matched placebo controls. In each response rate group the patients receiving Ab6 had a significantly greater response rate than placebo-treated controls, with p values of 0.0155, 0.0034, and 0.0006 in each respective group as indicated. The administered antibody was produced in *P. pastoris* and consisted of the light chain polypeptide of SEQ ID NO: 221 and the heavy chain polypeptide of SEQ ID NO: 201.

Use of anti-CGRP antibodies for treatment of medication overuse headache is described herein. Additionally, anti-CGRP antibodies are demonstrated herein to be effective for treatment of chronic migraine. The treatment was shown to have a very rapid onset of efficacy, with relief from migraine observed on the first day following administration.

Definitions

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims. As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

As used herein, the term "medication overuse headache" refers to a headache that meets the criteria for that condition specified in ICHD-3 (Headache Classification Committee of the International Headache Society (IHS), The International Classification of Headache Disorders, 3rd edition, Cephalalgia. 2018 January; 38(1):1-211). The term includes subtypes of medication overuse headache, as defined in the ICHD-3, such as triptan-overuse headache, non-opioid analgesic overuse headache, opioid overuse headache, etc.

As used herein, the term "reduction in migraine prevalence" refers to a reduction (e.g., a stated percentage reduction, such as 50%) in the likelihood of a patient having a migraine in the stated period, such as the 18 hour, 20 hour, 24 hour, 28 hour, or 30 hour period, preferably the 24 hour period, after a first dosage of an antibody, or on the first day following the day of antibody administration (i.e., on the first full day following the day on which the antibody administration is completed). It is to be understood that a given patient may or may not have a migraine during that period, as the reduction in likelihood may be observable over a large number of patients irrespective of the outcome for an individual patient.

As used herein, the term "chronic migraine" refers to a condition wherein a patient exhibits, on average, at least 15 migraine days and/or headache per month. The term "episodic migraine" refers to a condition wherein a patient exhibits, on average, less than 15 headache and/or migraine days per month.

As used herein, the term "diagnosed with chronic migraine" refers to a patient meeting the clinical criteria for chronic migraine, whether or not a formal diagnosis of that patient was performed.

As used herein, the term "intravenously administering" refers to a mode of administration wherein a substance, e.g., an antibody, is introduced directly into the circulation of that patient, most typically into the venous circulation. The substance may be introduced in a carrier fluid, such as an aqueous solution, e.g., normal saline. The substance may be administered in a single formulation or in multiple formulations, as long as the administration is completed over a short period of time (e.g., within 1 day, preferably within 12 hours, more preferably within 6 hours, and most preferably within 1-2 hours).

As used herein, the term "the baseline number of migraine days" refers to the number of migraine days exhibited by a patient in a specified time period, e.g., prior to treatment. For example, the baseline number of migraine days may be determined over a period of one month, or longer, e.g., by recording each day whether or not a migraine occurred.

As used herein, the term "migraine days per month" refers to the number of days per month on which a patient has a migraine, i.e., at any time during that day, the patient has symptoms that meet the clinical definition of migraine. The number of migraine days per month may be determined by recording each day whether or not a migraine occurred.

As used herein, the term "headache days per month" refers to the number of days per month on which a patient has a headache, i.e., at any time during that day, the patient has symptoms that meet the clinical definition of a headache. The number of headache days per month may be determined by recording each day whether or not a headache occurred.

Calcitonin Gene Related Peptide (CGRP): As used herein, CGRP encompasses not only the following *Homo sapiens* CGRP-alpha and *Homo sapiens* CGRP-beta amino acid sequences available from American Peptides (Sunnyvale CA) and Bachem (Torrance, CA):

CGRP-alpha: ACDTATCVTHR-LAGLLSRSGGVVKNNFVPTNVGSKAF-NH$_2$ (SEQ ID NO: 561), wherein the terminal phenylalanine is amidated;

CGRP-beta: ACNTATCVTHR-LAGLLSRSGGMVKSNFVPTNVGSKAF-NH$_2$ (SEQ ID NO: 562), wherein the terminal phenylalanine is amidated; but also any membrane-bound forms of these CGRP amino acid sequences, as well as mutants (mutiens), splice variants, isoforms, orthologs, homologues and variants of this sequence.

Expression Vector: These DNA vectors contain elements that facilitate manipulation for the expression of a foreign protein within the target host cell, e.g., a yeast or mammalian cell such as *Pichia pastoris* or CHO cells. Conveniently, manipulation of sequences and production of DNA for transformation is first performed in a bacterial host, e.g. *E. coli*, and usually vectors will include sequences to facilitate such manipulations, including a bacterial origin of replication and appropriate bacterial selection marker. Selection markers encode proteins necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, (b) complement auxotrophic deficiencies, or (c) supply critical nutrients not available from complex media. Exemplary vectors and methods for transformation of yeast are described, for example, in Burke, D., Dawson, D., & Steams, T. (2000). Methods in yeast genetics: a Cold Spring Harbor Laboratory course manual. Plainview, N.Y.: Cold Spring Harbor Laboratory Press.

Expression vectors for use in yeast or mammalian cells will generally further include yeast or mammalian specific sequences, including a selectable auxotrophic or drug marker for identifying transformed yeast strains or transformed mammalian cells. A drug marker may further be used to amplify copy number of the vector in the host cell.

The polypeptide coding sequence of interest is operably linked to transcriptional and translational regulatory sequences that provide for expression of the polypeptide in host cells, e.g., *Pichia pastoris* or CHO cells. These vector components may include, but are not limited to, one or more of the following: an enhancer element, a promoter, and a transcription termination sequence. Sequences for the secretion of the polypeptide may also be included, e.g. a signal sequence, and the like. A yeast or mammalian origin of replication is optional, as expression vectors are often integrated into the host cell genome. In one embodiment of the invention, the polypeptide of interest is operably linked, or fused, to sequences providing for optimized secretion of the polypeptide from yeast diploid cells.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites or alternatively via a PCR/recombination method familiar to those skilled in the art (Gateway® Technology; Invitrogen, Carlsbad California). If such sites do not exist, the synthetic oligonucleotide adapters or linkers are used in accordance with conventional practice.

Promoters are untranslated sequences located upstream (5') to the start codon of a structural gene (generally within about 100 to 1000 bp) that control the transcription and translation of particular nucleic acid sequences to which they are operably linked. Such promoters fall into several classes: inducible, constitutive, and repressible promoters (that increase levels of transcription in response to absence of a repressor). Inducible promoters may initiate increased levels of transcription from DNA under their control in response to some change in culture conditions, e.g., the presence or absence of a nutrient or a change in temperature.

The promoter fragment may also serve as the site for homologous recombination and integration of the expression vector into the same site in the host genome; alternatively a selectable marker is used as the site for homologous recombination. Examples of suitable promoters from *Pichia* include the AOX1 and promoter (Cregg et al. (1989) *Mol. Cell. Biol.* 9:1316-1323); ICL1 promoter (Menendez et al. (2003) *Yeast* 20(13):1097-108); glyceraldehyde-3-phosphate dehydrogenase promoter (GAP) (Waterham et al. (1997) *Gene* 186(1):37-44); and FLD1 promoter (Shen et al. (1998) *Gene* 216(1):93-102). The GAP promoter is a strong constitutive promoter and the AOX and FLD1 promoters are inducible.

Other yeast promoters include ADH1, alcohol dehydrogenase II, GAL4, PHO3, PHO5, Pyk, and chimeric promoters derived therefrom. Additionally, non-yeast promoters may be used in the invention such as mammalian, insect, plant, reptile, amphibian, viral, and avian promoters. Most typically the promoter will comprise a mammalian promoter (potentially endogenous to the expressed genes) or will comprise a yeast or viral promoter that provides for efficient transcription in yeast systems.

Examples of mammalian promoters include cytomegalovirus (CMV) derived promoters, chicken 3-actin (CBM) derived promoters, adenomatous polyposis *coli* (APC) derived promoters, leucine-rich repeat containing G protein-coupled receptor 5 (LGR5) promoters, CAG promoter, Beta actin promoter, elongation factor-1 (EF1) promoter, early growth response 1 (EGR-1) promoter, eukaryotic initiation factor 4A (EIF4A1) promoter, simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter, among others. Combinations of two or more of the foregoing promoters may also be used. Further, inducible promoters may be used. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

The polypeptides of interest may be produced recombinantly not only directly, but also as a fusion polypeptide with a heterologous polypeptide, e.g. a signal sequence or other polypeptide having a specific cleavage site at the N-terminus of the mature protein or polypeptide. In general, the signal sequence may be a component of the vector, or it may be a part of the polypeptide coding sequence that is inserted into the vector. The heterologous signal sequence selected preferably is one that is recognized and processed through one of the standard pathways available within the host cell. The *S. cerevisiae* alpha factor pre-pro signal has proven effective in the secretion of a variety of recombinant proteins from *P. pastoris*. Other yeast signal sequences include the alpha mating factor signal sequence, the invertase signal sequence, and signal sequences derived from other secreted yeast polypeptides. Additionally, these signal peptide sequences may be engineered to provide for enhanced secretion in diploid yeast expression systems. Secretion signals for use in mammalian as well as yeast cells include mammalian signal sequences, which may be heterologous to the protein being secreted, or may be a native sequence for the protein being secreted. Signal sequences include pre-peptide sequences, and in some instances may include propeptide sequences. Many such signal sequences are known in the art, including the signal sequences found on immunoglobulin chains, e.g., K28 preprotoxin sequence, PHA-E, FACE, human MCP-1, human serum albumin signal sequences, human Ig heavy chain, human Ig light chain, and the like. For example, see Hashimoto et. al. Protein Eng 11(2) 75 (1998); and Kobayashi et. al. Therapeutic Apheresis 2(4) 257 (1998).

Transcription may be increased by inserting a transcriptional activator sequence into the vector. These activators are cis-acting elements of DNA, usually about from 10 to 300 bp, which act on a promoter to increase its transcription. Transcriptional enhancers are relatively orientation and position independent, having been found 5' and 3' to the transcription unit, within an intron, as well as within the coding sequence itself. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from 3' to the translation termination codon, in untranslated regions of eukaryotic or viral DNAs or cDNAs. These regions contain nucleotide segments transcribed as polyadenylated fragments in the untranslated portion of the mRNA.

Construction of suitable vectors containing one or more of the above-listed components employs standard ligation techniques or PCR/recombination methods. Isolated plasmids or DNA fragments are cleaved, tailored, and re-ligated in the form desired to generate the plasmids required or via recombination methods. For analysis to confirm correct sequences in plasmids constructed, the ligation mixtures are used to transform host cells, and successful transformants selected by antibiotic resistance (e.g. ampicillin or Zeocin) where appropriate. Plasmids from the transformants are prepared, analyzed by restriction endonuclease digestion and/or sequenced.

As an alternative to restriction and ligation of fragments, recombination methods based on att sites and recombination enzymes may be used to insert DNA sequences into a vector. Such methods are described, for example, by Landy (1989) *Ann. Rev. Biochem.* 58:913-949; and are known to those of skill in the art. Such methods utilize intermolecular DNA recombination that is mediated by a mixture of lambda and *E. coli*-encoded recombination proteins. Recombination occurs between specific attachment (att) sites on the interacting DNA molecules. For a description of att sites see Weisberg and Landy (1983) Site-Specific Recombination in Phage Lambda, in *Lambda II*, Weisberg, ed. (Cold Spring Harbor, NY: Cold Spring Harbor Press), pp. 211-250. The DNA segments flanking the recombination sites are switched, such that after recombination, the att sites are hybrid sequences comprised of sequences donated by each parental vector. The recombination can occur between DNAs of any topology.

Att sites may be introduced into a sequence of interest by ligating the sequence of interest into an appropriate vector; generating a PCR product containing att B sites through the use of specific primers; generating a cDNA library cloned into an appropriate vector containing att sites; and the like.

Folding, as used herein, refers to the three-dimensional structure of polypeptides and proteins, where interactions between amino acid residues act to stabilize the structure. Proper folding is typically the arrangement of a polypeptide that results in optimal biological activity, and in the case of antibodies can conveniently be monitored by assays for activity, e.g. antigen binding.

The expression host may be further modified by the introduction of sequences encoding one or more enzymes that enhance folding and disulfide bond formation, i.e. foldases, chaperonins, etc. Such sequences may be constitutively or inducibly expressed in the yeast host cell, using vectors, markers, etc. as known in the art. Preferably the sequences, including transcriptional regulatory elements sufficient for the desired pattern of expression, are stably integrated in the yeast genome through a targeted methodology.

For example, the eukaryotic PDI is not only an efficient catalyst of protein cysteine oxidation and disulfide bond isomerization, but also exhibits chaperone activity. Co-expression of PDI can facilitate the production of active proteins having multiple disulfide bonds. Also of interest is the expression of BIP (immunoglobulin heavy chain binding protein); cyclophilin; and the like. In one embodiment of the invention, each of the haploid parental strains expresses a distinct folding enzyme, e.g. one strain may express BIP, and the other strain may express PDI or combinations thereof.

The terms "desired protein" or "desired antibody" are used interchangeably and refer generally to a parent antibody specific to a target, i.e., CGRP or a chimeric or humanized antibody or a binding portion thereof derived therefrom as described herein. The term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies." A preferred source for producing antibodies useful as starting material according to the invention is rabbits. Numerous antibody coding sequences have been described; and others may be raised by methods well-known in the art. Examples thereof include chimeric antibodies, human antibodies and other non-human mammalian antibodies, humanized antibodies, single chain antibodies (such as scFvs), camelbodies, nanobodies, IgNAR (single-chain antibodies derived from sharks), small-modular immuno-pharmaceuticals (SMIPs), and antibody fragments such as Fabs, Fab', F(ab')$_2$ and the like. See Streltsov V A, et al., Structure of a shark IgNAR antibody variable domain and modeling of an early-developmental isotype, Protein Sci. 2005 Nov.; 14(11):2901-9. Epub 2005 Sep. 30; Greenberg A S, et al., A new antigen receptor gene family that undergoes rearrangement and extensive somatic diversification in sharks, Nature. 1995 Mar. 9; 374(6518):168-73; Nuttall S D, et al., Isolation of the new antigen receptor from wobbegong sharks, and use as a scaffold for the display of protein loop libraries, Mol Immunol. 2001 August; 38(4):313-26; Hamers-Casterman C, et al., Naturally occurring antibodies devoid of light chains, Nature. 1993 Jun. 3; 363(6428):446-8; Gill D S, et al., Biopharmaceutical drug discovery using novel protein scaffolds, Curr Opin Biotechnol. 2006 Dec.; 17(6):653-8. Epub 2006 Oct. 19.

For example, antibodies or antigen binding fragments may be produced by genetic engineering. In this technique, as with other methods, antibody-producing cells are sensitized to the desired antigen or immunogen. The messenger RNA isolated from antibody producing cells is used as a template to make cDNA using PCR amplification. A library of vectors, each containing one heavy chain gene and one light chain gene retaining the initial antigen specificity, is produced by insertion of appropriate sections of the amplified immunoglobulin cDNA into the expression vectors. A combinatorial library is constructed by combining the heavy chain gene library with the light chain gene library. This results in a library of clones which co-express a heavy and light chain (resembling the Fab fragment or antigen binding fragment of an antibody molecule). The vectors that carry these genes are co-transfected into a host cell. When antibody gene synthesis is induced in the transfected host, the heavy and light chain proteins self-assemble to produce active antibodies that can be detected by screening with the antigen or immunogen.

Antibody coding sequences of interest include those encoded by native sequences, as well as nucleic acids that, by virtue of the degeneracy of the genetic code, are not identical in sequence to the disclosed nucleic acids, and variants thereof. Variant polypeptides can include amino acid (aa) substitutions, additions or deletions. The amino acid substitutions can be conservative amino acid substitutions or substitutions to eliminate non-essential amino acids, such as to alter a glycosylation site, or to minimize misfolding by substitution or deletion of one or more cysteine residues that are not necessary for function. Variants can be designed so as to retain or have enhanced biological activity of a particular region of the protein (e.g., a functional domain, catalytic amino acid residues, etc). Variants also include fragments of the polypeptides disclosed herein, particularly biologically active fragments and/or fragments corresponding to functional domains. Techniques for in vitro mutagenesis of cloned genes are known. Also included in the subject invention are polypeptides that have been modified using ordinary molecular biological techniques so as to improve their resistance to proteolytic degradation or to optimize solubility properties or to render them more suitable as a therapeutic agent.

Chimeric antibodies may be made by recombinant means by combining the variable light and heavy chain regions ($V_L$ and $V_H$), obtained from antibody producing cells of one species with the constant light and heavy chain regions from another. Typically chimeric antibodies utilize rodent or rabbit variable regions and human constant regions, in order to produce an antibody with predominantly human domains. The production of such chimeric antibodies is well known in the art, and may be achieved by standard means (as described, e.g., in U.S. Pat. No. 5,624,659, incorporated herein by reference in its entirety). It is further contemplated that the human constant regions of chimeric antibodies of the invention may be selected from IgG1, IgG2, IgG3, and IgG4 constant regions.

Humanized antibodies are engineered to contain even more human-like immunoglobulin domains, and incorporate only the complementarity-determining regions of the animal-derived antibody. This is accomplished by carefully examining the sequence of the hyper-variable loops of the variable regions of the monoclonal antibody, and fitting them to the structure of the human antibody chains. Although facially complex, the process is straightforward in practice. See, e.g., U.S. Pat. No. 6,187,287, incorporated fully herein by reference.

In addition to entire immunoglobulins (or their recombinant counterparts), immunoglobulin fragments comprising the epitope binding site (e.g., Fab', F(ab')$_2$, or other fragments) may be synthesized. "Fragment," or minimal immunoglobulins may be designed utilizing recombinant immunoglobulin techniques. For instance "Fv" immunoglobulins for use in the present invention may be produced by synthesizing a fused variable light chain region and a variable heavy chain region. Combinations of antibodies are also of interest, e.g. diabodies, which comprise two distinct Fv specificities. In another embodiment of the invention, SMIPs (small molecule immunopharmaceuticals), camelbodies, nanobodies, and IgNAR are encompassed by immunoglobulin fragments.

Immunoglobulins and fragments thereof may be modified post-translationally, e.g. to add effector moieties such as chemical linkers, detectable moieties, such as fluorescent dyes, enzymes, toxins, substrates, bioluminescent materials, radioactive materials, chemiluminescent moieties and the like, or specific binding moieties, such as streptavidin, avidin, or biotin, and the like may be utilized in the methods and compositions of the present invention. Examples of additional effector molecules are provided infra.

A polynucleotide sequence "corresponds" to a polypeptide sequence if translation of the polynucleotide sequence in accordance with the genetic code yields the polypeptide sequence (i.e., the polynucleotide sequence "encodes" the polypeptide sequence), one polynucleotide sequence "corresponds" to another polynucleotide sequence if the two sequences encode the same polypeptide sequence.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A "coding sequence" is an in-frame sequence of codons that (in view of the genetic code) correspond to or encode a protein or peptide sequence. Two coding sequences correspond to each other if the sequences or their complementary sequences encode the same amino acid sequences. A coding sequence in association with appropriate regulatory sequences may be transcribed and translated into a polypeptide. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. Promoter sequences typically contain additional sites for binding of regulatory molecules (e.g., transcription factors) which affect the transcription of the coding sequence. A coding sequence is "under the control" of the promoter sequence or "operatively linked" to the promoter when RNA polymerase binds the promoter sequence in a cell and transcribes the coding sequence into mRNA, which is then in turn translated into the protein encoded by the coding sequence.

Vectors are used to introduce a foreign substance, such as DNA, RNA or protein, into an organism or host cell. Typical vectors include recombinant viruses (for polynucleotides) and liposomes (for polypeptides). A "DNA vector" is a replicon, such as plasmid, phage or cosmid, to which another polynucleotide segment may be attached so as to bring about the replication of the attached segment. An "expression vector" is a DNA vector which contains regulatory sequences which will direct polypeptide synthesis by an appropriate host cell. This usually means a promoter to bind RNA polymerase and initiate transcription of mRNA, as well as ribosome binding sites and initiation signals to direct translation of the mRNA into a polypeptide(s). Incorporation of a polynucleotide sequence into an expression vector at the proper site and in correct reading frame, followed by transformation of an appropriate host cell by the vector, enables the production of a polypeptide encoded by said polynucleotide sequence.

"Amplification" of polynucleotide sequences is the in vitro production of multiple copies of a particular nucleic acid sequence. The amplified sequence is usually in the form of DNA. A variety of techniques for carrying out such amplification are described in a review article by Van Brunt (1990, Bio/Technol., 8(4):291-294). Polymerase chain reaction or PCR is a prototype of nucleic acid amplification, and use of PCR herein should be considered exemplary of other suitable amplification techniques.

The general structure of antibodies in vertebrates now is well understood (Edelman, G. M., Ann. N.Y. Acad. Sci., 190: 5 (1971)). Antibodies consist of two identical light polypeptide chains of molecular weight approximately 23,000 daltons (the "light chain"), and two identical heavy chains of molecular weight 53,000-70,000 (the "heavy chain"). The four chains are joined by disulfide bonds in a "Y" configuration wherein the light chains bracket the heavy chains starting at the mouth of the "Y" configuration. The "branch" portion of the "Y" configuration is designated the $F_{ab}$ region; the stem portion of the "Y" configuration is designated the Fc region. The amino acid sequence orientation runs from the N-terminal end at the top of the "Y" configuration to the C-terminal end at the bottom of each chain. The N-terminal end possesses the variable region having specificity for the antigen that elicited it, and is approximately 100 amino acids in length, there being slight variations between light and heavy chain and from antibody to antibody.

The variable region is linked in each chain to a constant region that extends the remaining length of the chain and that within a particular class of antibody does not vary with the specificity of the antibody (i.e., the antigen eliciting it). There are five known major classes of constant regions that determine the class of the immunoglobulin molecule (IgG, IgM, IgA, IgD, and IgE corresponding to γ, μ, α, δ, and ε (gamma, mu, alpha, delta, or epsilon) heavy chain constant regions). The constant region or class determines subsequent effector function of the antibody, including activation of complement (Kabat, E. A., Structural Concepts in Immunology and Immunochemistry, 2nd Ed., p. 413-436, Holt, Rinehart, Winston (1976)), and other cellular responses (Andrews, D. W., et al., Clinical Immunobiology, pp 1-18, W. B. Sanders (1980); Kohl, S., et al., Immunology, 48: 187 (1983)); while the variable region determines the antigen with which it will react. Light chains are classified as either κ (kappa) or λ (lambda). Each heavy chain class can be prepared with either kappa or lambda light chain. The light and heavy chains are covalently bonded to each other, and the "tail" portions of the two heavy chains are bonded to each other by covalent disulfide linkages when the immunoglobulins are generated either by hybridomas or by B cells.

The expression "variable region" or "VR" refers to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

The expressions "complementarity determining region," "hypervariable region," or "CDR" refer to one or more of the hyper-variable or complementarity determining regions (CDRs) found in the variable regions of light or heavy chains of an antibody (See Kabat, E. A. et al., Sequences of Proteins of Immunological Interest, National Institutes of Health, Bethesda, Md., (1987)). These expressions include the hypervariable regions as defined by Kabat et al. ("Sequences of Proteins of Immunological Interest," Kabat E., et al., US Dept. of Health and Human Services, 1983) or the hypervariable loops in 3-dimensional structures of antibodies (Chothia and Lesk, *J Mol. Biol.* 196 901-917 (1987)). The CDRs in each chain are held in close proximity by framework regions and, with the CDRs from the other chain, contribute to the formation of the antigen binding site. Within the CDRs there are select amino acids that have been described as the selectivity determining regions (SDRs) which represent the critical contact residues used by the CDR in the antibody-antigen interaction (Kashmiri, S., Methods, 36:25-34 (2005)). In the present invention when specific antibody amino acid or nucleic acid residues are referenced by number this generally refers to its position within a specified amino acid or nucleic acid sequence (i.e., particular sequence identifier) and/or in accordance with Kabat et al numbering.

The expressions "framework region" or "FR" refer to one or more of the framework regions within the variable regions of the light and heavy chains of an antibody (See Kabat, E. A. et al., Sequences of Proteins of Immunological Interest, National Institutes of Health, Bethesda, Md., (1987)). These expressions include those amino acid sequence regions interposed between the CDRs within the variable regions of the light and heavy chains of an antibody.

"Cmax" refers to the maximum (or peak) concentration that an antibody or other compound achieves in tested area (e.g., in the serum or another compartment such as cerebrospinal fluid) after the drug has been administered. For example, serum Cmax may be measured from serum, e.g., prepared by collecting a blood sample, allowing it to clot and separating solid components by centrifugation or other means to yield serum (blood containing neither blood cells nor clotting factors), and then detecting the concentration of the analyte in the serum by ELISA or other means known in the art.

"AUC" refers to the area under the concentration-time curve which is expressed in units of mg/mL*hr (or equivalently mg*hr/ml) unless otherwise specified. "$AUC_{0-t}$" refers to the area under the concentration-time curve from time=0 to last quantifiable concentration. "$AUC_{0-inf}$" refers to the area under the concentration-time curve from time=0 extrapolated to infinity.

"$I_{max}$" refers to the maximal pharmacodynamic response elicited by an anti-CGRP antibody dosage, preferably a dosage of 350 mg or more, more typically at least 750 or 1000 mg, as compared to the response elicited by a lower anti-CGRP antibody doses, e.g., wherein such response may be detected by the inhibition of vasodilation after topical application of capsaicin.

Anti-CGRP Antibodies and Binding Fragments Thereof Having Binding Specificity for CGRP The invention specifically includes the use of specific anti-CGRP antibodies and antibody fragments referred to herein as Ab1-Ab14 which comprise or consist of the CDR, VL, VH, CL, CH polypeptides sequences identified in FIGS. 1A-12. The polypeptides comprised in an especially preferred anti-CGRP antibody, Ab6 is further described below.

Antibody Ab6

In a preferred exemplary embodiment, the invention includes humanized antibodies having binding specificity to CGRP and possessing a variable light chain sequence comprising the sequence set forth below:

(SEQ ID NO: 222)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKR.

The invention also includes humanized antibodies having binding specificity to CGRP and possessing a light chain sequence comprising the sequence set forth below:

(SEQ ID NO: 221)
QVLTQSPSSLSASVGDRVTINCQASQSVYHNTYLAWYQQKPGKVPKQLIY

DASTLASGVPSRFSGSGSGTDFTLTISSLQPEDVATYYCLGSYDCTNGDC

FVFGGGTKVEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC.

The invention further includes humanized antibodies having binding specificity to CGRP and possessing a variable heavy chain sequence comprising the sequence set forth below:

(SEQ ID NO: 202)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSS.

The invention also includes humanized antibodies having binding specificity to CGRP and possessing a heavy chain sequence comprising the sequence set forth below:

(SEQ ID NO: 201)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPGK.

Alternatively, the heavy chain of Ab6 may lack the C-terminal lysine of SEQ ID NO: 201, i.e., a heavy chain sequence comprising the sequence set forth below:

(SEQ ID NO: 566)
EVQLVESGGGLVQPGGSLRLSCAVSGIDLSGYYMNWVRQAPGKGLEWVGV

IGINGATYYASWAKGRFTISRDNSKTTVYLQMNSLRAEDTAVYFCARGDI

WGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKP

SNTKVDARVEPKSCDKTHTCPPCPAPELLGGPSVFLFPPKPKDTLMISRT

PEVTCVVVDVSHEDPEVKFNWYVDGVEVHNAKTKPREEQYASTYRVVSVL

TVLHQDWLNGKEYKCKVSNKALPAPIEKTISKAKGQPREPQVYTLPPSRE

EMTKNQVSLTCLVKGFYPSDIAVEWESNGQPENNYKTTPPVLDSDGSFFL

YSKLTVDKSRWQQGNVFSCSVMHEALHNHYTQKSLSLSPG.

The invention further contemplates antibodies comprising one or more of the polypeptide sequences of SEQ ID NO: 224; SEQ ID NO: 226; and SEQ ID NO: 228 which correspond to the complementarity-determining regions (CDRs, or hypervariable regions) of the variable light chain sequence of SEQ ID NO: 222 or the light chain sequence of SEQ ID NO: 221, and/or one or more of the polypeptide sequences of SEQ ID NO: 204; SEQ ID NO: 206; and SEQ ID NO: 208 which correspond to the complementarity-determining regions (CDRs, or hypervariable regions) of the variable heavy chain sequence of SEQ ID NO: 202 or the heavy chain sequence of SEQ ID NO: 201 or SEQ ID NO: 566, or combinations of these polypeptide sequences. In another embodiment of the invention, the antibodies of the invention or fragments thereof comprise, or alternatively consist of, combinations of one or more of the CDRs, the variable heavy and variable light chain sequences, and the heavy and light chain sequences set forth above, including all of them.

The invention also contemplates fragments of the antibody having binding specificity to CGRP. In one embodiment of the invention, antibody fragments of the invention comprise, or alternatively consist of, the polypeptide sequence of SEQ ID NO: 222 or SEQ ID NO: 221. In another embodiment of the invention, antibody fragments of the invention comprise, or alternatively consist of, the polypeptide sequence of SEQ ID NO: 202 or SEQ ID NO: 201 or SEQ ID NO: 566.

In a further embodiment of the invention, fragments of the antibody having binding specificity to CGRP comprise, or alternatively consist of, one or more of the polypeptide sequences of SEQ ID NO: 224; SEQ ID NO: 226; and SEQ ID NO: 228 which correspond to the complementarity-determining regions (CDRs, or hypervariable regions) of the variable light chain sequence of SEQ ID NO: 222 or the light chain sequence of SEQ ID NO: 221.

In a further embodiment of the invention, fragments of the antibody having binding specificity to CGRP comprise, or alternatively consist of, one or more of the polypeptide sequences of SEQ ID NO: 204; SEQ ID NO: 206; and SEQ ID NO: 208 which correspond to the complementarity-determining regions (CDRs, or hypervariable regions) of the variable heavy chain sequence of SEQ ID NO: 202 or the heavy chain sequence of SEQ ID NO: 201 or SEQ ID NO: 566.

The invention also contemplates antibody fragments which include one or more of the antibody fragments described herein. In one embodiment of the invention, fragments of the antibodies having binding specificity to CGRP comprise, or alternatively consist of, one, two, three or more, including all of the following antibody fragments: the variable light chain region of SEQ ID NO: 222; the variable heavy chain region of SEQ ID NO: 202; the complementarity-determining regions (SEQ ID NO: 224; SEQ ID NO: 226; and SEQ ID NO: 228) of the variable light chain region of SEQ ID NO: 222; and the complementarity-determining regions (SEQ ID NO: 204; SEQ ID NO: 206; and SEQ ID NO: 208) of the variable heavy chain region of SEQ ID NO: 202.

In a particularly preferred embodiment of the invention, the humanized anti-CGRP antibody is Ab6, comprising, or alternatively consisting of, SEQ ID NO: 221 and SEQ ID NO: 201 or SEQ ID NO: 566, and having at least one of the biological activities set forth herein.

In a further particularly preferred embodiment of the invention, antibody fragments comprise, or alternatively consist of, Fab (fragment antigen binding) fragments having binding specificity for CGRP. With respect to antibody Ab6, the Fab fragment includes the variable light chain sequence of SEQ ID NO: 222 and the variable heavy chain sequence of SEQ ID NO: 202. This embodiment of the invention further contemplates additions, deletions, and variants of SEQ ID NO: 222 and/or SEQ ID NO: 202 in said Fab while retaining binding specificity for CGRP.

In another particularly preferred embodiment of the invention, said anti-CGRP antibody may comprise the antibody expression product isolated from recombinant cells which express nucleic acid sequences encoding the variable light chain polypeptide of SEQ ID NO: 222 and the variable heavy chain polypeptide of SEQ ID NO: 202, which polypeptides optionally are respectively linked to human light and heavy constant region polypeptides, e.g., human IgG1, IgG2, IgG3 or IgG4 constant regions, which constant regions optionally may be modified to alter glycosylation or proteolysis, wherein said recombinant cells optionally comprise yeast or mammalian cells, e.g., *Pichia pastoris* or CHO cells.

In another particularly preferred embodiment of the invention, said anti-CGRP antibody may comprise the antibody expression product isolated from recombinant cells which express nucleic acid sequences encoding the light chain of SEQ ID NO: 221 and the heavy chain polypeptide of SEQ ID NO: 201 or SEQ ID NO: 566, wherein said recombinant cells optionally comprise yeast or mammalian cells, e.g., *Pichia pastoris* or CHO cells, wherein the constant regions thereof optionally may be modified to alter glycosylation or proteolysis or other effector functions.

In another particularly preferred embodiment of the invention, any of the aforementioned anti-CGRP antibodies or antibody fragments may be optionally comprised in a formulation as disclosed herein, e.g., comprising histidine (L-histidine), sorbitol, polysorbate 80, such as, per 1 mL volume, about 100 mg anti-CGRP antibody, about 3.1 mg L-Histidine, about 40.5 mg Sorbitol, and about 0.15 mg Polysorbate 80, having a pH of about 5.8.

In one embodiment of the invention described herein (infra), Fab fragments may be produced by enzymatic digestion (e.g., papain) of Ab6. In another embodiment of the invention, anti-CGRP antibodies such as Ab6 or Fab fragments thereof may be produced via expression in mammalian cells such as CHO, NSO or HEK 293 cells, fungal, insect, or microbial systems such as yeast cells (for example diploid yeast such as diploid *Pichia*) and other yeast strains. Suitable *Pichia* species include, but are not limited to, *Pichia pastoris*.

In another embodiment, antibody fragments may be present in one or more of the following non-limiting forms: Fab, Fab', F(ab')₂, Fv and single chain Fv antibody forms. In a preferred embodiment, the anti-CGRP antibodies described herein further comprises the kappa constant light chain sequence comprising the sequence set forth below:

(SEQ ID NO: 563)
TVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKS

FNRGEC.

In another preferred embodiment, the anti-CGRP antibodies described herein further comprises the gamma-1 constant heavy chain polypeptide sequence comprising the sequence set forth below or the same sequence lacking the carboxy terminal lysine residue (SEQ ID NO: 564 and SEQ ID NO: 565, respectively):

(SEQ ID NO: 564)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

(SEQ ID NO: 565)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYASTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPG.

For clarity, any antibody disclosed herein is intended to include any variant of the disclosed constant region variant sequences, e.g., Ab6 may comprise the constant region of SEQ ID NO: 564 containing the C-terminal lysine or may comprise the constant region of SEQ ID NO: 565 lacking the C-terminal lysine. Thus, every disclosure herein of the heavy chain of SEQ ID NO: 201 also includes a variant lacking the C-terminal lysine residue thereof, i.e., having the heavy chain variable region sequence of Ab6 (SEQ ID NO: 202) and the constant region sequence of SEQ ID NO: 565. For example, the sequence encoding an antibody comprising a C-terminal lysine in the heavy chain may, when expressed in cell lines such as CHO cells, produce an antibody lacking said C-terminal lysine due to proteolysis, or a mixture of heavy chains containing or lacking said C-terminal lysine.

In another embodiment, the invention contemplates use of an isolated anti-CGRP antibody comprising a VH polypeptide sequence selected from: SEQ ID NO: 2, SEQ ID NO: 42, SEQ ID NO: 82, SEQ ID NO: 122, SEQ ID NO: 162, SEQ ID NO: 202, SEQ ID NO: 242, SEQ ID NO: 282, SEQ ID NO: 322, SEQ ID NO: 362, SEQ ID NO: 402, SEQ ID NO: 442, SEQ ID NO: 482, or SEQ ID NO: 522, or a variant thereof; and further comprising a $V_L$ polypeptide sequence selected from: SEQ ID NO: 22, SEQ ID NO: 62, SEQ ID NO: 102, SEQ ID NO: 142, SEQ ID NO: 182, SEQ ID NO: 222, SEQ ID NO: 262, SEQ ID NO: 302, SEQ ID NO: 342, SEQ ID NO: 382, SEQ ID NO: 422, SEQ ID NO: 462, SEQ ID NO: 502, or SEQ ID NO: 542, or a variant thereof, wherein one or more of the framework residues (FR residues) in said $V_H$ or $V_L$ polypeptide has been substituted with another amino acid residue resulting in an anti-CGRP antibody that specifically binds CGRP. The invention contemplates humanized and chimeric forms of these antibodies. The chimeric antibodies may include an Fc derived from IgG1, IgG2, IgG3, or IgG4 constant regions.

In one embodiment of the invention, the antibodies or VH or $V_L$ polypeptides originate or are selected from one or more rabbit B cell populations prior to initiation of the humanization process referenced herein.

In another embodiment of the invention, the anti-CGRP antibodies and fragments thereof do not have binding specificity for CGRP-R. In a further embodiment of the invention, the anti-CGRP antibodies and fragments thereof inhibit the association of CGRP with CGRP-R. In another embodiment of the invention, the anti-CGRP antibodies and fragments thereof inhibit the association of CGRP with CGRP-R and/or additional proteins and/or multimers thereof, and/or antagonizes the biological effects thereof.

As stated herein, antibodies and fragments thereof may be modified post-translationally to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

Antibodies or fragments thereof may also be chemically modified to provide additional advantages such as increased solubility, stability and circulating time (in vivo half-life) of the polypeptide, or decreased immunogenicity (See U.S. Pat. No. 4,179,337). The chemical moieties for derivatization may be selected from water soluble polymers such as polyethylene glycol, ethylene glycol/propylene glycol copolymers, carboxymethylcellulose, dextran, polyvinyl alcohol and the like. The antibodies and fragments thereof may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa. Branched polyethylene glycols are described, for example, in U.S. Pat. No. 5,643,575; Morpurgo et al., Appl. Biochem. Biotechnol. 56:59-72 (1996); Vorobjev et al., Nucleosides Nucleotides 18:2745-2750 (1999); and Caliceti et al., Bioconjug. Chem. 10:638-646 (1999), the disclosures of each of which are incorporated herein by reference.

There are a number of attachment methods available to those skilled in the art, See e.g., EP 0 401 384, herein incorporated by reference (coupling PEG to G-CSF), See also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to polypeptides via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) or to more than one type of amino acid residue (e.g., lysine, histidine, aspartic acid, glutamic acid, cysteine and combinations thereof).

Alternatively, antibodies or fragments thereof may have increased in vivo half-lives via fusion with albumin (including but not limited to recombinant human serum albumin or fragments or variants thereof (See, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety)) or other circulating blood proteins such as transferrin or ferritin. In a preferred embodiment, polypeptides and/or antibodies of the present invention (including fragments or variants thereof) are fused with the mature form of human serum albumin (i.e., amino acids 1-585 of human serum albumin as shown in FIGS. 1 and 2 of EP Patent 0 322 094) which is herein incorporated by reference in its entirety. Polynucleotides encoding fusion proteins of the invention are also encompassed by the invention.

Regarding detectable moieties, further exemplary enzymes include, but are not limited to, horseradish peroxidase, acetylcholinesterase, alkaline phosphatase, beta-galactosidase and luciferase. Further exemplary fluorescent materials include, but are not limited to, rhodamine, fluorescein, fluorescein isothiocyanate, umbelliferone, dichlorotriazinylamine, phycoerythrin and dansyl chloride. Further exemplary chemiluminescent moieties include, but are not limited to, luminol. Further exemplary bioluminescent materials include, but are not limited to, luciferin and aequorin. Further exemplary radioactive materials include, but are not limited to, Iodine 125 ($^{125}$I), Carbon 14 ($^{14}$C), Sulfur 35 ($^{35}$S), Tritium ($^{3}$H) and Phosphorus 32 ($^{32}$P).

Regarding functional moieties, exemplary cytotoxic agents include, but are not limited to, methotrexate, aminopterin, 6-mercaptopurine, 6-thioguanine, cytarabine, 5-fluorouracil decarbazine; alkylating agents such as mechlorethamine, thioepa chlorambucil, melphalan, carmustine (BSNU), mitomycin C, lomustine (CCNU), 1-methylnitrosourea, cyclothosphamide, mechlorethamine, busulfan, dibromomannitol, streptozotocin, mitomycin C, cis-dichlorodiamine platinum (II) (DDP) cisplatin and carboplatin (paraplatin); anthracyclines include daunorubicin (formerly daunomycin), doxorubicin (adriamycin), detorubicin, carminomycin, idarubicin, epirubicin, mitoxantrone and bisantrene; antibiotics include dactinomycin (actinomycin D), bleomycin, calicheamicin, mithramycin, and anthramycin (AMC); and antimytotic agents such as the *vinca* alkaloids, vincristine and vinblastine. Other cytotoxic agents include paclitaxel (taxol), ricin, *pseudomonas* exotoxin, gemcitabine, cytochalasin B, gramicidin D, ethidium bromide, emetine, etoposide, tenoposide, colchicin, dihydroxy anthracin dione, 1-dehydrotestosterone, glucocorticoids, procaine, tetracaine, lidocaine, propranolol, puromycin, procarbazine, hydroxyurea, asparaginase, corticosteroids, mytotane (O,P'-(DDD)), interferons, and mixtures of these cytotoxic agents.

Further cytotoxic agents include, but are not limited to, chemotherapeutic agents such as carboplatin, cisplatin, paclitaxel, gemcitabine, calicheamicin, doxorubicin, 5-fluorouracil, mitomycin C, actinomycin D, cyclophosphamide, vincristine and bleomycin. Toxic enzymes from plants and bacteria such as ricin, diphtheria toxin and *Pseudomonas* toxin may be conjugated to the humanized or chimeric antibodies, or binding fragments thereof, to generate cell-type-specific-killing reagents (Youle, et al., Proc. Nat'l Acad. Sci. USA 77:5483 (1980); Gilliland, et al., Proc. Nat'l Acad. Sci. USA 77:4539 (1980); Krolick, et al., Proc. Nat'l Acad. Sci. USA 77:5419 (1980)).

Other cytotoxic agents include cytotoxic ribonucleases as described by Goldenberg in U.S. Pat. No. 6,653,104. Embodiments of the invention also relate to radioimmunoconjugates where a radionuclide that emits alpha or beta particles is stably coupled to the antibody, or binding fragments thereof, with or without the use of a complex-forming agent. Such radionuclides include beta-emitters such as Phosphorus-32 ($^{32}$P), Scandium-47 ($^{47}$Sc), Copper-67 ($^{67}$Cu), Gallium-67 ($^{67}$Ga), Yttrium-88 ($^{88}$Y), Yttrium-90 ($^{90}$Y), Iodine-125 ($^{125}$I), Iodine-131 ($^{131}$I), Samarium-153 ($^{153}$Sm), Lutetium-177 ($^{177}$Lu), Rhenium-186 ($^{186}$Re) or Rhenium-188 ($^{188}$Re), and alpha-emitters such as Astatine-211 ($^{211}$At), Lead-212 ($^{212}$Pb), Bismuth-212 ($^{212}$Bi) or -213 ($^{213}$Bi) or Actinium-225 ($^{225}$Ac).

Methods are known in the art for conjugating an antibody or binding fragment thereof to a detectable moiety and the like, such as for example those methods described by Hunter et al, Nature 144:945 (1962); David et al, Biochemistry 13:1014 (1974); Pain et al, J. Immunol. Meth. 40:219 (1981); and Nygren, J., Histochem. and Cytochem. 30:407 (1982).

Embodiments described herein further include variants and equivalents that are substantially homologous to the antibodies, antibody fragments, diabodies, SMIPs, camelbodies, nanobodies, IgNAR, polypeptides, variable regions and CDRs set forth herein. These may contain, e.g., conservative substitution mutations, (i.e., the substitution of one or more amino acids by similar amino acids). For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

In another embodiment, the invention contemplates polypeptide sequences having at least 90% or greater sequence homology to any one or more of the polypeptide sequences of antibody fragments, variable regions and CDRs set forth herein. More preferably, the invention contemplates polypeptide sequences having at least 95% or greater sequence homology, even more preferably at least 98% or greater sequence homology, and still more preferably at least 99% or greater sequence homology to any one or more of the polypeptide sequences of antibody fragments, variable regions and CDRs set forth herein. Methods for determining homology between nucleic acid and amino acid sequences are well known to those of ordinary skill in the art.

In another embodiment, the invention further contemplates the above-recited polypeptide homologs of the antibody fragments, variable regions and CDRs set forth herein further having anti-CGRP activity. Non-limiting examples of anti-CGRP activity are set forth herein.

The present invention also contemplates anti-CGRP antibodies comprising any of the polypeptide or polynucleotide sequences described herein substituted for any of the other polynucleotide sequences described herein. For example, without limitation thereto, the present invention contemplates antibodies comprising the combination of any of the variable light chain and variable heavy chain sequences described herein, and further contemplates antibodies resulting from substitution of any of the CDR sequences described herein for any of the other CDR sequences described herein.

Additional Exemplary Embodiments of the Invention

In another embodiment, the invention contemplates treatment methods using one or more anti-human CGRP antibodies or antibody fragments thereof which specifically bind to the same overlapping linear or conformational epitope(s) and/or competes for binding to the same overlapping linear or conformational epitope(s) on an intact human CGRP polypeptide or fragment thereof as an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment, the anti-human CGRP antibody or fragment thereof specifically binds to the same overlapping linear or conformational epitope(s) and/or competes for binding to the same overlapping linear or conformational epitope(s) on an intact human CGRP polypeptide or a fragment thereof as Ab3, Ab6, Ab13, or Ab14.

A preferred embodiment of the invention is directed to treatment methods using chimeric or humanized antibodies and fragments thereof (including Fab fragments) having binding specificity for CGRP and inhibiting biological activities mediated by the binding of CGRP to the CGRP receptor. In a particularly preferred embodiment of the invention, the chimeric or humanized anti-CGRP antibodies are selected from Ab3, Ab6, Ab13, or Ab14.

In another embodiment of the invention, the anti-human CGRP antibody used in the described treatment methods is an antibody which specifically binds to the same overlapping linear or conformational epitopes on an intact CGRP polypeptide or fragment thereof that is (are) specifically bound by Ab3, Ab6, Ab13, or Ab14 as ascertained by epitopic mapping using overlapping linear peptide fragments which span the full length of the native human CGRP polypeptide.

The invention is also directed to treatment methods using an anti-CGRP antibody that binds with the same CGRP epitope and/or competes with an anti-CGRP antibody for binding to CGRP as an antibody or antibody fragment disclosed herein, including but not limited to an anti-CGRP antibody selected from Ab1, Ab2, Ab3, Ab4, Ab5, Ab6, Ab7, Ab8, Ab9, Ab10, Ab11, Ab12, Ab13, or Ab14.

In another embodiment, the invention is also directed to treatment methods using an isolated anti-CGRP antibody or antibody fragment comprising one or more of the CDRs contained in the VH polypeptide sequences selected from: 3, 13, 23, 33, 43, 53, 63, 73, 83, 93, 103, 113, 123, or 133, or a variant thereof, and/or one or more of the CDRs contained in the $V_L$ polypeptide sequences selected from: 1, 11, 21, 31, 41, 51, 61, 71, 81, 91, 101, 111, 121, or 131, or a variant thereof.

In one embodiment of the invention, the anti-human CGRP antibody discussed in the two prior paragraphs comprises at least 2 complementarity determining regions (CDRs) in each the variable light and the variable heavy regions which are identical to those contained in an anti-human CGRP antibody selected from Ab1, Ab2, Ab3, Ab4, Ab5, Ab6, Ab7, Ab8, Ab9, Ab10, Ab11, Ab12, Ab13, or Ab14.

In a preferred embodiment, the anti-human CGRP antibody used in the described treatment methods comprises at least 2 complementarity determining regions (CDRs) in each the variable light and the variable heavy regions which are identical to those contained in Ab3 or Ab6. In another embodiment, all of the CDRs of the anti-human CGRP antibody discussed above are identical to the CDRs contained in an anti-human CGRP antibody selected from Ab1, Ab2, Ab3, Ab4, Ab5, Ab6, Ab7, Ab8, Ab9, Ab10, Ab11, Ab12, Ab13, or Ab14. In a preferred embodiment of the invention, all of the CDRs of the anti-human CGRP antibody discussed above are identical to the CDRs contained in an anti-human CGRP antibody selected from Ab3 or Ab6.

The invention further contemplates treatment methods wherein the one or more anti-human CGRP antibodies discussed above are aglycosylated or if glycosylated are only mannosylated; that contain an Fc region that has been modified to alter effector function, half-life, proteolysis, and/or glycosylation; are human, humanized, single chain or chimeric; and are a humanized antibody derived from a rabbit (parent) anti-human CGRP antibody. An exemplary mutation which impairs glycosylation comprises the mutation of the Asn residue at position 297 of an IgG heavy chain constant region such as IgG1 to another amino acid, such as Ala as described in U.S. Pat. No. 5,624,821, which is incorporated by reference in its entirety.

The invention further contemplates one or more anti-human CGRP antibodies wherein the framework regions (FRs) in the variable light region and the variable heavy regions of said antibody respectively are human FRs which are unmodified or which have been modified by the substitution of one or more human FR residues in the variable light or heavy chain region with the corresponding FR residues of the parent rabbit antibody, and wherein said human FRs have been derived from human variable heavy and light chain antibody sequences which have been selected from a library of human germline antibody sequences based on their high level of homology to the corresponding rabbit variable heavy or light chain regions relative to other human germline antibody sequences contained in the library.

The invention also contemplates a method of treating or preventing medication overuse headache, e.g., associated with the overuse of anti-migraine drugs and/or associated with triptan and/or ergot and/or analgesic overuse, comprising administering to a patient exhibiting medication overuse headache or at risk of developing medication overuse headache a therapeutically effective amount of at least one anti-human CGRP antibody or fragment described herein. The invention also contemplates that the treatment method may involve the administration of two or more anti-CGRP antibodies or fragments thereof and disclosed herein. If more than one antibody is administered to the patient, the multiple antibodies may be administered simultaneously or concurrently, or may be staggered in their administration. The anti-CGRP activity of the anti-CGRP antibodies of the present invention, and fragments thereof having binding specificity to CGRP, may also be described by their strength of binding or their affinity for CGRP. In one embodiment of the invention, the anti-CGRP antibodies of the present invention, and fragments thereof having binding specificity to CGRP, bind to CGRP with a dissociation constant ($K_D$) of less than or equal to $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, or $10^{-13}$ M. Preferably, the anti-CGRP antibodies and fragments thereof bind CGRP with a dissociation constant of less than or equal to $10^{-11}$ M, $5\times10^{-12}$ M, or $10^{-12}$ M. In another embodiment of the invention, the anti-CGRP antibodies of the present invention, and fragments thereof having binding specificity to CGRP, bind to a linear or conformational CGRP epitope.

In another embodiment of the invention, the anti-CGRP activity of the anti-CGRP antibodies of the present invention, and fragments thereof having binding specificity to CGRP, bind to CGRP with an off-rate of less than or equal to $10^{-4}$ $S^{-1}$, $5\times10^{-5}$ $S^{-1}$, $10^{-5}$ $S^{-1}$, $5\times10^{-6}$ $S^{-1}$, $10^{-6}$ $S^{-1}$, $5\times10^{-7}$ $S^{-1}$, or $10^{-7}$ $S^{-1}$.

In a further embodiment of the invention, the anti-CGRP activity of the anti-CGRP antibodies of the present invention, and fragments thereof having binding specificity to CGRP, exhibit anti-CGRP activity by preventing, ameliorating or reducing the symptoms of, or alternatively treating, diseases and disorders associated with CGRP. Non-limiting examples of diseases and disorders associated with CGRP are set forth herein and include headache and migraine disorders.

Polynucleotides Encoding Anti-CGRP Antibody Polypeptides

As aforementioned the invention specifically includes the use of specific anti-CGRP antibodies and antibody fragments referred to herein as Ab1-Ab14 which comprise or consist of the CDR, VL, VH, CL, and CH polypeptides having the sequences identified in FIGS. 1A-12. The nucleic acid sequences encoding the foregoing VL, VH, CL, and CH polypeptides comprised in Ab1-Ab14 are also comprised in FIGS. 1A-12. The nucleic acid sequences which encode the CDR, VL, VH, CL, and CH polypeptides of an especially preferred anti-CGRP antibody, Ab6, are further described below.

Antibody Ab6

The invention is further directed to polynucleotides encoding antibody polypeptides having binding specificity to CGRP. In one embodiment of the invention, polynucleotides of the invention comprise, or alternatively consist of, the following polynucleotide sequence encoding the variable light chain polypeptide sequence of SEQ ID NO: 222:

(SEQ ID NO: 232)
CAAGTGCTGacccagtctccatcctccctgtctgcatctgtaggagacag agtcaccatcAATtgcCAGGCCAGTCAGAGTGTTTATCATAACACCTACC TGGCCtggtatcagcagaaaccagggaaagttcctaagCAActgatctat GATGCATCCACTCTGGCATCTggggtcccatctcgtttcagtggcagtgg atctgggacagatttcactctcaccatcagcagcctgcagcctgaagatg ttgcaacttattactgtCTGGGCAGTTATGATTGTACTAATGGTGATTGT TTTGTTttcggcggaggaaccaaggtggaaatcaaacgt.

In one embodiment of the invention, polynucleotides of the invention comprise, or alternatively consist of, the following polynucleotide sequence encoding the light chain polypeptide sequence of SEQ ID NO: 221:

(SEQ ID NO: 231)
CAAGTGCTGacccagtctccatcctccctgtctgcatctgtaggagacag agtcaccatcAATtgcCAGGCCAGTCAGAGTGTTTATCATAACACCTACC TGGCCtggtatcagcagaaaccagggaaagttcctaagCAActgatctat GATGCATCCACTCTGGCATCTggggtcccatctcgtttcagtggcagtgg atctgggacagatttcactctcaccatcagcagcctgcagcctgaagatg ttgcaacttattactgtCTGGGCAGTTATGATTGTACTAATGGTGATTGT TTTGTTttcggcggaggaaccaaggtggaaatcaaacgtACGGTGGCTGC

ACCATCGTCTTCATCTTCCCGCCATCTGATGAGCAGTTGAAATCTGGAA

CTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAG

TGTCACAGAGCAGGACAGCAAGGACAGCACCTACAGCCTCAGCAGCACCC

TGACGCTGAGCAAAGCAGACTACGAGAAACACAAAGTCTACGCCTGCGAA

GTCACCCATCAGGGCCTGAGCTCGCCCGTCACAAAGAGCTTCAACAGGGG

AGAGTGTTAG.

In another embodiment of the invention, polynucleotides of the invention comprise, or alternatively consist of, the following polynucleotide sequence encoding the variable heavy chain polypeptide sequence of SEQ ID NO: 202:

(SEQ ID NO: 212)
gaggtgcagctTgtggagtctgggggaggcttggtccagcctgggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGC.

In one embodiment of the invention, polynucleotides of the invention comprise, or alternatively consist of, the following polynucleotide sequence encoding the heavy chain polypeptide sequence of SEQ ID NO: 201:

(SEQ ID NO: 211)
gaggtgcagctTgtggagtctgggggaggcttggtccagcctgggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGCGCCTCCACCAAGGGCCC ATCGGTCTTCCCCCTGGCAcCCTCCTCCaAGAGCACCTCTGGGGGCACAG

CGGCCCTGGGCTGCCTGGTCAAGGACTACTTCCCCGAACCGGTGACGGTG

TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGGACCGTCAG

TCTTCCTCTTCCCCCCAAAACCCAAGGACACCCTCATGaTCTCCCgGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTAAATGA.

In one embodiment of the invention, polynucleotides of the invention comprise, or alternatively consist of, the following polynucleotide sequence encoding the heavy chain polypeptide sequence of SEQ ID NO: 566:

(SEQ ID NO: 567)
gaggtgcagctTgtggagtctgggggaggcttggtccagcctgggggtc cctgagactctcctgtgcaGTCtctggaATCGACCTCagtGGCTACTACA TGAACtgggtccgtcaggctccagggaaggggctggagtgggtcGGAGTC ATTGGTATTAATGGTGCCACATACTACGCGAGCTGGGCGAAAGGCcgatt caccatctccagagacaattccaagACCACGGTGtatcttcaaatgaaca gcctgagagctgaggacactgctgtgtatTTCtgtGCTAGAGGGGACATC tggggccaagggaccctcgtcaccgtcTCGAGCGCCTCCACCAAGGGCCC ATCGGTCTTCCCCCTGGCAcCCTCCTCCaAGAGCACCTCTGGGGGCACAG

CGGCCCTGGGCTGCCTGGTCAAGGACTACTTCCCCGAACCGGTGACGGTG

-continued
```
TCGTGGAACTCAGGCGCCCTGACCAGCGGCGTGCACACCTTCCCGGCTGT

CCTACAGTCCTCAGGACTCTACTCCCTCAGCAGCGTGGTGACCGTGCCCT

CCAGCAGCTTGGGCACCCAGACCTACATCTGCAACGTGAATCACAAGCCC

AGCAACACCAAGGTGGACGCGAGAGTTGAGCCCAAATCTTGTGACAAAAC

TCACACATGCCCACCGTGCCCAGCACCTGAACTCCTGGGGGACCGTCAG

TCTTCCTCTTCCCCCCAAAACCCAAGGACACCCTCATGaTCTCCcgGACC

CCTGAGGTCACATGCGTGGTGGTGGACGTGAGCCACGAAGACCCTGAGGT

CAAGTTCAACTGGTACGTGGACGGCGTGGAGGTGCATAATGCCAAGACAA

AGCCGCGGGAGGAGCAGTACGCCAGCACGTACCGTGTGGTCAGCGTCCTC

ACCGTCCTGCACCAGGACTGGCTGAATGGCAAGGAGTACAAGTGCAAGGT

CTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAG

GAGATGACCAAGAACCAGGTCAGCCTGACCTGCCTGGTCAAAGGCTTCTA

TCCCAGCGACATCGCCGTGGAGTGGGAGAGCAATGGGCAGCCGGAGAACA

ACTACAAGACCACGCCTCCCGTGCTGGACTCCGACGGCTCCTTCTTCCTC

TACAGCAAGCTCACCGTGGACAAGAGCAGGTGGCAGCAGGGGAACGTCTT

CTCATGCTCCGTGATGCATGAGGCTCTGCACAACCACTACACGCAGAAGA

GCCTCTCCCTGTCTCCGGGTTGA.
```

In a further embodiment of the invention, polynucleotides encoding antibody fragments having binding specificity to CGRP comprise, or alternatively consist of, one or more of the polynucleotide sequences of SEQ ID NO: 234; SEQ ID NO: 236; and SEQ ID NO: 238 which correspond to polynucleotides encoding the complementarity-determining regions (CDRs, or hypervariable regions) of the light chain variable sequence of SEQ ID NO: 222 or the light chain sequence of SEQ ID NO: 221.

In a further embodiment of the invention, polynucleotides encoding antibody fragments having binding specificity to CGRP comprise, or alternatively consist of, one or more of the polynucleotide sequences of SEQ ID NO: 214; SEQ ID NO: 216; and SEQ ID NO: 218 which correspond to polynucleotides encoding the complementarity-determining regions (CDRs, or hypervariable regions) of the heavy chain variable sequence of SEQ ID NO: 202 or the heavy chain sequence of SEQ ID NO: 201 or SEQ ID NO: 566.

The invention also contemplates polynucleotide sequences including one or more of the polynucleotide sequences encoding antibody fragments described herein. In one embodiment of the invention, polynucleotides encoding antibody fragments having binding specificity to CGRP comprise, or alternatively consist of, one, two, three or more, including all of the following polynucleotides encoding antibody fragments: the polynucleotide SEQ ID NO: 232 encoding the light chain variable sequence of SEQ ID NO: 222; the polynucleotide SEQ ID NO: 231 encoding the light chain sequence of SEQ ID NO: 221; the polynucleotide SEQ ID NO: 212 encoding the heavy chain variable sequence of SEQ ID NO: 202; the polynucleotide SEQ ID NO: 211 encoding the heavy chain sequence of SEQ ID NO: 201; the polynucleotide SEQ ID NO: 567 encoding the heavy chain sequence of SEQ ID NO: 566; polynucleotides encoding the complementarity-determining regions (SEQ ID NO: 234; SEQ ID NO: 236; and SEQ ID NO: 238) of the light chain variable sequence of SEQ ID NO: 222 or the light chain sequence of SEQ ID NO: 221; and polynucleotides encoding the complementarity-determining regions (SEQ ID NO: 214; SEQ ID NO: 216; and SEQ ID NO: 218) of the heavy chain variable sequence of SEQ ID NO: 202 or the heavy chain sequence of SEQ ID NO: 201 or SEQ ID NO: 566.

In a preferred embodiment of the invention, polynucleotides of the invention comprise, or alternatively consist of, polynucleotides encoding Fab (fragment antigen binding) fragments having binding specificity for CGRP. With respect to antibody Ab6, the polynucleotides encoding the full length Ab6 antibody comprise, or alternatively consist of, the polynucleotide SEQ ID NO: 231 encoding the light chain sequence of SEQ ID NO: 221 and the polynucleotide SEQ ID NO: 211 encoding the heavy chain sequence of SEQ ID NO: 201 or the polynucleotide SEQ ID NO: 567 encoding the heavy chain sequence of SEQ ID NO: 566.

Another embodiment of the invention contemplates these polynucleotides incorporated into an expression vector for expression in mammalian cells such as CHO, NSO, HEK-293, or in fungal, insect, or microbial systems such as yeast cells such as the yeast Pichia. Suitable Pichia species include, but are not limited to, Pichia pastoris. In one embodiment of the invention described herein (infra), Fab fragments may be produced by enzymatic digestion (e.g., papain) of Ab6 following expression of the full-length polynucleotides in a suitable host. In another embodiment of the invention, anti-CGRP antibodies such as Ab6 or Fab fragments thereof may be produced via expression of Ab6 polynucleotides in mammalian cells such as CHO, NSO or HEK 293 cells, fungal, insect, or microbial systems such as yeast cells (for example diploid yeast such as diploid Pichia) and other yeast strains. Suitable Pichia species include, but are not limited to, Pichia pastoris.

In one embodiment, the invention is directed to an isolated polynucleotide comprising a polynucleotide encoding an anti-CGRP VH antibody amino acid sequence selected from SEQ ID NO: 2, SEQ ID NO: 42, SEQ ID NO: 82, SEQ ID NO: 122, SEQ ID NO: 162, SEQ ID NO: 202, SEQ ID NO: 242, SEQ ID NO: 282, SEQ ID NO: 322, SEQ ID NO: 362, SEQ ID NO: 402, SEQ ID NO: 442, SEQ ID NO: 482, or SEQ ID NO: 522 or encoding a variant thereof wherein at least one framework residue (FR residue) has been substituted with an amino acid present at the corresponding position in a rabbit anti-CGRP antibody $V_H$ polypeptide or a conservative amino acid substitution.

In another embodiment, the invention is directed to an isolated polynucleotide comprising the polynucleotide sequence encoding an anti-CGRP $V_L$ antibody amino acid sequence of SEQ ID NO: 22, SEQ ID NO: 62, SEQ ID NO: 102, SEQ ID NO: 142, SEQ ID NO: 182, SEQ ID NO: 222, SEQ ID NO: 262, SEQ ID NO: 302, SEQ ID NO: 342, SEQ ID NO: 382, SEQ ID NO: 422, SEQ ID NO: 462, SEQ ID NO: 502, or SEQ ID NO: 542, or encoding a variant thereof wherein at least one framework residue (FR residue) has been substituted with an amino acid present at the corresponding position in a rabbit anti-CGRP antibody $V_L$ polypeptide or a conservative amino acid substitution.

In yet another embodiment, the invention is directed to one or more heterologous polynucleotides comprising a sequence encoding the polypeptides contained in SEQ ID NO: 22 and SEQ ID NO: 2; SEQ ID NO: 62 and SEQ ID NO: 42; SEQ ID NO: 102 and SEQ ID NO: 82; SEQ ID NO: 142 and SEQ ID NO: 122; SEQ ID NO: 182 and SEQ ID NO: 162; SEQ ID NO: 222 and SEQ ID NO: 202; SEQ ID NO: 262 and SEQ ID NO: 242; SEQ ID NO: 302 and SEQ ID NO: 282; SEQ ID NO: 342 and SEQ ID NO: 322; SEQ ID NO: 382 and SEQ ID NO: 362; SEQ ID NO: 422 and SEQ ID NO: 402; SEQ ID NO: 462 and SEQ ID NO: 442; SEQ ID NO: 502 and SEQ ID NO: 482; or SEQ ID NO: 542 and SEQ ID NO: 522.

In another embodiment, the invention is directed to an isolated polynucleotide that expresses a polypeptide containing at least one CDR polypeptide derived from an anti-CGRP antibody wherein said expressed polypeptide alone specifically binds CGRP or specifically binds CGRP when expressed in association with another polynucleotide sequence that expresses a polypeptide containing at least one CDR polypeptide derived from an anti-CGRP antibody wherein said at least one CDR is selected from those contained in the $V_L$ or VH polypeptides of SEQ ID NO: 22, SEQ ID NO: 2, SEQ ID NO: 62, SEQ ID NO: 42, SEQ ID NO: 102, SEQ ID NO: 82, SEQ ID NO: 142, SEQ ID NO: 122, SEQ ID NO: 182, SEQ ID NO: 162, SEQ ID NO: 222, SEQ ID NO: 202, SEQ ID NO: 262, SEQ ID NO: 242, SEQ ID NO: 302, SEQ ID NO: 282, SEQ ID NO: 342, SEQ ID NO: 322, SEQ ID NO: 382, SEQ ID NO: 362, SEQ ID NO: 422, SEQ ID NO: 402, SEQ ID NO: 462, SEQ ID NO: 442, SEQ ID NO: 502, SEQ ID NO: 482, SEQ ID NO: 542, or SEQ ID NO: 522.

Host Cells and Vectors Comprising Said Polynucleotides are Also Contemplated.

The invention further contemplates vectors comprising the polynucleotide sequences encoding the variable heavy and light chain polypeptide sequences, as well as the individual complementarity-determining regions (CDRs, or hypervariable regions), as set forth herein, as well as host cells comprising said vector sequences. In one embodiment of the invention, the host cell is a yeast cell. In another embodiment of the invention, the yeast host cell belongs to the genus *Pichia*.

Methods of Producing Antibodies and Fragments thereof

In another embodiment, the present invention contemplates methods for producing anti-CGRP antibodies and fragments thereof. Methods for producing antibodies and fragments thereof secreted from polyploidal, preferably diploid or tetraploid strains of mating competent yeast are taught, for example, in U.S. patent application publication no. US 2009/0022659 to Olson et al., and in U.S. Pat. No. 7,935,340 to Garcia-Martinez et al., the disclosures of each of which are herein incorporated by reference in their entireties. Methods for producing antibodies and fragments thereof in mammalian cells, e.g., CHO cells are further well known in the art.

Other methods of producing antibodies are also well known to those of ordinary skill in the art. For example, methods of producing chimeric antibodies are now well known in the art (See, for example, U.S. Pat. No. 4,816,567 to Cabilly et al.; Morrison et al., P.N.A.S. USA, 81:8651-55 (1984); Neuberger, M. S. et al., Nature, 314:268-270 (1985); Boulianne, G. L. et al., Nature, 312:643-46 (1984), the disclosures of each of which are herein incorporated by reference in their entireties).

Likewise, other methods of producing humanized antibodies are now well known in the art (See, for example, U.S. Pat. Nos. 5,530,101, 5,585,089, 5,693,762, and 6,180,370 to Queen et al; U.S. Pat. Nos. 5,225,539 and 6,548,640 to Winter; U.S. Pat. Nos. 6,054,297, 6,407,213 and 6,639,055 to Carter et al; U.S. Pat. No. 6,632,927 to Adair; Jones, P. T. et al, Nature, 321:522-525 (1986); Reichmann, L., et al, Nature, 332:323-327 (1988); Verhoeyen, M, et al, Science, 239:1534-36 (1988), the disclosures of each of which are herein incorporated by reference in their entireties).

The term "opioid analgesic" herein refers to all drugs, natural or synthetic, with morphine-like actions. The synthetic and semi-synthetic opioid analgesics are derivatives of five chemical classes of compound: phenanthrenes; phenylheptylamines; phenylpiperidines; morphinans; and benzomorphans, all of which are within the scope of the term. Exemplary opioid analgesics include codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine or pharmaceutically acceptable salts thereof.

The term "NSAID" refers to a non-steroidal anti-inflammatory compound. NSAIDs are categorized by virtue of their ability to inhibit cyclooxygenase. Cyclooxygenase 1 and cyclooxygenase 2 are two major isoforms of cyclooxygenase and most standard NSAIDs are mixed inhibitors of the two isoforms. Most standard NSAIDs fall within one of the following five structural categories: (1) propionic acid derivatives, such as ibuprofen, naproxen, naprosyn, diclofenac, and ketoprofen; (2) acetic acid derivatives, such as tolmetin and slindac; (3) fenamic acid derivatives, such as mefenamic acid and meclofenamic acid; (4) biphenylcarboxylic acid derivatives, such as diflunisal and flufenisal; and (5) oxicams, such as piroxim, sudoxicam, and isoxicam. Another class of NSAID has been described which selectively inhibit cyclooxygenase 2. Cox-2 inhibitors have been described, e.g., in U.S. Pat. Nos. 5,616,601; 5,604,260; 5,593,994; 5,550,142; 5,536,752; 5,521,213; 5,475,995; 5,639,780; 5,604,253; 5,552,422; 5,510,368; 5,436,265; 5,409,944; and 5,130,311, all of which are hereby incorporated by reference. Certain exemplary COX-2 inhibitors include celecoxib (SC-58635), DUP-697, flosulide (CGP-28238), meloxicam, 6-methoxy-2 naphthylacetic acid (6-MNA), rofecoxib, MK-966, nabumetone (prodrug for 6-MNA), nimesulide, NS-398, SC-5766, SC-58215, T-614; or combinations thereof.

In some embodiments, aspirin and/or acetaminophen may be taken in conjunction with the subject CGRP antibody or fragment. Aspirin is another type of non-steroidal anti-inflammatory compound.

The subject to which the pharmaceutical formulation is administered can be, e.g., any human or non-human animal that is in need of such treatment, prevention and/or amelioration, or who would otherwise benefit from the inhibition or attenuation of medication overuse headache. For example, the subject can be an individual that is diagnosed with, or who is deemed to be at risk of being afflicted by medication overuse headache. The present invention further includes the use of any of the pharmaceutical formulations disclosed herein in the manufacture of a medicament for the treatment, prevention and/or amelioration of medication overuse headache.

Administration

In one embodiment of the invention, the anti-CGRP antibodies described herein, or CGRP binding fragments thereof, as well as combinations of said antibodies or antibody fragments, are administered to a subject at a concentration of between about 0.1 and 100.0 mg/kg of body weight of recipient subject. In a preferred embodiment of the invention, the anti-CGRP antibodies described herein, or CGRP binding fragments thereof, as well as combinations of said antibodies or antibody fragments, are administered to a subject at a concentration of about 0.4 mg/kg of body weight of recipient subject and/or at a dosage of 100 or 300 mg. In a preferred embodiment of the invention, the anti-CGRP antibodies described herein, or CGRP binding fragments thereof, as well as combinations of said antibodies or antibody fragments, are administered to a recipient subject with a frequency of once every twenty-six weeks or six months or less, such as once every sixteen weeks or four months or less, once every eight weeks or two months or less, once every four weeks or monthly or less, once every two weeks or bimonthly or less, once every week or less, or once daily or less. In general the administration of sequential doses may vary by plus or minus a few days from the aforementioned schedule, e.g., administration every 3 months or every 12 weeks includes administration of a dose varying from the schedule day by plus or minus 1, 2, 3, 4, 5, 5, or 7 days.

Fab fragments may be administered every two weeks or less, every week or less, once daily or less, multiple times per day, and/or every few hours. In one embodiment of the invention, a patient receives Fab fragments of 0.1 mg/kg to 40 mg/kg per day given in divided doses of 1 to 6 times a day, or in a sustained release form, effective to obtain desired results.

It is to be understood that the concentration of the antibody or Fab administered to a given patient may be greater or lower than the exemplary administration concentrations set forth above.

A person of skill in the art would be able to determine an effective dosage and frequency of administration through routine experimentation, for example guided by the disclosure herein and the teachings in Goodman, L. S., Gilman, A., Brunton, L. L., Lazo, J. S., & Parker, K. L. (2006). Goodman & Gilman's the pharmacological basis of therapeutics. New York: McGraw-Hill; Howland, R. D., Mycek, M. J., Harvey, R. A., Champe, P. C., & Mycek, M. J. (2006). Pharmacology. Lippincott's illustrated reviews. Philadelphia: Lippincott Williams & Wilkins; and Golan, D. E. (2008). Principles of pharmacology: the pathophysiologic basis of drug therapy. Philadelphia, Pa., [etc.]: Lippincott Williams & Wilkins.

In another embodiment of the invention, the anti-CGRP antibodies described herein, or CGRP binding fragments thereof, as well as combinations of said antibodies or antibody fragments, are administered to a subject in a pharmaceutical formulation.

A "pharmaceutical composition" refers to a chemical or biological composition suitable for administration to a mammal. Such compositions may be specifically formulated for administration via one or more of a number of routes, including but not limited to buccal, epicutaneous, epidural, inhalation, intraarterial, intracardial, intracerebroventricular, intradermal, intramuscular, intranasal, intraocular, intraperitoneal, intraspinal, intrathecal, intravenous, oral, parenteral, rectally via an enema or suppository, subcutaneous, subdermal, sublingual, transdermal, and transmucosal, preferably intravenous. In addition, administration can occur by means of injection, powder, liquid, gel, drops, or other means of administration.

A "pharmaceutical excipient" or a "pharmaceutically acceptable excipient" is a carrier, usually a liquid, in which an active therapeutic agent is formulated. In one embodiment of the invention, the active therapeutic agent is a humanized antibody described herein, or one or more fragments thereof. The excipient generally does not provide any pharmacological activity to the formulation, though it may provide chemical and/or biological stability, and release characteristics. Exemplary formulations can be found, for example, in Remington's Pharmaceutical Sciences, 19$^{th}$ Ed., Grennaro, A., Ed., 1995 which is incorporated by reference.

As used herein "pharmaceutically acceptable carrier" or "excipient" includes any and all solvents, dispersion media, coatings, antibacterial and antifungal agents, isotonic and absorption delaying agents that are physiologically compatible. In one embodiment, the carrier is suitable for parenteral administration. Alternatively, the carrier can be suitable for intravenous, intraperitoneal, intramuscular, or sublingual administration. Pharmaceutically acceptable carriers include sterile aqueous solutions or dispersions and sterile powders for the extemporaneous preparation of sterile injectable solutions or dispersions. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Pharmaceutical compositions typically must be sterile and stable under the conditions of manufacture and storage. The invention contemplates that the pharmaceutical composition is present in lyophilized form. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol), and suitable mixtures thereof. The invention further contemplates the inclusion of a stabilizer in the pharmaceutical composition. The proper fluidity can be maintained, for example, by the maintenance of the required particle size in the case of dispersion and by the use of surfactants.

In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the alkaline polypeptide can be formulated in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are known to those skilled in the art.

An exemplary composition comprises, consists essentially of, or consists of an anti-CGRP antibody or fragment thereof (e.g., Ab6), an excipient such as histidine, an isotonic agent such as sorbitol, and a surfactant such as polysorbate 80 in an aqueous solution. For example, the composition may comprise, consist essentially of, or consist of histidine (L-histidine), sorbitol, polysorbate 80, such as, per 1 mL volume, about 100 mg anti-CGRP antibody (e.g., Ab6), about 3.1 mg L-Histidine, about 40.5 mg Sorbitol, and about 0.15 mg Polysorbate 80, having a pH of about 5.8, or approximately that constitution, e.g., within 10% of those values, within 5% of those values, within 1% of those values, within 0.5% of those values, or within 0.10% of those values, and water. For example, the pH value may be within 10% of 5.8, i.e., between 5.22 and 6.38. The Ab6 antibody may comprise or consist of the variable light and heavy chain polypeptides of SEQ ID NO: 222 and SEQ ID NO: 202 respectively, or the light and heavy chain polypeptides of SEQ ID NO: 221 and SEQ ID NO: 201 respectively, or the light and heavy chain polypeptides of SEQ ID NO: 221 and SEQ ID NO: 566 respectively. The composition may be in the form of an aqueous solution, or a concentrate (e.g., lyophilized) which when reconstituted, e.g., by addition of water, yields the aforementioned constitution. An exemplary composition consists of, per mL, 100 mg of the light and heavy chain polypeptides of SEQ ID NO: 221 and SEQ ID NO: 201 respectively, about 3.1 mg L-Histidine, about 40.5 mg Sorbitol, and about 0.15 mg Polysorbate 80, and water Q.S, or approximately that constitution, e.g., within 10% of those quantities, within 5% of those quantities, within 1% of those quantities, within 0.5% of those quantities, or within 0.1% of those quantities. Another exemplary composition consists of, per mL, 100 mg of the light and heavy chain polypeptides of SEQ ID NO: 221 and SEQ ID NO: 566 respectively, about 3.1 mg L-Histidine, about 40.5 mg Sorbitol, and about 0.15 mg Polysorbate 80, and water Q.S, or approximately that constitution, e.g., within 10% of those quantities, within 5% of those quantities, within 1% of those quantities, within 0.5% of those quantities, or within 0.10% of those quantities. The composition may be suitable for intravenous or subcutaneous administration, preferably intravenous administration. For example, the composition may be suitable for mixing with an intravenous solution (such as 0.9% sodium chloride) at an amount of between about 100 mg and about 300 mg antibody added to 100 mL of intravenous solution. Preferably the composition may be shelf-stable for at least 1, 3, 6, 12, 18, or 24 months, e.g., showing formation of aggregates of no more than 5% or no more than 10% of the antibody or fragment after storage at room temperature or when refrigerated at 4° C. for the specified duration, or in an accelerated aging test that simulates storage for that duration.

For each of the recited embodiments, the compounds can be administered by a variety of dosage forms. Any biologically-acceptable dosage form known to persons of ordinary skill in the art, and combinations thereof, are contemplated. Examples of such dosage forms include, without limitation, reconstitutable powders, elixirs, liquids, solutions, suspensions, emulsions, powders, granules, particles, microparticles, dispersible granules, cachets, inhalants, aerosol inhalants, patches, particle inhalants, implants, depot implants, injectables (including subcutaneous, intramuscular, intravenous, and intradermal, preferably intravenous), infusions, and combinations thereof.

The above description of various illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. The teachings provided herein of the invention can be applied to other purposes, other than the examples described above.

These and other changes can be made to the invention in light of the above detailed description. In general, in the following claims, the terms used should not be construed to limit the invention to the specific embodiments disclosed in the specification and the claims. Accordingly, the invention is not limited by the disclosure, but instead the scope of the invention is to be determined entirely by the following claims.

The invention may be practiced in ways other than those particularly described in the foregoing description and examples. Numerous modifications and variations of the invention are possible in light of the above teachings and, therefore, are within the scope of the appended claims.

Certain CGRP antibody polynucleotides and polypeptides are disclosed in the sequence listing accompanying this patent application filing, and the disclosure of said sequence listing is herein incorporated by reference in its entirety.

The entire disclosure of each document cited (including patents, patent applications, journal articles, abstracts, manuals, books, or other disclosures) in the Background of the Invention, Detailed Description, and Examples is herein incorporated by reference in their entireties.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

ADDITIONAL EXEMPLARY EMBODIMENTS

Additional exemplary embodiments of the invention are provided as follows:
- S1. Use of an anti-CGRP antibody for the manufacturing of a medicament for treating acute migraine, comprising administering to a patient an anti-CGRP antibody while the patient has a headache and within 30 hours of headache onset, preferably within 24 hours of headache onset.
- S2. Use of the anti-CGRP antibody of embodiment 1, wherein the medicament is for administration within 18 hours, within 12 hours, within 6 hours, within 5 hours, within 4 hours, within 3 hours, within 2 hours, or within 1 hour of headache onset, such as between 1-6 hours from headache onset.
- S3. Use of the anti-CGRP antibody of any one of the foregoing embodiments, wherein said medicament is for intravenous or subcutaneous infusion.
- S4. Use of the anti-CGRP antibody of any one of the foregoing embodiments, wherein said medicament is for intravenous infusion.
- S5. Use of the anti-CGRP antibody of any one of the foregoing embodiments, wherein said patient is headache free 2 hours post-completion of administration or infusion.
- S6. Use of the anti-CGRP antibody of any one of the foregoing embodiments, wherein said patient is free from the most bothersome symptom (MBS) at 2 hours post-completion of administration or infusion.
- S7. Use of the anti-CGRP antibody of any one of the foregoing embodiments, wherein the administration of said medicament improves one or more of the following: time to pain relief; time to pain freedom; headache pain freedom at 2 hours with sustained headache pain freedom for 24 and 48 hours post completion of infusion; use of rescue medication by 24 hours and by 48 hours post completion of infusion; absence of photophobia at 2 hours post completion of infusion; absence of phonophobia at 2 hours post completion of infusion; absence of nausea at 2 hours post completion of infusion; change from baseline in Headache Impact Test (HIT-6) at Week 4; or change from baseline in Migraine Treatment Optimization Questionnaire-6 (MTOQ-6) at Week 4.
- S8. Use of the anti-CGRP antibody of any one of the foregoing embodiments, wherein said anti-CGRP antibody comprises any one of Ab1-Ab14.

S9. Use of the anti-CGRP antibody of any one of the foregoing embodiments, wherein said anti-CGRP antibody comprises Ab6.

S10. Use of the anti-CGRP antibody of any one of the foregoing embodiments, wherein said anti-CGRP antibody comprises the light chain complementarity-determining region (CDR) 1, 2, and 3 polypeptide sequences of SEQ ID NO: 224; SEQ ID NO: 226; and SEQ ID NO: 228, respectively.

S11. Use of the anti-CGRP antibody of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively.

S12. Use of the anti-CGRP antibody of any one of the foregoing embodiments, wherein said anti-CGRP antibody comprises the heavy chain CDR 1, 2, and 3 polypeptide sequences of SEQ ID NO: 204; SEQ ID NO: 206; and SEQ ID NO: 208, respectively.

S13. Use of the anti-CGRP antibody of any one of the foregoing embodiments, wherein said anti-CGRP antibody comprises the heavy chain CDR 1, 2, and 3 polypeptide sequences encoded by SEQ ID NO: 214; SEQ ID NO: 216; and SEQ ID NO: 218, respectively.

S14. Use of the anti-CGRP antibody of any one of the foregoing embodiments, wherein said anti-CGRP antibody comprises the light chain CDR 1, 2, and 3 polypeptide sequences of SEQ ID NO: 224; SEQ ID NO: 226; and SEQ ID NO: 228, respectively and heavy chain CDR 1, 2, and 3 polypeptide sequences of SEQ ID NO: 204; SEQ ID NO: 206; and SEQ ID NO: 208, respectively.

S15. Use of the anti-CGRP antibody of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively.

S16. Use of the anti-CGRP antibody of any one of the foregoing embodiments, wherein said anti-CGRP antibody comprises the variable light chain polypeptide of SEQ ID NO: 222.

S17. Use of the anti-CGRP antibody of any one of the foregoing embodiments, wherein said anti-CGRP antibody comprises the variable light chain polypeptide encoded by SEQ ID NO: 232.

S18. Use of the anti-CGRP antibody of any one of the foregoing embodiments, wherein said anti-CGRP antibody comprises the variable heavy chain polypeptide of SEQ ID NO: 202.

S19. Use of the anti-CGRP antibody of any one of the foregoing embodiments, wherein said anti-CGRP antibody comprises the variable heavy chain polypeptide encoded by SEQ ID NO: 212.

S20. Use of the anti-CGRP antibody of any one of the foregoing embodiments, wherein said anti-CGRP antibody comprises the variable light chain polypeptide of SEQ ID NO: 222 and the variable heavy chain polypeptide of SEQ ID NO: 202.

S21. Use of the anti-CGRP antibody of any one of the foregoing embodiments, wherein said anti-CGRP antibody comprises the variable light chain polypeptide encoded by SEQ ID NO: 232 and the variable heavy chain polypeptide encoded by SEQ ID NO: 212.

S22. Use of the anti-CGRP antibody of any one of the foregoing embodiments, wherein said anti-CGRP antibody comprises the light chain polypeptide of SEQ ID NO: 221.

S23. Use of the anti-CGRP antibody of any one of the foregoing embodiments, wherein said anti-CGRP antibody comprises the light chain polypeptide encoded by SEQ ID NO: 231.

S24. Use of the anti-CGRP antibody of any one of the foregoing embodiments, wherein said anti-CGRP antibody comprises the heavy chain polypeptide of SEQ ID NO: 201 or SEQ ID NO: 566.

S25. Use of the anti-CGRP antibody of any one of the foregoing embodiments, wherein said anti-CGRP antibody comprises the heavy chain polypeptide encoded by SEQ ID NO: 211 or SEQ ID NO: 567.

S26. Use of the anti-CGRP antibody of any one of the foregoing embodiments, wherein said anti-CGRP antibody comprises the light chain polypeptide of SEQ ID NO: 221 and the heavy chain polypeptide of SEQ ID NO: 201 or SEQ ID NO: 566.

S27. Use of the anti-CGRP antibody of any one of the foregoing embodiments, wherein said anti-CGRP antibody comprises the light chain polypeptide encoded by SEQ ID NO: 231 and the heavy chain polypeptide encoded by SEQ ID NO: 211 or SEQ ID NO: 567.

S28. Use of the anti-CGRP antibody of any one of the foregoing embodiments, wherein the administered amount of said anti-CGRP antibody is between about 100 mg and about 300 mg, or is about 100 mg, or is about 300 mg.

S29. Use of the anti-CGRP antibody of any one of the foregoing embodiments, wherein the administered amount of said anti-CGRP antibody is 100 mg.

S30. Use of the anti-CGRP antibody of any one of the foregoing embodiments, wherein said medicament is for intravenous administration in a dosage of 100 mg of said anti-CGRP antibody every 10-14 weeks, preferably every 11-13 weeks, more preferably every 12 weeks.

S31. Use of the anti-CGRP antibody of any one of embodiments S1-S29, wherein said medicament is for intravenous administration in a dosage of 300 mg of said anti-CGRP antibody every 10-14 weeks, preferably every 11-13 weeks, more preferably every 12 weeks.

S32. Use of the anti-CGRP antibody of any one of the foregoing embodiments, wherein said patient suffers from medication overuse headache.

S33. Use of the anti-CGRP antibody of any one of the foregoing embodiments wherein, prior to administration of said medicament, the patient exhibits between 1-10 migraine attacks per month in the month or in the 3 months prior to administration.

S34. Use of the anti-CGRP antibody of any one of the foregoing embodiments wherein, prior to administration of said medicament, the patient exhibits between 2-8 migraine attacks per month in the month or in the 3 months prior to administration.

S35. Use of the anti-CGRP antibody of any one of the foregoing embodiments wherein, prior to administration of said medicament, the patient exhibits between 3-7 migraine attacks per month in the month or in the 3 months prior to administration.

S36. Use of the anti-CGRP antibody of any one of the foregoing embodiments wherein, prior to administration of said medicament, the patient exhibits less than 25 headache days per month in the month or in the 3 months prior to administration.

S37. Use of the anti-CGRP antibody of any one of the foregoing embodiments wherein, prior to administration of said medicament, the patient exhibits less than 20 headache days per month in the month or in the 3 months prior to administration.

S38. Use of the anti-CGRP antibody of any one of the foregoing embodiments wherein, prior to administration of said medicament, the patient exhibits less than 15 headache days per month in the month or in the 3 months prior to administration.

S39. Use of the anti-CGRP antibody of any one of the foregoing embodiments wherein, prior to administration of said medicament, the patient exhibits less than 10 headache days per month in the month or in the 3 months prior to administration.

S40. Use of the anti-CGRP antibody of any one of the foregoing embodiments wherein said patient was diagnosed with migraine at least 10 years prior to administration of said medicament.

S41. Use of the anti-CGRP antibody of any one of the foregoing embodiments wherein said patient was diagnosed with migraine at least 15 years prior to administration of said medicament.

S42. Use of the anti-CGRP antibody of any one of the foregoing embodiments wherein said patient was diagnosed with migraine at least 18 or at least 19 years prior to administration of said medicament.

S43. Use of the anti-CGRP antibody of any one of the foregoing embodiments, wherein said patient has a reduction in the number of migraine days by at least 50% in the one month period after being administered said antibody relative to the baseline number of migraine days experienced by that patient prior to administration of said medicament.

S44. Use of the anti-CGRP antibody of any one of the foregoing embodiments, wherein said patient has a reduction in the number of migraine days by at least 75% in the one month period after being administered said antibody relative to the baseline number of migraine days experienced by that patient prior to administration of said medicament.

S45. Use of the anti-CGRP antibody of any one of the foregoing embodiments, wherein said patient has a reduction in the number of migraine days by 100% in the one month period after being administered said antibody relative to the baseline number of migraine days experienced by that patient prior to administration of said medicament.

S46. Use of the anti-CGRP antibody of any one of the foregoing embodiments, wherein said patient has a reduction in the number of migraine days by at least 50% in the 12 week period after being administered said antibody relative to the baseline number of migraine days experienced by that patient prior to administration of said medicament.

S47. Use of the anti-CGRP antibody of any one of the foregoing embodiments, wherein said patient has a reduction in the number of migraine days by at least 75% in the 12 week period after being administered said antibody relative to the baseline number of migraine days experienced by that patient prior to administration of said medicament.

S48. Use of the anti-CGRP antibody of any one of the foregoing embodiments, wherein said patient has a reduction in the number of migraine days by 100% in the 12 week period after being administered said antibody relative to the baseline number of migraine days experienced by that patient prior to administration of said medicament.

S49. Use of the anti-CGRP antibody of any one of the foregoing embodiments, wherein said medicament is further for administration in a second dose of said anti-CGRP antibody about 10-14 weeks, preferably 11-13 weeks, more preferably about 12 weeks or about 3 months after administration of said medicament.

S50. Use of the anti-CGRP antibody of any one of the foregoing embodiments, wherein said medicament comprises about 100 mg, about 125 mg, about 150 mg, about 175 mg, about 200 mg, about 225 mg, about 250 mg, about 275 mg, or about 300 mg of said anti-CGRP antibody.

S51. Use of the anti-CGRP antibody of any one of the foregoing embodiments, wherein said anti-CGRP antibody is aglycosylated or if glycosylated only contains only mannose residues.

S52. Use of the anti-CGRP antibody of any one of the foregoing embodiments, wherein said anti-CGRP antibody consists of the light chain polypeptide of SEQ ID NO: 221 and the heavy chain polypeptide of SEQ ID NO: 201 or SEQ ID NO: 566.

S53. Use of the anti-CGRP antibody of any one of the foregoing embodiments, wherein said anti-CGRP antibody consists of the light chain polypeptide encoded by SEQ ID NO: 231 and the heavy chain polypeptide encoded by SEQ ID NO: 211 or SEQ ID NO: 567.

S54. Use of the anti-CGRP antibody of any one of embodiments S7-S53, wherein said rescue medication comprises one or more of a triptan, non-opioid analgesics (such as paracetamol (acetaminophen), acetylsalicylic acid (aspirin), another NSAID, or another non-opioid analgesic), a combination of two or more drug classes, wherein said triptan use optionally comprises use of one or more of sumatriptan, zolmitriptan, naratriptan, rizatriptan, eletriptan, almotriptan, and frovatriptan, and/or wherein said opioid use optionally comprises use of one or more of oxycodone, tramadol, butorphanol, morphine, codeine, and hydrocodone, and/or wherein said combination of two or more drug class optionally comprises two drugs with analgesic effects (for example, paracetamol and codeine) or acting as adjuvants (for example, caffeine), optionally wherein said combination-analgesics combine non-opioid analgesic includes at least one opioid (such as tramadol, butorphanol, morphine, codeine, hydrocodone, or any combination thereof), barbiturate such as butalbital and/or caffeine.

S55. Use of the anti-CGRP antibody of any one of the foregoing embodiments, wherein said headache or said migraine is diagnosed according to the third edition of the International Classification of Headache Disorders.

S56. Use of the anti-CGRP antibody of any of any one of the foregoing embodiments, wherein said anti-CGRP antibody is expressed in or obtained by expression in *Pichia pastoris*.

S57. Use of the anti-CGRP antibody of any of any one of embodiments S1-S55, wherein said anti-CGRP antibody is expressed in or obtained by expression in CHO cells.

S58. Use of the anti-CGRP antibody of any one of the foregoing embodiments, wherein said anti-CGRP antibody or anti-CGRP antibody fragment is comprised in a formulation comprising or consisting of histidine (L-histidine), sorbitol, polysorbate 80, and water.

S59. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

S60. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

S61. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

S62. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

S63. Use of the anti-CGRP antibody of embodiment S58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

S64. Use of an anti-CGRP antibody for the manufacture of a medicament for treating chronic migraine, wherein said medicament is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein in the first 24 hours after administration of said first dosage the patient exhibits at least a 50% reduction in migraine prevalence.

S65. Use of an anti-CGRP antibody for the manufacture of a medicament for treating chronic migraine, wherein said medicament is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein on the first day following the day of administration the patient exhibits at least a 50% reduction in migraine prevalence.

S66. Use of the anti-CGRP antibody of embodiment S64 or embodiment S65, wherein the first dosage of said anti-CGRP antibody is 100 mg.

S67. Use of the anti-CGRP antibody of embodiment S64 or embodiment S65, wherein the first dosage of said anti-CGRP antibody is 300 mg.

S68. Use of the anti-CGRP antibody of embodiment S64, S65, or S66, wherein said medicament is for intravenous administration in a dosage of 100 mg of said anti-CGRP antibody every 10-14 weeks, preferably 11-13 weeks, more preferably every 12 weeks.

S69. Use of the anti-CGRP antibody of embodiment S64, S65, or S67, wherein said medicament is for intravenous administration in a dosage of 300 mg of said anti-CGRP antibody every 10-14 weeks, preferably 11-13 weeks, more preferably every 12 weeks.

S70. Use of the anti-CGRP antibody of any one of embodiments S64-S69 wherein, prior to said first dosage, the patient exhibits between about 10 and about 22 migraine days per month.

S71. Use of the anti-CGRP antibody of any one of embodiments S64-S70 wherein, prior to said first dosage, the patient exhibits between about 13 and about 19 migraine days per month.

S72. Use of the anti-CGRP antibody of any one of embodiments S64-S71 wherein, prior to said first dosage, the patient exhibits about 16 migraine days per month.

S73. Use of the anti-CGRP antibody of any one of embodiments S64-S72 wherein, prior to said first dosage, the patient exhibits between about 14 and about 27 headache days per month.

S74. Use of the anti-CGRP antibody of any one of embodiments S64-S73 wherein, prior to said first dosage, the patient exhibits between about 17 and about 24 headache days per month.

S75. Use of the anti-CGRP antibody of any one of embodiments S64-S74 wherein, prior to said first dosage, the patient exhibits about 20 or about 21 headache days per month.

S76. Use of the anti-CGRP antibody of any one of embodiments S64-S75 wherein said patient was diagnosed with migraine at least 10 years prior to said first dosage.

S77. Use of the anti-CGRP antibody of any one of embodiments S64-S76 wherein said patient was diagnosed with migraine at least 15 years prior to said first dosage.

S78. Use of the anti-CGRP antibody of any one of embodiments S64-S77 wherein said patient was diagnosed with migraine at least 18 or at least 19 years prior to said first dosage.

S79. Use of the anti-CGRP antibody of any one of embodiments S64-S78 wherein said patient was diagnosed with chronic migraine at least 5 years prior to said first dosage.

S80. Use of the anti-CGRP antibody of any one of embodiments S64-S79 wherein said patient was diagnosed with chronic migraine at least 8 years prior to said first dosage.

S81. Use of the anti-CGRP antibody of any one of embodiments S64-S80 wherein said patient was diagnosed with chronic migraine at least 11 or at least 12 years prior to said first dosage.

S82. Use of the anti-CGRP antibody of any one of embodiments S64-S81 wherein said medicament is for administration of said first dosage when the patient has a headache.

S83. Use of the anti-CGRP antibody of any one of embodiments S64-S82 wherein said medicament is for administration of said first dosage when the patient has a migraine.

S84. Use of the anti-CGRP antibody of any one of embodiments S64-S83 wherein said medicament is for administration of said first dosage when the patient has a migraine with aura.

S85. Use of the anti-CGRP antibody of any one of embodiments S64-S84, wherein said patient has a reduction in the number of migraine days by at least 50% in the one month period after being administered said first dose relative to the baseline number of migraine days experienced by that patient prior to said first dose.

S86. Use of the anti-CGRP antibody of any one of embodiments S64-S85, wherein said patient has a reduction in the number of migraine days by at least 75% in the one month period after being administered said first dose relative to the baseline number of migraine days experienced by that patient prior to said first dose.

S87. Use of the anti-CGRP antibody of any one of embodiments S64-S86, wherein said patient has a reduction in the number of migraine days by 100% in the one month period after being administered said first dose relative to the baseline number of migraine days experienced by that patient prior to said first dose.

S88. Use of the anti-CGRP antibody of any one of embodiments S64-S87, wherein said patient has a reduction in the number of migraine days by at least 50% in the 12 week period after being administered said first dose relative to the baseline number of migraine days experienced by that patient prior to said first dose.

S89. Use of the anti-CGRP antibody of any one of embodiments S64-S88, wherein said patient has a reduction in the number of migraine days by at least 75% in the 12 week period after being administered said first dose relative to the baseline number of migraine days experienced by that patient prior to said first dose.

S90. Use of the anti-CGRP antibody of any one of embodiments S64-S89, wherein said patient has a reduction in the number of migraine days by 100% in the 12 week period after being administered said first dose relative to the baseline number of migraine days experienced by that patient prior to said first dose.

S91. Use of the anti-CGRP antibody of any one of embodiments S64-S90, further comprising administering a second dose of said anti-CGRP antibody to said patient about 12 weeks or about 3 months after said first dose.

S92. Use of the anti-CGRP antibody of any one of embodiments S64-S91, wherein said first dose comprises about 100 mg, about 125 mg, about 150 mg, about 175 mg, about 200 mg, about 225 mg, about 250 mg, about 275 mg, or about 300 mg of said anti-CGRP antibody.

S93. Use of the anti-CGRP antibody of any one of embodiments S64-S92, wherein said anti-CGRP antibody or antibody fragment is aglycosylated or if glycosylated only contains only mannose residues.

S94. Use of the anti-CGRP antibody of any one of embodiments S64-S93, wherein said anti-CGRP antibody consists of the light chain polypeptide of the light chain polypeptide of SEQ ID NO: 221 and the heavy chain polypeptide of SEQ ID NO: 201 or SEQ ID NO: 566.

S95. Use of the anti-CGRP antibody of any of any one of embodiments S64-S94, wherein said anti-CGRP antibody is expressed in or obtained by expression in *Pichia pastoris.*

S96. Use of the anti-CGRP antibody of any of any one of embodiments S64-S94, wherein said anti-CGRP antibody is expressed in or obtained by expression in CHO cells.

S97. Use of the anti-CGRP antibody of any one of embodiments S64-S96, wherein said anti-CGRP antibody or anti-CGRP antibody fragment is comprised in a formulation comprising or consisting of histidine (L-histidine), sorbitol, polysorbate 80, and water.

S98. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

S99. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

S100. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

S101. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

S102. Use of the anti-CGRP antibody of embodiment S97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

FURTHER EXEMPLARY EMBODIMENTS

Further exemplary embodiments of the invention are provided as follows:

E1. An anti-CGRP antibody for use in treating acute migraine while the patient has a headache and within 30 hours of headache onset, preferably within 24 hours of headache onset.

E2. The anti-CGRP antibody for use of embodiment E1, wherein the anti-CGRP antibody is for administration within 18 hours, within 12 hours, within 6 hours, within 5 hours, within 4 hours, within 3 hours, within 2 hours, or within 1 hour of headache onset, such as between 1-6 hours from headache onset.

E3. The anti-CGRP antibody for use of any one of the foregoing embodiments, wherein said anti-CGRP antibody is for intravenous or subcutaneous infusion.

E4. The anti-CGRP antibody for use of any one of the foregoing embodiments, wherein said anti-CGRP antibody is for intravenous infusion.

E5. The anti-CGRP antibody for use of any one of the foregoing embodiments, wherein said patient is headache free 2 hours post-completion of administration or infusion.

E6. The anti-CGRP antibody for use of any one of the foregoing embodiments, wherein said patient is free from the most bothersome symptom (MBS) at 2 hours post-completion of administration or infusion.

E7. The anti-CGRP antibody for use of any one of the foregoing embodiments, wherein the administration of said anti-CGRP antibody improves one or more of the following: time to pain relief, time to pain freedom; headache pain freedom at 2 hours with sustained headache pain freedom for 24 and 48 hours post completion of infusion; use of rescue medication by 24 hours and by 48 hours post completion of infusion; absence of photophobia at 2 hours post completion of infusion; absence of phonophobia at 2 hours post completion of infusion; absence of nausea at 2 hours post completion of infusion; change from baseline in Headache Impact Test (HIT-6) at Week 4; or change from baseline in Migraine Treatment Optimization Questionnaire-6 (MTOQ-6) at Week 4.

E8. The anti-CGRP antibody for use of any one of the foregoing embodiments, wherein said anti-CGRP antibody comprises any one of Ab1-Ab14.

E9. The anti-CGRP antibody for use of any one of the foregoing embodiments, wherein said anti-CGRP antibody comprises Ab6.

E10. The anti-CGRP antibody for use of any one of the foregoing embodiments, wherein said anti-CGRP antibody comprises the light chain complementarity-determining region (CDR) 1, 2, and 3 polypeptide sequences of SEQ ID NO: 224; SEQ ID NO: 226; and SEQ ID NO: 228, respectively.

E11. The anti-CGRP antibody for use of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively.

E12. The anti-CGRP antibody for use of any one of the foregoing embodiments, wherein said anti-CGRP antibody comprises the heavy chain CDR 1, 2, and 3 polypeptide sequences of SEQ ID NO: 204; SEQ ID NO: 206; and SEQ ID NO: 208, respectively.

E13. The anti-CGRP antibody for use of any one of the foregoing embodiments, wherein said anti-CGRP antibody comprises the heavy chain CDR 1, 2, and 3 polypeptide sequences encoded by SEQ ID NO: 214; SEQ ID NO: 216; and SEQ ID NO: 218, respectively.

E14. The anti-CGRP antibody for use of any one of the foregoing embodiments, wherein said anti-CGRP antibody comprises the light chain CDR 1, 2, and 3 polypeptide sequences of SEQ ID NO: 224; SEQ ID NO: 226; and SEQ ID NO: 228, respectively and heavy chain CDR 1, 2, and 3 polypeptide sequences of SEQ ID NO: 204; SEQ ID NO: 206; and SEQ ID NO: 208, respectively.

E15. The anti-CGRP antibody for use of any one of the foregoing embodiments, wherein said anti-CGRP antibody comprises the light chain CDR 1, 2, and 3 polypeptide sequences encoded by SEQ ID NO: 234; SEQ ID NO: 236; and SEQ ID NO: 238, respectively and heavy chain CDR 1, 2, and 3 polypeptide sequences encoded by SEQ ID NO: 214; SEQ ID NO: 216; and SEQ ID NO: 218, respectively.

E16. The anti-CGRP antibody for use of any one of the foregoing embodiments, wherein said anti-CGRP antibody comprises the variable light chain polypeptide of SEQ ID NO: 222.

E17. The anti-CGRP antibody for use of any one of the foregoing embodiments, wherein said anti-CGRP antibody comprises the variable light chain polypeptide encoded by SEQ ID NO: 232.

E18. The anti-CGRP antibody for use of any one of the foregoing embodiments, wherein said anti-CGRP antibody comprises the variable heavy chain polypeptide of SEQ ID NO: 202.

E19. The anti-CGRP antibody for use of any one of the foregoing embodiments, wherein said anti-CGRP antibody comprises the variable heavy chain polypeptide encoded by SEQ ID NO: 212.

E20. The anti-CGRP antibody for use of any one of the foregoing embodiments, wherein said anti-CGRP antibody comprises the variable light chain polypeptide of SEQ ID NO: 222 and the variable heavy chain polypeptide of SEQ ID NO: 202.

E21. The anti-CGRP antibody for use of any one of the foregoing embodiments, wherein said anti-CGRP antibody comprises the variable light chain polypeptide encoded by SEQ ID NO: 232 and the variable heavy chain polypeptide encoded by SEQ ID NO: 212.

E22. The anti-CGRP antibody for use of any one of the foregoing embodiments, wherein said anti-CGRP antibody comprises the light chain polypeptide of SEQ ID NO: 221.

E23. The anti-CGRP antibody for use of any one of the foregoing embodiments, wherein said anti-CGRP antibody comprises the light chain polypeptide encoded by SEQ ID NO: 231.

E24. The anti-CGRP antibody for use of any one of the foregoing embodiments, wherein said anti-CGRP antibody comprises the heavy chain polypeptide of SEQ ID NO: 201 or SEQ ID NO: 566.

E25. The anti-CGRP antibody for use of any one of the foregoing embodiments, wherein said anti-CGRP antibody comprises the heavy chain polypeptide encoded by SEQ ID NO: 211 or SEQ ID NO: 567.

E26. The anti-CGRP antibody for use of any one of the foregoing embodiments, wherein said anti-CGRP antibody comprises the light chain polypeptide of SEQ ID NO: 221 and the heavy chain polypeptide of SEQ ID NO: 201 or SEQ ID NO: 566.

E27. The anti-CGRP antibody for use of any one of the foregoing embodiments, wherein said anti-CGRP antibody comprises the light chain polypeptide encoded by SEQ ID NO: 231 and the heavy chain polypeptide encoded by SEQ ID NO: 211 or SEQ ID NO: 567.

E28. The anti-CGRP antibody for use of any one of the foregoing embodiments, wherein the administered amount of said anti-CGRP antibody is between about 100 mg and about 300 mg, or is about 100 mg, or is about 300 mg.

E29. The anti-CGRP antibody for use of any one of the foregoing embodiments, wherein the administered amount of said anti-CGRP antibody is 100 mg.

E30. The anti-CGRP antibody for use of any one of the foregoing embodiments, wherein said anti-CGRP antibody is for intravenous administration in a dosage of 100 mg of said anti-CGRP antibody every 10-14 weeks, preferably every 11-13 weeks, more preferably every 12 weeks.

E31. The anti-CGRP antibody for use of any one of embodiments E1-E29, wherein said anti-CGRP antibody is for intravenous administration in a dosage of administering 300 mg of said anti-CGRP antibody every $10^{-14}$ weeks, preferably every 11-13 weeks, more preferably every 12 weeks.

E32. The anti-CGRP antibody for use of any one of the foregoing embodiments, wherein said patient suffers from medication overuse headache.

E33. The anti-CGRP antibody for use of any one of the foregoing embodiments wherein, prior to administration of said anti-CGRP antibody, the patient exhibits between 1-10 migraine attacks per month in the month or in the 3 months prior to administration.

E34. The anti-CGRP antibody for use of any one of the foregoing embodiments wherein, prior to administration of said anti-CGRP antibody, the patient exhibits between 2-8 migraine attacks per month in the month or in the 3 months prior to administration.

E35. The anti-CGRP antibody for use of any one of the foregoing embodiments wherein, prior to administration of said anti-CGRP antibody, the patient exhibits between 3-7 migraine attacks per month in the month or in the 3 months prior to administration.

E36. The anti-CGRP antibody for use of any one of the foregoing embodiments wherein, prior to administration of said anti-CGRP antibody, the patient exhibits less than 25 headache days per month in the month or in the 3 months prior to administration.

E37. The anti-CGRP antibody for use of any one of the foregoing embodiments wherein, prior to administration of said anti-CGRP antibody, the patient exhibits less than 20 headache days per month in the month or in the 3 months prior to administration.

E38. The anti-CGRP antibody for use of any one of the foregoing embodiments wherein, prior to administration of said anti-CGRP antibody, the patient exhibits less than 15 headache days per month in the month or in the 3 months prior to administration.

E39. The anti-CGRP antibody for use of any one of the foregoing embodiments wherein, prior to administration of said anti-CGRP antibody, the patient exhibits less than 10 headache days per month in the month or in the 3 months prior to administration.

E40. The anti-CGRP antibody for use of any one of the foregoing embodiments wherein said patient was diagnosed with migraine at least 10 years prior to the administration of said anti-CGRP antibody.

E41. The anti-CGRP antibody for use of any one of the foregoing embodiments wherein said patient was diagnosed with migraine at least 15 years prior to the administration of said anti-CGRP antibody.

E42. The anti-CGRP antibody for use of any one of the foregoing embodiments wherein said patient was diagnosed with migraine at least 18 or at least 19 years prior to the administration of said anti-CGRP antibody.

E43. The anti-CGRP antibody for use of any one of the foregoing embodiments, wherein said patient has a reduction in the number of migraine days by at least 50% in the one month period after being administered said antibody relative to the baseline number of migraine days experienced by that patient prior to the administration of said anti-CGRP antibody.

E44. The anti-CGRP antibody for use of any one of the foregoing embodiments, wherein said patient has a reduction in the number of migraine days by at least 75% in the one month period after being administered said antibody relative to the baseline number of migraine days experienced by that patient prior to the administration of said anti-CGRP antibody.

E45. The anti-CGRP antibody for use of any one of the foregoing embodiments, wherein said patient has a reduction in the number of migraine days by 100% in the one month period after being administered said antibody relative to the baseline number of migraine days experienced by that patient prior to the administration of said anti-CGRP antibody.

E46. The anti-CGRP antibody for use of any one of the foregoing embodiments, wherein said patient has a reduction in the number of migraine days by at least 50% in the 12 week period after being administered said antibody relative to the baseline number of migraine days experienced by that patient prior to the administration of said anti-CGRP antibody.

E47. The anti-CGRP antibody for use of any one of the foregoing embodiments, wherein said patient has a reduction in the number of migraine days by at least 75% in the 12 week period after being administered said antibody relative to the baseline number of migraine days experienced by that patient prior to the administration of said anti-CGRP antibody.

E48. The anti-CGRP antibody for use of any one of the foregoing embodiments, wherein said patient has a reduction in the number of migraine days by 100% in the 12 week period after being administered said antibody relative to the baseline number of migraine days experienced by that patient prior to the administration of said anti-CGRP antibody.

E49. The anti-CGRP antibody for use of any one of the foregoing embodiments, wherein said use comprises administering a second dose of said anti-CGRP antibody to said patient about 10-14 weeks, preferably 11-13 weeks, more preferably about 12 weeks or about 3 months after the administration of said anti-CGRP antibody.

E50. The anti-CGRP antibody for use of any one of the foregoing embodiments, wherein said use comprises administering about 100 mg, about 125 mg, about 150 mg, about 175 mg, about 200 mg, about 225 mg, about 250 mg, about 275 mg, or about 300 mg of said anti-CGRP antibody.

E51. The anti-CGRP antibody for use of any one of the foregoing embodiments, wherein said anti-CGRP antibody is aglycosylated or if glycosylated only contains only mannose residues.

E52. The anti-CGRP antibody for use of any one of the foregoing embodiments, wherein said anti-CGRP antibody consists of the light chain polypeptide of SEQ ID NO: 221 and the heavy chain polypeptide of SEQ ID NO: 201 or SEQ ID NO: 566.

E53. The anti-CGRP antibody for use of any one of the foregoing embodiments, wherein said anti-CGRP antibody consists of the light chain polypeptide encoded by SEQ ID NO: 231 and the heavy chain polypeptide encoded by SEQ ID NO: 211 or SEQ ID NO: 567.

E54. The anti-CGRP antibody for use of any one of embodiments E7-E53, wherein said rescue medication comprises one or more of a triptan, non-opioid analgesics (such as paracetamol (acetaminophen), acetylsalicylic acid (aspirin), another NSAID, or another non-opioid analgesic), a combination of two or more drug classes, wherein said triptan use optionally comprises use of one or more of sumatriptan, zolmitriptan, naratriptan, rizatriptan, eletriptan, almotriptan, and frovatriptan, and/or wherein said opioid use optionally comprises use of one or more of oxycodone, tramadol, butorphanol, morphine, codeine, and hydrocodone, and/or wherein said combination of two or more drug class optionally comprises two drugs with analgesic effects (for example, paracetamol and codeine) or acting as adjuvants (for example, caffeine), optionally wherein said combination-analgesics combine non-opioid analgesic includes at least one opioid (such as tramadol, butorphanol, morphine, codeine, hydrocodone, or any combination thereof), barbiturate such as butalbital and/or caffeine.

E55. The anti-CGRP antibody for use of any one of the foregoing embodiments, wherein said headache or said migraine is diagnosed according to the third edition of the International Classification of Headache Disorders.

E56. The anti-CGRP antibody for use of any of any one of the foregoing embodiments, wherein said anti-CGRP antibody is expressed in or obtained by expression in *Pichia pastoris*.

E57. The anti-CGRP antibody for use of any of any one of embodiments E1-E55, wherein said anti-CGRP antibody is expressed in or obtained by expression in CHO cells.

E58. The anti-CGRP antibody for use of any one of the foregoing embodiments, wherein said anti-CGRP antibody or anti-CGRP antibody fragment is comprised in a formulation comprising or consisting of histidine (L-histidine), sorbitol, polysorbate 80, and water.

E59. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

E60. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

E61. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

E62. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

E63. The anti-CGRP antibody for use of embodiment E58, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

E64. An anti-CGRP antibody for use in treating chronic migraine, wherein said antibody is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein in the first 24 hours after administration of said first dosage the patient exhibits at least a 50% reduction in migraine prevalence.

E65. An anti-CGRP antibody for use in treating chronic migraine, wherein said antibody is for intravenous administration in a first dosage comprising between about 100 mg and about 300 mg of an anti-CGRP antibody, wherein said anti-CGRP antibody comprises the light chain polypeptide of SEQ ID NO: 221 and the heavy chain polypeptide of SEQ ID NO: 201 or SEQ ID NO: 566, wherein on the first day following the day of administration the patient exhibits at least a 50% reduction in migraine prevalence.

E66. The anti-CGRP antibody for use of embodiment E64 or embodiment E65, wherein the first dosage of said anti-CGRP antibody is 100 mg.

E67. The anti-CGRP antibody for use of embodiment E64 or embodiment E65, wherein the first dosage of said anti-CGRP antibody is 300 mg.

E68. The anti-CGRP antibody for use of embodiment E64, E65, or E66, wherein said anti-CGRP antibody is for intravenous administration in a dosage of 100 mg of said anti-CGRP antibody every 10-14 weeks, preferably 11-13 weeks, more preferably every 12 weeks.

E69. The anti-CGRP antibody for use of embodiment E64, E65, or E67, wherein said anti-CGRP antibody is for intravenous administration in a dosage of 300 mg of said anti-CGRP antibody every 10-14 weeks, preferably 11-13 weeks, more preferably every 12 weeks.

E70. The anti-CGRP antibody for use of any one of embodiments E64-E69 wherein, prior to said first dosage, the patient exhibits between about 10 and about 22 migraine days per month.

E71. The anti-CGRP antibody for use of any one of embodiments E64-E70 wherein, prior to said first dosage, the patient exhibits between about 13 and about 19 migraine days per month.

E72. The anti-CGRP antibody for use of any one of embodiments E64-E71 wherein, prior to said first dosage, the patient exhibits about 16 migraine days per month.

E73. The anti-CGRP antibody for use of any one of embodiments E64-E72 wherein, prior to said first dosage, the patient exhibits between about 14 and about 27 headache days per month.

E74. The anti-CGRP antibody for use of any one of embodiments E64-E73 wherein, prior to said first dosage, the patient exhibits between about 17 and about 24 headache days per month.

E75. The anti-CGRP antibody for use of any one of embodiments E64-E74 wherein, prior to said first dosage, the patient exhibits about 20 or about 21 headache days per month.

E76. The anti-CGRP antibody for use of any one of embodiments E64-E75 wherein said patient was diagnosed with migraine at least 10 years prior to said first dosage.

E77. The anti-CGRP antibody for use of any one of embodiments E64-E76 wherein said patient was diagnosed with migraine at least 15 years prior to said first dosage.

E78. The anti-CGRP antibody for use of any one of embodiments E64-E77 wherein said patient was diagnosed with migraine at least 18 or at least 19 years prior to said first dosage.

E79. The anti-CGRP antibody for use of any one of embodiments E64-E78 wherein said patient was diagnosed with chronic migraine at least 5 years prior to said first dosage.

E80. The anti-CGRP antibody for use of any one of embodiments E64-E79 wherein said patient was diagnosed with chronic migraine at least 8 years prior to said first dosage.

E81. The anti-CGRP antibody for use of any one of embodiments E64-E80 wherein said patient was diagnosed with chronic migraine at least 11 or at least 12 years prior to said first dosage.

E82. The anti-CGRP antibody for use of any one of embodiments E64-E81 wherein said anti-CGRP antibody is for administration of said first dosage when the patient has a headache.

E83. The anti-CGRP antibody for use of any one of embodiments E64-E82 wherein said anti-CGRP antibody is for administration of said first dosage when the patient has a migraine.

E84. The anti-CGRP antibody for use of any one of embodiments E64-E83 wherein said anti-CGRP antibody is for administration of said first dosage when the patient has a migraine with aura.

E85. The anti-CGRP antibody for use of any one of embodiments E64-E84, wherein said patient has a reduction in the number of migraine days by at least 50% in the one month period after being administered said first dose relative to the baseline number of migraine days experienced by that patient prior to said first dose.

E86. The anti-CGRP antibody for use of any one of embodiments E64-E85, wherein said patient has a reduction in the number of migraine days by at least 75% in the one month period after being administered said first dose relative to the baseline number of migraine days experienced by that patient prior to said first dose.

E87. The anti-CGRP antibody for use of any one of embodiments E64-E86, wherein said patient has a reduction in the number of migraine days by 100% in the one month period after being administered said first dose relative to the baseline number of migraine days experienced by that patient prior to said first dose.

E88. The anti-CGRP antibody for use of any one of embodiments E64-E87, wherein said patient has a reduction in the number of migraine days by at least 50% in the 12 week period after being administered said first dose relative to the baseline number of migraine days experienced by that patient prior to said first dose.

E89. The anti-CGRP antibody for use of any one of embodiments E64-E88, wherein said patient has a reduction in the number of migraine days by at least 75% in the 12 week period after being administered said first dose relative to the baseline number of migraine days experienced by that patient prior to said first dose.

E90. The anti-CGRP antibody for use of any one of embodiments E64-E89, wherein said patient has a reduction in the number of migraine days by 100% in the 12 week period after being administered said first dose relative to the baseline number of migraine days experienced by that patient prior to said first dose.

E91. The anti-CGRP antibody for use of any one of embodiments E64-E90, further comprising administering a second dose of said anti-CGRP antibody to said patient about 12 weeks or about 3 months after said first dose.

E92. The anti-CGRP antibody for use of any one of embodiments E64-E91, wherein said first dose comprises about 100 mg, about 125 mg, about 150 mg, about 175 mg, about 200 mg, about 225 mg, about 250 mg, about 275 mg, or about 300 mg of said anti-CGRP antibody.

E93. The anti-CGRP antibody for use of any one of embodiments E64-E92, wherein said anti-CGRP antibody or antibody fragment is aglycosylated or if glycosylated only contains only mannose residues.

E94. The anti-CGRP antibody for use of any one of embodiments E64-E93, wherein said anti-CGRP antibody consists of the light chain polypeptide of the light chain polypeptide of SEQ ID NO: 221 and the heavy chain polypeptide of SEQ ID NO: 201 or SEQ ID NO: 566.

E95. The anti-CGRP antibody for use of any of any one of embodiments E64-E94, wherein said anti-CGRP antibody is expressed in or obtained by expression in *Pichia pastoris*.

E96. The anti-CGRP antibody for use of any of any one of embodiments E64-E94, wherein said anti-CGRP antibody is expressed in or obtained by expression in CHO cells.

E97. The anti-CGRP antibody for use of any one of embodiments E64-E96, wherein said anti-CGRP antibody or anti-CGRP antibody fragment is comprised in a formulation comprising or consisting of histidine (L-histidine), sorbitol, polysorbate 80, and water.

E98. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−10% of said values, and having a pH of 5.8 or within +/−10% of said value.

E99. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−5% of said values, and/or having a pH of 5.8 or within +/−5% of said value.

E100. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−1% of said values, and/or having a pH of 5.8 or within +/−1% of said value.

E101. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.5% of said values, and/or having a pH of 5.8 or within +/−0.5% of said value.

E102. The anti-CGRP antibody for use of embodiment E97, wherein said formulation comprises or consists of, per 1 mL volume, 100 mg anti-CGRP antibody, 3.1 mg L-Histidine, 40.5 mg Sorbitol, and 0.15 mg Polysorbate 80, or having amounts of each constituent within +/−0.1% of said values, and/or having a pH of 5.8 or within +/−0.1% of said value.

EXAMPLES

The following examples are provided in order to illustrate the invention, but are not to be construed as limiting the scope of the claims in any way.

Example 1

Preparation of Antibodies that Bind CGRP

The preparation of exemplary anti-CGRP antibodies Ab1-Ab14 having the sequences in FIGS. 1A-12 is disclosed in commonly owned PCT Application WO/2012/162243, published on Nov. 29, 2012, the contents of which are incorporated by reference herein. This application exemplifies synthesis of these antibodies in *Pichia pastoris* cells. The present Applicant further contemplates synthesis of anti-CGRP antibodies Ab1-Ab14, and Ab6 in particular in CHO cells.

Example 2

Human Clinical Study Evaluating the Safety and Efficacy of an Anti-CGRP Antibody According to the Invention Clinical Treatment Protocol The humanized anti-CGRP IgG1 antibody identified herein as Ab6 was assessed in human subjects for its ability to inhibit, alleviate or prevent the number of, duration, and/or the intensity of migraine episodes. The Ab6 antibody contains the $V_L$ and light chain polypeptides respectively in SEQ ID NO: 222 and SEQ ID NO: 221, and contains the VH and heavy chain polypeptides respectively in SEQ ID NO: 202 and SEQ ID NO: 201. This antibody comprises an IgG1 constant region that contains a mutation in the heavy chain constant region (replacement of asparagine residue at position 297 with an alanine residue which substantially eliminates glycosylation and lytic activity (see U.S. Pat. No. 5,624,821).

Specifically, the clinical efficacy of the Ab6 antibody was tested in a placebo controlled double-blind, randomized study. The individuals in the study were all selected based on specific criteria. Particularly all were diagnosed as migraine sufferers at ≤50 years of age (ICHD-II, 2004 Section 1), and further had a history of migraine ≥12 months with ≥5 and ≤14 migraine days in each 28 day period in the 3 months prior to screening.

Further, all of the individuals in the study used acute migraine medications ≤14 days per 28 day period and, within those days, ≤10 days of triptan use per 28 day period in the 3 months prior to screening and the 28 day period of completion of eDiary prior to randomization.

Table 1 summarizes the demographic characteristics of the study population.

TABLE 1

Baseline Demographics and Clinical Characteristics

| Characteristic | Placebo iv (n = 82) | Ab6 1000 mg iv (n = 81) |
|---|---|---|
| Mean ± SD Age (years) | 39.0 (9.6) | 38.6 (10.8) |
| Mean ± SD Weight (kg) | 75.4 (14.4) | 75.0 (16.5) |
| Female Gender | 66 (80%) | 67 (83%) |
| Race: | | |
| Caucasian | 66 (80.5%) | 66 (81.5%) |
| African American | 9 (11.0%) | 10 (12.4%) |
| Asian | 3 (3.7%) | 4 (5.0%) |
| Other | 4 (4.8%) | 1 (1.1%) |
| Baseline (per 28 days): | | |
| Mean ± SD Migraine Days | 8.8 (2.7) | 8.4 (2.1) |
| Mean ± SD Migraine Episodes | 6.7 (2.4) | 6.0 (2.2) |
| Mean ± SD Headache Frequency | 9.6 (2.8) | 9.2 (2.6) |
| Mean ± SD Migraine Hours | 72.2 (51.0) | 80.1 (49.1) |
| Mean ± SD HIT-6 Score | 64.5 (4.44) | 63.8 (5.21) |
| Mean ± SD MSQ RFP Score | 49.0 (17.9) | 49.5 (21.2) |
| Mean ± SD MSQ RFR Score | 61.9 (22.7) | 63.9 (24.0) |
| Mean ± SD MSQ EF Score | 59.5 (22.9) | 59.8 (27.0) |

Throughout the study all of the individuals were required to record their migraine status daily using an e-diary. In the e-diary the subjects in the study were required to record the number of migraine days/month, migraine episodes/month, migraine hours/month, migraine severity, and the use of any abortive medicine such as triptans.

In addition, the study participants were required to use the e-diary to record their migraine status in the 28 day period prior to treatment with antibody or placebo in order to establish a migraine day/hour/episode baseline per month. Also, this allowed the subjects in the study to become familiar with the use of the e-diary.

Figure 17:
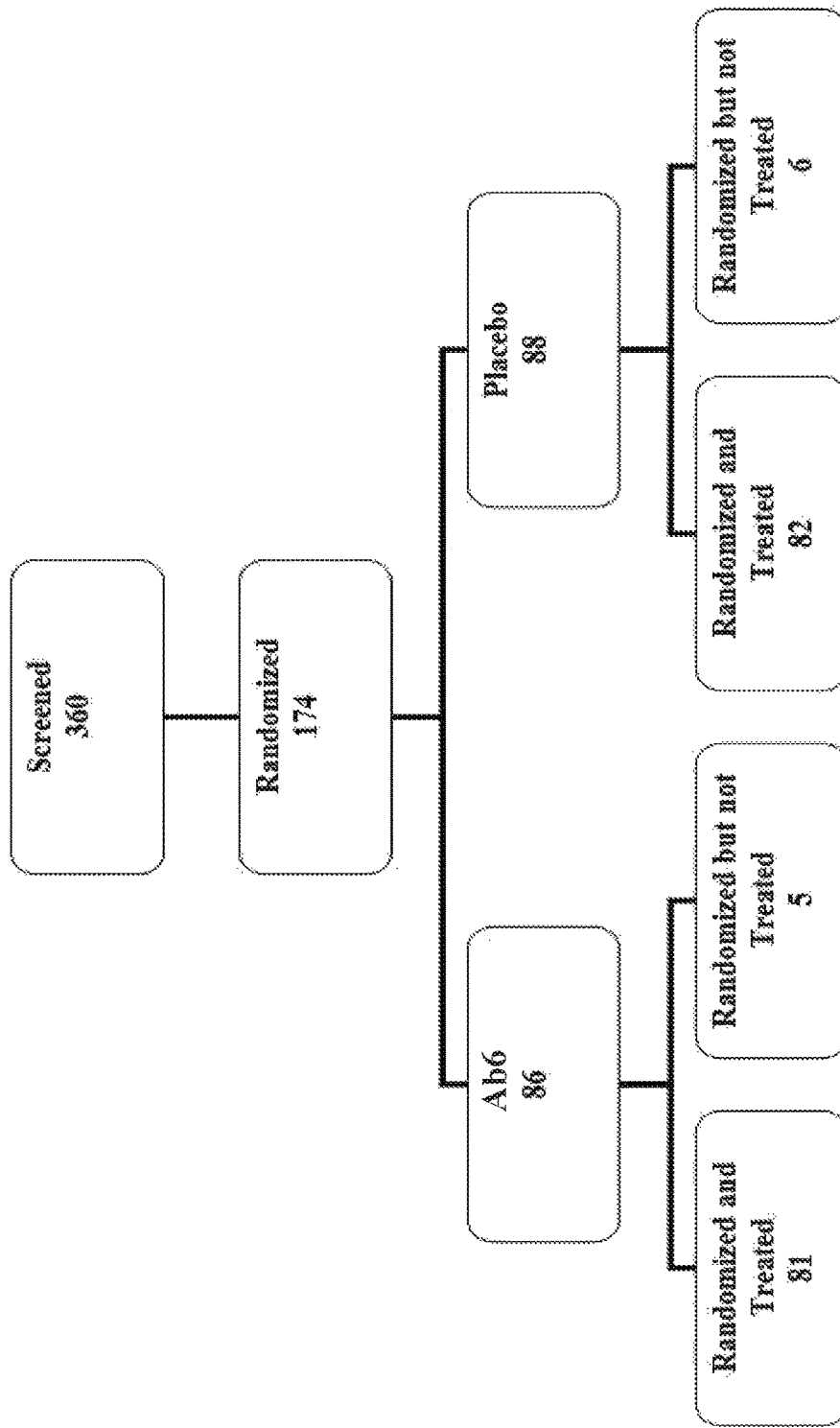
FIG. 17 summarizes the screening of patients, allocation into the treatment and control groups, and loss of patients through follow-up.

After the 28-day run-in the subjects in the study were broken into two groups, each including 80 subjects (FIG. 17). In the first group, i.e., the antibody treatment group, (n=80) each subject in the group was administered intravenously a single 1000 mg dose of Ab6. In the second group (n=80), i.e., the placebo group, each of the subjects was given an intravenous injection containing only the aqueous antibody carrier solution.

The individuals in the treated and placebo groups were assessed in the 24 weeks post-dose administration. Initially, a 12 week interim analysis was conducted. Subsequent to the 12 week interm analysis, a refined analysis was conducted. This refined analysis potentially included, for example, addition or removal of patient data in accord with the study protocol, e.g., updating data that had not been fully loaded from the e-diaries. This refinement resulted in slight changes but did not alter the overall conclusions.

The efficacy of the antibody versus the placebo was assessed in part based on the recorded data in the e-diary entries. For example, this analysis included a comparison of the number of recorded migraine days/month, migraine episodes/month, migraine hours/month in the subjects in the treated versus the placebo group. The percentage of responders in each group (i.e., the subjects with 50%, 75%, and 100% reduction in migraine days) in both groups was also compared.

In addition, the responses of the Ab6- and placebo-treated subjects in both groups to MSQ and HIT-6 questionnaires are to be evaluated and compared. MSQ is a frequently utilized disease-specific tool to assess the impact of migraine on health-related quality of life (HRQL). MSQ comprises a 16-item Migraine-Specific Quality-of-Life Questionnaire (Version 1.0), which was developed by Glaxo Wellcome Inc. MSQ is hypothesized to measure 3 parameters: (i) Role Function-Restrictive; (ii) Role Function-Preventive; and (iii) Emotional Function.

The HIT-6 or functional impact (also called the Headache Impact Test or HIT-6) similarly is a well known tool for assessing migraine intensity. This test uses six questions to capture the impact of headache and its treatment on an individual's functional health and well-being.

Also, the pharmacokinetic (PK) properties of the CGRP antibody and immunogenicity are to be assessed in the Ab6 antibody treated subjects.

Clinical Results and Analysis

The results of this human clinical trial and analysis through week 12 in the treated subjects are summarized in the Table 2 below.

TABLE 2

Responder analysis for migraine days

| Time period | % reduction migraine days | Placebo iv | Ab6 1000 mg iv | P value |
|---|---|---|---|---|
| Week 1-4 | | n = 80 | n = 75 | |
| | 50 | 40 (50.0) | 58 (77.3) | p = 0.0005 |
| | 75 | 19 (23.8) | 39 (52.0) | p = 0.0005 |
| | 100 | 4 (5.0) | 21 (28.0) | p = 0.0001 |
| Week 5-8 | | n = 80 | n = 78 | |
| | 50 | 43 (53.8) | 59 (75.6) | p = 0.0048 |
| | 75 | 28 (35.0) | 35 (44.9) | p = 0.2555 |
| | 100 | 12 (15.0) | 21 (26.9) | p = 0.0791 |
| Week 9-12 | | n = 77 | n = 72 | |
| | 50 | 51 (66.2) | 54 (75.0) | p = 0.2827 |
| | 75 | 24 (31.2) | 38 (52.8) | p = 0.0083 |
| | 100 | 13 (16.9) | 29 (40.3) | p = 0.0019 |

In addition, the results of the clinical study were compared based on the number of responders in the treatment and placebo groups. As shown in FIG. 13 the number of subjects who showed a 50, 75 or 100% reduction in migraine days for each month of the interim period were compared in the treatment and placebo groups. As shown in the figure, 60% of the Ab6-treated group had at least 50% reduction in headache days, 31% of the Ab6-treated group had at least 75% reduction in headache days and 15% of the Ab6 treated group had 100% reduction in headache days.

By contrast, 33% of the placebo-treated group had at least 50% reduction in headache days, 9% of the placebo-treated group had at least 75% reduction in headache days, and 0% (none) of the placebo-treated group had 100% reduction in headache days.

These results clearly show that the reduction in the number of migraine days was much greater in the Ab6-treated group. But for the significant placebo effect, the difference in these numbers would have been more pronounced. (Elevated placebo effect is not surprising as the phenomenon is often very high for migraine and other neurological drugs).

Figure 14:
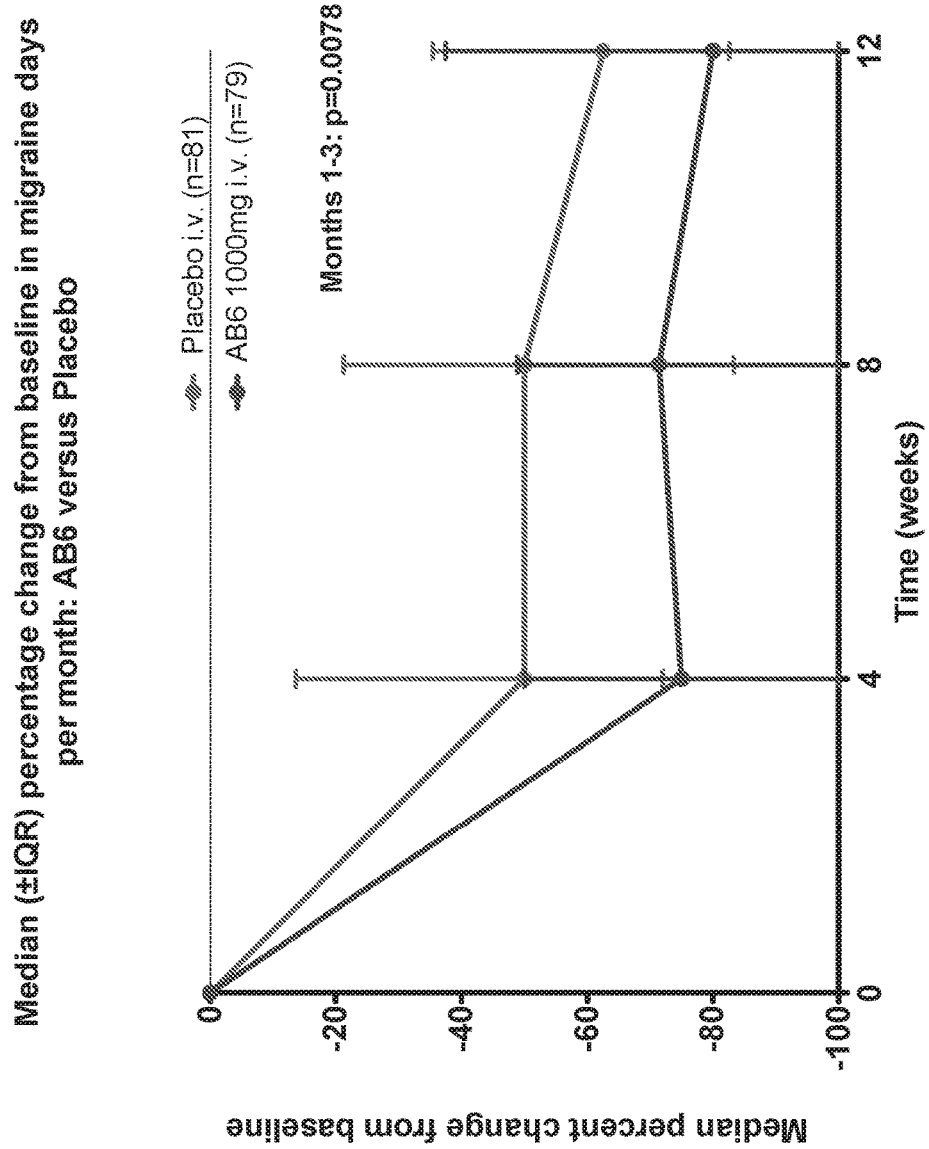
FIG. 14 shows the median (±QR) % change from baseline in the number of migraine days per month in the placebo and Ab6-treated group over the 12 weeks post-treatment. (p=0.0078). The upper (red) line and lower (blue) line show results for placebo-treated controls and patients administered 1000 mg Ab6, respectively.

In addition, the % change from baseline in the number of migraine days per month in the placebo and Ab6-treated group was compared. As shown in FIG. 14, the median (±QR) % change from baseline in the number of migraine days per month in the placebo and Ab6-treated group was compared for the 2 groups during the 12 weeks post-treatment. These results which are statistically significant (p=0.0078) clearly show the Ab6-treated group had a much greater reduction in the number of headache days per month compared to baseline than the placebo-treated group.

Figure 15:
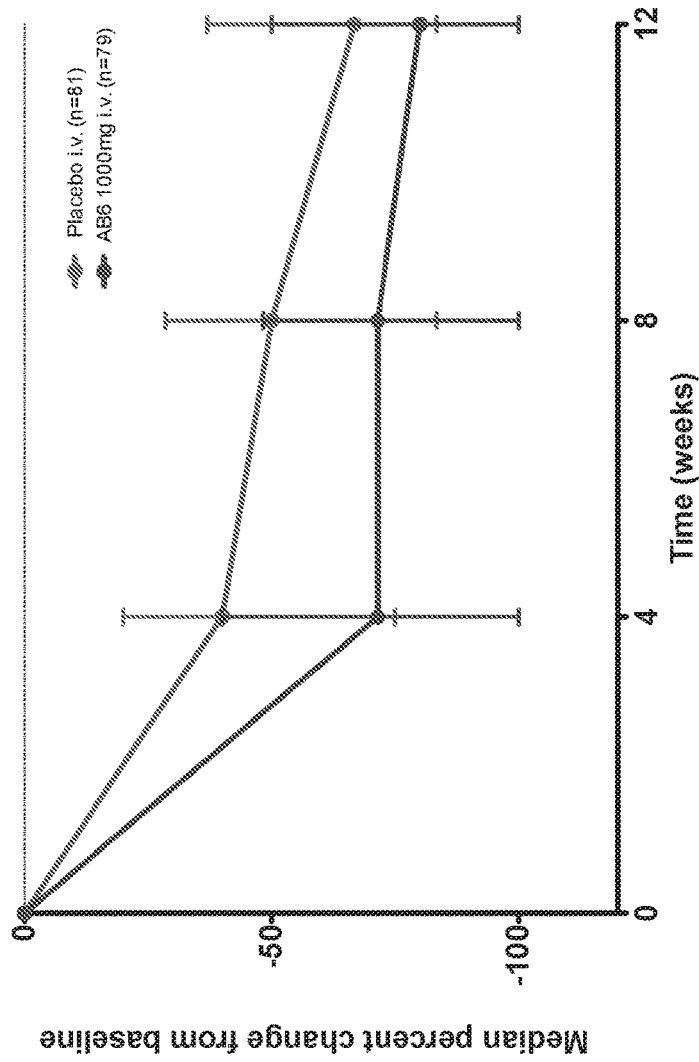
FIG. 15 shows the median (±QR) % change from baseline in the number of migraine episodes per month in the placebo and Ab6-treated group over the 12 weeks post-treatment. The upper (red) line and lower (blue) line show results for placebo-treated controls and patients administered 1000 mg Ab6, respectively.

Also, the % change from baseline in the number of migraine episodes per month in the placebo and Ab6-treated group was compared. As shown in FIG. 15 the median (±QR) % change from baseline in the number of migraine episodes per month in the placebo and Ab6-treated group was compared during the 12 weeks post-treatment. These results indicate that the Ab6-treated group had a significantly greater reduction in the number of migraine episodes per month compared to baseline than the placebo-treated group.

Figure 16:
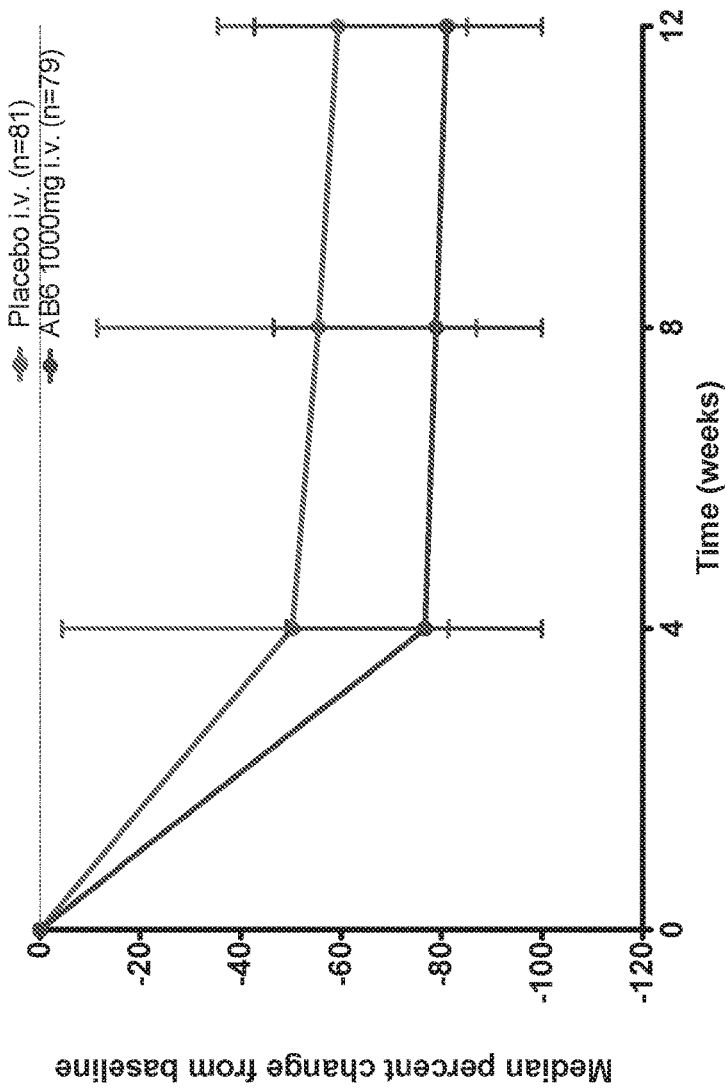
FIG. 16 shows the median (±QR) % change from baseline in the number of migraine hours per month in the placebo and Ab6-treated group over the 12 weeks post-treatment. The upper (red) line and lower (blue) line show results for placebo-treated controls and patients administered 1000 mg Ab6, respectively.

Further, the % change from baseline in the number of migraine hours per month in the placebo and Ab6-treated group was compared. As shown in FIG. 16, the median (±QR) % change from baseline in the number of migraine hours per month in the placebo and Ab6-treated group was compared for the 2 groups during the 12 weeks post-treatment. These results clearly show the Ab6-treated group had a greater reduction in the number of migraine hours per month compared to baseline than the placebo-treated group.

Figure 18:
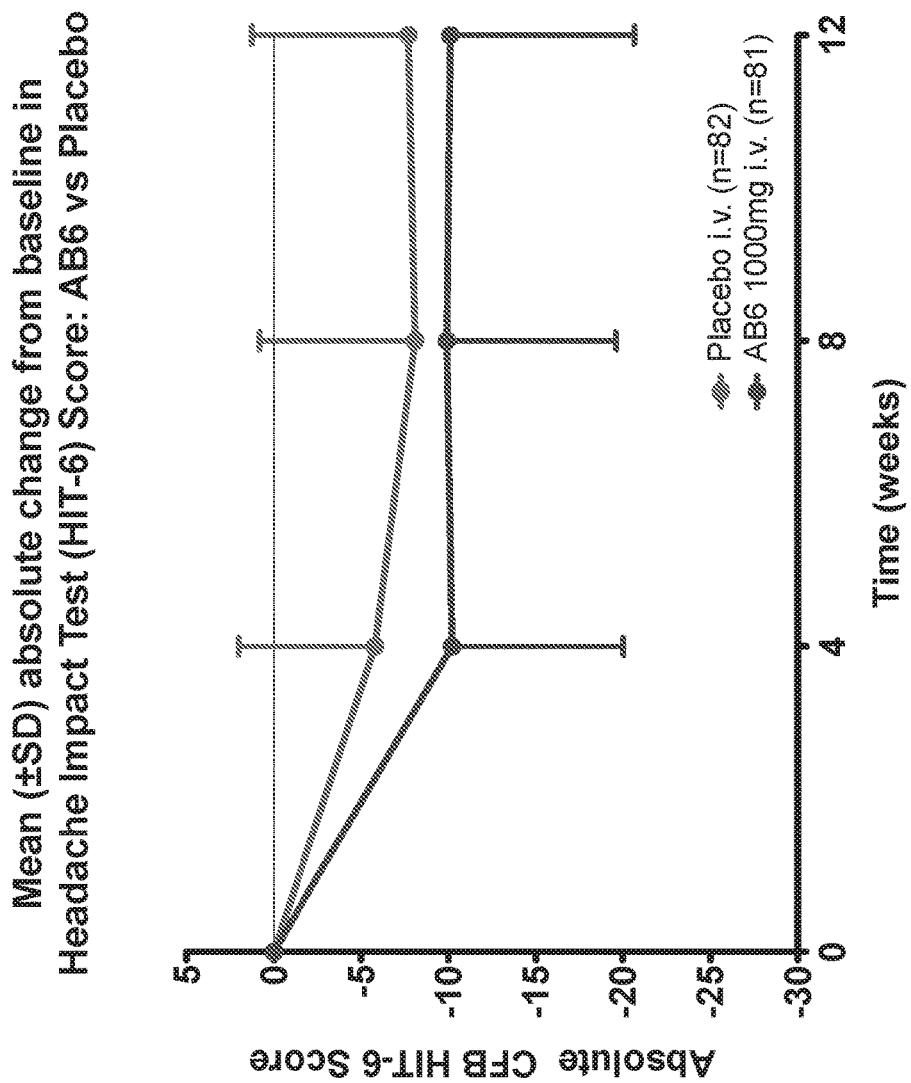
FIG. 18 compares the HIT-6 responder analysis for the Ab6-treated and placebo groups at baseline, week 4 after treatment, week 8 after treatment and week 12 after treatment.
Figure 19:
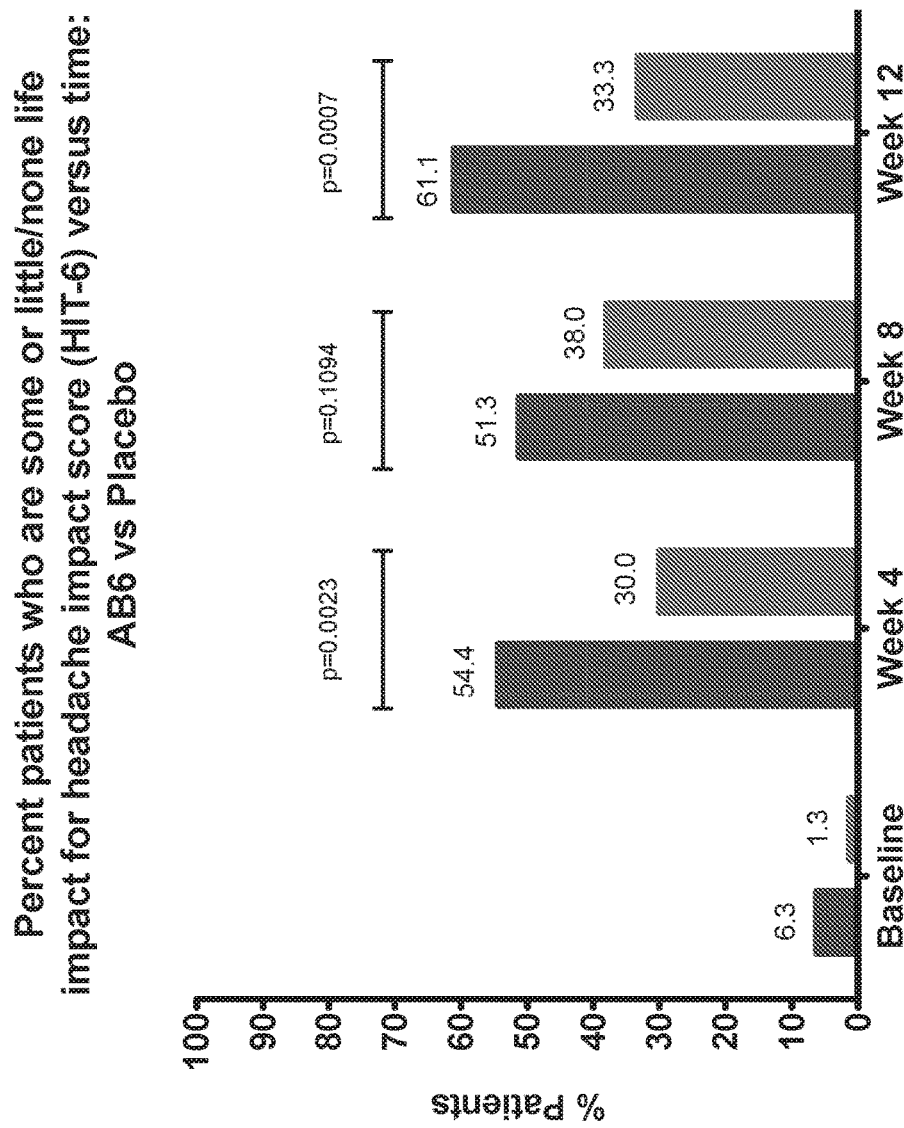
FIG. 19 shows the percentage of patients for whom the HIT-6 analysis indicated that the effect of headaches was only "some" or "little/none" at baseline and after Ab6 administration. At baseline most patients had either "substantial" or "severe" impact from migraines. At each subsequent time point, a significantly greater percentage of patients administered 1000 mg Ab6 had only "some" or "little/none" HIT-6 impact (left bar in each group, colored blue) as compared to placebo controls (right bar in each group, colored red).
Figure 22:
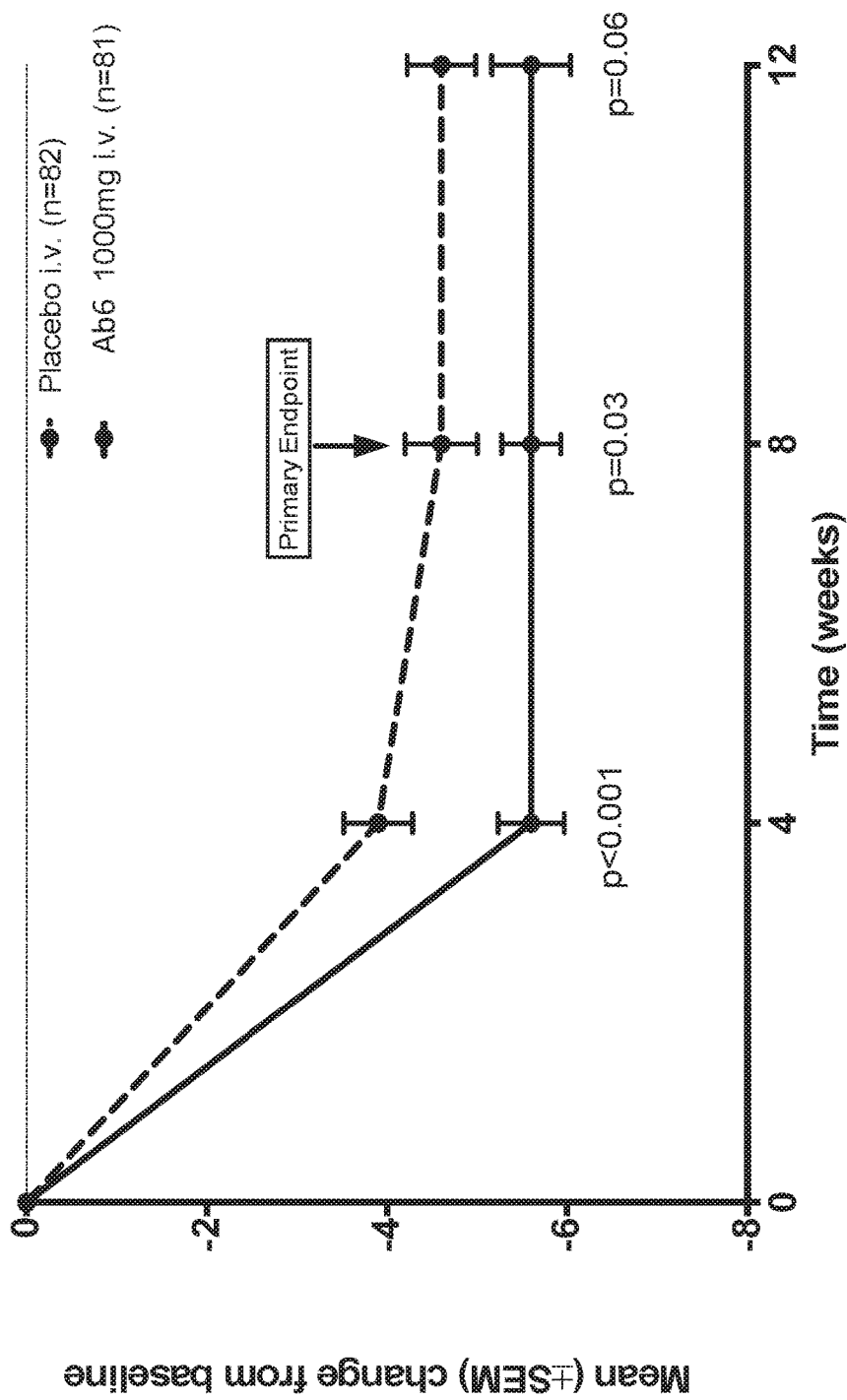
FIG. 22 shows the change (mean+−SEM) change from baseline in migraine days per month for Ab6 (1000 mg i.v.) versus placebo as a single dose for the study described in Example 2.

In addition, the HIT-6 results were compared for both groups. As noted, this questionnaire finds well accepted usage in assessing the migraine status of individuals with frequent/chronic migraine. FIG. 18 compares the HIT-6 responder analysis for the Ab6-treated and placebo groups at baseline, week 4 after treatment, week 8 after treatment and week 12 after treatment. The results at each time point reveal that the Ab6-treated group had a statistically significant improvement in the HIT-6 scores relative to the placebo group, i.e., 54.4% for the Ab6-treated compared to 30% for the placebo at week 4 (p=0.0023), 51.3% for the Ab6-treated compared to 38.0% for the placebo at week 8 (p=0.1094) and 61.1% for the Ab6-treated compared to 33.3% for the placebo at week 12 (p=0.0007). FIG. 19 shows the percentage of patients having a HIG-6 score of some or little/none over time in the placebo and Ab6 treatment groups (statistical significance a shown).

In addition, FIG. 20 contains the pharmacokinetic (PK) profile for Ab6 administered intravenously at a single dosage of 1000 mg in mg/mL over the 24 week period following Ab6 administration.

FIG. 21 contains plasma-free pharmacokinetic (PK) parameters N (number of patients), mean, and standard deviation (SD) for a single 1000 mg intravenous dosage of Ab6. The parameters shown in the table and the units are $C_{max}$ (µg/mL), $AUC_{0-\infty}$ (mg*hr/mL), half-life (days), $V_z$ (L) and $C_L$ (mL/hr).

Further analysis was conducted for patient data between 12-weeks and 24-weeks. The treatment group continued to exhibit decreased migraine days relative to the control group, however, the magnitude of the difference decreased over time. Additionally, the control group exhibited fewer migraine days per month than at baseline. This was thought to result at least in part from "diary fatigue" wherein patients potentially report no migraine on a day in which a migraine actually occurred, in order to avoid the time and effort of answering further queries about the migraine that would result from giving an affirmative answer to the question of whether they had a migraine on a given day.

Figure 23:
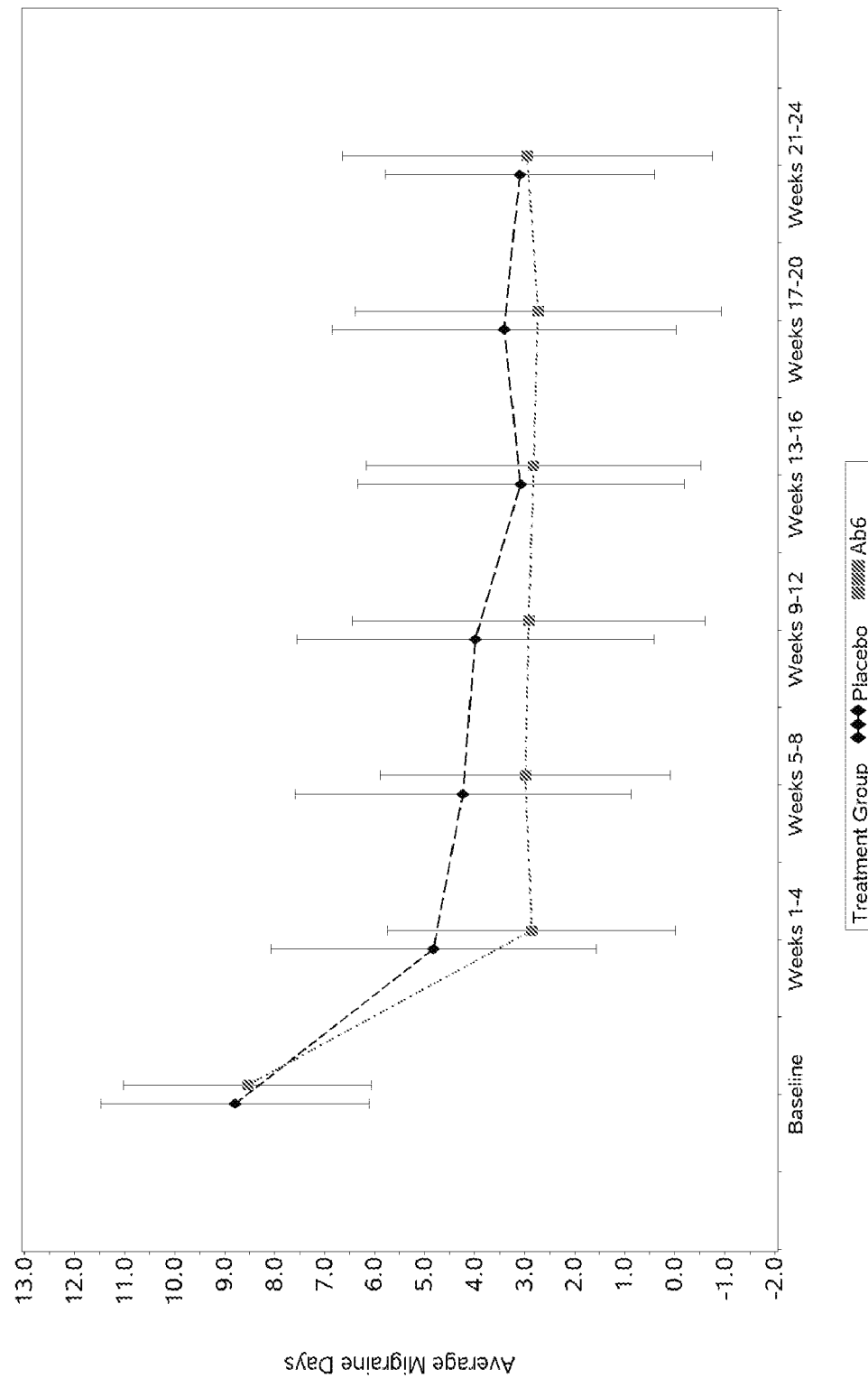
FIG. 23 shows the average migraine days (+/−SD) over time for the full analysis population for the study described in Example 2. Normalization was applied to visit intervals where eDiaries were completed for 21-27 days by multiplying the observed frequency by the inverse of the completion rate.
Figure 24:
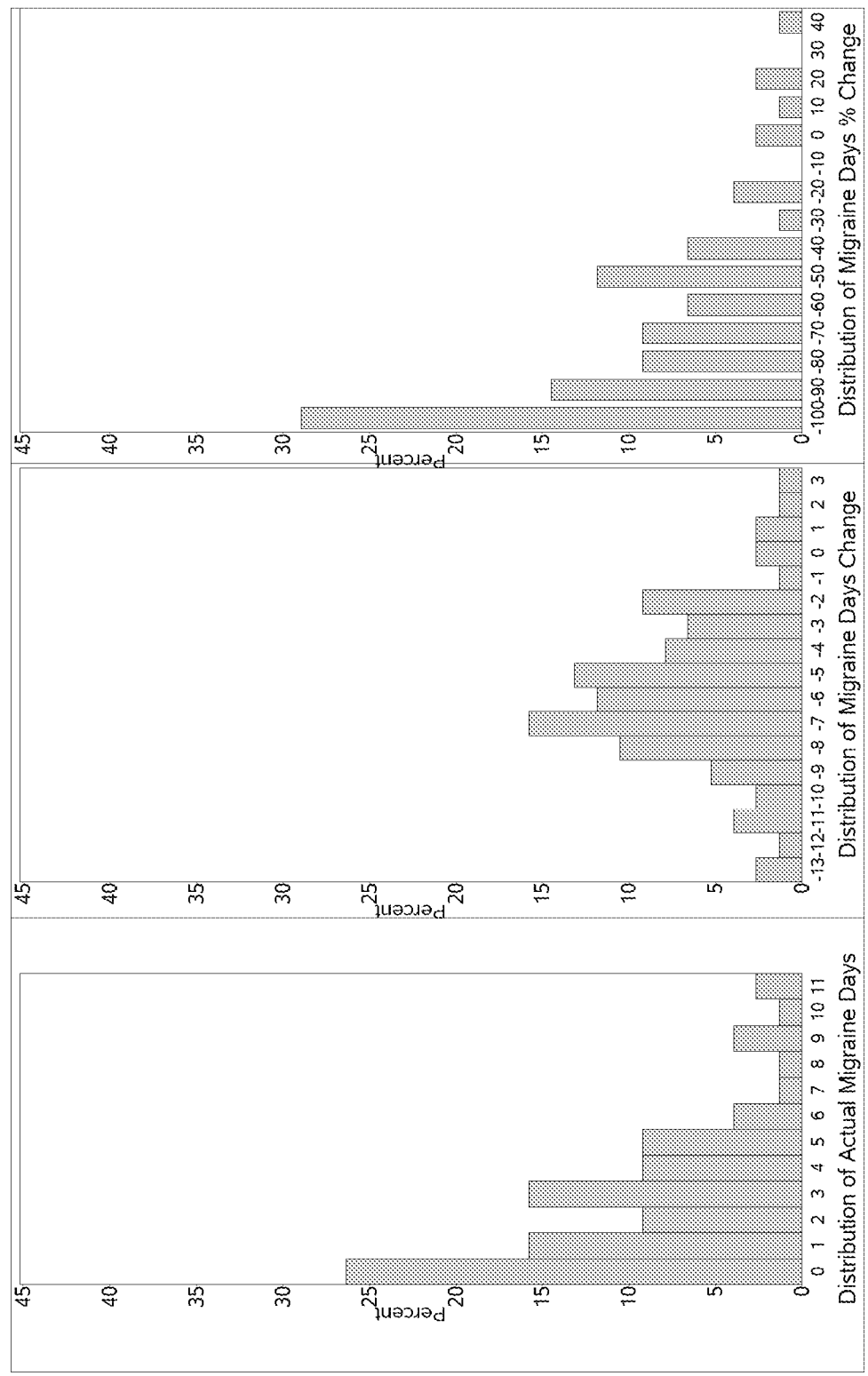
FIG. 24 shows the distribution of migraine days actual and change for the Ab6 treatment group during weeks 1-4 for the study described in Example 2.
Figure 25:
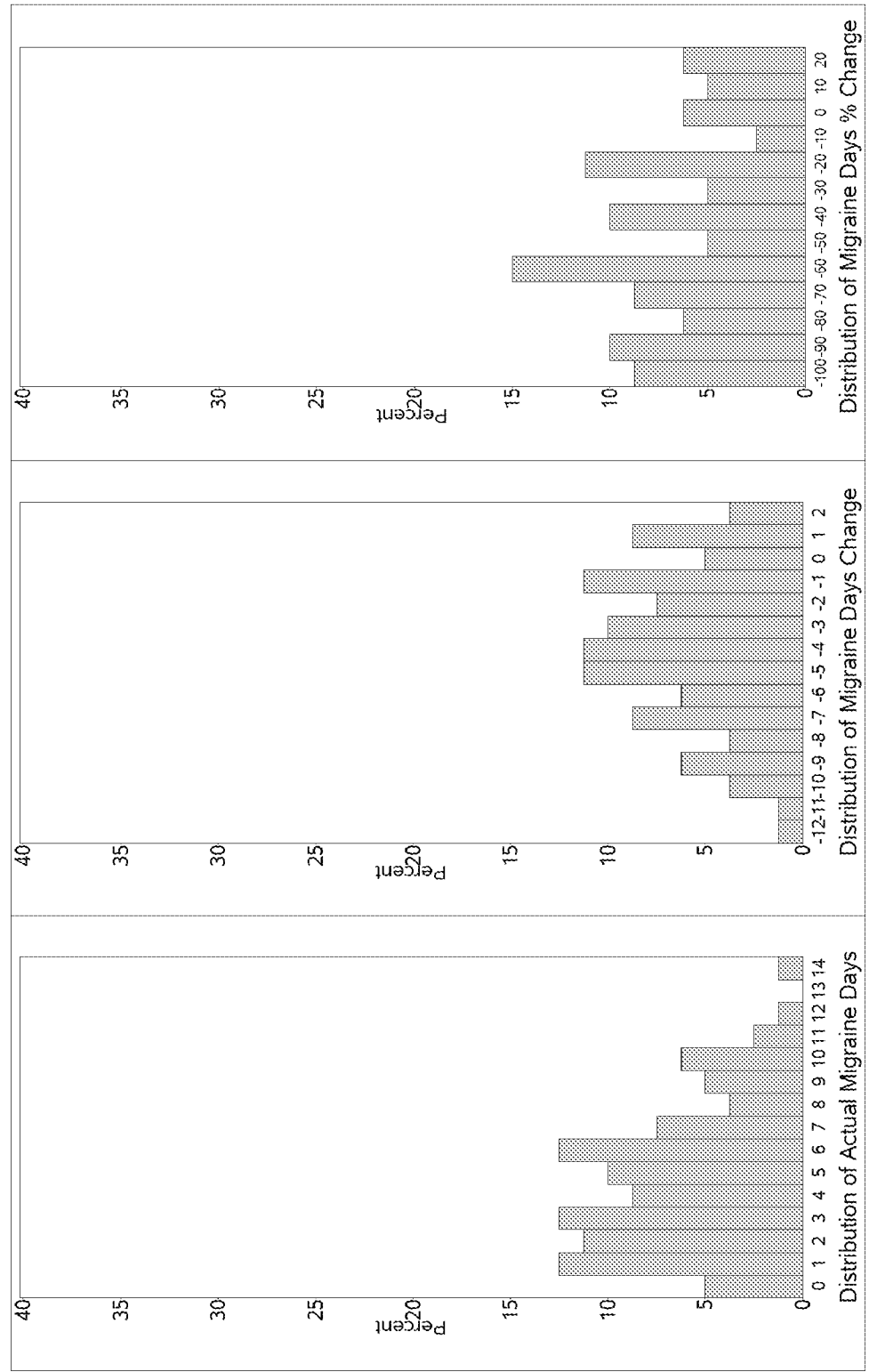
FIG. 25 shows the distribution of migraine days actual and change for the placebo group during weeks 1-4 for the study described in Example 2.
Figure 26:
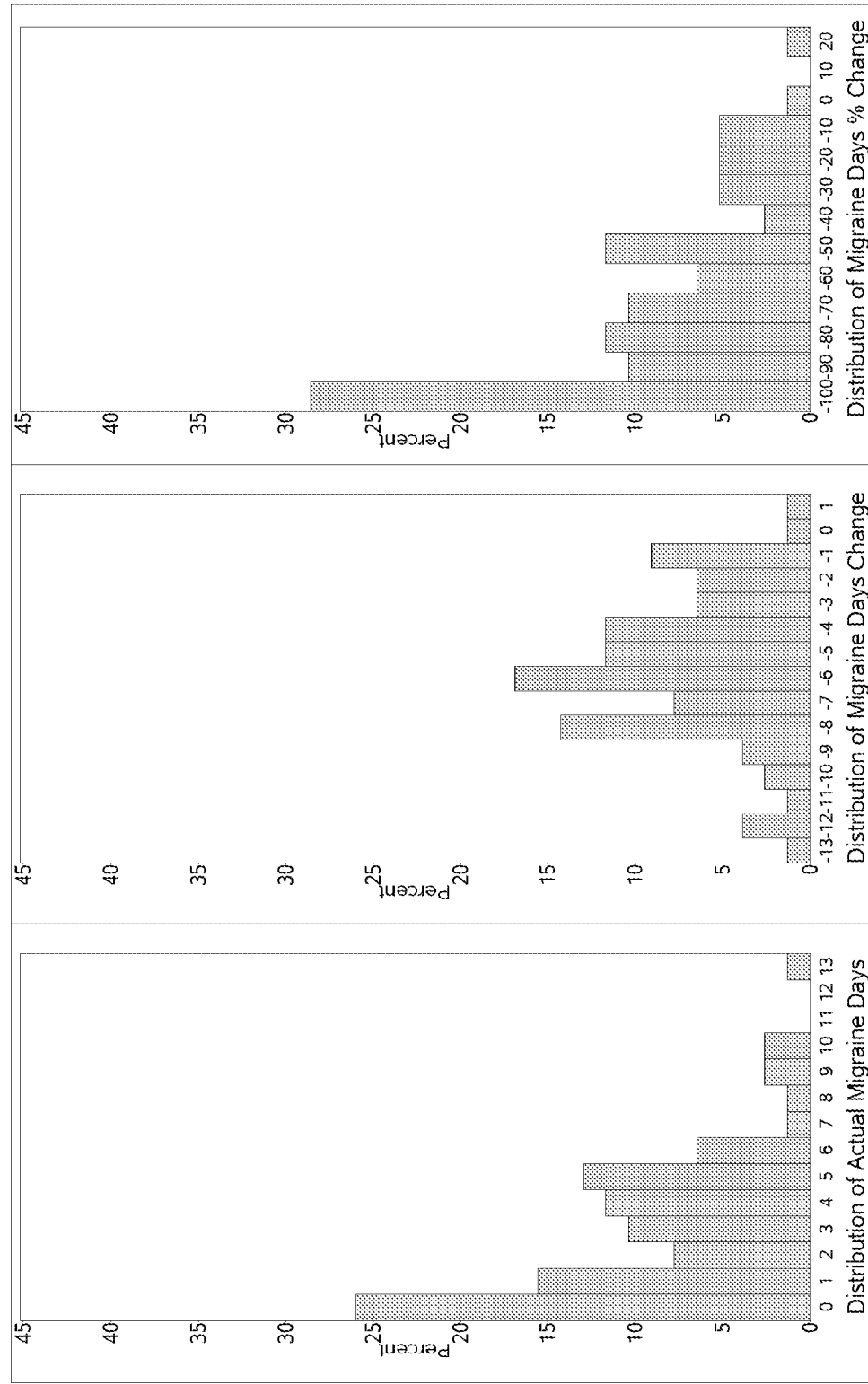
FIG. 26 shows the distribution of migraine days actual and change for the Ab6 treatment group during weeks 5-8 for the study described in Example 2.
Figure 27:
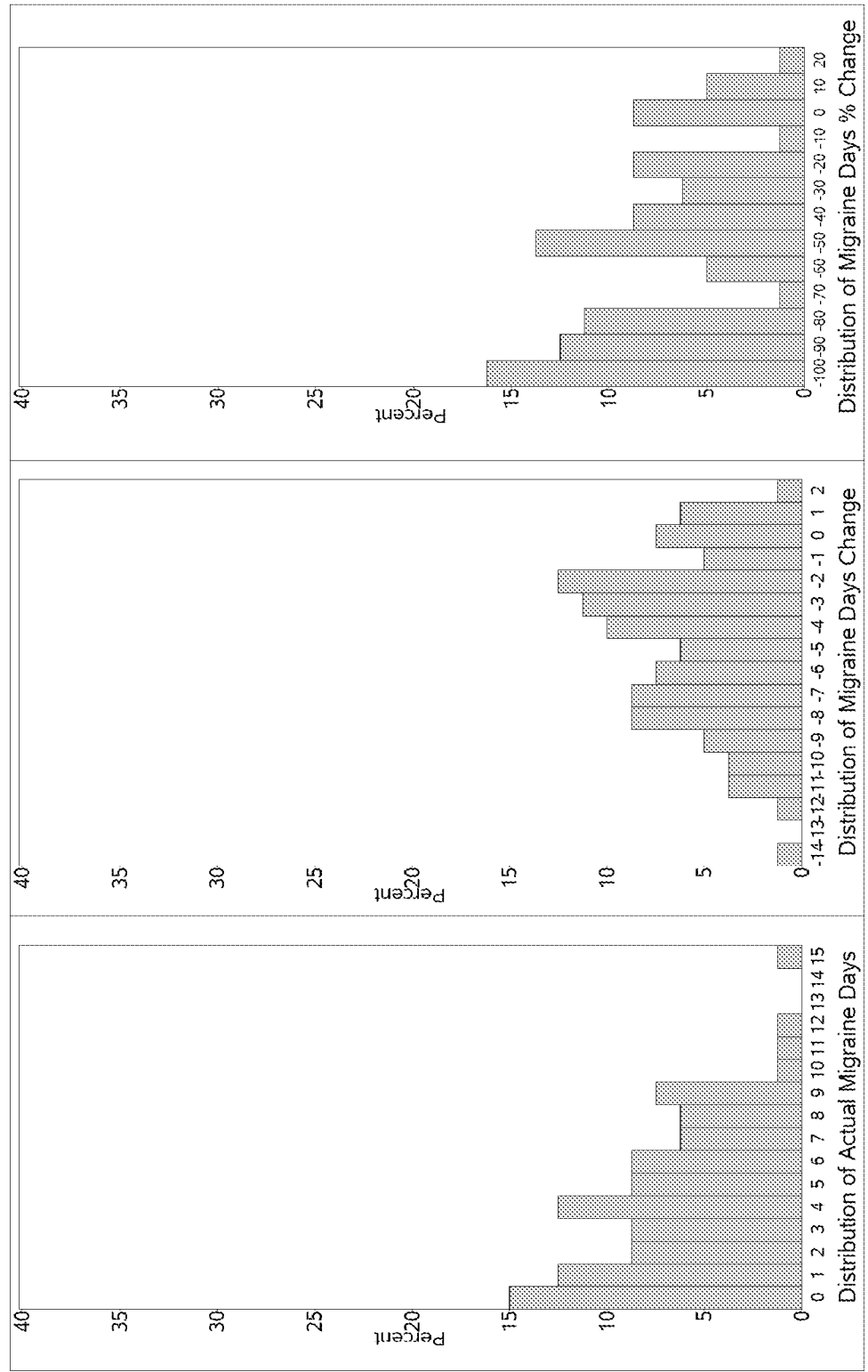
FIG. 27 shows the distribution of migraine days actual and change for the placebo group during weeks 5-8 for the study described in Example 2.
Figure 28:
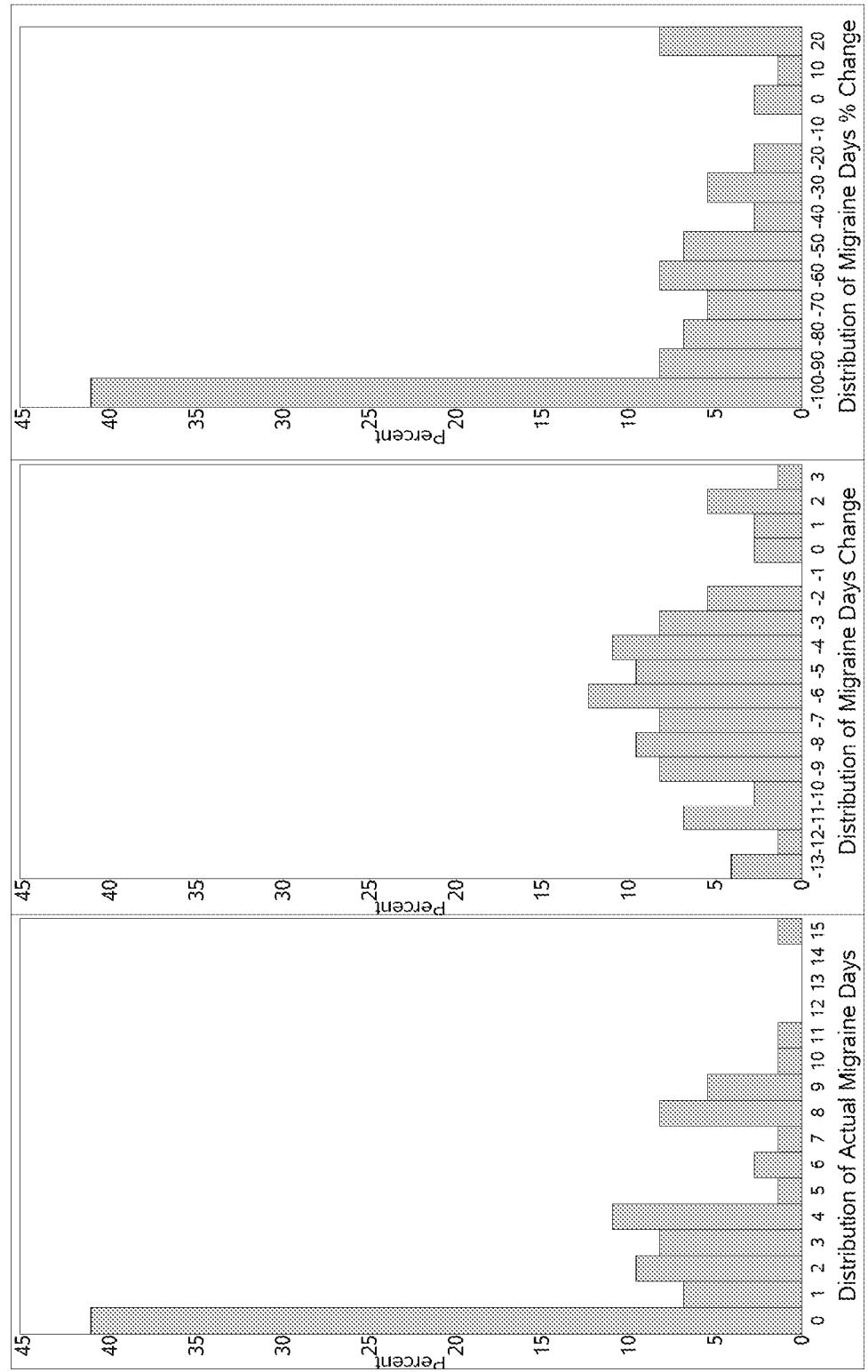
FIG. 28 shows the distribution of migraine days actual and change for the Ab6 treatment group during weeks 9-12 for the study described in Example 2.
Figure 29:
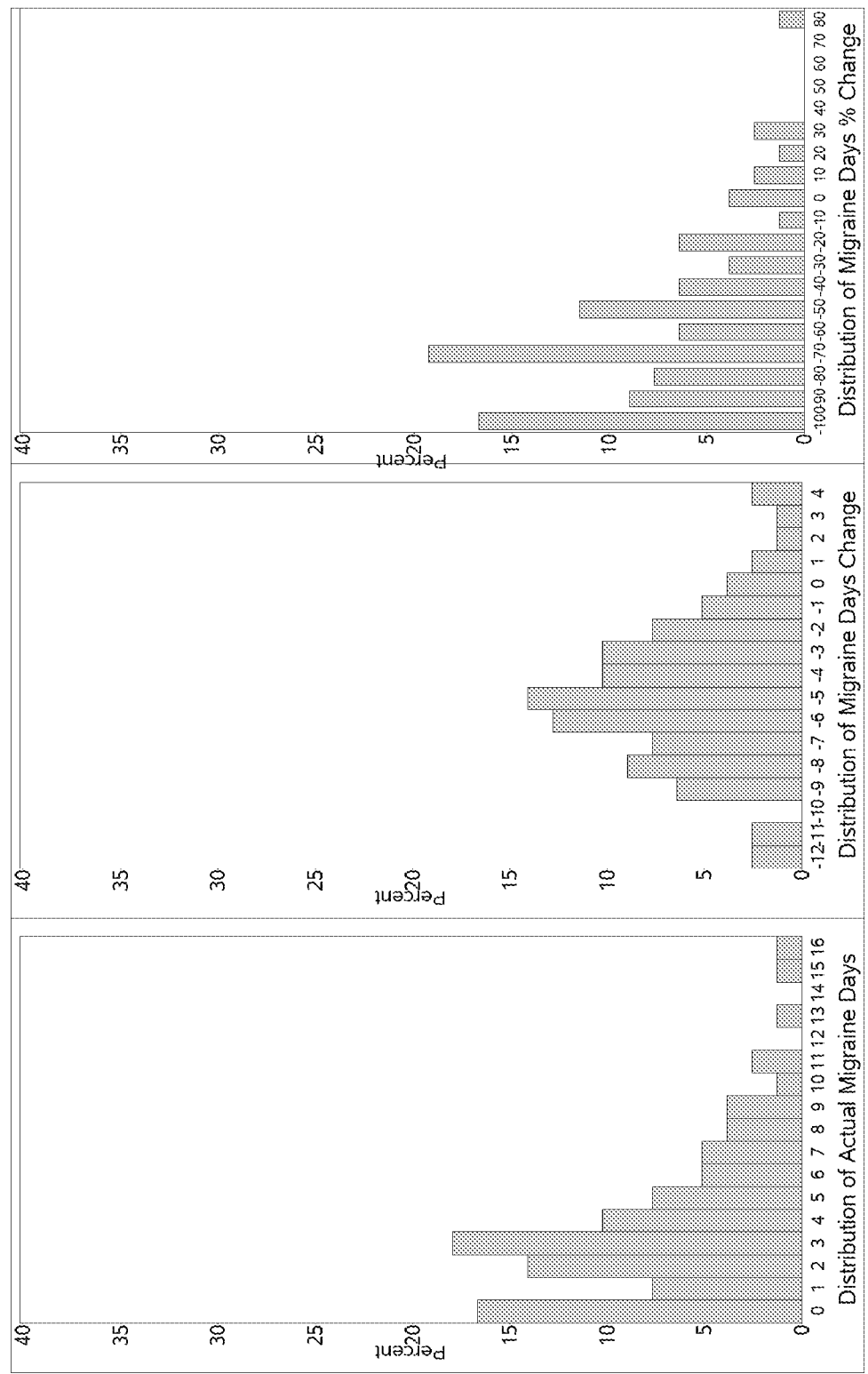
FIG. 29 shows the distribution of migraine days actual and change for the placebo group during weeks 9-12 for the study described in Example 2.

Further analysis of the study results are shown in FIGS. 22-33. These result include analysis of the change (mean+/−SEM) from baseline in migraine days per month for Ab6 (1000 mg i.v.) versus placebo (FIG. 22), change in average migraine days (+/−SD) over time for the full analysis population (FIG. 23). Additionally, shown are the distribution of migraine days actual and change for the Ab6 treatment group during weeks 1-4 (FIG. 24), distribution of migraine days actual and change for the placebo group during weeks 1-4 (FIG. 25), distribution of migraine days actual and change for the Ab6 treatment group during weeks 5-8 (FIG. 26), distribution of migraine days actual and change for the placebo group during weeks 5-8 (FIG. 27), distribution of migraine days actual and change for the Ab6 treatment group during weeks 9-12 (FIG. 28), and distribution of migraine days actual and change for the placebo group during weeks 9-12 (FIG. 29).

Figure 30:
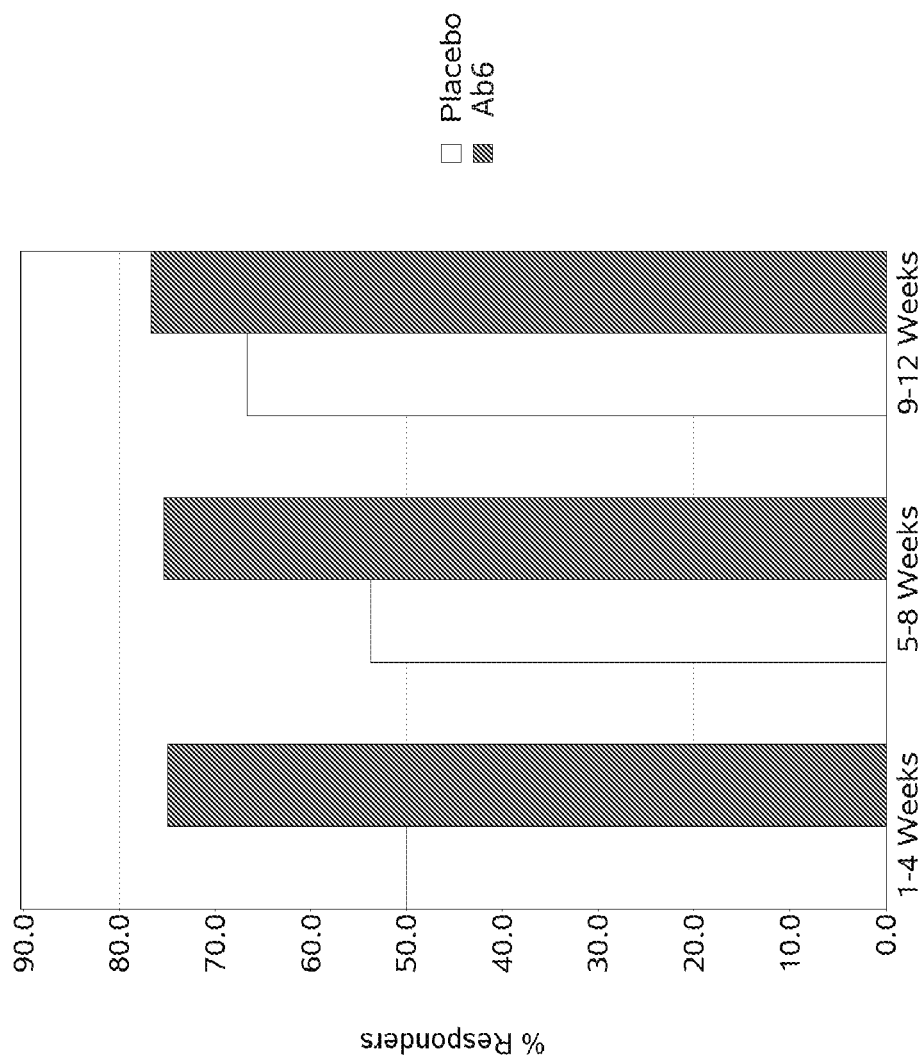
FIG. 30 shows the 50% responder rate for the Ab6 and placebo treatment groups for the study described in Example 2. Subjects with ≥50% reduction in migraine frequency were considered to be a 50% responder. Normalization was applied to visit intervals where eDiary was completed for 21-27 days by multiplying the observed frequency by the inverse of the completion rate.
Figure 31:
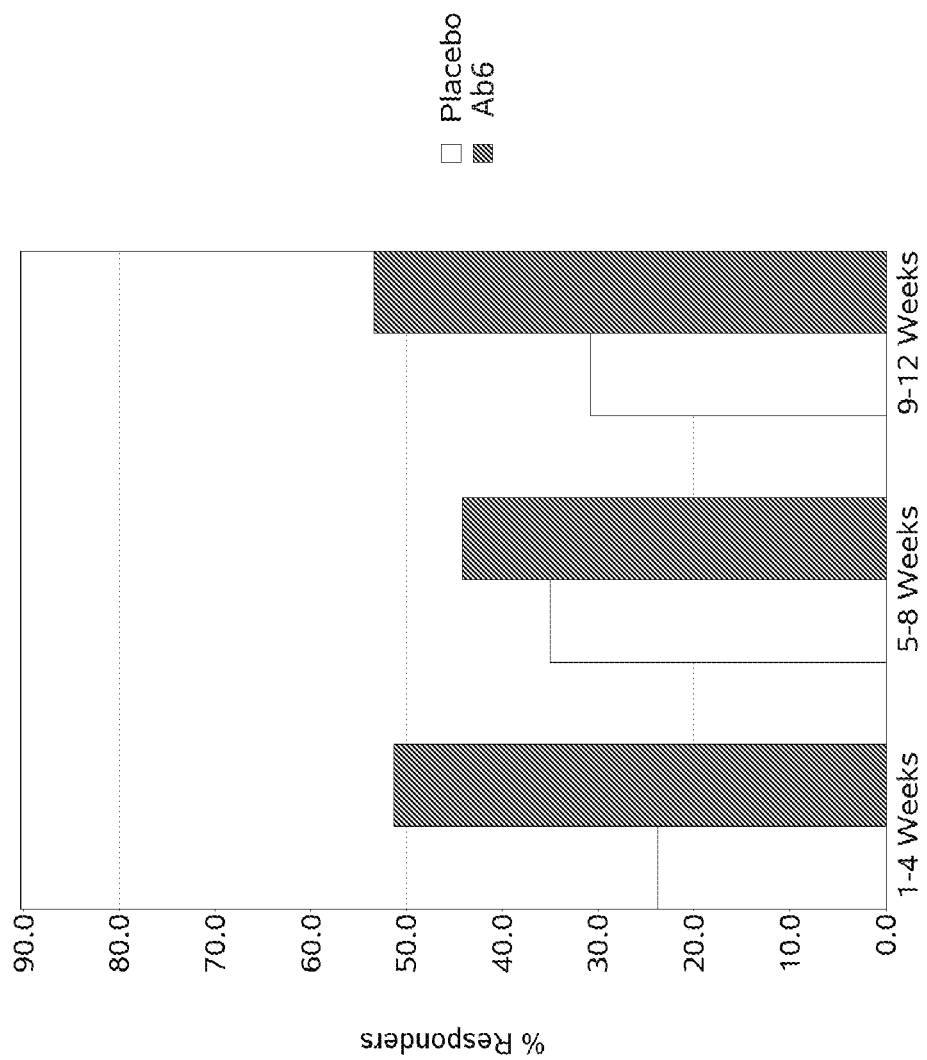
FIG. 31 shows the 75% responder rate for the Ab6 and placebo treatment groups for the study described in Example 2. Subjects with ≥75% reduction in migraine frequency were considered to be a 75% responder. Normalization was applied as described with FIG. 30.
Figure 32:
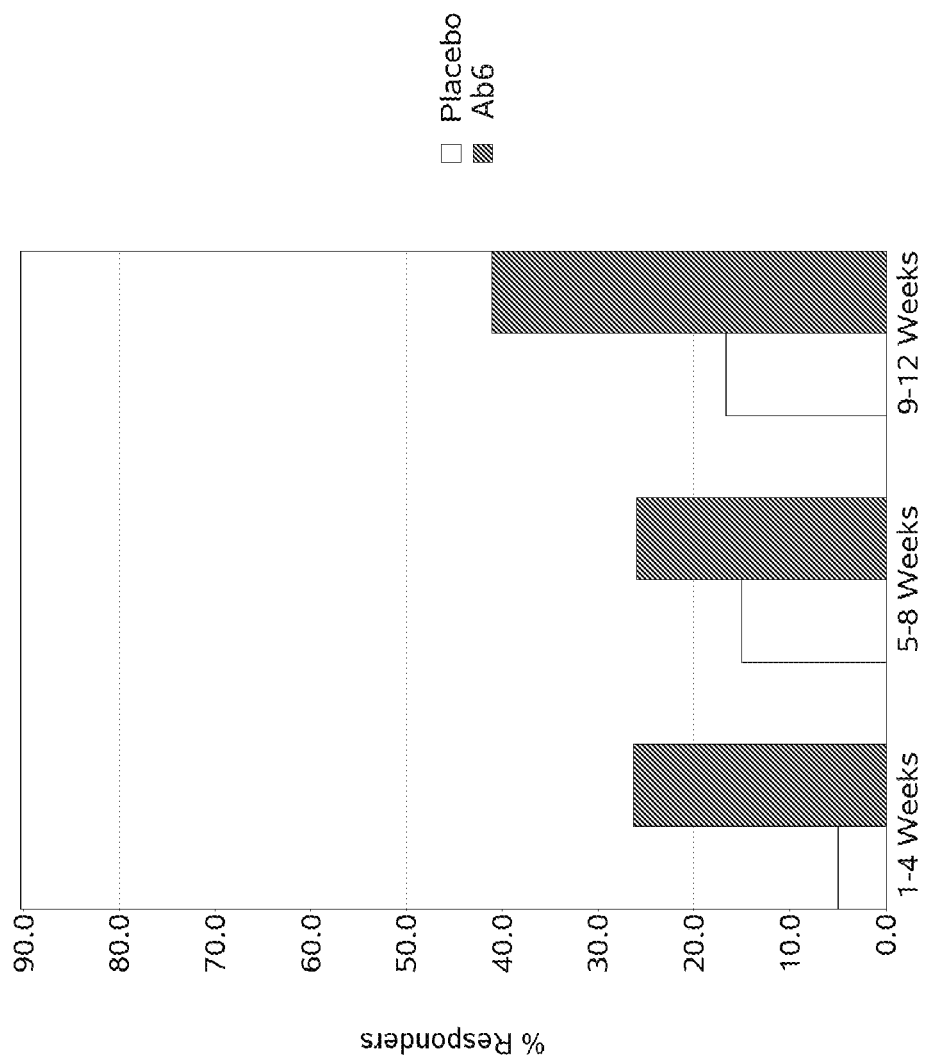
FIG. 32 shows the 100% responder rate for the Ab6 and placebo treatment group for the study described in Example 2. Subjects with 100% reduction in migraine frequency were considered to be a 100% responder. Normalization was applied as described with FIG. 30.

Responder rate analysis was also performed (FIGS. 30-32). These figures respectively show the 50%, 75%, and 100% responder rate for the Ab6 and placebo treatment groups. Subjects with ≥50% reduction in migraine frequency were considered to be a 50% responder. Subjects with ≥75% reduction in migraine frequency were considered to be a 75% responder. Likewise, subjects with 100% reduction in migraine frequency were considered to be a 100% responder.

In FIGS. 22 and 30-32, normalization was applied to visit intervals where eDiaries were completed for 21-27 days by multiplying the observed frequency by the inverse of the completion rate.

Figure 33:
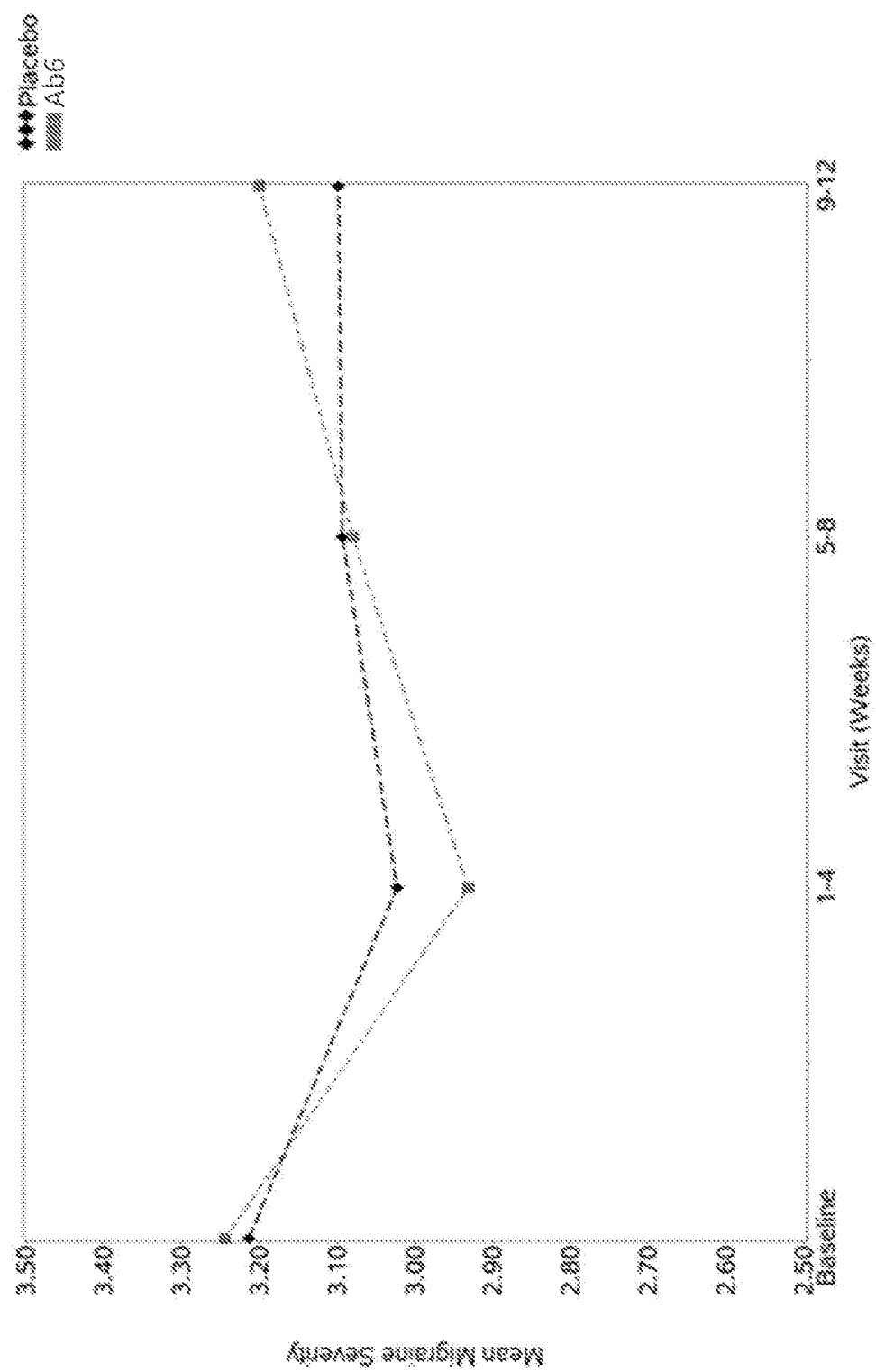
FIG. 33 shows the mean migraine severity over time for the full analysis population for the study described in Example 2. On the scale used, a mean migraine score of 3 represents "moderate pain."

Migraine severity was also analyzed. FIG. 33 shows the mean migraine severity over time for the full analysis population. On the scale used, a mean migraine score of 3 represents "moderate pain."

FIG. 34 summarizes the change from baseline in migraine days, migraine episodes, migraine hours, average migraine severity, headache frequency, and outcome measures including the HIT-6 score, MSQ (Migraine Specific Quality of Life Questionnaire) RFP (Role Function-Preventative), MSQ RFR (Role Function-Restrictive), and MSQ EF (Emotional Function).

Example 3

Human Clinical Study Evaluating the Safety and Efficacy of an Anti-CGRP Antibody in Chronic Migraine Patients This example describes a randomized, double-blind, placebo-controlled clinical trial evaluating the safety and efficacy of Ab6 for chronic migraine prevention. In the study, 1,072 patients were randomized to receive Ab6 (300 mg or 100 mg), or placebo administered by infusion once every 12 weeks. To be eligible for the trial, patients must have experienced at least 15 headache days per month, of which at least eight met criteria for migraine. Patients that participated in the trial had an average of 16.1 migraine days per month at baseline. Study endpoints included the mean change from baseline in monthly migraine days, reduction in migraine prevalence at day 1 and over days 1-28, and reduction of at least 50%, 75%, and 100% from baseline in mean monthly migraine days, change from baseline in mean monthly acute migraine-specific medication days, and reductions from baseline in patient-reported impact scores on the Headache Impact Test (HIT-6). The administered antibody, Ab6, is an anti-CGRP antibody consisting of the light chain polypeptide of SEQ ID NO: 221 and heavy chain polypeptide of SEQ ID NO: 201.

Patient characteristics are summarized in FIG. 39, with separate columns for patients receiving placebo, 100 mg of the antibody, or 300 mg of the antibody. Patients had a mean number of years from migraine diagnosis of between 17.0 and 19.0 years, a mean duration of suffering from chronic migraine of between 11.5 and 12.4 years, and between 44.3% and 45.2% of patients utilized at least one prophylactic medication. At baseline, in both antibody treatment groups the mean number of migraine days per month was 16.1, while for the placebo group, the mean number of migraine days per month was 16.2.

The reduction in a specified percentage (50%, 75%, or 100%) from baseline in mean monthly migraine days refers to the number or percentage of patients in a treatment group that exhibited the given percentage reduction in the number of migraine days per month. For example, a patient exhibiting 16 migraine days per month at baseline would be a 75% responder if the number of migraine days per month was decreased by at least 12 days per month over specified period.

Figure 35:
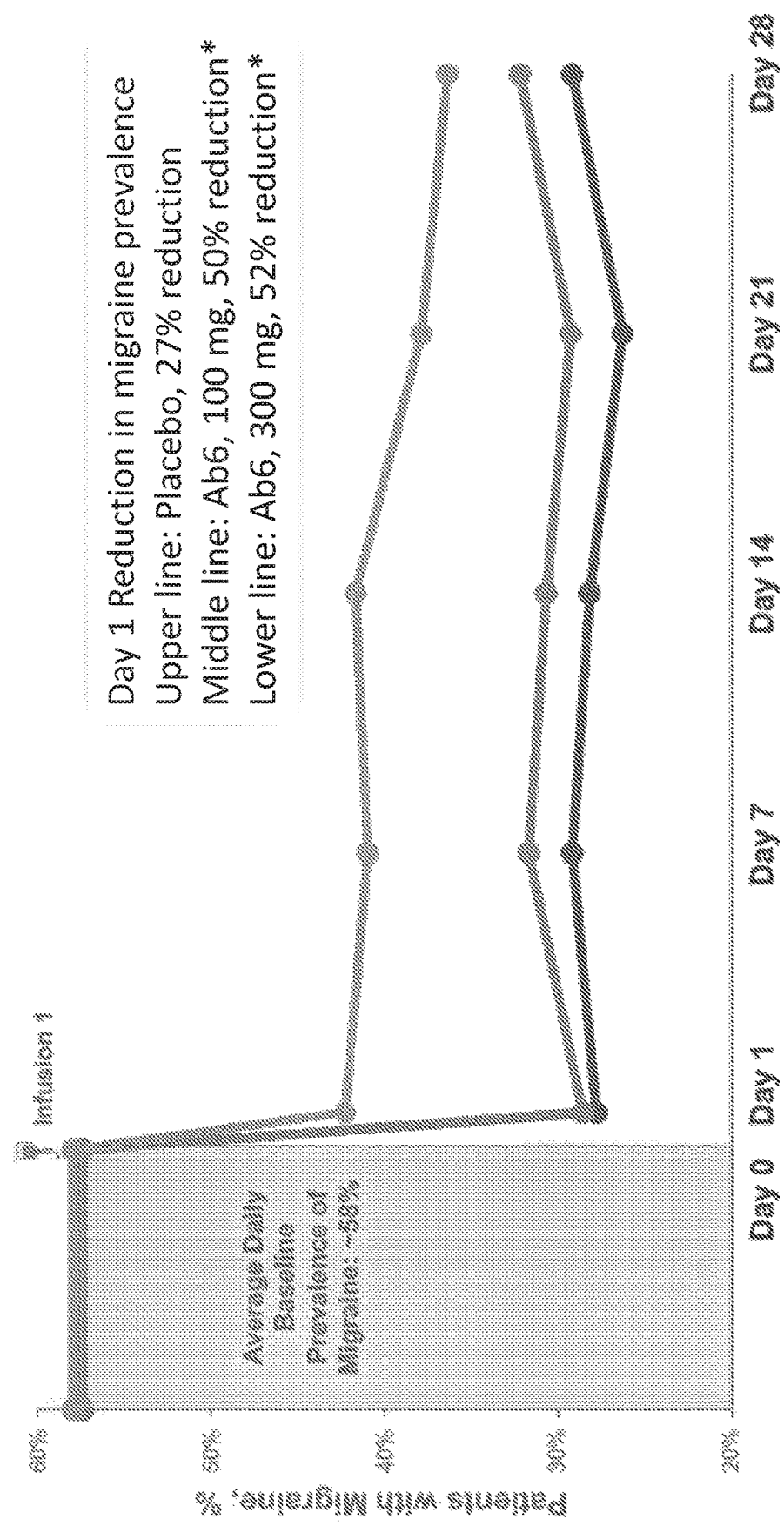
FIG. 35 shows the percentages of patients with migraine in the 300 mg, 100 mg, and placebo treatment groups at days 1, 7, 14, 21, and 28 in the clinical trial described in Example 3. The uppermost line shows results for placebo, the lowest line shows results for the 300 mg dosage, and the middle line shows results for the 100 mg dosage.

The results are shown in FIGS. 35-39. FIG. 35 shows the percentages of patients with migraine in the 300 mg, 100 mg, and placebo treatment groups at days 1, 7, 14, 21, and 28. The uppermost line shows results for placebo, the lowest line shows results for the 300 mg dosage, and the middle line shows results for the 100 mg dosage.

As shown in FIG. 35, at day 1 the percentage reduction in migraine prevalence was 52% for the 300 mg dosage, 50% at the 100 mg dosage, and 27% for placebo. The decrease was statistically significant compared to the placebo group for both the 100 mg and 300 mg treatment groups.

Figure 36:
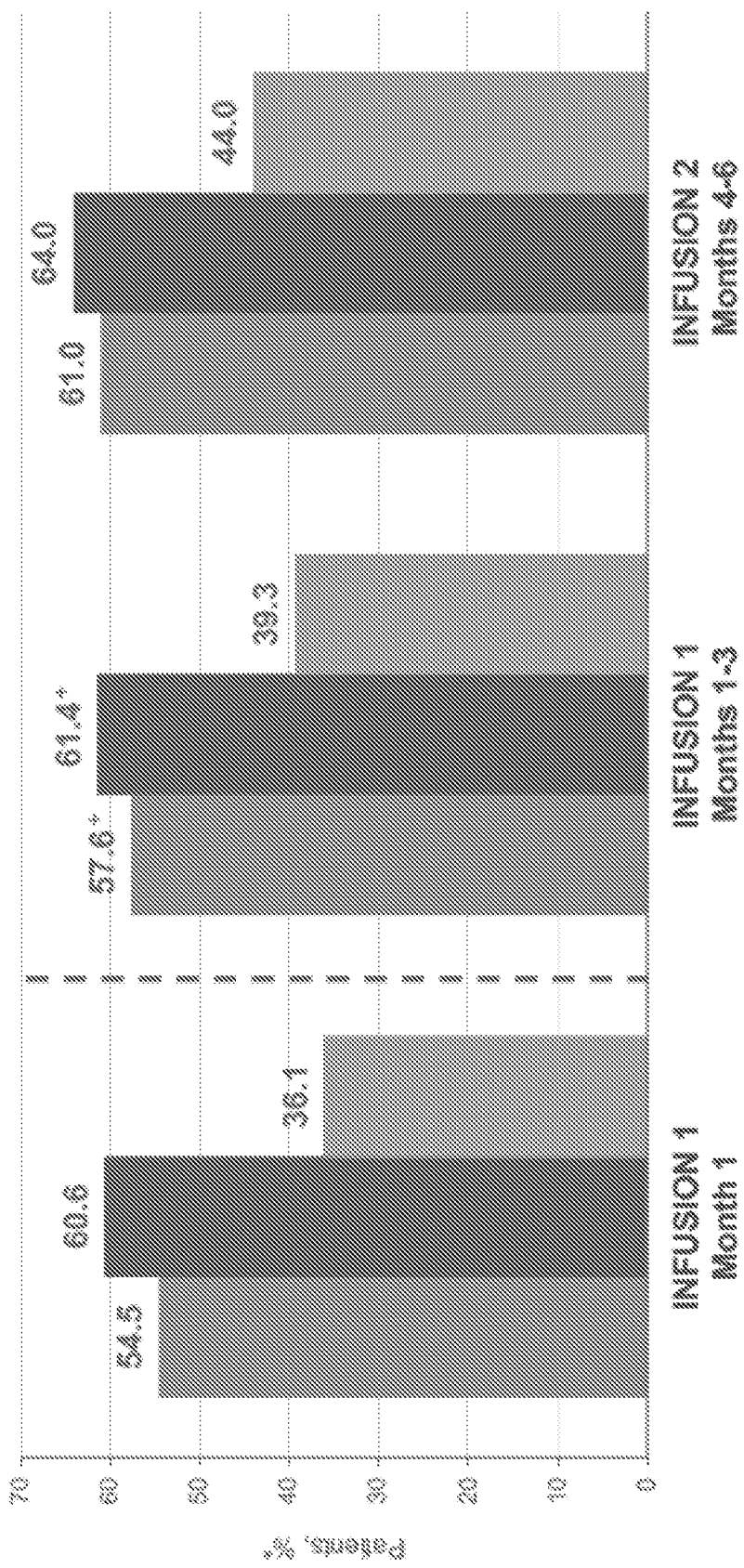
FIG. 36 show the percentage of patients in the 300 mg and 100 mg treatment groups achieving a 50% reduction in migraine days in month 1, over months 1-3 (after the 1st infusion), and over months 4-5 (after the 2nd infusion) in the clinical trial described in Example 3. In each graph, the data bars, from left to right, show results for the 100 mg, 300 mg, and placebo groups. Statistical significance is as shown. ++ indicates a statistically significant difference from placebo; + indicates a statistically significant difference from placebo (unadjusted); and § indicates a statistically significant difference from placebo (post hoc).
Figure 37:
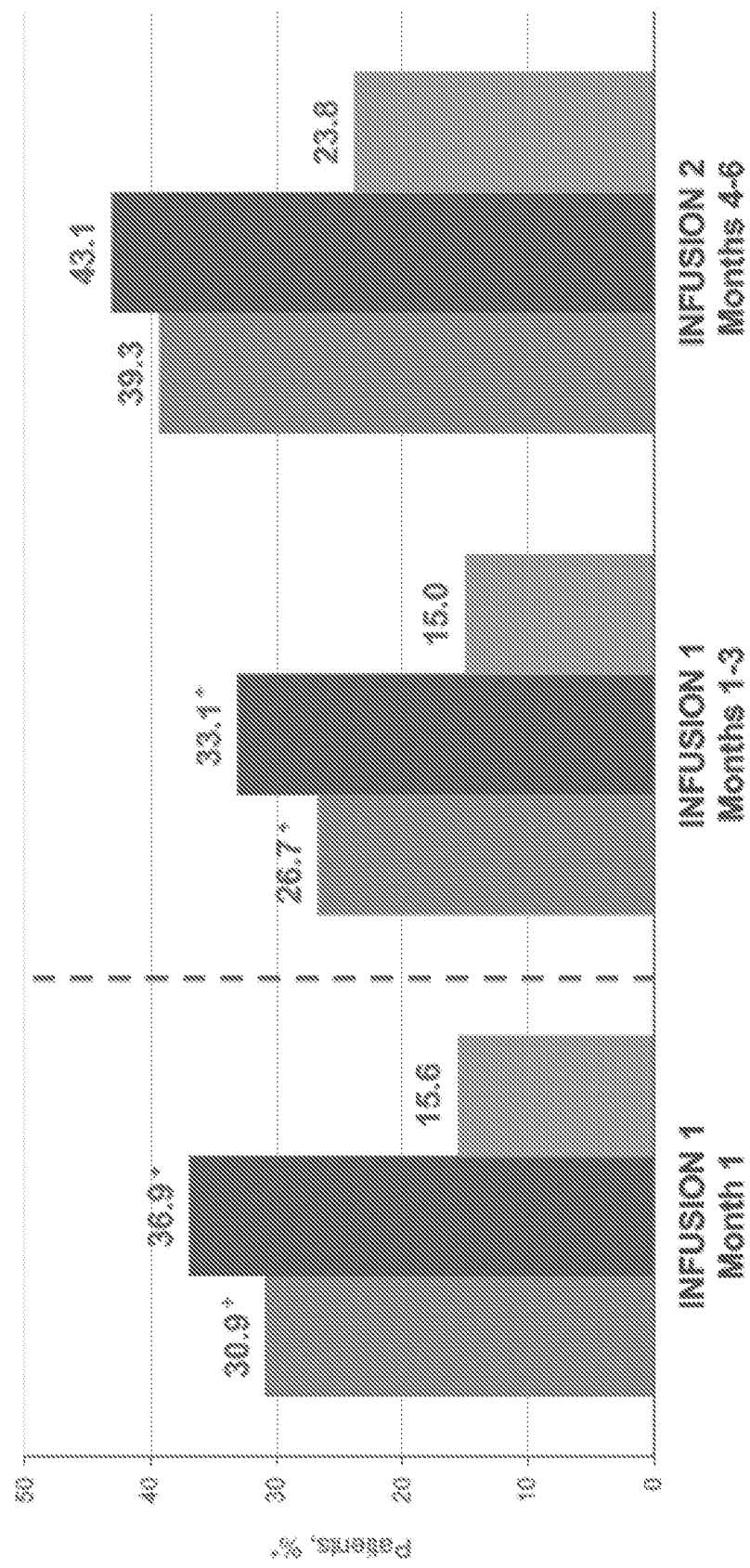
FIG. 37 show the percentage of patients in the 300 mg and 100 mg treatment groups achieving a 75% reduction in migraine days in month 1, over months 1-3 (after the 1st infusion), and over months 4-5 (after the 2nd infusion) in the clinical trial described in Example 3. Data order and statistical significance labels are as indicated with FIG. 36.
Figure 38:
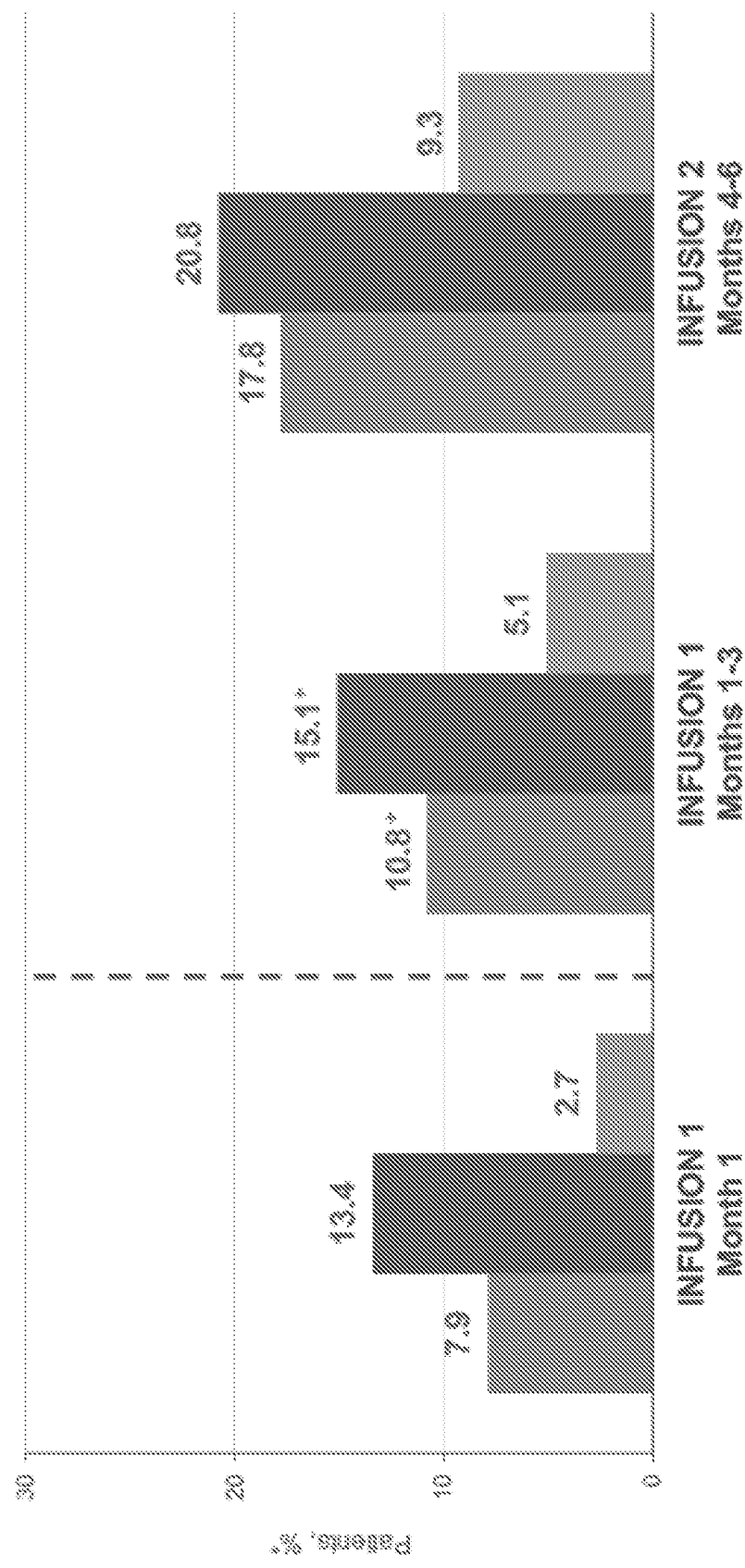
FIG. 38 show the percentage of patients in the 300 mg and 100 mg treatment groups achieving a 100% reduction in migraine days in month 1, over months 1-3 (after the 1st infusion), and over months 4-5 (after the 2nd infusion) in the clinical trial described in Example 3. Data order and statistical significance labels are as indicated with FIG. 36.

FIGS. 36-38 show the percentage of patients in the 300 mg and 100 mg treatment groups achieving, respectively, 50%, 75%, and 100% reduction in migraine days in month 1, over months 1-3 (after the 1st infusion), and over months 4-5 (after the 2nd infusion). In each graph, the data bars, from left to right, show results for the 100 mg, 300 mg, and placebo groups. Statistical significance is as shown. ++ indicates a statistically significant difference from placebo; + indicates a statistically significant difference from placebo (unadjusted); and § indicates a statistically significant difference from placebo (post hoc).

Example 4

Figure 41:
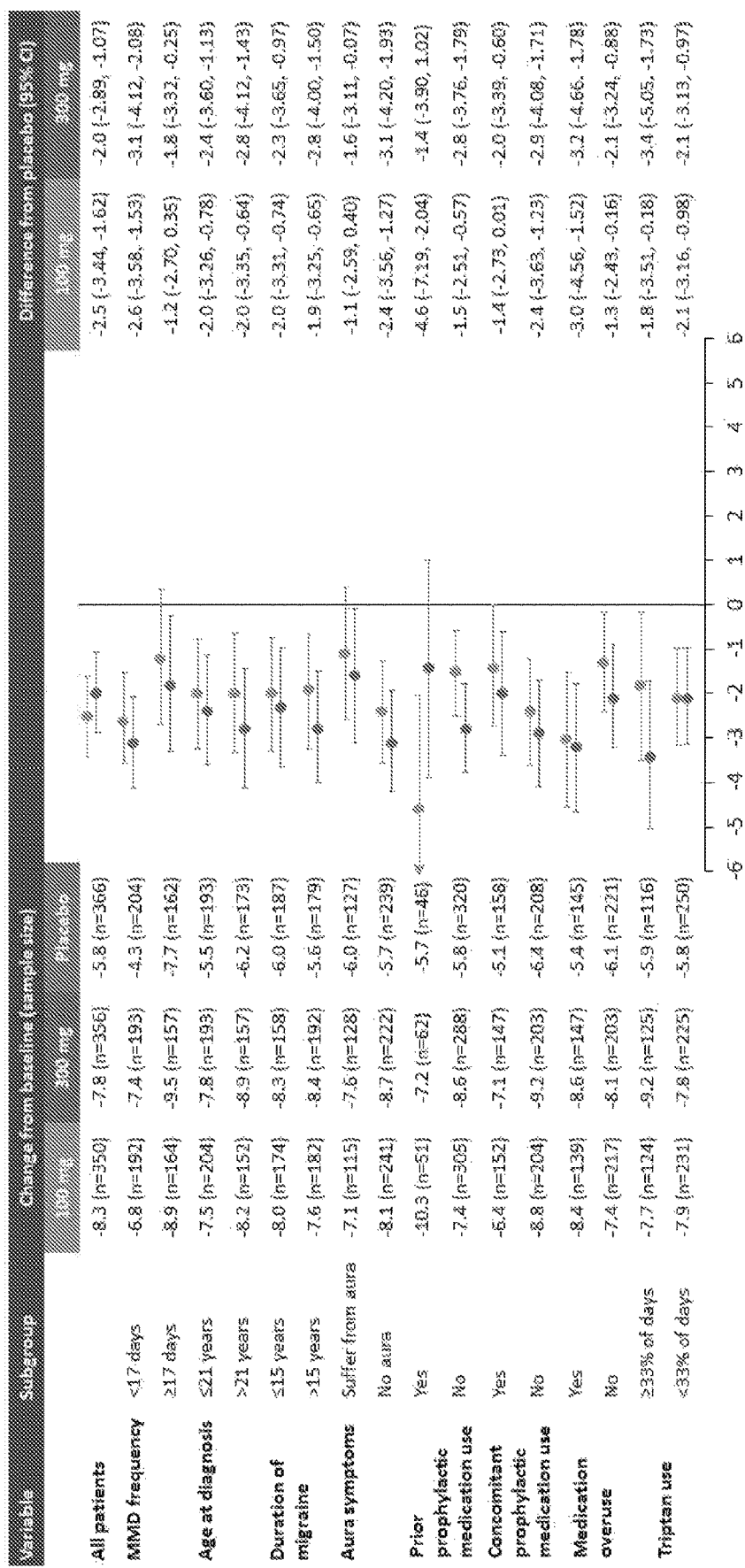
FIG. 41. Difference from placebo in change from baseline in mean migraine days (MMD) over months 1-3 by baseline subgroup for a human clinical trial of episodic migraine patients. The graph is labeled as in FIG. 40.

Baseline Subgroup Analysis for Human Clinical Studies Evaluating the Safety and Efficacy of an Anti-CGRP Antibody in Chronic or Episodic Migraine Patients In the study of Chronic Migraine described in Example 3, at intake, each patient was assessed for potential medication overuse headache (MOH). MOH was present in 39.9% (139 patients) in the 100 mg treatment group, 42.0% (147 patients) in the 300 mg treatment group, and 39.6% (145 patients) in the placebo group. Assessment of the treatment outcomes in this patient subset indicated that treatment with the anti-CGRP antibody was efficacious for MOH (FIG. 41). Specifically, in the 100 mg treatment group, mean migraine days per month changed by −3.0 days (95% CI, −4.56 to −1.52 days) in the patients having MOH at baseline, compared to MOH patients receiving placebo. Similarly, in the 300 mg treatment group, mean migraine days per month changed by −3.2 days (95% CI, −4.66 to −1.78 days) in the patients having MOH at baseline, compared to MOH patients receiving placebo. By contrast, for patients without MOH at baseline, in the 100 mg treatment group, mean migraine days per month changed by −1.3 days (95% CI, −2.43 to −0.16 days), compared to patients without MOH at baseline receiving placebo. Likewise, for patients without MOH at baseline in the 300 mg treatment group, mean migraine days per month changed by −2.1 days (95% CI, −3.24 to −0.88 days), compared to patients without MOH at baseline receiving placebo. Efficacy for other subgroups was shown as well, including efficacy for patients with mean migraine day (MMD) frequency less than 17 days or greater than or equal to 17 days, patients with an age at diagnosis of less than or equal to 21 years or greater than 21 years, patients having a duration of migraine of less than or equal to 15 year or greater than 15 years, patients suffering from migraine with aura or migraine with no aura, patients with prior prophylactic medication use or no prior prophylactic medication use, patients with concomitant prophylactic medication use or no concomitant prophylactic medication use, ant patients with triptan use on greater than or equal to 33% of days, or less than 33% of days. In each case, efficacy for each subgroup was shown (FIG. 41).

Figure 40:
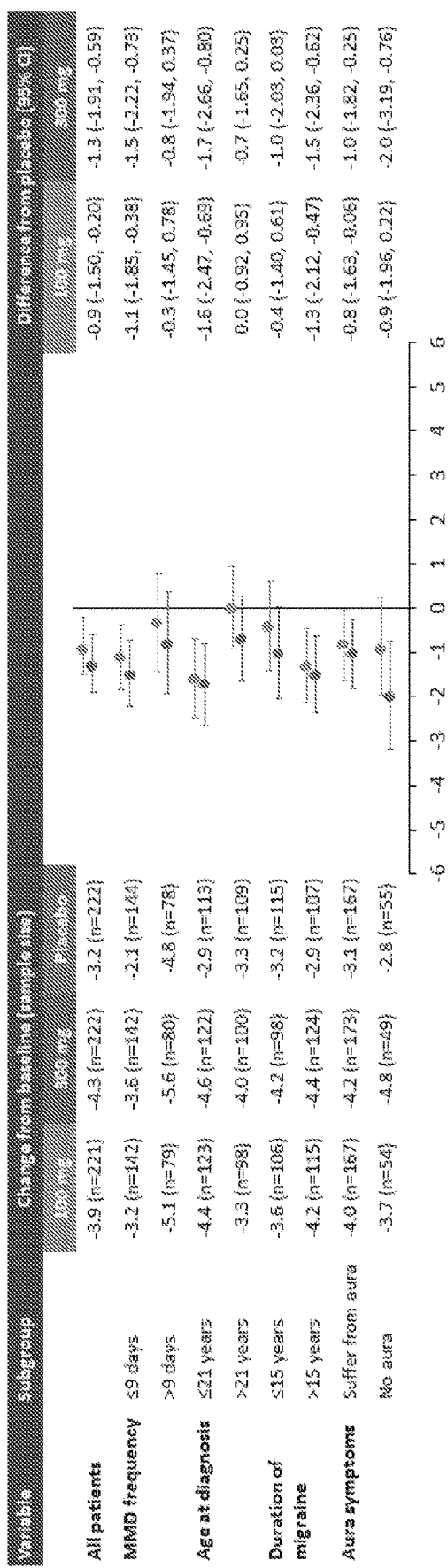
FIG. 40. Difference from placebo in change from baseline in mean migraine days (MMD) over months 1-3 by baseline subgroup for a human clinical trial of chronic migraine patients. In the graph, the data point refers to the mean value and the line shows the 95% confidence interval (CI) of the change from placebo for the 100 mg (upper line) or 300 mg (lower line) treatment group, for each subgroup as labeled at the far left.

In another human clinical trial of patients with episodic migraine, patients were randomized to receive Ab6 100 mg (n=221), 300 mg (n=222), or placebo (n=222) in a double blind, parallel study. After a 28 day screening period, patients were administered the drug or placebo intravenously every 3 months for 4 total infusions (FIG. 40). Efficacy was shown over months 1-3 for both the 100 mg and 300 mg treatment groups, with a mean change in migraine days of −3.9 for the 100 mg treatment group and −4.3 days for the 300 mg treatment group, compared to −3.2 days for the placebo group. Efficacy for subgroups of patients was also shown, including efficacy for patients with mean migraine day (MMD) frequency less than or equal to 9 days or greater than 9 days, patients with an age at diagnosis of less than or equal to 21 years or greater than 21 years, patients having a duration of migraine of less than or equal to 15 year or greater than 15 years, and patients suffering from migraine with aura or migraine with no aura.

Example 5

Effects of Ab6 Treatment on Medication Use in Chronic and Episodic Migraine Patients During the studies of chronic migraine patients described in Example 3 and episodic migraine patients described in Example 4, patients also recorded use of acute medication in a daily eDiary and were allowed to use acute medication at their own discretion. Acute medications for migraine included ergots, triptans, and analgesics (e.g., NSAIDS, opioids, and caffeine-containing combination analgesics).

For further analysis, patients were stratified by the number of days with acute medication use during the 28-day screening period (1-9 or ≥10 days; "baseline"). Acute medication days were calculated for individual types of acute medications and combined, meaning that if 2 or more types medications were used on the same calendar days, they were counted as separate medication use days. For example, if a patient took an opioid and a triptan on the same day, it counted as 2 days of acute medication use. These analyses included patients with at least 1 acute medication use day during the 28-day baseline screening period.

In both chronic migraine and episodic migraine patients who used acute medication during the 28-day baseline period, Ab6 treatment resulted in greater average reductions in monthly migraine days and acute medication days than placebo as early as Month 1 after dosing, with similar results across 2 dose intervals over 6 months.

Figure 42:
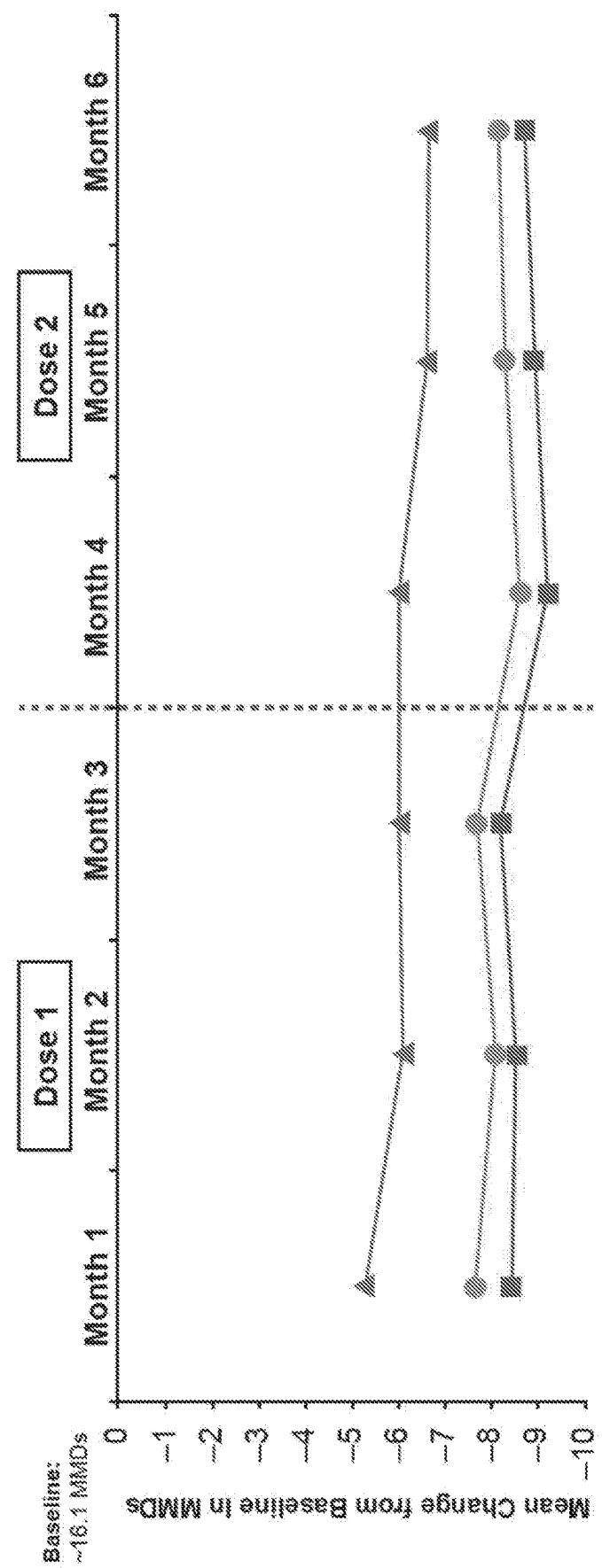
FIG. 42. Change from baseline in mean migraine days (MMDs) across 2 dose intervals in chronic migraine patients with at least 1 day of acute medication use per month at baseline. Triangle: placebo (n=366). Circle: 100 mg Ab6 per dose (n=356). Square: 300 mg Ab6 per dose (n=350).
Figure 43:
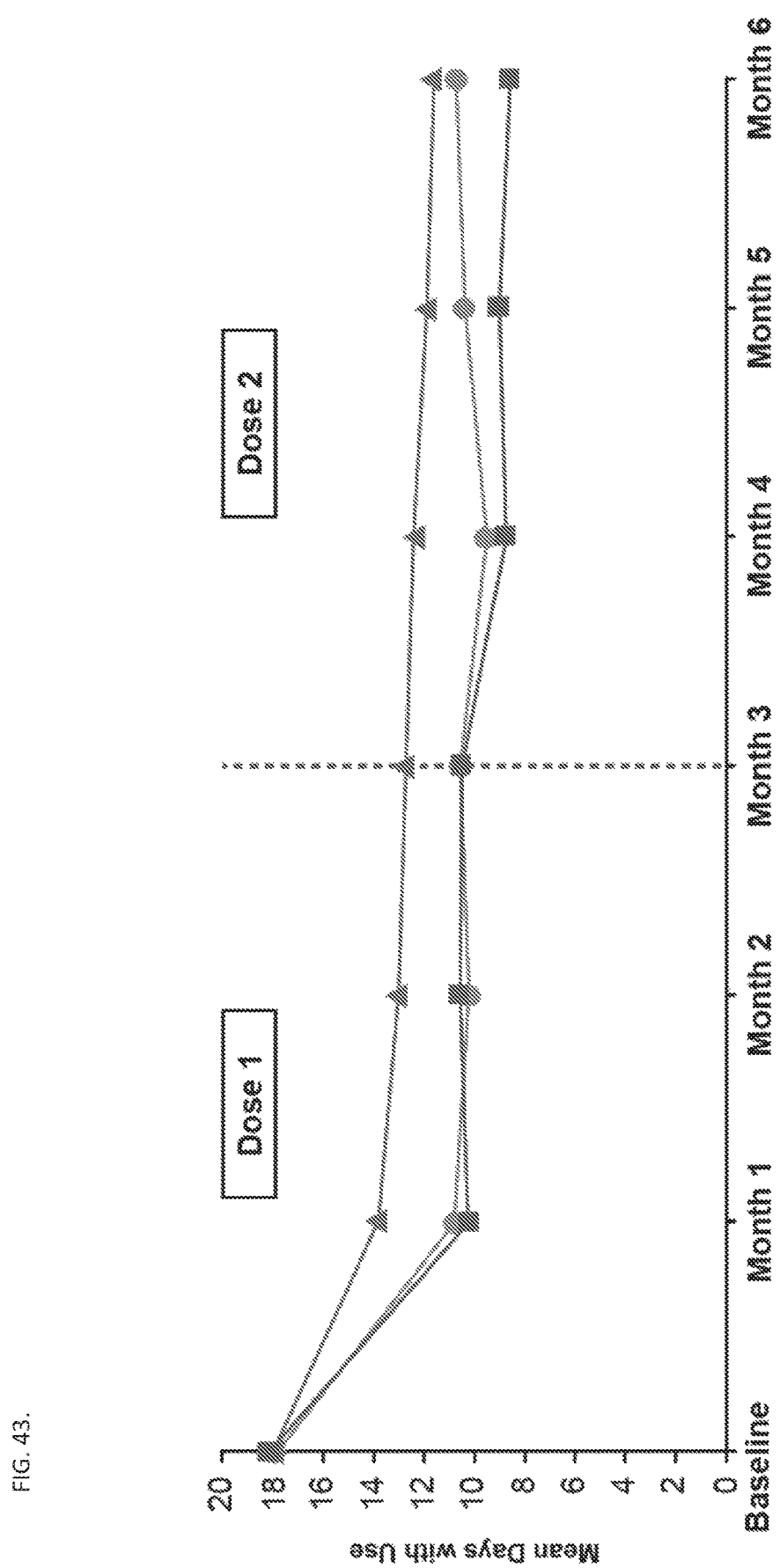
FIG. 43. Mean days with acute medication use in chronic migraine patients with at least one day per month of acute medication use at baseline. Triangle: placebo (n=366). Circle: 100 mg Ab6 per dose (n=356). Square: 300 mg Ab6 per dose (n=350).
Figure 44:
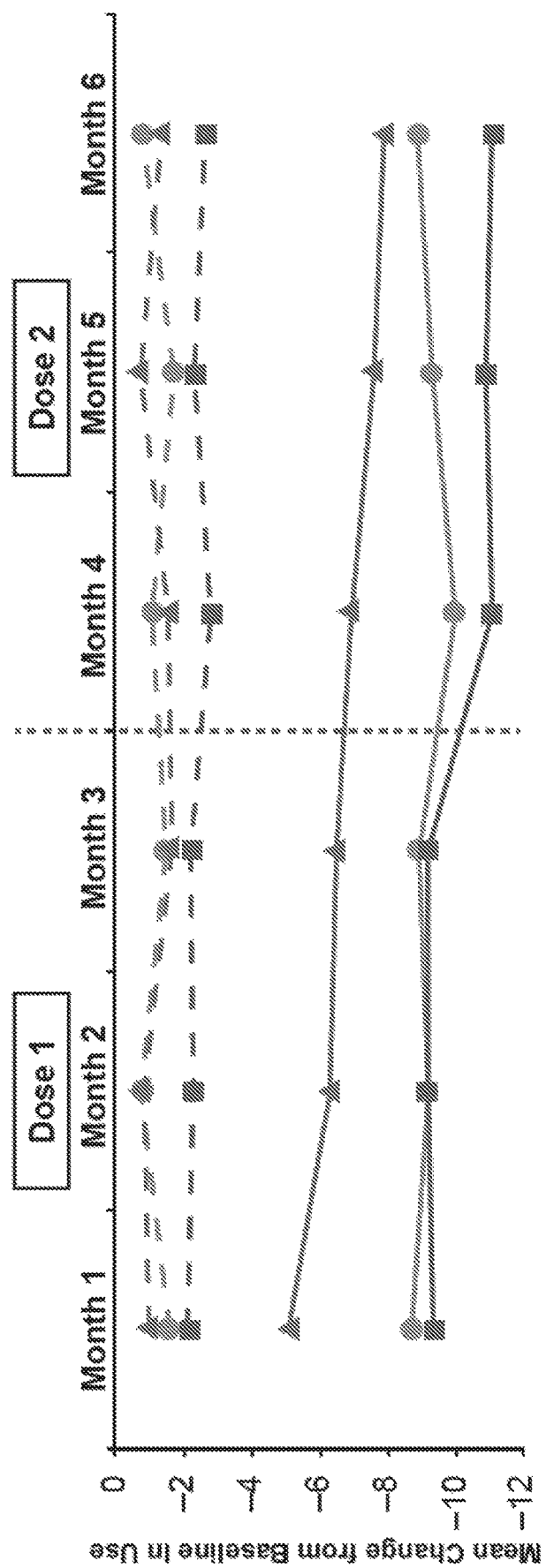
FIG. 44. Change from baseline in acute medication use by subgroups of chronic migraine patients with differing baseline days of acute medication use. Solid lines: patients with 10 or more days of acute medication use per month at baseline. Dashed lines: patients with at least 1 and less than 10 days of acute medication use per month at baseline. Triangle: placebo. Circle: 100 mg Ab6 per dose. Square: 300 mg Ab6 per dose.

Ab6 consistently demonstrated greater reductions in mean monthly migraine days over 6 months of treatment than placebo in chronic migraine patients taking ≥1 day of acute medication use during baseline (FIG. 42). Chronic migraine patients who had at least one day of acute medication use per month during baseline demonstrated greater decreases in acute medication use than placebo as early as month 1 after treatment and across the entire 6 month treatment period (FIG. 43). In the subgroup of chronic migraine patients who were taking 1-9 days of acute medication during baseline, the change from baseline in days of acute medication use was greater in the 300 mg Ab6 group than placebo across 6 months of treatment (FIG. 44). A clear decrease in medication days per month was observed for patients with at least 10 days of medication use per month at baseline for both Ab6 treatment group compared to placebo over the entire 6 month period. FIG. 45 shows the changes in medication use days at Month 1 and Month 6 in the subgroups of chronic migraine patients with ≥1, 1-9, and ≥10 days of acute medication use at baseline. With the exception of Ab6 100 mg at month 6 in patients with 1-9 days/month of use at baseline, Ab6 demonstrated a greater treatment effect in reducing acute medication use than placebo.

Figure 46:
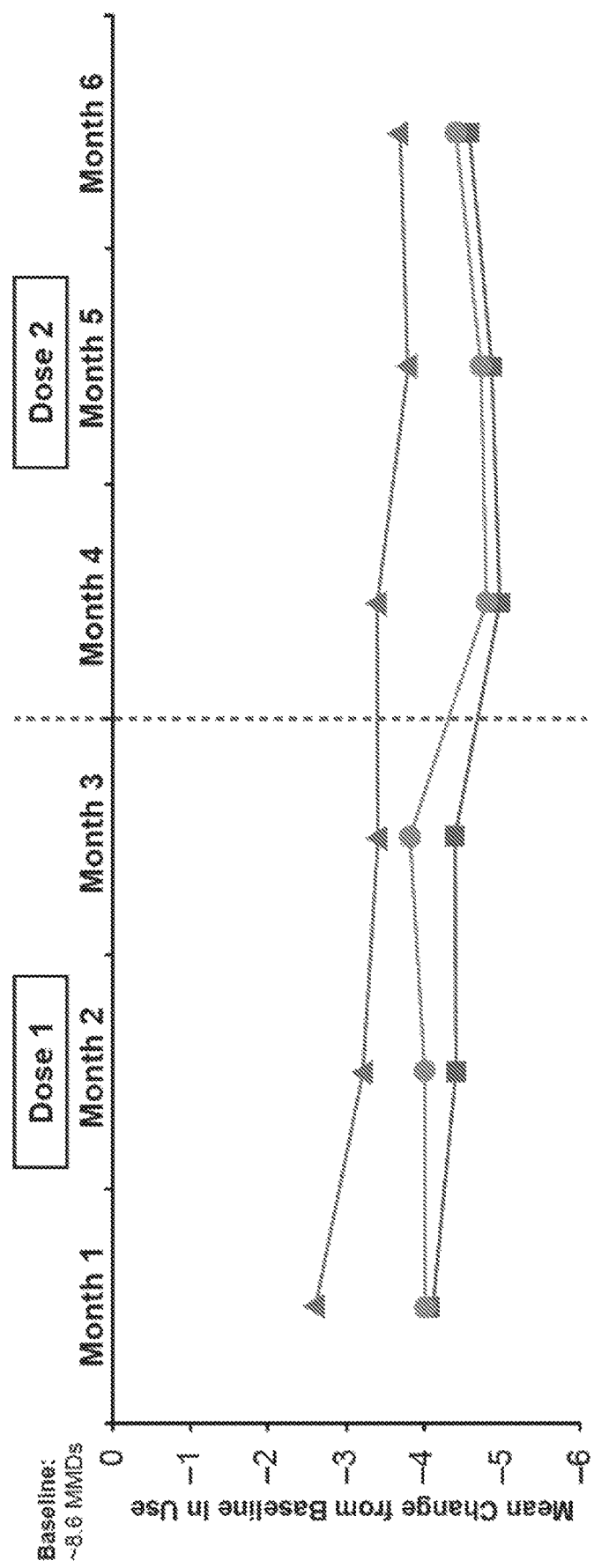
FIG. 46. Change from baseline in mean migraine days (MMDs) across 2 dose intervals in episodic migraine patients with at least 1 day of acute medication use per month at baseline. Triangle: placebo (n=222). Circle: 100 mg Ab6 per dose (n=221). Square: 300 mg Ab6 per dose (n=222).
Figure 47:
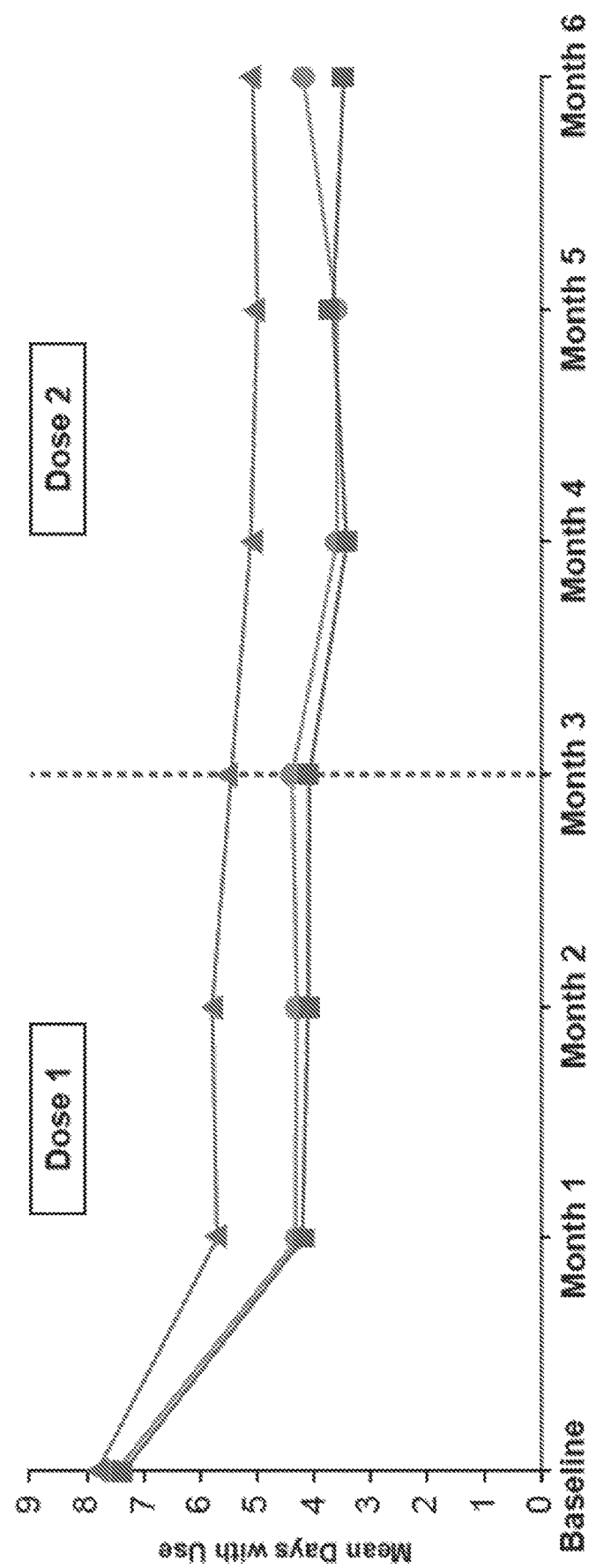
FIG. 47. Mean days with acute medication use in episodic migraine patients with at least one day per month of acute medication use at baseline. Triangle: placebo (n=222). Circle: 100 mg Ab6 per dose (n=221). Square: 300 mg Ab6 per dose (n=222).
Figure 48:
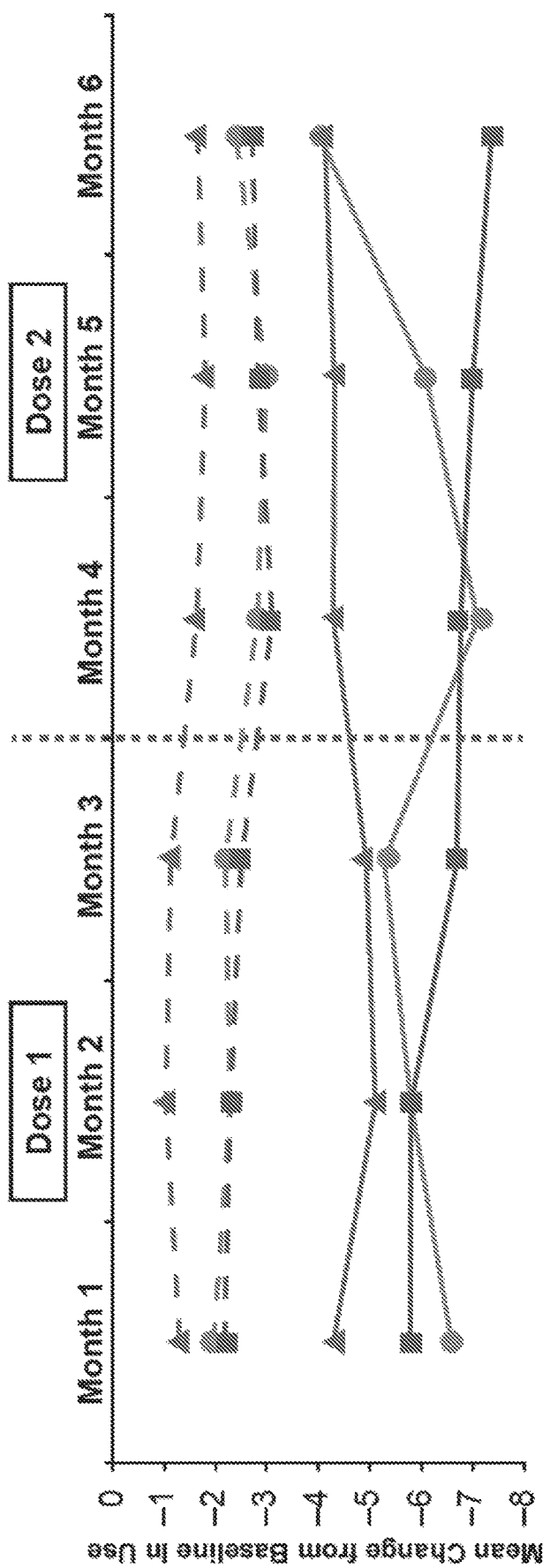
FIG. 48. Change from baseline in acute medication use by subgroups of episodic migraine patients with differing baseline days of acute medication use. Solid lines: patients with 10 or more days of acute medication use per month at baseline. Dashed lines: patients with at least 1 and less than 10 days of acute medication use per month at baseline. Triangle: placebo. Circle: 100 mg Ab6 per dose. Square: 300 mg Ab6 per dose.

Similarly, across 2 dose intervals over 6 months, episodic migraine patients with one or more days of acute medication use during baseline experienced greater reductions in mean monthly migraine days with Ab6 than Placebo (FIG. 46). Episodic migraine patients who had at least one day of acute medication use per month during baseline demonstrated greater decreases in acute medication use than placebo as early as month 1 after treatment and across the entire 6 month treatment period (FIG. 47). In the subgroup of episodic migraine patients who were taking 1-9 days of acute medication during baseline, the change from baseline in days of acute medication use was greater with Ab6 than placebo across 6 months of treatment (FIG. 48). A similar pattern was observed in the subgroup of patients who were taking ≥10 days of acute medication during baseline, though smaller sample sizes may have contributed to the less consistent pattern over time. FIG. 49 shows the changes in medication use days at Month 1 and Month 6 in the subgroups of episodic migraine patients with ≥1, 1-9, and ≥10 days of acute medication use at baseline. With the exception of Ab6 100 mg at Month 6 in patients with ≥10 days/month of use at baseline, the reduction in acute medication use was greater in the Ab6 treatment groups than placebo.

The results show that both episodic migraine and chronic migraine patients who were at risk for medication-overuse headache (≥10 days/month of acute medication use) demonstrated the greatest reductions in acute medication use, with Ab6 treatment generally resulting in larger decreases in medication use days than placebo.

The most frequently reported acute headache medications in >10% of subjects included Thomapyrin N (44.5%) (a combination of paracetamol, aspirin, and caffeine), ibuprofen (40.6%), sumatriptan (33.6%), paracetamol (acetaminophen) (20.3%), and naproxen sodium (10.2%). The most frequently reported preventive headache medication in >10% of subjects was topiramate (12.5%).

Example 6

Efficacy of Anti-CGRP Antibodies in Subjects Experiencing an Acute Attack of Migraine This example describes a randomized, double-blind, placebo-controlled clinical trial evaluating the safety and efficacy of Ab6 for the acute treatment of migraine. In the study, approximately 450 patients are randomized 1:1 to receive either 100 mg Ab6 or placebo. During a screening period (approx. 1-8 weeks) patients are assessed for migraine frequency and medication use frequency. Eligible patients have a migraine attack frequency of about 4-15 migraine days per month in the 3 months prior to screening. By history, the subject's typical migraine attack, if untreated, would be associated with headache pain of moderate to severe intensity and a most bothersome symptom of nausea, photophobia, or phonophobia. Subjects must be headache free for at least 24 hours prior to onset of a qualifying migraine in order to participate in the trial. On the day of treatment, the patient will travel to the study site and intravenous infusion of 100 mg Ab6 or placebo will commence between about 1-6 hours from the start of the attack. Patients will not have received any other monoclonal antibody (e.g., any CGRP antagonist antibody) within the 6 month period prior to screening.

Co-Primary Endpoints are time to headache pain freedom and time to absence of most bothersome symptom. Co-Key secondary are headache pain freedom at 2 hours and absence of most bothersome symptom at 2 hours. Secondary endpoints are time to headache pain relief, headache pain freedom at 2 hours with sustained headache pain freedom for 24 and 48 hours, use of rescue medication by 24 hours and by 48 hours, absence of photophobia at 2 hours, absence of phonophobia at 2 hours, absence of nausea at 2 hours, change from Baseline in Headache Impact Test (HIT 6) at Week 4, and change from Baseline in Migraine Treatment Optimization Questionnaire-6 (mTOQ-6) at Week 4. Exploratory Endpoints are absence of headache pain at all timepoints other than 2 hours, absence of photophobia at all timepoints other than 2 hours, absence of phonophobia at all timepoints other than 2 hours, absence of nausea at all timepoints other than 2 hours, pain relapse when the subject was headache pain-free at 2 hours, patient Global Impression of Change (PGIC) at Week 4, and time to next migraine. Headache pain is collected on a 4-point scale with 3 being severe, 2 being moderate, 1 being mild, and 0 being no pain. Pain freedom is no pain (0) with the absence of rescue medication (note that in the trial rescue medication is not to be used for 2 hours post completion of infusion in order to separate the effects of the antibody from the rescue medication, however, in the course of normal use, rescue medication optionally may be used; any use of rescue medication is collected as data).

Statistical analysis is performed to determine significance of the difference in endpoints between patients receiving Ab6 or placebo, including the time to pain freedom and time to absence of most bothersome symptom, and each of the other aforementioned endpoints.

Use of rescue medication refers to any intervention (medical or device) provided to the subject to provide relief of migraine. In the study this should not be provided sooner than 2 hours following completion of the study drug administration in order to separate the effects of the antibody from the effects of said rescue medication, however, rescue medication is not contraindicated. The proportion of subjects requiring rescue medication use is summarized in the study. Acute rescue medication includes any medication to treat migraine or migraine associated symptoms, e.g., triptans, analgesics such as non-opioids or opioids/narcotics, acetaminophen, NSAIDS, combination medications such as EXCEDRIN® or EXCEDRIN MIGRAINE®, antiemetic medications, ergotamines, ergot derivatives, etc.

Absence of Migraine-Associated Symptoms (Photophobia, Phonophobia and Nausea) refers to the absence or presence of each of the aforementioned migraine-associated symptoms, as reported by the subject. The proportion of subjects absent the symptoms, with no administration of rescue medication, is summarized in the study.

Headache Impact Test (HIT-6) is assessed as the change from baseline of the total score, and is summarized and compared between treatment groups in the study.

Migraine Treatment Optimization Questionnaire-6 (mTOQ-6) is assessed as the change from baseline of the total score and is summarized and compared between the treatment groups in the study.

Time to Headache Pain Relief is assessed as the first time point post completion of infusion at which the subject reports relief of pain meaning their headache pain has gone from moderate or severe (2 or 3) to mild or no pain (1 or 0) with no administration of rescue medication.

Pain Relapse is assessed as the occurrence of headache of any severity within 48 hours of drug administration for a patient who has no headache pain (0) at 2 hours. The proportion of subjects with recurrence of headache pain of any severity is summarized in the study.

The study shows that Ab6 is effective and safe for acute migraine treatment.

What is claimed is:

1. A method of acute treatment of migraine in a patient in need thereof, the method comprising intravenously administering to the patient:
   (A) about 100 mg or about 300 mg of a monoclonal antibody comprising:
      (a) a variable light chain polypeptide comprising light chain complementary determining region (CDR) 1, 2, and 3 polypeptide sequences of SEQ ID NO: 224, SEQ ID NO: 226, and SEQ ID NO: 228, respectively, and
      (b) a variable heavy chain polypeptide comprising heavy chain CDR 1, 2, and 3 polypeptide sequences of SEQ ID NO: 204, SEQ ID NO: 206, and SEQ ID NO: 208, respectively; and
   (B) one or more acute migraine medications,
wherein the administering begins while the patient is experiencing a headache, and wherein the administering is followed by preventive treatment once every three months using about 100 mg or about 300 mg of said monoclonal antibody.

2. The method according to claim 1, wherein the one or more acute migraine medications comprise triptan, an analgesic such as non-opioids or opioids/narcotics, acetaminophen, an non-steroidal anti-inflammatory drug (NSAID), a combination medication, an ergotamine, and/or an ergot derivative.

3. The method according to claim 2, wherein the patient suffers from chronic migraine.

4. The method according to claim 3, wherein the about 100 mg or about 300 mg of the monoclonal antibody is administered to the patient once every three months, for at least six months.

5. The method according to claim 2, wherein the patient suffers from episodic migraine.

6. The method according to claim 5, wherein the about 100 mg or about 300 mg of the monoclonal antibody is administered to the patient once every three months, for at least twelve months.

7. The method according to claim 2, wherein the monoclonal antibody comprises a human IgG1 constant region and is produced in Chinese hamster ovary (CHO) cells.

8. The method according to claim 2, wherein the monoclonal antibody comprises a human IgG1 constant region and is produced in *Pichia pastoris* yeast cells.

9. The method according to claim 2, wherein the monoclonal antibody is a humanized IgG1 monoclonal antibody.

10. The method according to claim 2, wherein:
    (A) the variable light chain polypeptide comprises the amino acid sequence of SEQ ID NO: 222; and
    (B) the variable heavy chain polypeptide comprises the amino acid sequence of SEQ ID NO: 202.

11. The method according to claim 10, wherein the monoclonal antibody is produced in CHO cells.

12. The method according to claim 10, wherein the monoclonal antibody further comprises the heavy chain constant region polypeptide sequence of SEQ ID NO: 565.

13. The method according to claim 2, wherein the monoclonal antibody comprises:
    (A) a light chain polypeptide comprising the amino acid sequence of SEQ ID NO: 221; and
    (B) a heavy chain polypeptide comprising the amino acid sequence of SEQ ID NO: 201.

14. The method according to claim 2, wherein the monoclonal antibody comprises:
    (A) a light chain polypeptide comprising the amino acid sequence of SEQ ID NO: 221; and
    (B) a heavy chain polypeptide comprising the amino acid sequence of SEQ ID NO: 566.

15. The method according to claim 2, wherein the patient experiences:
    (i) a reduction in the number of migraine days per month in the one-month period following the administration of the monoclonal antibody, relative to the number of migraine days per month experienced by the patient during the previous one-month period prior to said administration;
    (ii) a reduction in the number of migraine days per month in the three-month period following the administration of the monoclonal antibody, relative to the baseline number of migraine days per month experienced by the patient prior to said administration, wherein said baseline number of migraine days per month is determined over a period of one month or longer; and/or
    (iii) a reduction in migraine prevalence in the one-month period after being administered the monoclonal antibody, relative to the patient's migraine prevalence during the previous one-month period prior to said administration.

16. The method according to claim 1, wherein said administering is completed within 1-2 hours.

17. A method of reducing the occurrence of migraine in a patient in need thereof, the method comprising intravenously administering to the patient, about 100 mg or about 300 mg of a monoclonal antibody comprising:
    (A) a variable light chain polypeptide comprising light chain complementary determining region (CDR) 1, 2, and 3 polypeptide sequences of SEQ ID NO: 224, SEQ ID NO: 226, and SEQ ID NO: 228, respectively, and
    (B) a variable heavy chain polypeptide comprising heavy chain CDR 1, 2, and 3 polypeptide sequences of SEQ ID NO: 204, SEQ ID NO: 206, and SEQ ID NO: 208, respectively,
wherein the administering begins while the patient is experiencing a headache, and wherein the administering is followed by administration of about 100 mg or about 300 mg of said monoclonal antibody once every three months.

18. The method according to claim 17, wherein the patient suffers from chronic migraine.

19. The method according to claim 18, wherein the about 100 mg or about 300 mg of the monoclonal antibody is intravenously administered to the patient once every three months, for at least six months.

20. The method according to claim 17, wherein the patient suffers from episodic migraine.

21. The method according to claim 20, wherein the about 100 mg or about 300 mg of the monoclonal antibody is intravenously administered to the patient once every three months, for at least twelve months.

22. The method according to claim 17, wherein the monoclonal antibody comprises a human IgG1 constant region and is produced in CHO cells.

23. The method according to claim 17, wherein the monoclonal antibody comprises a human IgG1 constant region and is produced in *Pichia pastoris* yeast cells.

24. The method according to claim 17, wherein the monoclonal antibody is a humanized IgG1 monoclonal antibody.

25. The method according to of claim 17, wherein:
    (A) the variable light chain polypeptide comprises the amino acid sequence of SEQ ID NO: 222; and
    (B) the variable heavy chain polypeptide comprises the amino acid sequence of SEQ ID NO: 202.

26. The method according to claim 25, wherein the monoclonal antibody is produced in CHO cells.

27. The method according to claim 25, wherein the monoclonal antibody further comprises the heavy chain constant region polypeptide sequence of SEQ ID NO: 565.

28. The method according to claim 17, wherein the monoclonal antibody comprises:
   (A) a light chain polypeptide comprising the amino acid sequence of SEQ ID NO: 221; and
   (B) a heavy chain polypeptide comprising the amino acid sequence of SEQ ID NO: 201.

29. The method according to claim 17, wherein the monoclonal antibody comprises:
   (A) a light chain polypeptide comprising the amino acid sequence of SEQ ID NO: 221; and
   (B) a heavy chain polypeptide comprising the amino acid sequence of SEQ ID NO: 566.

30. The method according to claim 17, wherein the patient experiences:
   (i) a reduction in the number of migraine days per month in the one-month period following the administration of the monoclonal antibody, relative to the number of migraine days per month experienced by the patient during the previous one-month period prior to said administration;
   (ii) a reduction in the number of migraine days per month in the three-month period following the administration of the monoclonal antibody, relative to the baseline number of migraine days per month experienced by the patient prior to said administration, wherein said baseline number of migraine days per month is determined over a period of one month or longer; and/or
   (iii) a reduction in migraine prevalence in the one-month period following the administration of the monoclonal antibody, relative to the patient's migraine prevalence during the previous one-month period prior to said administration.

31. The method according to claim 17, wherein said administering is completed within 1-2 hours.

* * * * *